United States Patent
Spencer et al.

(10) Patent No.: US 10,654,910 B2
(45) Date of Patent: May 19, 2020

(54) FACTOR VIII PROTEINS HAVING ANCESTRAL SEQUENCES, EXPRESSION VECTORS, AND USES RELATED THERETO

(71) Applicants: Emory University, Atlanta, GA (US); Georgia Tech Research Corporation, Atlanta, GA (US)

(72) Inventors: H. Trent Spencer, Marietta, GA (US); Christopher Doering, Atlanta, GA (US); Philip M. Zakas, Atlanta, GA (US); Eric Gaucher, Atlanta, GA (US)

(73) Assignees: Emory University, Atlanta, GA (US); Georgia Tech Research Corporation, Atlanta, GA (US)

(*) Notice: Subject to any disclaimer, the term of this patent is extended or adjusted under 35 U.S.C. 154(b) by 0 days.

(21) Appl. No.: 15/547,742

(22) PCT Filed: Jan. 27, 2016

(86) PCT No.: PCT/US2016/015092
§ 371 (c)(1),
(2) Date: Jul. 31, 2017

(87) PCT Pub. No.: WO2016/123200
PCT Pub. Date: Aug. 4, 2016

(65) Prior Publication Data
US 2018/0009873 A1    Jan. 11, 2018

Related U.S. Application Data

(60) Provisional application No. 62/109,964, filed on Jan. 30, 2015.

(51) Int. Cl.
C07K 14/755    (2006.01)
A61K 38/00    (2006.01)

(52) U.S. Cl.
CPC ............ *C07K 14/755* (2013.01); *A61K 38/00* (2013.01)

(58) Field of Classification Search
None
See application file for complete search history.

(56) References Cited

U.S. PATENT DOCUMENTS

| | | |
|---|---|---|
| 2004/0197875 A1 | 10/2004 | Hauser et al. |
| 2007/0166283 A1 | 7/2007 | High et al. |
| 2012/0065136 A1 | 3/2012 | Fay et al. |
| 2013/0296244 A1 | 11/2013 | Lai et al. |

FOREIGN PATENT DOCUMENTS

| | | |
|---|---|---|
| WO | WO 2012/061689 A2 | 5/2012 |
| WO | WO 2013/123457 | 8/2013 |

OTHER PUBLICATIONS

Gunasekera, et al Factor VIII gene variants and inhibitor risk in African American hemophilia A patients, Blood, Aug. 13, 2015 x vol. 126, No. 7, 895-904 11 pages total. (Year: 2015).*
Brown et al. "Bioengineered coagulation factor VIII enables long-term correction of murine hemophilia A following liver-directed adeno-associated viral vector delivery," *Molecular Therapy-Methods & Clinical Development* 1 (2014): 14036.
Doering et al. "Identification of porcine coagulation factor VIII domains responsible for high level expression via enhanced secretion." *Journal of Biological Chemistry* 279, No. 8 (2004): 6546-6552.
Hussain et al. "Three novel F8 mutations in sporadic haemophilia A cases." *Springer Plus* 1, No. 1 (2012): 10.
McIntosh et al. "Therapeutic levels of FVIII following a single peripheral vein administration of rAAV vector encoding a novel human factor VIII variant." *Blood* 121, No. 17 (2013): 3335-3344.
Schwarz et al. "F8 haplotype and inhibitor risk: results from the Hemophilia Inhibitor Genetics Study (HIGS) Combined Cohort." *Haemophilia* 19, No. 1 (2013): 113-118.
Zakas et al. "Expanding the ortholog approach for hemophilia treatment complicated by factor VIII inhibitors." *Journal of Thrombosis and Haemostasis* 13, No. 1 (2015): 72-81.
Extended European Search Report for EP Application No. 16744021.3, mailed by the European Patent Office dated Sep. 3, 2018 (8 pages).
Lind, et al. "Novel forms of B-domain-deleted recombinant factor VIII molecules: construction and biochemical characterization." *European Journal of Biochemistry* 232.1 (1995): 19-27.
Powell. "Recombinant factor VIII in the management of hemophilia A: current use and future promise." *Therapeutics and Clinical Risk Management* 5 (2009): 391-402.
Ngo et al., "Crystal Structure of Human Factor VIII: Implications for the Formation of the Factor IXa-Factor VIIIa Complex," *Structure* 16:597-606, 2008.
Shen et al., "The tertiary structure and doman organization of coagulation factor VIII," *Blood* 111:1240-1247, 2008.

* cited by examiner

*Primary Examiner* — Thomas S Heard
(74) *Attorney, Agent, or Firm* — Kilpatrick Townsend & Stockton LLP

(57) ABSTRACT

This disclosure relates to recombinant or chimeric FVIII proteins, variants, and vectors encoding the proteins containing one or more ancestral mutations. In certain embodiments, one or more protein domains comprise amino acid sequences that are derived from ancestrally reconstructed amino acid sequences. In certain embodiments, the disclosure relates to pharmaceutical compositions comprising the proteins or vectors and related methods of inducing blood clotting.

18 Claims, 8 Drawing Sheets

Specification includes a Sequence Listing.

SEQUENCE LISTING

<160> NUMBER OF SEQ ID NOS: 281

<210> SEQ ID NO 1
<211> LENGTH: 2351
<212> TYPE: PRT
<213> ORGANISM: Homo sapiens

<400> SEQUENCE: 1

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365
```

-continued

```
Leu Thr Asp Ser Glu Met Asp Val Val Arg Phe Asp Asp Asn Ser
    370             375                 380
Pro Ser Phe Ile Gln Ile Arg Ser Val Ala Lys Lys His Pro Lys Thr
385             390                 395                 400
Trp Val His Tyr Ile Ala Ala Glu Glu Asp Trp Asp Tyr Ala Pro
                405                 410                 415
Leu Val Leu Ala Pro Asp Asp Arg Ser Tyr Lys Ser Gln Tyr Leu Asn
            420                 425                 430
Asn Gly Pro Gln Arg Ile Gly Arg Lys Tyr Lys Lys Val Arg Phe Met
        435                 440                 445
Ala Tyr Thr Asp Glu Thr Phe Lys Thr Arg Glu Ala Ile Gln His Glu
    450                 455                 460
Ser Gly Ile Leu Gly Pro Leu Leu Tyr Gly Glu Val Gly Asp Thr Leu
465                 470                 475                 480
Leu Ile Ile Phe Lys Asn Gln Ala Ser Arg Pro Tyr Asn Ile Tyr Pro
                485                 490                 495
His Gly Ile Thr Asp Val Arg Pro Leu Tyr Ser Arg Arg Leu Pro Lys
            500                 505                 510
Gly Val Lys His Leu Lys Asp Phe Pro Ile Leu Pro Gly Glu Ile Phe
        515                 520                 525
Lys Tyr Lys Trp Thr Val Thr Val Glu Asp Gly Pro Thr Lys Ser Asp
    530                 535                 540
Pro Arg Cys Leu Thr Arg Tyr Tyr Ser Ser Phe Val Asn Met Glu Arg
545                 550                 555                 560
Asp Leu Ala Ser Gly Leu Ile Gly Pro Leu Leu Ile Cys Tyr Lys Glu
                565                 570                 575
Ser Val Asp Gln Arg Gly Asn Gln Ile Met Ser Asp Lys Arg Asn Val
            580                 585                 590
Ile Leu Phe Ser Val Phe Asp Glu Asn Arg Ser Trp Tyr Leu Thr Glu
        595                 600                 605
Asn Ile Gln Arg Phe Leu Pro Asn Pro Ala Gly Val Gln Leu Glu Asp
    610                 615                 620
Pro Glu Phe Gln Ala Ser Asn Ile Met His Ser Ile Asn Gly Tyr Val
625                 630                 635                 640
Phe Asp Ser Leu Gln Leu Ser Val Cys Leu His Glu Val Ala Tyr Trp
                645                 650                 655
Tyr Ile Leu Ser Ile Gly Ala Gln Thr Asp Phe Leu Ser Val Phe Phe
            660                 665                 670
Ser Gly Tyr Thr Phe Lys His Lys Met Val Tyr Glu Asp Thr Leu Thr
        675                 680                 685
Leu Phe Pro Phe Ser Gly Glu Thr Val Phe Met Ser Met Glu Asn Pro
    690                 695                 700
Gly Leu Trp Ile Leu Gly Cys His Asn Ser Asp Phe Arg Asn Arg Gly
705                 710                 715                 720
Met Thr Ala Leu Leu Lys Val Ser Ser Cys Asp Lys Asn Thr Gly Asp
                725                 730                 735
Tyr Tyr Glu Asp Ser Tyr Glu Asp Ile Ser Ala Tyr Leu Leu Ser Lys
            740                 745                 750
Asn Asn Ala Ile Glu Pro Arg Ser Phe Ser Gln Asn Ser Arg His Pro
        755                 760                 765
Ser Thr Arg Gln Lys Gln Phe Asn Ala Thr Thr Ile Pro Glu Asn Asp
    770                 775                 780
Ile Glu Lys Thr Asp Pro Trp Phe Ala His Arg Thr Pro Met Pro Lys
```

-continued

```
            785                 790                 795                 800
        Ile Gln Asn Val Ser Ser Ser Asp Leu Leu Met Leu Leu Arg Gln Ser
                            805                 810                 815
        Pro Thr Pro His Gly Leu Ser Leu Ser Asp Leu Gln Glu Ala Lys Tyr
                            820                 825                 830
        Glu Thr Phe Ser Asp Asp Pro Ser Pro Gly Ala Ile Asp Ser Asn Asn
                            835                 840                 845
        Ser Leu Ser Glu Met Thr His Phe Arg Pro Gln Leu His His Ser Gly
        850                     855                 860
        Asp Met Val Phe Thr Pro Glu Ser Gly Leu Gln Leu Arg Leu Asn Glu
        865                     870                 875                 880
        Lys Leu Gly Thr Thr Ala Ala Thr Glu Leu Lys Lys Leu Asp Phe Lys
                            885                 890                 895
        Val Ser Ser Thr Ser Asn Asn Leu Ile Ser Thr Ile Pro Ser Asp Asn
                            900                 905                 910
        Leu Ala Ala Gly Thr Asp Asn Thr Ser Ser Leu Gly Pro Pro Ser Met
                            915                 920                 925
        Pro Val His Tyr Asp Ser Gln Leu Asp Thr Thr Leu Phe Gly Lys Lys
                            930                 935                 940
        Ser Ser Pro Leu Thr Glu Ser Gly Gly Pro Leu Ser Leu Ser Glu Glu
        945                     950                 955                 960
        Asn Asn Asp Ser Lys Leu Leu Glu Ser Gly Leu Met Asn Ser Gln Glu
                            965                 970                 975
        Ser Ser Trp Gly Lys Asn Val Ser Ser Thr Glu Ser Gly Arg Leu Phe
                            980                 985                 990
        Lys Gly Lys Arg Ala His Gly Pro Ala Leu Leu Thr Lys Asp Asn Ala
                            995                 1000                1005
        Leu Phe Lys Val Ser Ile Ser Leu Leu Lys Thr Asn Lys Thr Ser
                            1010                1015                1020
        Asn Asn Ser Ala Thr Asn Arg Lys Thr His Ile Asp Gly Pro Ser
                            1025                1030                1035
        Leu Leu Ile Glu Asn Ser Pro Ser Val Trp Gln Asn Ile Leu Glu
                            1040                1045                1050
        Ser Asp Thr Glu Phe Lys Lys Val Thr Pro Leu Ile His Asp Arg
                            1055                1060                1065
        Met Leu Met Asp Lys Asn Ala Thr Ala Leu Arg Leu Asn His Met
                            1070                1075                1080
        Ser Asn Lys Thr Thr Ser Ser Lys Asn Met Glu Met Val Gln Gln
                            1085                1090                1095
        Lys Lys Glu Gly Pro Ile Pro Pro Asp Ala Gln Asn Pro Asp Met
                            1100                1105                1110
        Ser Phe Phe Lys Met Leu Phe Leu Pro Glu Ser Ala Arg Trp Ile
                            1115                1120                1125
        Gln Arg Thr His Gly Lys Asn Ser Leu Asn Ser Gly Gln Gly Pro
                            1130                1135                1140
        Ser Pro Lys Gln Leu Val Ser Leu Gly Pro Glu Lys Ser Val Glu
                            1145                1150                1155
        Gly Gln Asn Phe Leu Ser Glu Lys Asn Lys Val Val Gly Lys
                            1160                1165                1170
        Gly Glu Phe Thr Lys Asp Val Gly Leu Lys Glu Met Val Phe Pro
                            1175                1180                1185
        Ser Ser Arg Asn Leu Phe Leu Thr Asn Leu Asp Asn Leu His Glu
                            1190                1195                1200
```

```
Asn Asn Thr His Asn Gln Glu Lys Lys Ile Gln Glu Glu Ile Glu
1205                 1210                1215

Lys Lys Glu Thr Leu Ile Gln Glu Asn Val Val Leu Pro Gln Ile
1220                 1225                1230

His Thr Val Thr Gly Thr Lys Asn Phe Met Lys Asn Leu Phe Leu
1235                 1240                1245

Leu Ser Thr Arg Gln Asn Val Glu Gly Ser Tyr Asp Gly Ala Tyr
1250                 1255                1260

Ala Pro Val Leu Gln Asp Phe Arg Ser Leu Asn Asp Ser Thr Asn
1265                 1270                1275

Arg Thr Lys Lys His Thr Ala His Phe Ser Lys Lys Gly Glu Glu
1280                 1285                1290

Glu Asn Leu Glu Gly Leu Gly Asn Gln Thr Lys Gln Ile Val Glu
1295                 1300                1305

Lys Tyr Ala Cys Thr Thr Arg Ile Ser Pro Asn Thr Ser Gln Gln
1310                 1315                1320

Asn Phe Val Thr Gln Arg Ser Lys Arg Ala Leu Lys Gln Phe Arg
1325                 1330                1335

Leu Pro Leu Glu Glu Thr Glu Leu Glu Lys Arg Ile Ile Val Asp
1340                 1345                1350

Asp Thr Ser Thr Gln Trp Ser Lys Asn Met Lys His Leu Thr Pro
1355                 1360                1365

Ser Thr Leu Thr Gln Ile Asp Tyr Asn Glu Lys Glu Lys Gly Ala
1370                 1375                1380

Ile Thr Gln Ser Pro Leu Ser Asp Cys Leu Thr Arg Ser His Ser
1385                 1390                1395

Ile Pro Gln Ala Asn Arg Ser Pro Leu Pro Ile Ala Lys Val Ser
1400                 1405                1410

Ser Phe Pro Ser Ile Arg Pro Ile Tyr Leu Thr Arg Val Leu Phe
1415                 1420                1425

Gln Asp Asn Ser Ser His Leu Pro Ala Ala Ser Tyr Arg Lys Lys
1430                 1435                1440

Asp Ser Gly Val Gln Glu Ser Ser His Phe Leu Gln Gly Ala Lys
1445                 1450                1455

Lys Asn Asn Leu Ser Leu Ala Ile Leu Thr Leu Glu Met Thr Gly
1460                 1465                1470

Asp Gln Arg Glu Val Gly Ser Leu Gly Thr Ser Ala Thr Asn Ser
1475                 1480                1485

Val Thr Tyr Lys Lys Val Glu Asn Thr Val Leu Pro Lys Pro Asp
1490                 1495                1500

Leu Pro Lys Thr Ser Gly Lys Val Glu Leu Leu Pro Lys Val His
1505                 1510                1515

Ile Tyr Gln Lys Asp Leu Phe Pro Thr Glu Thr Ser Asn Gly Ser
1520                 1525                1530

Pro Gly His Leu Asp Leu Val Glu Gly Ser Leu Leu Gln Gly Thr
1535                 1540                1545

Glu Gly Ala Ile Lys Trp Asn Glu Ala Asn Arg Pro Gly Lys Val
1550                 1555                1560

Pro Phe Leu Arg Val Ala Thr Glu Ser Ser Ala Lys Thr Pro Ser
1565                 1570                1575

Lys Leu Leu Asp Pro Leu Ala Trp Asp Asn His Tyr Gly Thr Gln
1580                 1585                1590
```

-continued

```
Ile Pro Lys Glu Glu Trp Lys Ser Gln Glu Lys Ser Pro Glu Lys
1595                1600                1605

Thr Ala Phe Lys Lys Lys Asp Thr Ile Leu Ser Leu Asn Ala Cys
1610                1615                1620

Glu Ser Asn His Ala Ile Ala Ile Asn Glu Gly Gln Asn Lys
1625                1630                1635

Pro Glu Ile Glu Val Thr Trp Ala Lys Gln Gly Arg Thr Glu Arg
1640                1645                1650

Leu Cys Ser Gln Asn Pro Pro Val Leu Lys Arg His Gln Arg Glu
1655                1660                1665

Ile Thr Arg Thr Thr Leu Gln Ser Asp Gln Glu Glu Ile Asp Tyr
1670                1675                1680

Asp Asp Thr Ile Ser Val Glu Met Lys Lys Glu Asp Phe Asp Ile
1685                1690                1695

Tyr Asp Glu Asp Glu Asn Gln Ser Pro Arg Ser Phe Gln Lys Lys
1700                1705                1710

Thr Arg His Tyr Phe Ile Ala Ala Val Glu Arg Leu Trp Asp Tyr
1715                1720                1725

Gly Met Ser Ser Ser Pro His Val Leu Arg Asn Arg Ala Gln Ser
1730                1735                1740

Gly Ser Val Pro Gln Phe Lys Lys Val Val Phe Gln Glu Phe Thr
1745                1750                1755

Asp Gly Ser Phe Thr Gln Pro Leu Tyr Arg Gly Glu Leu Asn Glu
1760                1765                1770

His Leu Gly Leu Leu Gly Pro Tyr Ile Arg Ala Glu Val Glu Asp
1775                1780                1785

Asn Ile Met Val Thr Phe Arg Asn Gln Ala Ser Arg Pro Tyr Ser
1790                1795                1800

Phe Tyr Ser Ser Leu Ile Ser Tyr Glu Glu Asp Gln Arg Gln Gly
1805                1810                1815

Ala Glu Pro Arg Lys Asn Phe Val Lys Pro Asn Glu Thr Lys Thr
1820                1825                1830

Tyr Phe Trp Lys Val Gln His His Met Ala Pro Thr Lys Asp Glu
1835                1840                1845

Phe Asp Cys Lys Ala Trp Ala Tyr Phe Ser Asp Val Asp Leu Glu
1850                1855                1860

Lys Asp Val His Ser Gly Leu Ile Gly Pro Leu Leu Val Cys His
1865                1870                1875

Thr Asn Thr Leu Asn Pro Ala His Gly Arg Gln Val Thr Val Gln
1880                1885                1890

Glu Phe Ala Leu Phe Phe Thr Ile Phe Asp Glu Thr Lys Ser Trp
1895                1900                1905

Tyr Phe Thr Glu Asn Met Glu Arg Asn Cys Arg Ala Pro Cys Asn
1910                1915                1920

Ile Gln Met Glu Asp Pro Thr Phe Lys Glu Asn Tyr Arg Phe His
1925                1930                1935

Ala Ile Asn Gly Tyr Ile Met Asp Thr Leu Pro Gly Leu Val Met
1940                1945                1950

Ala Gln Asp Gln Arg Ile Arg Trp Tyr Leu Leu Ser Met Gly Ser
1955                1960                1965

Asn Glu Asn Ile His Ser Ile His Phe Ser Gly His Val Phe Thr
1970                1975                1980

Val Arg Lys Lys Glu Glu Tyr Lys Met Ala Leu Tyr Asn Leu Tyr
```

```
                    1985                1990                1995
Pro Gly Val Phe Glu Thr Val Glu Met Leu Pro Ser Lys Ala Gly
    2000                2005                2010

Ile Trp Arg Val Glu Cys Leu Ile Gly Glu His Leu His Ala Gly
    2015                2020                2025

Met Ser Thr Leu Phe Leu Val Tyr Ser Asn Lys Cys Gln Thr Pro
    2030                2035                2040

Leu Gly Met Ala Ser Gly His Ile Arg Asp Phe Gln Ile Thr Ala
    2045                2050                2055

Ser Gly Gln Tyr Gly Gln Trp Ala Pro Lys Leu Ala Arg Leu His
    2060                2065                2070

Tyr Ser Gly Ser Ile Asn Ala Trp Ser Thr Lys Glu Pro Phe Ser
    2075                2080                2085

Trp Ile Lys Val Asp Leu Leu Ala Pro Met Ile Ile His Gly Ile
    2090                2095                2100

Lys Thr Gln Gly Ala Arg Gln Lys Phe Ser Ser Leu Tyr Ile Ser
    2105                2110                2115

Gln Phe Ile Ile Met Tyr Ser Leu Asp Gly Lys Lys Trp Gln Thr
    2120                2125                2130

Tyr Arg Gly Asn Ser Thr Gly Thr Leu Met Val Phe Phe Gly Asn
    2135                2140                2145

Val Asp Ser Ser Gly Ile Lys His Asn Ile Phe Asn Pro Pro Ile
    2150                2155                2160

Ile Ala Arg Tyr Ile Arg Leu His Pro Thr His Tyr Ser Ile Arg
    2165                2170                2175

Ser Thr Leu Arg Met Glu Leu Met Gly Cys Asp Leu Asn Ser Cys
    2180                2185                2190

Ser Met Pro Leu Gly Met Glu Ser Lys Ala Ile Ser Asp Ala Gln
    2195                2200                2205

Ile Thr Ala Ser Ser Tyr Phe Thr Asn Met Phe Ala Thr Trp Ser
    2210                2215                2220

Pro Ser Lys Ala Arg Leu His Leu Gln Gly Arg Ser Asn Ala Trp
    2225                2230                2235

Arg Pro Gln Val Asn Asn Pro Lys Glu Trp Leu Gln Val Asp Phe
    2240                2245                2250

Gln Lys Thr Met Lys Val Thr Gly Val Thr Thr Gln Gly Val Lys
    2255                2260                2265

Ser Leu Leu Thr Ser Met Tyr Val Lys Glu Phe Leu Ile Ser Ser
    2270                2275                2280

Ser Gln Asp Gly His Gln Trp Thr Leu Phe Phe Gln Asn Gly Lys
    2285                2290                2295

Val Lys Val Phe Gln Gly Asn Gln Asp Ser Phe Thr Pro Val Val
    2300                2305                2310

Asn Ser Leu Asp Pro Pro Leu Leu Thr Arg Tyr Leu Arg Ile His
    2315                2320                2325

Pro Gln Ser Trp Val His Gln Ile Ala Leu Arg Met Glu Val Leu
    2330                2335                2340

Gly Cys Glu Ala Gln Asp Leu Tyr
    2345                2350

<210> SEQ ID NO 2
<211> LENGTH: 2324
<212> TYPE: PRT
<213> ORGANISM: artificial sequence
```

```
<220> FEATURE:
<223> OTHER INFORMATION: ancestral

<400> SEQUENCE: 2
```

| | | | | | | | | | | | | | | |
|---|---|---|---|---|---|---|---|---|---|---|---|---|---|---|
| Met | Gln | Ile | Ala | Leu | Phe | Thr | Cys | Phe | Phe | Leu | Ser | Leu | Phe | Asn | Phe |
| 1 | | | | 5 | | | | | 10 | | | | | 15 | |

| Cys | Ser | Ser | Ala | Thr | Arg | Arg | Tyr | Tyr | Leu | Gly | Ala | Val | Glu | Leu | Ser |
| | | | 20 | | | | | 25 | | | | | 30 | | |

| Trp | Asn | Tyr | Met | Gln | Ser | Asp | Leu | Leu | Ser | Val | Leu | His | Thr | Asp | Thr |
| | | 35 | | | | | 40 | | | | | 45 | | | |

| Arg | Phe | Leu | Pro | Arg | Met | Pro | Thr | Ser | Phe | Pro | Phe | Asn | Thr | Ser | Ile |
| | 50 | | | | | 55 | | | | | 60 | | | | |

| Met | Tyr | Lys | Lys | Thr | Val | Phe | Val | Glu | Tyr | Met | Asp | His | Leu | Phe | Asn |
| 65 | | | | | 70 | | | | | 75 | | | | | 80 |

| Ile | Ala | Lys | Pro | Arg | Pro | Pro | Trp | Met | Gly | Leu | Leu | Gly | Pro | Thr | Ile |
| | | | | 85 | | | | | 90 | | | | | 95 | |

| Trp | Thr | Glu | Val | His | Asp | Thr | Val | Val | Ile | Thr | Leu | Lys | Asn | Met | Ala |
| | | | 100 | | | | | 105 | | | | | 110 | | |

| Ser | His | Pro | Val | Ser | Leu | His | Ala | Val | Gly | Val | Ser | Tyr | Trp | Lys | Ala |
| | | 115 | | | | | 120 | | | | | 125 | | | |

| Ser | Glu | Gly | Ala | Glu | Tyr | Glu | Asp | Gln | Thr | Ser | Gln | Arg | Glu | Lys | Glu |
| | 130 | | | | | 135 | | | | | 140 | | | | |

| Asp | Asp | Lys | Val | Phe | Pro | Gly | Glu | Ser | His | Thr | Tyr | Val | Trp | Gln | Val |
| 145 | | | | | 150 | | | | | 155 | | | | | 160 |

| Leu | Lys | Glu | Asn | Gly | Pro | Met | Ala | Ser | Asp | Pro | Pro | Cys | Leu | Thr | Tyr |
| | | | | 165 | | | | | 170 | | | | | 175 | |

| Ser | Tyr | Leu | Ser | His | Val | Asp | Leu | Val | Lys | Asp | Leu | Asn | Ser | Gly | Leu |
| | | | 180 | | | | | 185 | | | | | 190 | | |

| Ile | Gly | Ala | Leu | Leu | Val | Cys | Lys | Glu | Gly | Ser | Leu | Ser | Lys | Glu | Arg |
| | | 195 | | | | | 200 | | | | | 205 | | | |

| Thr | Gln | Met | Leu | His | Gln | Phe | Val | Leu | Leu | Phe | Ala | Val | Phe | Asp | Glu |
| | 210 | | | | | 215 | | | | | 220 | | | | |

| Gly | Lys | Ser | Trp | His | Ser | Glu | Thr | Lys | Asp | Ser | Phe | Thr | Gln | Ala | Met |
| 225 | | | | | 230 | | | | | 235 | | | | | 240 |

| Asp | Ser | Ala | Ser | Thr | Arg | Ala | Trp | Pro | Lys | Met | His | Thr | Val | Asn | Gly |
| | | | | 245 | | | | | 250 | | | | | 255 | |

| Tyr | Val | Asn | Arg | Ser | Leu | Pro | Gly | Leu | Ile | Gly | Cys | His | Arg | Lys | Ser |
| | | | 260 | | | | | 265 | | | | | 270 | | |

| Val | Tyr | Trp | His | Val | Ile | Gly | Met | Gly | Thr | Thr | Pro | Glu | Val | His | Ser |
| | | 275 | | | | | 280 | | | | | 285 | | | |

| Ile | Phe | Leu | Glu | Gly | His | Thr | Phe | Leu | Val | Arg | Asn | His | Arg | Gln | Ala |
| | 290 | | | | | 295 | | | | | 300 | | | | |

| Ser | Leu | Glu | Ile | Ser | Pro | Ile | Thr | Phe | Leu | Thr | Ala | Gln | Thr | Leu | Leu |
| 305 | | | | | 310 | | | | | 315 | | | | | 320 |

| Ile | Asp | Leu | Gly | Gln | Phe | Leu | Leu | Phe | Cys | His | Ile | Ser | Ser | His | Lys |
| | | | | 325 | | | | | 330 | | | | | 335 | |

| His | Asp | Gly | Met | Glu | Ala | Tyr | Val | Lys | Val | Asp | Ser | Cys | Pro | Glu | Glu |
| | | | 340 | | | | | 345 | | | | | 350 | | |

| Pro | Gln | Trp | Gln | Lys | Lys | Asn | Asn | Glu | Glu | Met | Glu | Asp | Tyr | Asp | Asp |
| | | 355 | | | | | 360 | | | | | 365 | | | |

| Asp | Leu | Asp | Ser | Glu | Met | Asp | Met | Phe | Thr | Leu | Asp | Asp | Asp | Asn | Ser |
| | 370 | | | | | 375 | | | | | 380 | | | | |

| Pro | Phe | Ile | Gln | Ile | Arg | Ser | Val | Ala | Lys | Lys | Tyr | Pro | Lys | Thr | Trp |
| 385 | | | | | 390 | | | | | 395 | | | | | 400 |

-continued

```
Ile His Tyr Ile Ser Ala Glu Glu Asp Trp Asp Tyr Ala Pro Ser
                405                 410                 415

Val Leu Thr Ser Asp Asp Gly Ser Tyr Lys Ser Gln Tyr Leu Ser Asn
                420                 425                 430

Gly Pro His Arg Ile Gly Arg Lys Tyr Lys Val Arg Phe Ile Ala
                435                 440                 445

Tyr Thr Asp Glu Thr Phe Lys Thr Arg Glu Thr Ile Gln His Glu Ser
                450                 455                 460

Gly Ile Leu Gly Pro Leu Leu Tyr Gly Glu Val Gly Asp Thr Leu Leu
465                 470                 475                 480

Ile Ile Phe Lys Asn Gln Ala Ser Arg Pro Tyr Asn Ile Tyr Pro His
                485                 490                 495

Gly Ile Thr Asp Val Ser Pro Leu His Ser Arg Arg Leu Pro Arg Gly
                500                 505                 510

Ile Lys His Val Lys Asp Leu Pro Ile Arg Pro Gly Glu Ile Phe Lys
                515                 520                 525

Tyr Lys Trp Thr Val Thr Val Glu Asp Gly Pro Thr Lys Ser Asp Pro
                530                 535                 540

Arg Cys Leu Thr Arg Tyr Tyr Ser Ser Phe Ile Asn Pro Glu Arg Asp
545                 550                 555                 560

Leu Ala Ser Gly Leu Ile Gly Pro Leu Leu Ile Cys Tyr Lys Glu Ser
                565                 570                 575

Val Asp Gln Arg Gly Asn Gln Met Met Ser Asp Lys Arg Asn Val Ile
                580                 585                 590

Leu Phe Ser Val Phe Asp Glu Asn Gln Ser Trp Tyr Ile Thr Glu Asn
                595                 600                 605

Met Gln Arg Phe Leu Pro Asn Ala Ala Asp Thr Gln Pro Gln Asp Pro
                610                 615                 620

Glu Phe Gln Ala Ser Asn Ile Met His Ser Ile Asn Gly Tyr Val Phe
625                 630                 635                 640

Asp Ser Leu Gln Leu Thr Val Cys Leu His Glu Val Ala Tyr Trp Tyr
                645                 650                 655

Ile Leu Ser Val Gly Ala Gln Thr Asp Phe Leu Ser Ile Phe Phe Ser
                660                 665                 670

Gly Tyr Thr Phe Lys His Lys Met Val Tyr Glu Asp Thr Leu Thr Leu
                675                 680                 685

Phe Pro Phe Ser Gly Glu Thr Val Phe Met Ser Met Glu Asn Pro Gly
                690                 695                 700

Leu Trp Val Leu Gly Cys His Asn Ser Asp Phe Arg Lys Arg Gly Met
705                 710                 715                 720

Thr Ala Leu Leu Lys Val Ser Ser Cys Asp Lys Ser Thr Ser Asp Tyr
                725                 730                 735

Tyr Glu Glu Ile Tyr Glu Asp Ile Pro Thr Gln Leu Val Asn Asp Asn
                740                 745                 750

Asn Val Ile Glu Pro Arg Ser Phe Gln Asn Ser Asn His Pro Asn
                755                 760                 765

Thr Arg Lys Lys Lys Phe Lys Ala Thr Thr Ile Pro Glu Asn Asp Ile
                770                 775                 780

Glu Lys Ile Glu Pro Gln Phe Gly Glu Thr Ala Glu Met Leu Lys Val
785                 790                 795                 800

Gln Ser Val Ser Ser Ser Asp Leu Leu Met Leu Leu Gly Gln Ser Pro
                805                 810                 815
```

```
Thr Pro His Gly Leu Ser Leu Ser Asp Asn Gln Glu Ala Ile Tyr Glu
            820                 825                 830

Ala Ile Pro Asp Asp His Ser Pro Asp Ala Ile Asp Ser Asn Glu Gly
            835                 840                 845

Pro Ser Lys Val Thr Gln Leu Arg Pro Glu Leu His His Ser Gly Lys
            850                 855                 860

Ile Val Phe Thr Pro Glu Pro Gly Leu Gln Leu Arg Ser Asn Lys Asn
865                 870                 875                 880

Leu Glu Thr Thr Ile Glu Val Lys Trp Lys Lys Leu Asp Leu Gln Val
                885                 890                 895

Ser Ser Leu Pro Asn Asn Leu Met Thr Thr Thr Ile Leu Ser Asp Asn
            900                 905                 910

Leu Thr Ala Thr Ser Glu Lys Thr Asp Ser Ser Gly Ser Pro Asp Met
            915                 920                 925

Pro Val His Phe Ser Ser Lys Leu Ser Thr Thr Ala Phe Gly Lys Lys
            930                 935                 940

Ser Tyr Pro Leu Ile Gly Ser His Val Pro Leu Asn Ile Ser Glu Arg
945                 950                 955                 960

Asn Ser Asp Ser Asn Leu Leu Asp Ala Thr Leu Met Asn Asn Gln Glu
            965                 970                 975

Ser Ser Leu Gly Asp Asn Ile Ser Ser Met Glu Asn Asp Arg Leu Leu
            980                 985                 990

Lys Glu Lys Arg Phe His Gly Ile Ala Leu Leu Thr Lys Asp Asn Thr
            995                 1000                1005

Leu Phe Lys Asp Asn Ile Ser Leu Met Lys Thr Asn Lys Thr Tyr
      1010                1015                1020

Asn His Ser Thr Thr Asn Gly Lys Ala His Ile Asp Ser Pro Thr
      1025                1030                1035

Ser Ile Glu Asn Ser Thr Ala Val Leu Gln Asp Thr Ile Leu Lys
      1040                1045                1050

Ile Asn Ser Glu Ile Gln Glu Val Thr Ser Leu Ile His Asp Gly
      1055                1060                1065

Thr Leu Ser Gly Lys Asn Thr Thr Tyr Leu Arg Leu Asn His Met
      1070                1075                1080

Leu Asn Arg Thr Thr Ser Ser Lys Asn Lys Glu Ile Phe His Gln
      1085                1090                1095

Lys Asp Glu Asp Pro Val Pro Gln Asp Thr Glu Asn Thr Ile Met
      1100                1105                1110

Pro Phe Phe Lys Met Leu Phe Leu Pro Glu Ser Ala Asn Trp Met
      1115                1120                1125

Lys Arg Thr Asn Gly Asn Asn Ser Leu Asn Ser Glu Gln Gly Pro
      1130                1135                1140

Ser Pro Lys Gln Leu Val Tyr Leu Met Leu Glu Lys Ser Val Lys
      1145                1150                1155

Asn Gln Asn Phe Leu Ser Glu Lys Asn Lys Val Ile Val Glu Gln
      1160                1165                1170

Asp Glu Phe Thr Lys Asp Thr Gly Leu Lys Asp Met Val Phe Pro
      1175                1180                1185

Ser Asn Met Ser Ile Phe Leu Thr Thr Leu Ala Asn Val Gln Glu
      1190                1195                1200

Asn Asp Met His Asn Gln Glu Lys Asn Ile Gln Glu Glu Ile Glu
      1205                1210                1215

Lys Glu Ala Leu Ile Glu Glu Lys Val Val Leu Pro Gln Val His
```

-continued

```
              1220            1225            1230
Ile Ala Thr Gly Ser Lys Asn Phe Leu Lys Asp Ile Phe Phe Leu
    1235            1240            1245

Gly Thr Arg Gln Asn Val Ser Leu Asp Glu Asp Ile Tyr Val Pro
    1250            1255            1260

Val Leu Gln Asp Ile Ser Ser Ile Asn Asn Ser Thr Asn Thr Val
    1265            1270            1275

Glu Ile His Met Ala His Phe Phe Lys Arg Arg Glu Asp Glu Glu
    1280            1285            1290

Thr Asn Ser Glu Gly Leu Val Asn Lys Thr Arg Glu Met Val Lys
    1295            1300            1305

Asn Tyr Pro Ser Gln Lys Asn Ile Ile Thr Gln Arg Ser Lys Arg
    1310            1315            1320

Ala Leu Gly Gln Phe Arg Leu Pro Leu Ala Ser Thr Gln Trp Pro
    1325            1330            1335

Gln Thr Met Asn Tyr Leu Thr Gln Ser Ile Ile Thr Gln Ile Asp
    1340            1345            1350

His Ser Lys Glu Gly Glu Lys Ser Ile Thr Gln Ser Ser Leu Ser
    1355            1360            1365

Asp Ser Ser Met Ile Lys Ser Thr Thr Gln Thr Asn Ser Ser Gly
    1370            1375            1380

Leu His Ile Val Lys Thr Ser Ala Phe Pro Pro Thr Asp Leu Lys
    1385            1390            1395

Arg Ile Pro Phe Gln Asp Lys Phe Phe His Val Leu Ala Ser Ser
    1400            1405            1410

Tyr Thr Tyr Asp Phe Lys Thr Lys Ser Ser Arg Ile Gln Glu Ser
    1415            1420            1425

Ser His Phe Leu Lys Glu Thr Lys Ile Asn Asn Ser Ser Leu Ala
    1430            1435            1440

Ile Leu Pro Trp Glu Met Ile Ile Asn Gln Gly Lys Phe Ala Ser
    1445            1450            1455

Pro Gly Thr Ser Asn Thr Asn Ser Val Thr Tyr Lys Lys Leu Glu
    1460            1465            1470

Asn Ile Val Leu Leu Lys Pro Val Leu Pro Glu Glu Ser Gly Lys
    1475            1480            1485

Val Glu Leu Leu Pro Gln Val Ser Ile His Glu Glu Leu Leu
    1490            1495            1500

Pro Thr Glu Thr Ser His Gly Ser Pro Gly His Leu Asp Leu Met
    1505            1510            1515

Lys Glu Val Phe Leu Gln Lys Thr Gln Gly Pro Ile Lys Trp Asn
    1520            1525            1530

Lys Ala Lys Arg His Gly Glu Ser Glu Leu Lys Gly Thr Thr Glu
    1535            1540            1545

Ser Ser Glu Lys Thr Pro Ser Lys Leu Leu Asp His Leu Ala Trp
    1550            1555            1560

Asp Asn His Tyr Ala Ala Gln Ile Pro Lys Asp Lys Trp Lys Ser
    1565            1570            1575

Lys Glu Lys Ser Pro Glu Ile Thr Ser Ile Lys Arg Glu Asp Thr
    1580            1585            1590

Ile Leu Ser Leu Asn Pro His Glu Asn Asn His Ser Ile Val Ala
    1595            1600            1605

Asn Glu Lys Gln Asn Trp Pro Gln Arg Glu Ala Thr Trp Val Lys
    1610            1615            1620
```

```
Gln Gly Gln Thr Gln Arg Leu Cys Ser Gln Asn Pro Pro Val Leu
        1625                1630                1635

Lys Arg His Gln Arg Glu Leu Ser Ala Leu Gln Ser Glu Gln Glu
        1640                1645                1650

Ala Thr Asp Tyr Asp Asp Ser Ile Thr Ile Glu Thr Asn Glu Asp
        1655                1660                1665

Phe Asp Ile Tyr Gly Glu Asp Ile Lys Gln Gly Pro Arg Ser Phe
        1670                1675                1680

Gln Gln Lys Thr Arg His Tyr Phe Ile Ala Ala Val Glu Arg Leu
        1685                1690                1695

Trp Asp Tyr Gly Met Ser Thr Ser Pro His Val Leu Arg Asn Arg
        1700                1705                1710

Asp Gln Ser Gly Asn Ala Pro Gln Phe Lys Lys Val Val Phe Gln
        1715                1720                1725

Glu Phe Thr Asp Gly Ser Phe Ser Gln Pro Leu Tyr Arg Gly Glu
        1730                1735                1740

Leu Asn Glu His Leu Gly Leu Leu Gly Pro Tyr Ile Arg Ala Glu
        1745                1750                1755

Val Glu Asp Asn Ile Met Val Thr Phe Lys Asn Gln Ala Ser Arg
        1760                1765                1770

Pro Tyr Ser Phe Tyr Ser Ser Leu Ile Ser Tyr Lys Glu Asp Gln
        1775                1780                1785

Arg Gln Gly Glu Glu Pro Arg Arg Asn Phe Val Lys Pro Asn Glu
        1790                1795                1800

Thr Lys Ile Tyr Phe Trp Lys Val Gln His His Met Ala Pro Thr
        1805                1810                1815

Glu Asp Glu Phe Asp Cys Lys Ala Trp Ala Tyr Phe Ser Asp Val
        1820                1825                1830

Asp Leu Glu Arg Asp Met His Ser Gly Leu Ile Gly Pro Leu Leu
        1835                1840                1845

Ile Cys His Thr Asn Thr Leu Asn Pro Ala His Gly Arg Gln Val
        1850                1855                1860

Ala Val Gln Glu Phe Ala Leu Phe Phe Thr Ile Phe Asp Glu Thr
        1865                1870                1875

Lys Ser Trp Tyr Phe Thr Glu Asn Val Glu Arg Asn Cys Lys Thr
        1880                1885                1890

Pro Cys Asn Ile Gln Met Glu Asp Pro Thr Leu Lys Glu Asn Tyr
        1895                1900                1905

Arg Phe His Ala Ile Asn Gly Tyr Val Met Asp Thr Leu Pro Gly
        1910                1915                1920

Leu Val Met Ala Gln Asp Gln Arg Ile Arg Trp Tyr Leu Leu Ser
        1925                1930                1935

Met Gly Ser Asn Glu Asn Ile Gln Ser Ile His Phe Ser Gly His
        1940                1945                1950

Val Phe Thr Val Arg Lys Lys Glu Glu Tyr Lys Met Ala Val Tyr
        1955                1960                1965

Asn Leu Tyr Pro Gly Val Phe Glu Thr Val Glu Met Leu Pro Ser
        1970                1975                1980

Arg Ala Gly Ile Trp Arg Val Glu Cys Leu Ile Gly Glu His Leu
        1985                1990                1995

Gln Ala Gly Met Ser Thr Leu Phe Leu Val Tyr Ser Lys Gln Cys
        2000                2005                2010
```

Gln Ile Pro Leu Gly Met Ala Ser Gly Ser Ile Arg Asp Phe Gln
    2015                2020                2025

Ile Thr Ala Ser Gly His Tyr Gly Gln Trp Ala Pro Asn Leu Ala
    2030                2035                2040

Arg Leu His His Ser Gly Ser Ile Asn Ala Trp Ser Thr Lys Glu
    2045                2050                2055

Pro Phe Ser Trp Ile Lys Val Asp Leu Leu Thr Pro Met Ile Ile
    2060                2065                2070

His Gly Ile Lys Thr Gln Gly Ala Arg Gln Lys Phe Ser Ser Leu
    2075                2080                2085

Tyr Ile Ser Gln Phe Ile Ile Met Tyr Ser Leu Asp Gly Lys Lys
    2090                2095                2100

Trp Leu Ser Tyr Arg Gly Asn Ser Thr Gly Thr Leu Met Val Phe
    2105                2110                2115

Phe Gly Asn Val Asp Ser Ser Gly Ile Lys His Asn Ser Phe Asn
    2120                2125                2130

Pro Pro Ile Ile Ala Arg Tyr Ile Arg Leu His Pro Thr His Ser
    2135                2140                2145

Ser Ile Arg Ser Thr Leu Arg Met Glu Leu Met Gly Cys Asp Leu
    2150                2155                2160

Asn Ser Cys Ser Ile Pro Leu Gly Met Glu Asn Lys Val Ile Ser
    2165                2170                2175

Asp Thr Gln Ile Thr Ala Ser Ser Tyr Phe Thr Asn Met Phe Ala
    2180                2185                2190

Thr Trp Ser Pro Ser Gln Ala Arg Leu His Leu Gln Gly Arg Thr
    2195                2200                2205

Asn Ala Trp Arg Pro Gln Val Asn Asp Pro Lys Glu Trp Leu Gln
    2210                2215                2220

Val Asp Leu Gln Lys Thr Met Lys Val Thr Gly Ile Ile Thr Gln
    2225                2230                2235

Gly Val Lys Ser Leu Phe Thr Ser Met Phe Val Lys Glu Phe Leu
    2240                2245                2250

Ile Ser Ser Ser Gln Asp Gly His His Trp Thr His Ile Leu His
    2255                2260                2265

Asn Gly Lys Val Lys Val Phe Gln Gly Asn Gln Asp Ser Ser Thr
    2270                2275                2280

Pro Met Val Asn Ser Leu Asp Pro Pro Leu Leu Thr Arg Tyr Leu
    2285                2290                2295

Arg Ile His Pro Gln Ile Trp Glu His Gln Ile Ala Leu Arg Leu
    2300                2305                2310

Glu Ile Leu Gly Cys Glu Ala Gln Gln Leu Tyr
    2315                2320

<210> SEQ ID NO 3
<211> LENGTH: 19
<212> TYPE: PRT
<213> ORGANISM: artificial sequence
<220> FEATURE:
<223> OTHER INFORMATION: ancestral

<400> SEQUENCE: 3

Met Gln Ile Ala Leu Phe Thr Cys Phe Phe Leu Ser Leu Phe Asn Phe
1               5                   10                  15

Cys Ser Ser

```
<210> SEQ ID NO 4
<211> LENGTH: 372
<212> TYPE: PRT
<213> ORGANISM: artificial sequence
<220> FEATURE:
<223> OTHER INFORMATION: ancestral

<400> SEQUENCE: 4

Ala Thr Arg Arg Tyr Tyr Leu Gly Ala Val Glu Leu Ser Trp Asn Tyr
1               5                   10                  15

Met Gln Ser Asp Leu Leu Ser Val Leu His Thr Asp Thr Arg Phe Leu
            20                  25                  30

Pro Arg Met Pro Thr Ser Phe Pro Phe Asn Thr Ser Ile Met Tyr Lys
        35                  40                  45

Lys Thr Val Phe Val Glu Tyr Met Asp His Leu Phe Asn Ile Ala Lys
    50                  55                  60

Pro Arg Pro Pro Trp Met Gly Leu Leu Gly Pro Thr Ile Trp Thr Glu
65                  70                  75                  80

Val His Asp Thr Val Val Ile Thr Leu Lys Asn Met Ala Ser His Pro
                85                  90                  95

Val Ser Leu His Ala Val Gly Val Ser Tyr Trp Lys Ala Ser Glu Gly
            100                 105                 110

Ala Glu Tyr Glu Asp Gln Thr Ser Gln Arg Glu Lys Glu Asp Asp Lys
        115                 120                 125

Val Phe Pro Gly Glu Ser His Thr Tyr Val Trp Gln Val Leu Lys Glu
    130                 135                 140

Asn Gly Pro Met Ala Ser Asp Pro Pro Cys Leu Thr Tyr Ser Tyr Leu
145                 150                 155                 160

Ser His Val Asp Leu Val Lys Asp Leu Asn Ser Gly Leu Ile Gly Ala
                165                 170                 175

Leu Leu Val Cys Lys Glu Gly Ser Leu Ser Lys Glu Arg Thr Gln Met
            180                 185                 190

Leu His Gln Phe Val Leu Leu Phe Ala Val Phe Asp Glu Gly Lys Ser
        195                 200                 205

Trp His Ser Glu Thr Lys Asp Ser Phe Thr Gln Ala Met Asp Ser Ala
    210                 215                 220

Ser Thr Arg Ala Trp Pro Lys Met His Thr Val Asn Gly Tyr Val Asn
225                 230                 235                 240

Arg Ser Leu Pro Gly Leu Ile Gly Cys His Arg Lys Ser Val Tyr Trp
                245                 250                 255

His Val Ile Gly Met Gly Thr Thr Pro Glu Val His Ser Ile Phe Leu
            260                 265                 270

Glu Gly His Thr Phe Leu Val Arg Asn His Arg Gln Ala Ser Leu Glu
        275                 280                 285

Ile Ser Pro Ile Thr Phe Leu Thr Ala Gln Thr Leu Leu Ile Asp Leu
    290                 295                 300

Gly Gln Phe Leu Leu Phe Cys His Ile Ser Ser His Lys His Asp Gly
305                 310                 315                 320

Met Glu Ala Tyr Val Lys Val Asp Ser Cys Pro Glu Glu Pro Gln Trp
                325                 330                 335

Gln Lys Lys Asn Asn Glu Glu Met Glu Asp Tyr Asp Asp Leu Asp
            340                 345                 350

Ser Glu Met Asp Met Phe Thr Leu Asp Asp Asn Ser Pro Phe Ile
        355                 360                 365

Gln Ile Arg Ser
```

<210> SEQ ID NO 5
<211> LENGTH: 367
<212> TYPE: PRT
<213> ORGANISM: artificial sequence
<220> FEATURE:
<223> OTHER INFORMATION: ancestral

<400> SEQUENCE: 5

Val Ala Lys Lys Tyr Pro Lys Thr Trp Ile His Tyr Ile Ser Ala Glu
1               5                   10                  15

Glu Glu Asp Trp Asp Tyr Ala Pro Ser Val Leu Thr Ser Asp Asp Gly
            20                  25                  30

Ser Tyr Lys Ser Gln Tyr Leu Ser Asn Gly Pro His Arg Ile Gly Arg
        35                  40                  45

Lys Tyr Lys Lys Val Arg Phe Ile Ala Tyr Thr Asp Glu Thr Phe Lys
    50                  55                  60

Thr Arg Glu Thr Ile Gln His Glu Ser Gly Ile Leu Gly Pro Leu Leu
65                  70                  75                  80

Tyr Gly Glu Val Gly Asp Thr Leu Leu Ile Ile Phe Lys Asn Gln Ala
                85                  90                  95

Ser Arg Pro Tyr Asn Ile Tyr Pro His Gly Ile Thr Asp Val Ser Pro
            100                 105                 110

Leu His Ser Arg Arg Leu Pro Arg Gly Ile Lys His Val Lys Asp Leu
        115                 120                 125

Pro Ile Arg Pro Gly Glu Ile Phe Lys Tyr Lys Trp Thr Val Thr Val
130                 135                 140

Glu Asp Gly Pro Thr Lys Ser Asp Pro Arg Cys Leu Thr Arg Tyr Tyr
145                 150                 155                 160

Ser Ser Phe Ile Asn Pro Glu Arg Asp Leu Ala Ser Gly Leu Ile Gly
                165                 170                 175

Pro Leu Leu Ile Cys Tyr Lys Glu Ser Val Asp Gln Arg Gly Asn Gln
            180                 185                 190

Met Met Ser Asp Lys Arg Asn Val Ile Leu Phe Ser Val Phe Asp Glu
        195                 200                 205

Asn Gln Ser Trp Tyr Ile Thr Glu Asn Met Gln Arg Phe Leu Pro Asn
210                 215                 220

Ala Ala Asp Thr Gln Pro Gln Asp Pro Glu Phe Gln Ala Ser Asn Ile
225                 230                 235                 240

Met His Ser Ile Asn Gly Tyr Val Phe Asp Ser Leu Gln Leu Thr Val
                245                 250                 255

Cys Leu His Glu Val Ala Tyr Trp Tyr Ile Leu Ser Val Gly Ala Gln
            260                 265                 270

Thr Asp Phe Leu Ser Ile Phe Phe Ser Gly Tyr Thr Phe Lys His Lys
        275                 280                 285

Met Val Tyr Glu Asp Thr Leu Thr Leu Phe Pro Phe Ser Gly Glu Thr
290                 295                 300

Val Phe Met Ser Met Glu Asn Pro Gly Leu Trp Val Leu Gly Cys His
305                 310                 315                 320

Asn Ser Asp Phe Arg Lys Arg Gly Met Thr Ala Leu Leu Lys Val Ser
                325                 330                 335

Ser Cys Asp Lys Ser Thr Ser Asp Tyr Tyr Glu Glu Ile Tyr Glu Asp
            340                 345                 350

Ile Pro Thr Gln Leu Val Asn Asp Asn Asn Val Ile Glu Pro Arg

```
                    355                 360                 365

<210> SEQ ID NO 6
<211> LENGTH: 885
<212> TYPE: PRT
<213> ORGANISM: artificial sequence
<220> FEATURE:
<223> OTHER INFORMATION: ancestral

<400> SEQUENCE: 6

Ser Phe Phe Gln Asn Ser Asn His Pro Asn Thr Arg Lys Lys Lys Phe
1               5                   10                  15

Lys Ala Thr Thr Ile Pro Glu Asn Asp Ile Glu Lys Ile Glu Pro Gln
            20                  25                  30

Phe Gly Glu Thr Ala Glu Met Leu Lys Val Gln Ser Val Ser Ser Ser
        35                  40                  45

Asp Leu Leu Met Leu Leu Gly Gln Ser Pro Thr Pro His Gly Leu Ser
    50                  55                  60

Leu Ser Asp Asn Gln Glu Ala Ile Tyr Glu Ala Ile Pro Asp Asp His
65                  70                  75                  80

Ser Pro Asp Ala Ile Asp Ser Asn Glu Gly Pro Ser Lys Val Thr Gln
                85                  90                  95

Leu Arg Pro Glu Leu His His Ser Gly Lys Ile Val Phe Thr Pro Glu
            100                 105                 110

Pro Gly Leu Gln Leu Arg Ser Asn Lys Asn Leu Glu Thr Thr Ile Glu
        115                 120                 125

Val Lys Trp Lys Lys Leu Asp Leu Gln Val Ser Ser Leu Pro Asn Asn
    130                 135                 140

Leu Met Thr Thr Thr Ile Leu Ser Asp Asn Leu Thr Ala Thr Ser Glu
145                 150                 155                 160

Lys Thr Asp Ser Ser Gly Ser Pro Asp Met Pro Val His Phe Ser Ser
                165                 170                 175

Lys Leu Ser Thr Thr Ala Phe Gly Lys Lys Ser Tyr Pro Leu Ile Gly
            180                 185                 190

Ser His Val Pro Leu Asn Ile Ser Glu Arg Asn Ser Asp Ser Asn Leu
        195                 200                 205

Leu Asp Ala Thr Leu Met Asn Asn Gln Glu Ser Ser Leu Gly Asp Asn
    210                 215                 220

Ile Ser Ser Met Glu Asn Asp Arg Leu Leu Lys Glu Lys Arg Phe His
225                 230                 235                 240

Gly Ile Ala Leu Leu Thr Lys Asp Asn Thr Leu Phe Lys Asp Asn Ile
                245                 250                 255

Ser Leu Met Lys Thr Asn Lys Thr Tyr Asn His Ser Thr Thr Asn Gly
            260                 265                 270

Lys Ala His Ile Asp Ser Pro Thr Ser Ile Glu Asn Ser Thr Ala Val
        275                 280                 285

Leu Gln Asp Thr Ile Leu Lys Ile Asn Ser Glu Ile Gln Glu Val Thr
    290                 295                 300

Ser Leu Ile His Asp Gly Thr Leu Ser Gly Lys Asn Thr Thr Tyr Leu
305                 310                 315                 320

Arg Leu Asn His Met Leu Asn Arg Thr Thr Ser Ser Lys Asn Lys Glu
                325                 330                 335

Ile Phe His Gln Lys Asp Glu Asp Pro Val Pro Gln Asp Thr Glu Asn
            340                 345                 350

Thr Ile Met Pro Phe Phe Lys Met Leu Phe Leu Pro Glu Ser Ala Asn
```

```
                355                 360                 365
Trp Met Lys Arg Thr Asn Gly Asn Asn Ser Leu Asn Ser Glu Gln Gly
            370                 375                 380

Pro Ser Pro Lys Gln Leu Val Tyr Leu Met Leu Glu Lys Ser Val Lys
385                 390                 395                 400

Asn Gln Asn Phe Leu Ser Glu Lys Asn Lys Val Ile Val Glu Gln Asp
                405                 410                 415

Glu Phe Thr Lys Asp Thr Gly Leu Lys Asp Met Val Phe Pro Ser Asn
            420                 425                 430

Met Ser Ile Phe Leu Thr Thr Leu Ala Asn Val Gln Glu Asn Asp Met
        435                 440                 445

His Asn Gln Glu Lys Asn Ile Gln Glu Glu Ile Glu Lys Glu Ala Leu
    450                 455                 460

Ile Glu Glu Lys Val Val Leu Pro Gln Val His Ile Ala Thr Gly Ser
465                 470                 475                 480

Lys Asn Phe Leu Lys Asp Ile Phe Phe Leu Gly Thr Arg Gln Asn Val
                485                 490                 495

Ser Leu Asp Glu Asp Ile Tyr Val Pro Val Leu Gln Asp Ile Ser Ser
            500                 505                 510

Ile Asn Asn Ser Thr Asn Thr Val Glu Ile His Met Ala His Phe Phe
        515                 520                 525

Lys Arg Arg Glu Asp Glu Glu Thr Asn Ser Gly Leu Val Asn Lys
    530                 535                 540

Thr Arg Glu Met Val Lys Asn Tyr Pro Ser Gln Lys Asn Ile Ile Thr
545                 550                 555                 560

Gln Arg Ser Lys Arg Ala Leu Gly Gln Phe Arg Leu Pro Leu Ala Ser
                565                 570                 575

Thr Gln Trp Pro Gln Thr Met Asn Tyr Leu Thr Gln Ser Ile Ile Thr
            580                 585                 590

Gln Ile Asp His Ser Lys Glu Gly Glu Lys Ser Ile Thr Gln Ser Ser
        595                 600                 605

Leu Ser Asp Ser Ser Met Ile Lys Ser Thr Thr Gln Thr Asn Ser Ser
    610                 615                 620

Gly Leu His Ile Val Lys Thr Ser Ala Phe Pro Pro Thr Asp Leu Lys
625                 630                 635                 640

Arg Ile Pro Phe Gln Asp Lys Phe Phe His Val Leu Ala Ser Ser Tyr
                645                 650                 655

Thr Tyr Asp Phe Lys Thr Lys Ser Ser Arg Ile Gln Glu Ser Ser His
            660                 665                 670

Phe Leu Lys Glu Thr Lys Ile Asn Asn Ser Ser Leu Ala Ile Leu Pro
        675                 680                 685

Trp Glu Met Ile Ile Asn Gln Gly Lys Phe Ala Ser Pro Gly Thr Ser
    690                 695                 700

Asn Thr Asn Ser Val Thr Tyr Lys Lys Leu Glu Asn Ile Val Leu Leu
705                 710                 715                 720

Lys Pro Val Leu Pro Glu Ser Gly Lys Val Glu Leu Leu Pro Gln
                725                 730                 735

Val Ser Ile His Glu Glu Leu Leu Pro Thr Glu Thr Ser His Gly
            740                 745                 750

Ser Pro Gly His Leu Asp Leu Met Lys Glu Val Phe Leu Gln Lys Thr
        755                 760                 765

Gln Gly Pro Ile Lys Trp Asn Lys Ala Lys Arg His Gly Glu Ser Glu
    770                 775                 780
```

Leu Lys Gly Thr Thr Glu Ser Glu Lys Thr Pro Ser Lys Leu Leu
785                 790                 795                 800

Asp His Leu Ala Trp Asp Asn His Tyr Ala Gln Ile Pro Lys Asp
            805                 810                 815

Lys Trp Lys Ser Lys Glu Lys Ser Pro Glu Ile Thr Ser Ile Lys Arg
        820                 825                 830

Glu Asp Thr Ile Leu Ser Leu Asn Pro His Glu Asn Asn His Ser Ile
            835                 840                 845

Val Ala Asn Glu Lys Gln Asn Trp Pro Gln Arg Glu Ala Thr Trp Val
850                 855                 860

Lys Gln Gly Gln Thr Gln Arg Leu Cys Ser Gln Asn Pro Pro Val Leu
865                 870                 875                 880

Lys Arg His Gln Arg
            885

<210> SEQ ID NO 7
<211> LENGTH: 38
<212> TYPE: PRT
<213> ORGANISM: artificial sequence
<220> FEATURE:
<223> OTHER INFORMATION: ancestral

<400> SEQUENCE: 7

Glu Leu Ser Ala Leu Gln Ser Glu Gln Glu Ala Thr Asp Tyr Asp Asp
1               5                   10                  15

Ser Ile Thr Ile Glu Thr Asn Glu Asp Phe Asp Ile Tyr Gly Glu Asp
            20                  25                  30

Ile Lys Gln Gly Pro Arg
        35

<210> SEQ ID NO 8
<211> LENGTH: 330
<212> TYPE: PRT
<213> ORGANISM: artificial sequence
<220> FEATURE:
<223> OTHER INFORMATION: ancestral

<400> SEQUENCE: 8

Ser Phe Gln Gln Lys Thr Arg His Tyr Phe Ile Ala Ala Val Glu Arg
1               5                   10                  15

Leu Trp Asp Tyr Gly Met Ser Thr Ser Pro His Val Leu Arg Asn Arg
            20                  25                  30

Asp Gln Ser Gly Asn Ala Pro Gln Phe Lys Lys Val Val Phe Gln Glu
        35                  40                  45

Phe Thr Asp Gly Ser Phe Ser Gln Pro Leu Tyr Arg Gly Glu Leu Asn
    50                  55                  60

Glu His Leu Gly Leu Leu Gly Pro Tyr Ile Arg Ala Glu Val Glu Asp
65                  70                  75                  80

Asn Ile Met Val Thr Phe Lys Asn Gln Ala Ser Arg Pro Tyr Ser Phe
            85                  90                  95

Tyr Ser Ser Leu Ile Ser Tyr Lys Glu Asp Gln Arg Gln Gly Glu Glu
        100                 105                 110

Pro Arg Arg Asn Phe Val Lys Pro Asn Glu Thr Lys Ile Tyr Phe Trp
    115                 120                 125

Lys Val Gln His His Met Ala Pro Thr Glu Asp Glu Phe Asp Cys Lys
130                 135                 140

Ala Trp Ala Tyr Phe Ser Asp Val Asp Leu Glu Arg Asp Met His Ser

```
                145                 150                 155                 160
Gly Leu Ile Gly Pro Leu Leu Ile Cys His Thr Asn Thr Leu Asn Pro
                165                 170                 175

Ala His Gly Arg Gln Val Ala Val Gln Glu Phe Ala Leu Phe Phe Thr
                180                 185                 190

Ile Phe Asp Glu Thr Lys Ser Trp Tyr Phe Thr Glu Asn Val Glu Arg
                195                 200                 205

Asn Cys Lys Thr Pro Cys Asn Ile Gln Met Glu Asp Pro Thr Leu Lys
210                 215                 220

Glu Asn Tyr Arg Phe His Ala Ile Asn Gly Tyr Val Met Asp Thr Leu
225                 230                 235                 240

Pro Gly Leu Val Met Ala Gln Asp Gln Arg Ile Arg Trp Tyr Leu Leu
                245                 250                 255

Ser Met Gly Ser Asn Glu Asn Ile Gln Ser Ile His Phe Ser Gly His
                260                 265                 270

Val Phe Thr Val Arg Lys Lys Glu Glu Tyr Lys Met Ala Val Tyr Asn
                275                 280                 285

Leu Tyr Pro Gly Val Phe Glu Thr Val Glu Met Leu Pro Ser Arg Ala
                290                 295                 300

Gly Ile Trp Arg Val Glu Cys Leu Ile Gly Glu His Leu Gln Ala Gly
305                 310                 315                 320

Met Ser Thr Leu Phe Leu Val Tyr Ser Lys
                325                 330

<210> SEQ ID NO 9
<211> LENGTH: 153
<212> TYPE: PRT
<213> ORGANISM: artificial sequence
<220> FEATURE:
<223> OTHER INFORMATION: ancestral

<400> SEQUENCE: 9

Gln Cys Gln Ile Pro Leu Gly Met Ala Ser Gly Ser Ile Arg Asp Phe
1               5                   10                  15

Gln Ile Thr Ala Ser Gly His Tyr Gly Gln Trp Ala Pro Asn Leu Ala
                20                  25                  30

Arg Leu His His Ser Gly Ser Ile Asn Ala Trp Ser Thr Lys Glu Pro
                35                  40                  45

Phe Ser Trp Ile Lys Val Asp Leu Leu Thr Pro Met Ile Ile His Gly
            50                  55                  60

Ile Lys Thr Gln Gly Ala Arg Gln Lys Phe Ser Ser Leu Tyr Ile Ser
65                  70                  75                  80

Gln Phe Ile Ile Met Tyr Ser Leu Asp Gly Lys Lys Trp Leu Ser Tyr
                85                  90                  95

Arg Gly Asn Ser Thr Gly Thr Leu Met Val Phe Phe Gly Asn Val Asp
                100                 105                 110

Ser Ser Gly Ile Lys His Asn Ser Phe Asn Pro Pro Ile Ile Ala Arg
                115                 120                 125

Tyr Ile Arg Leu His Pro Thr His Ser Ser Ile Arg Ser Thr Leu Arg
            130                 135                 140

Met Glu Leu Met Gly Cys Asp Leu Asn
145                 150

<210> SEQ ID NO 10
<211> LENGTH: 160
<212> TYPE: PRT
```

```
<213> ORGANISM: artificial sequence
<220> FEATURE:
<223> OTHER INFORMATION: ancestral

<400> SEQUENCE: 10

Ser Cys Ser Ile Pro Leu Gly Met Glu Asn Lys Val Ile Ser Asp Thr
1               5                   10                  15

Gln Ile Thr Ala Ser Ser Tyr Phe Thr Asn Met Phe Ala Thr Trp Ser
            20                  25                  30

Pro Ser Gln Ala Arg Leu His Leu Gln Gly Arg Thr Asn Ala Trp Arg
        35                  40                  45

Pro Gln Val Asn Asp Pro Lys Glu Trp Leu Gln Val Asp Leu Gln Lys
    50                  55                  60

Thr Met Lys Val Thr Gly Ile Ile Thr Gln Gly Val Lys Ser Leu Phe
65                  70                  75                  80

Thr Ser Met Phe Val Lys Glu Phe Leu Ile Ser Ser Gln Asp Gly
                85                  90                  95

His His Trp Thr His Ile Leu His Asn Gly Lys Val Lys Val Phe Gln
            100                 105                 110

Gly Asn Gln Asp Ser Ser Thr Pro Met Val Asn Ser Leu Asp Pro Pro
        115                 120                 125

Leu Leu Thr Arg Tyr Leu Arg Ile His Pro Gln Ile Trp Glu His Gln
    130                 135                 140

Ile Ala Leu Arg Leu Glu Ile Leu Gly Cys Glu Ala Gln Gln Leu Tyr
145                 150                 155                 160

<210> SEQ ID NO 11
<211> LENGTH: 2354
<212> TYPE: PRT
<213> ORGANISM: artificial sequence
<220> FEATURE:
<223> OTHER INFORMATION: ancestral

<400> SEQUENCE: 11

Met Gln Ile Glu Leu Ser Thr Cys Phe Phe Leu Cys Leu Leu Gln Phe
1               5                   10                  15

Ser Phe Ser Ala Thr Arg Arg Tyr Tyr Leu Gly Ala Val Glu Leu Ser
            20                  25                  30

Trp Asp Tyr Met Gln Ser Asp Leu Leu Ser Glu Leu His Val Asp Thr
        35                  40                  45

Arg Phe Pro Pro Arg Val Pro Arg Ser Phe Pro Phe Asn Thr Ser Val
    50                  55                  60

Met Tyr Lys Lys Thr Val Phe Val Glu Phe Thr Asp His Leu Phe Asn
65                  70                  75                  80

Ile Ala Lys Pro Arg Pro Pro Trp Met Gly Leu Leu Gly Pro Thr Ile
                85                  90                  95

Gln Ala Glu Val Tyr Asp Thr Val Val Ile Thr Leu Lys Asn Met Ala
            100                 105                 110

Ser His Pro Val Ser Leu His Ala Val Gly Val Ser Tyr Trp Lys Ala
        115                 120                 125

Ser Glu Gly Ala Glu Tyr Asp Asp Gln Thr Ser Gln Arg Glu Lys Glu
    130                 135                 140

Asp Asp Lys Val Phe Pro Gly Glu Ser His Thr Tyr Val Trp Gln Val
145                 150                 155                 160

Leu Lys Glu Asn Gly Pro Met Ala Ser Asp Pro Pro Cys Leu Thr Tyr
                165                 170                 175
```

```
Ser Tyr Leu Ser His Val Asp Leu Val Lys Asp Leu Asn Ser Gly Leu
            180                 185                 190

Ile Gly Ala Leu Leu Val Cys Arg Glu Gly Ser Leu Ala Lys Glu Arg
        195                 200                 205

Thr Gln Thr Leu His Lys Phe Val Leu Leu Phe Ala Val Phe Asp Glu
    210                 215                 220

Gly Lys Ser Trp His Ser Glu Thr Lys Asp Ser Leu Met Gln Asp Met
225                 230                 235                 240

Asp Ser Ala Ser Ala Arg Ala Trp Pro Lys Met His Thr Val Asn Gly
                245                 250                 255

Tyr Val Asn Arg Ser Leu Pro Gly Leu Ile Gly Cys His Arg Lys Ser
            260                 265                 270

Val Tyr Trp His Val Ile Gly Met Gly Thr Thr Pro Glu Val His Ser
        275                 280                 285

Ile Phe Leu Glu Gly His Thr Phe Leu Val Arg Asn His Arg Gln Ala
    290                 295                 300

Ser Leu Glu Ile Ser Pro Ile Thr Phe Leu Thr Ala Gln Thr Leu Leu
305                 310                 315                 320

Met Asp Leu Gly Gln Phe Leu Leu Phe Cys His Ile Ser Ser His Gln
                325                 330                 335

His Asp Gly Met Glu Ala Tyr Val Lys Val Asp Ser Cys Pro Glu Glu
            340                 345                 350

Pro Gln Leu Arg Met Lys Asn Asn Glu Glu Glu Asp Tyr Asp Asp
        355                 360                 365

Asp Leu Ala Asp Ser Glu Met Asp Val Val Arg Phe Asp Asp Asp Asn
    370                 375                 380

Ser Pro Ser Phe Ile Gln Ile Arg Ser Val Ala Lys Lys His Pro Lys
385                 390                 395                 400

Thr Trp Val His Tyr Ile Ala Ala Glu Glu Glu Asp Trp Asp Tyr Ala
                405                 410                 415

Pro Ser Val Leu Thr Pro Asp Asp Arg Ser Tyr Lys Ser Gln Tyr Leu
            420                 425                 430

Asn Asn Gly Pro Gln Arg Ile Gly Arg Lys Tyr Lys Lys Val Arg Phe
        435                 440                 445

Met Ala Tyr Thr Asp Glu Thr Phe Lys Thr Arg Glu Ala Ile Gln Tyr
    450                 455                 460

Glu Ser Gly Ile Leu Gly Pro Leu Leu Tyr Gly Glu Val Gly Asp Thr
465                 470                 475                 480

Leu Leu Ile Ile Phe Lys Asn Gln Ala Ser Arg Pro Tyr Asn Ile Tyr
                485                 490                 495

Pro His Gly Ile Thr Asp Val Arg Pro Leu His Ser Gly Arg Leu Pro
            500                 505                 510

Lys Gly Val Lys His Leu Lys Asp Leu Pro Ile Leu Pro Gly Glu Ile
        515                 520                 525

Phe Lys Tyr Lys Trp Thr Val Thr Val Glu Asp Gly Pro Thr Lys Ser
    530                 535                 540

Asp Pro Arg Cys Leu Thr Arg Tyr Tyr Ser Ser Phe Ile Asn Leu Glu
545                 550                 555                 560

Arg Asp Leu Ala Ser Gly Leu Ile Gly Pro Leu Leu Ile Cys Tyr Lys
                565                 570                 575

Glu Ser Val Asp Gln Arg Gly Asn Gln Met Met Ser Asp Lys Arg Asn
            580                 585                 590

Val Ile Leu Phe Ser Val Phe Asp Glu Asn Arg Ser Trp Tyr Leu Thr
```

```
            595                 600                 605

Glu Asn Met Gln Arg Phe Leu Pro Asn Ala Ala Gly Val Gln Pro Gln
            610                 615                 620

Asp Pro Glu Phe Gln Ala Ser Asn Ile Met His Ser Ile Asn Gly Tyr
625                 630                 635                 640

Val Phe Asp Ser Leu Gln Leu Ser Val Cys Leu His Glu Val Ala Tyr
                645                 650                 655

Trp Tyr Ile Leu Ser Ile Gly Ala Gln Thr Asp Phe Leu Ser Val Phe
                660                 665                 670

Phe Ser Gly Tyr Thr Phe Lys His Lys Met Val Tyr Glu Asp Thr Leu
                675                 680                 685

Thr Leu Phe Pro Phe Ser Gly Glu Thr Val Phe Met Ser Met Glu Asn
            690                 695                 700

Pro Gly Leu Trp Val Leu Gly Cys His Asn Ser Asp Phe Arg Asn Arg
705                 710                 715                 720

Gly Met Thr Ala Leu Leu Lys Val Ser Ser Cys Asp Arg Asn Thr Gly
                725                 730                 735

Asp Tyr Tyr Glu Asp Thr Tyr Glu Asp Ile Ser Thr Tyr Leu Leu Ser
                740                 745                 750

Glu Asn Asn Val Ile Glu Pro Arg Ser Phe Ser Gln Asn Ser Arg His
                755                 760                 765

Pro Ser Thr Arg Gln Lys Gln Phe Lys Ala Thr Thr Ile Pro Glu Asn
770                 775                 780

Asp Ile Glu Lys Ile Asp Pro Gln Phe Gly Glu Arg Thr Gln Met Leu
785                 790                 795                 800

Lys Val Gln Ser Val Ser Ser Asp Leu Leu Met Leu Leu Gly Gln
                805                 810                 815

Ser Pro Thr Pro His Gly Leu Ser Leu Ser Asp Leu Gln Glu Ala Thr
                820                 825                 830

Tyr Glu Ala Ile Pro Asp Asp His Ser Pro Gly Ala Ile Asp Ser Asn
                835                 840                 845

Glu Gly Pro Ser Glu Val Ala His Leu Arg Pro Glu Leu His His Ser
                850                 855                 860

Gly Asp Met Val Phe Thr Pro Glu Pro Gly Leu Gln Leu Arg Leu Asn
865                 870                 875                 880

Glu Asn Leu Gly Thr Thr Ile Ala Val Glu Leu Lys Lys Leu Asp Leu
                885                 890                 895

Lys Val Ser Ser Ser Asn Asn Leu Met Thr Ser Pro Thr Ile Pro
                900                 905                 910

Ser Asp Asn Leu Ala Ala Gly Thr Glu Lys Thr Gly Ser Leu Gly Pro
            915                 920                 925

Pro Asn Met Pro Val His Phe Asp Ser Gln Leu Asp Thr Thr Val Phe
            930                 935                 940

Gly Lys Lys Ser Ser Pro Leu Ile Gly Ser Gly Val Pro Leu Ser Leu
945                 950                 955                 960

Ser Glu Arg Asn Asn Asp Ser Lys Leu Leu Glu Ala Ala Leu Met Asn
                965                 970                 975

Ser Gln Glu Ser Ser Leu Gly Lys Asn Val Ser Ser Met Glu Ser Asp
            980                 985                 990

Arg Leu Phe Lys Glu Lys Arg Ala His Gly Pro Ala Leu Leu Thr Lys
                995                 1000                1005

Asp Asn Ala Leu Phe Lys Val Asn Ile Ser Leu Val Lys Thr Asn
    1010                1015                1020
```

```
Lys Thr Ser Asn Asn Ser Thr Thr Asn Arg Lys Thr His Ile Asp
    1025            1030            1035

Gly Pro Thr Leu Leu Ile Glu Asn Ser Thr Ser Val Trp Gln Asp
    1040            1045            1050

Ile Leu Glu Ser Asp Thr Glu Phe Gln Glu Val Thr Ser Leu Ile
    1055            1060            1065

His Asp Lys Met Leu Met Asp Lys Asn Thr Thr Ala Leu Arg Leu
    1070            1075            1080

Asn His Val Ser Asn Lys Thr Thr Ser Ser Lys Asn Met Glu Met
    1085            1090            1095

Val His Gln Lys Lys Glu Gly Pro Val Pro Pro Asp Ala Glu Asn
    1100            1105            1110

Pro Asp Met Ser Phe Phe Lys Met Leu Phe Leu Pro Glu Ser Ala
    1115            1120            1125

Asn Trp Ile Lys Arg Thr His Gly Lys Asn Ser Leu Asn Ser Gly
    1130            1135            1140

Gln Gly Pro Ser Pro Lys Gln Leu Ile Ser Leu Gly Ser Glu Lys
    1145            1150            1155

Ser Val Lys Asp Gln Asn Phe Leu Ser Glu Lys Asn Lys Val Val
    1160            1165            1170

Val Gly Glu Asp Glu Phe Thr Lys Asp Thr Gly Leu Lys Glu Met
    1175            1180            1185

Ile Phe Pro Ser Ser Arg Asn Ile Phe Leu Thr Asn Leu Ala Asn
    1190            1195            1200

Val His Glu Asn Asp Thr His Asn Gln Glu Lys Lys Ile Gln Glu
    1205            1210            1215

Glu Ile Glu Arg Lys Glu Thr Leu Ile Gln Glu Asn Val Val Leu
    1220            1225            1230

Pro Gln Val Tyr Thr Val Thr Gly Thr Lys Asn Phe Met Lys Asn
    1235            1240            1245

Leu Phe Leu Leu Ser Thr Arg Gln Asn Val Glu Gly Leu Asp Glu
    1250            1255            1260

Gly Ala Tyr Ala Pro Val Leu Gln Asp Thr Arg Ser Leu Asn Asp
    1265            1270            1275

Ser Thr Asn Arg Thr Glu Ile His Met Ala His Phe Ser Lys Lys
    1280            1285            1290

Arg Glu Glu Glu Asn Leu Glu Gly Leu Gly Asn Gln Thr Lys Gln
    1295            1300            1305

Met Val Glu Lys Tyr Pro Ser Thr Thr Arg Met Ser Pro Asn Pro
    1310            1315            1320

Ser Gln Gln Asn Val Ile Thr Gln Arg Gly Lys Arg Ala Leu Lys
    1325            1330            1335

Gln Phe Arg Leu Pro Leu Glu Thr Glu Leu Glu Lys Gly Leu
    1340            1345            1350

Ile Val Asp Asp Thr Ser Thr Gln Trp Ser Lys Asn Met Lys Tyr
    1355            1360            1365

Leu Thr Gln Ser Thr Leu Thr Gln Ile Asp Tyr Asn Glu Lys Glu
    1370            1375            1380

Lys Lys Ala Ile Thr Gln Ser Pro Leu Ser Asp Cys Leu Met Arg
    1385            1390            1395

Asn His Ser Ile Thr Gln Thr Asn Ser Ser Ala Leu Pro Ile Ala
    1400            1405            1410
```

-continued

```
Lys Val Ser Ala Phe Pro Ser Ile Arg Pro Thr Asp Leu Thr Arg
1415                1420                1425

Val Pro Ser Gln Asp Asn Ser Ser His Leu Leu Ala Ser Ala Tyr
1430                1435                1440

Arg Lys Lys Ser Ser Gly Val Gln Glu Ser Ser His Phe Leu Gln
1445                1450                1455

Gly Ala Lys Arg Asn Asn Leu Ser Leu Ala Ile Leu Thr Leu Glu
1460                1465                1470

Met Ile Gly Asn Gln Arg Lys Val Gly Ser Leu Gly Thr Ser Ala
1475                1480                1485

Thr Asn Ser Val Met Tyr Lys Lys Leu Glu Asn Thr Val Leu Leu
1490                1495                1500

Lys Pro Gly Leu Pro Glu Ala Ser Gly Lys Val Glu Leu Leu Pro
1505                1510                1515

Lys Val His Ile His Gln Lys Asp Leu Phe Pro Thr Glu Thr Ser
1520                1525                1530

Asn Gly Ser Pro Gly His Leu Asp Leu Met Glu Glu Ile Leu Leu
1535                1540                1545

Gln Lys Thr Gln Gly Ala Ile Lys Trp Asn Lys Thr Asn Arg Pro
1550                1555                1560

Gly Lys Val Pro Phe Leu Lys Gly Ala Thr Glu Ser Ser Glu Lys
1565                1570                1575

Thr Pro Ser Lys Leu Leu Gly Pro Leu Ala Trp Asp Asn Gln Tyr
1580                1585                1590

Ala Thr Gln Ile Pro Lys Glu Glu Trp Lys Ser Gln Glu Lys Ser
1595                1600                1605

Pro Glu Asn Thr Ala Phe Lys Thr Lys Asp Thr Ile Leu Ser Leu
1610                1615                1620

Asn Pro Cys Glu Ser Asn His Ala Ile Ala Ala Ile Asn Glu Gly
1625                1630                1635

Gln Asp Arg Pro Gln Arg Glu Ala Thr Trp Ala Lys Gln Gly Gly
1640                1645                1650

Thr Gly Arg Leu Cys Ser Gln Asn Pro Pro Val Leu Lys Arg His
1655                1660                1665

Gln Arg Glu Ile Thr Leu Thr Thr Leu Gln Ser Asp Gln Glu Glu
1670                1675                1680

Ile Asp Tyr Asp Asp Thr Ile Ser Ile Glu Thr Lys Arg Glu Asp
1685                1690                1695

Phe Asp Ile Tyr Gly Glu Asp Glu Asn Gln Ser Pro Arg Ser Phe
1700                1705                1710

Gln Lys Lys Thr Arg His Tyr Phe Ile Ala Ala Val Glu Arg Leu
1715                1720                1725

Trp Asp Tyr Gly Met Ser Arg Ser Pro His Val Leu Arg Asn Arg
1730                1735                1740

Ala Gln Ser Gly Ser Val Pro Gln Phe Lys Lys Val Val Phe Gln
1745                1750                1755

Glu Phe Thr Asp Gly Ser Phe Thr Gln Pro Leu Tyr Arg Gly Glu
1760                1765                1770

Leu Asn Glu His Leu Gly Leu Leu Gly Pro Tyr Ile Arg Ala Glu
1775                1780                1785

Val Glu Asp Asn Ile Met Val Thr Phe Lys Asn Gln Ala Ser Arg
1790                1795                1800

Pro Tyr Ser Phe Tyr Ser Ser Leu Ile Ser Tyr Glu Glu Asp Gln
```

```
                1805                1810                1815
Arg Gln Gly Ala Glu Pro Arg Lys Asn Phe Val Lys Pro Asn Glu
                1820                1825                1830
Thr Lys Thr Tyr Phe Trp Lys Val Gln His His Met Ala Pro Thr
                1835                1840                1845
Lys Asp Glu Phe Asp Cys Lys Ala Trp Ala Tyr Phe Ser Asp Val
                1850                1855                1860
Asp Leu Glu Lys Asp Met His Ser Gly Leu Ile Gly Pro Leu Leu
                1865                1870                1875
Ile Cys His Thr Asn Thr Leu Asn Pro Ala His Gly Arg Gln Val
                1880                1885                1890
Thr Val Gln Glu Phe Ala Leu Phe Phe Thr Ile Phe Asp Glu Thr
                1895                1900                1905
Lys Ser Trp Tyr Phe Thr Glu Asn Met Glu Arg Asn Cys Arg Ala
                1910                1915                1920
Pro Cys Asn Ile Gln Met Glu Asp Pro Thr Phe Lys Glu Asn Tyr
                1925                1930                1935
Arg Phe His Ala Ile Asn Gly Tyr Val Met Asp Thr Leu Pro Gly
                1940                1945                1950
Leu Val Met Ala Gln Asp Gln Arg Ile Arg Trp Tyr Leu Leu Ser
                1955                1960                1965
Met Gly Ser Asn Glu Asn Ile His Ser Ile His Phe Ser Gly His
                1970                1975                1980
Val Phe Thr Val Arg Lys Lys Glu Glu Tyr Lys Met Ala Val Tyr
                1985                1990                1995
Asn Leu Tyr Pro Gly Val Phe Glu Thr Val Glu Met Leu Pro Ser
                2000                2005                2010
Lys Ala Gly Ile Trp Arg Val Glu Cys Leu Ile Gly Glu His Leu
                2015                2020                2025
His Ala Gly Met Ser Thr Leu Phe Leu Val Tyr Ser Lys Gln Cys
                2030                2035                2040
Gln Thr Pro Leu Gly Met Ala Ser Gly His Ile Arg Asp Phe Gln
                2045                2050                2055
Ile Thr Ala Ser Gly Gln Tyr Gly Gln Trp Ala Pro Lys Leu Ala
                2060                2065                2070
Arg Leu His Tyr Ser Gly Ser Ile Asn Ala Trp Ser Thr Lys Glu
                2075                2080                2085
Pro Phe Ser Trp Ile Lys Val Asp Leu Leu Ala Pro Met Ile Ile
                2090                2095                2100
His Gly Ile Lys Thr Gln Gly Ala Arg Gln Lys Phe Ser Ser Leu
                2105                2110                2115
Tyr Ile Ser Gln Phe Ile Ile Met Tyr Ser Leu Asp Gly Lys Lys
                2120                2125                2130
Trp Gln Thr Tyr Arg Gly Asn Ser Thr Gly Thr Leu Met Val Phe
                2135                2140                2145
Phe Gly Asn Val Asp Ser Ser Gly Ile Lys His Asn Ile Phe Asn
                2150                2155                2160
Pro Pro Ile Ile Ala Arg Tyr Ile Arg Leu His Pro Thr His Tyr
                2165                2170                2175
Ser Ile Arg Ser Thr Leu Arg Met Glu Leu Met Gly Cys Asp Leu
                2180                2185                2190
Asn Ser Cys Ser Met Pro Leu Gly Met Glu Ser Lys Ala Ile Ser
                2195                2200                2205
```

```
Asp Ala Gln Ile Thr Ala Ser Ser Tyr Phe Thr Asn Met Phe Ala
    2210            2215                2220

Thr Trp Ser Pro Ser Gln Ala Arg Leu His Leu Gln Gly Arg Thr
2225            2230                2235

Asn Ala Trp Arg Pro Gln Val Asn Asn Pro Lys Glu Trp Leu Gln
    2240            2245                2250

Val Asp Phe Gln Lys Thr Met Lys Val Thr Gly Ile Thr Thr Gln
    2255            2260                2265

Gly Val Lys Ser Leu Leu Thr Ser Met Tyr Val Lys Glu Phe Leu
    2270            2275                2280

Ile Ser Ser Ser Gln Asp Gly His His Trp Thr Leu Phe Phe Gln
    2285            2290                2295

Asn Gly Lys Val Lys Val Phe Gln Gly Asn Gln Asp Ser Phe Thr
    2300            2305                2310

Pro Val Val Asn Ser Leu Asp Pro Pro Leu Leu Thr Arg Tyr Leu
    2315            2320                2325

Arg Ile His Pro Gln Ser Trp Val His Gln Ile Ala Leu Arg Leu
    2330            2335                2340

Glu Val Leu Gly Cys Glu Ala Gln Gln Leu Tyr
    2345            2350
```

<210> SEQ ID NO 12
<211> LENGTH: 19
<212> TYPE: PRT
<213> ORGANISM: artificial sequence
<220> FEATURE:
<223> OTHER INFORMATION: ancestral

<400> SEQUENCE: 12

```
Met Gln Ile Glu Leu Ser Thr Cys Phe Phe Leu Cys Leu Leu Gln Phe
1               5                   10                  15

Ser Phe Ser
```

<210> SEQ ID NO 13
<211> LENGTH: 374
<212> TYPE: PRT
<213> ORGANISM: artificial sequence
<220> FEATURE:
<223> OTHER INFORMATION: ancestral

<400> SEQUENCE: 13

```
Ala Thr Arg Arg Tyr Tyr Leu Gly Ala Val Glu Leu Ser Trp Asp Tyr
1               5                   10                  15

Met Gln Ser Asp Leu Leu Ser Glu Leu His Val Asp Thr Arg Phe Pro
            20                  25                  30

Pro Arg Val Pro Arg Ser Phe Pro Phe Asn Thr Ser Val Met Tyr Lys
        35                  40                  45

Lys Thr Val Phe Val Glu Phe Thr Asp His Leu Phe Asn Ile Ala Lys
    50                  55                  60

Pro Arg Pro Pro Trp Met Gly Leu Leu Gly Pro Thr Ile Gln Ala Glu
65                  70                  75                  80

Val Tyr Asp Thr Val Val Ile Thr Leu Lys Asn Met Ala Ser His Pro
                85                  90                  95

Val Ser Leu His Ala Val Gly Val Ser Tyr Trp Lys Ala Ser Glu Gly
            100                 105                 110

Ala Glu Tyr Asp Asp Gln Thr Ser Gln Arg Glu Lys Glu Asp Asp Lys
        115                 120                 125
```

Val Phe Pro Gly Glu Ser His Thr Tyr Val Trp Gln Val Leu Lys Glu
    130                 135                 140

Asn Gly Pro Met Ala Ser Asp Pro Pro Cys Leu Thr Tyr Ser Tyr Leu
145                 150                 155                 160

Ser His Val Asp Leu Val Lys Asp Leu Asn Ser Gly Leu Ile Gly Ala
                165                 170                 175

Leu Leu Val Cys Arg Glu Gly Ser Leu Ala Lys Glu Arg Thr Gln Thr
            180                 185                 190

Leu His Lys Phe Val Leu Leu Phe Ala Val Phe Asp Glu Gly Lys Ser
        195                 200                 205

Trp His Ser Glu Thr Lys Asp Ser Leu Met Gln Asp Met Asp Ser Ala
    210                 215                 220

Ser Ala Arg Ala Trp Pro Lys Met His Thr Val Asn Gly Tyr Val Asn
225                 230                 235                 240

Arg Ser Leu Pro Gly Leu Ile Gly Cys His Arg Lys Ser Val Tyr Trp
                245                 250                 255

His Val Ile Gly Met Gly Thr Thr Pro Glu Val His Ser Ile Phe Leu
            260                 265                 270

Glu Gly His Thr Phe Leu Val Arg Asn His Arg Gln Ala Ser Leu Glu
        275                 280                 285

Ile Ser Pro Ile Thr Phe Leu Thr Ala Gln Thr Leu Leu Met Asp Leu
    290                 295                 300

Gly Gln Phe Leu Leu Phe Cys His Ile Ser Ser His Gln His Asp Gly
305                 310                 315                 320

Met Glu Ala Tyr Val Lys Val Asp Ser Cys Pro Glu Glu Pro Gln Leu
                325                 330                 335

Arg Met Lys Asn Asn Glu Glu Glu Asp Tyr Asp Asp Asp Leu Ala
            340                 345                 350

Asp Ser Glu Met Asp Val Val Arg Phe Asp Asp Asp Asn Ser Pro Ser
        355                 360                 365

Phe Ile Gln Ile Arg Ser
    370

<210> SEQ ID NO 14
<211> LENGTH: 367
<212> TYPE: PRT
<213> ORGANISM: artificial sequence
<220> FEATURE:
<223> OTHER INFORMATION: ancestral

<400> SEQUENCE: 14

Val Ala Lys Lys His Pro Lys Thr Trp Val His Tyr Ile Ala Ala Glu
1               5                   10                  15

Glu Glu Asp Trp Asp Tyr Ala Pro Ser Val Leu Thr Pro Asp Asp Arg
            20                  25                  30

Ser Tyr Lys Ser Gln Tyr Leu Asn Asn Gly Pro Gln Arg Ile Gly Arg
        35                  40                  45

Lys Tyr Lys Lys Val Arg Phe Met Ala Tyr Thr Asp Glu Thr Phe Lys
    50                  55                  60

Thr Arg Glu Ala Ile Gln Tyr Glu Ser Gly Ile Leu Gly Pro Leu Leu
65                  70                  75                  80

Tyr Gly Glu Val Gly Asp Thr Leu Leu Ile Ile Phe Lys Asn Gln Ala
                85                  90                  95

Ser Arg Pro Tyr Asn Ile Tyr Pro His Gly Ile Thr Asp Val Arg Pro
            100                 105                 110

-continued

```
Leu His Ser Gly Arg Leu Pro Lys Gly Val Lys His Leu Lys Asp Leu
        115                 120                 125

Pro Ile Leu Pro Gly Glu Ile Phe Lys Tyr Lys Trp Thr Val Thr Val
        130                 135                 140

Glu Asp Gly Pro Thr Lys Ser Asp Pro Arg Cys Leu Thr Arg Tyr Tyr
145                 150                 155                 160

Ser Ser Phe Ile Asn Leu Glu Arg Asp Leu Ala Ser Gly Leu Ile Gly
                165                 170                 175

Pro Leu Leu Ile Cys Tyr Lys Glu Ser Val Asp Gln Arg Gly Asn Gln
            180                 185                 190

Met Met Ser Asp Lys Arg Asn Val Ile Leu Phe Ser Val Phe Asp Glu
        195                 200                 205

Asn Arg Ser Trp Tyr Leu Thr Glu Asn Met Gln Arg Phe Leu Pro Asn
        210                 215                 220

Ala Ala Gly Val Gln Pro Gln Asp Pro Glu Phe Gln Ala Ser Asn Ile
225                 230                 235                 240

Met His Ser Ile Asn Gly Tyr Val Phe Asp Ser Leu Gln Leu Ser Val
                245                 250                 255

Cys Leu His Glu Val Ala Tyr Trp Tyr Ile Leu Ser Ile Gly Ala Gln
            260                 265                 270

Thr Asp Phe Leu Ser Val Phe Phe Ser Gly Tyr Thr Phe Lys His Lys
        275                 280                 285

Met Val Tyr Glu Asp Thr Leu Thr Leu Phe Pro Phe Ser Gly Glu Thr
        290                 295                 300

Val Phe Met Ser Met Glu Asn Pro Gly Leu Trp Val Leu Gly Cys His
305                 310                 315                 320

Asn Ser Asp Phe Arg Asn Arg Gly Met Thr Ala Leu Leu Lys Val Ser
                325                 330                 335

Ser Cys Asp Arg Asn Thr Gly Asp Tyr Tyr Glu Asp Thr Tyr Glu Asp
            340                 345                 350

Ile Ser Thr Tyr Leu Leu Ser Glu Asn Asn Val Ile Glu Pro Arg
        355                 360                 365

<210> SEQ ID NO 15
<211> LENGTH: 910
<212> TYPE: PRT
<213> ORGANISM: artificial sequence
<220> FEATURE:
<223> OTHER INFORMATION: ancestral

<400> SEQUENCE: 15

Ser Phe Ser Gln Asn Ser Arg His Pro Ser Thr Arg Gln Lys Gln Phe
1               5                   10                  15

Lys Ala Thr Thr Ile Pro Glu Asn Asp Ile Glu Lys Ile Asp Pro Gln
            20                  25                  30

Phe Gly Glu Arg Thr Gln Met Leu Lys Val Gln Ser Val Ser Ser Ser
        35                  40                  45

Asp Leu Leu Met Leu Leu Gly Gln Ser Pro Thr Pro His Gly Leu Ser
    50                  55                  60

Leu Ser Asp Leu Gln Glu Ala Thr Tyr Glu Ala Ile Pro Asp Asp His
65                  70                  75                  80

Ser Pro Gly Ala Ile Asp Ser Asn Glu Gly Pro Ser Glu Val Ala His
                85                  90                  95

Leu Arg Pro Glu Leu His His Ser Gly Asp Met Val Phe Thr Pro Glu
            100                 105                 110
```

```
Pro Gly Leu Gln Leu Arg Leu Asn Glu Asn Leu Gly Thr Thr Ile Ala
        115                 120                 125

Val Glu Leu Lys Lys Leu Asp Leu Lys Val Ser Ser Ser Asn Asn
    130                 135                 140

Leu Met Thr Ser Pro Thr Ile Pro Ser Asp Asn Leu Ala Ala Gly Thr
145                 150                 155                 160

Glu Lys Thr Gly Ser Leu Gly Pro Pro Asn Met Pro Val His Phe Asp
                165                 170                 175

Ser Gln Leu Asp Thr Thr Val Phe Gly Lys Lys Ser Ser Pro Leu Ile
                180                 185                 190

Gly Ser Gly Val Pro Leu Ser Leu Ser Glu Arg Asn Asn Asp Ser Lys
            195                 200                 205

Leu Leu Glu Ala Ala Leu Met Asn Ser Gln Glu Ser Ser Leu Gly Lys
210                 215                 220

Asn Val Ser Ser Met Glu Ser Asp Arg Leu Phe Lys Glu Lys Arg Ala
225                 230                 235                 240

His Gly Pro Ala Leu Leu Thr Lys Asp Asn Ala Leu Phe Lys Val Asn
                245                 250                 255

Ile Ser Leu Val Lys Thr Asn Lys Thr Ser Asn Asn Ser Thr Thr Asn
            260                 265                 270

Arg Lys Thr His Ile Asp Gly Pro Thr Leu Leu Ile Glu Asn Ser Thr
        275                 280                 285

Ser Val Trp Gln Asp Ile Leu Glu Ser Asp Thr Glu Phe Gln Glu Val
    290                 295                 300

Thr Ser Leu Ile His Asp Lys Met Leu Met Asp Lys Asn Thr Thr Ala
305                 310                 315                 320

Leu Arg Leu Asn His Val Ser Asn Lys Thr Thr Ser Ser Lys Asn Met
                325                 330                 335

Glu Met Val His Gln Lys Lys Glu Gly Pro Val Pro Pro Asp Ala Glu
                340                 345                 350

Asn Pro Asp Met Ser Phe Phe Lys Met Leu Phe Leu Pro Glu Ser Ala
            355                 360                 365

Asn Trp Ile Lys Arg Thr His Gly Lys Asn Ser Leu Asn Ser Gly Gln
        370                 375                 380

Gly Pro Ser Pro Lys Gln Leu Ile Ser Leu Gly Ser Glu Lys Ser Val
385                 390                 395                 400

Lys Asp Gln Asn Phe Leu Ser Glu Lys Asn Lys Val Val Gly Glu
                405                 410                 415

Asp Glu Phe Thr Lys Asp Thr Gly Leu Lys Glu Met Ile Phe Pro Ser
            420                 425                 430

Ser Arg Asn Ile Phe Leu Thr Asn Leu Ala Asn Val His Glu Asn Asp
        435                 440                 445

Thr His Asn Gln Glu Lys Lys Ile Gln Glu Glu Ile Glu Arg Lys Glu
    450                 455                 460

Thr Leu Ile Gln Glu Asn Val Val Leu Pro Gln Val Tyr Thr Val Thr
465                 470                 475                 480

Gly Thr Lys Asn Phe Met Lys Asn Leu Phe Leu Leu Ser Thr Arg Gln
                485                 490                 495

Asn Val Glu Gly Leu Asp Glu Gly Ala Tyr Ala Pro Val Leu Gln Asp
            500                 505                 510

Thr Arg Ser Leu Asn Asp Ser Thr Asn Arg Thr Glu Ile His Met Ala
        515                 520                 525
```

```
His Phe Ser Lys Lys Arg Glu Glu Asn Leu Glu Gly Leu Gly Asn
            530                 535                 540
Gln Thr Lys Gln Met Val Glu Lys Tyr Pro Ser Thr Thr Arg Met Ser
545                 550                 555                 560
Pro Asn Pro Ser Gln Gln Asn Val Ile Thr Gln Arg Gly Lys Arg Ala
                565                 570                 575
Leu Lys Gln Phe Arg Leu Pro Leu Glu Glu Thr Glu Leu Glu Lys Gly
            580                 585                 590
Leu Ile Val Asp Asp Thr Ser Thr Gln Trp Ser Lys Asn Met Lys Tyr
        595                 600                 605
Leu Thr Gln Ser Thr Leu Thr Gln Ile Asp Tyr Asn Glu Lys Glu Lys
    610                 615                 620
Lys Ala Ile Thr Gln Ser Pro Leu Ser Asp Cys Leu Met Arg Asn His
625                 630                 635                 640
Ser Ile Thr Gln Thr Asn Ser Ser Ala Leu Pro Ile Ala Lys Val Ser
                645                 650                 655
Ala Phe Pro Ser Ile Arg Pro Thr Asp Leu Thr Arg Val Pro Ser Gln
            660                 665                 670
Asp Asn Ser Ser His Leu Leu Ala Ser Ala Tyr Arg Lys Lys Ser Ser
        675                 680                 685
Gly Val Gln Glu Ser Ser His Phe Leu Gln Gly Ala Lys Arg Asn Asn
    690                 695                 700
Leu Ser Leu Ala Ile Leu Thr Leu Glu Met Ile Gly Asn Gln Arg Lys
705                 710                 715                 720
Val Gly Ser Leu Gly Thr Ser Ala Thr Asn Ser Val Met Tyr Lys Lys
                725                 730                 735
Leu Glu Asn Thr Val Leu Leu Lys Pro Gly Leu Pro Glu Ala Ser Gly
            740                 745                 750
Lys Val Glu Leu Leu Pro Lys Val His Ile His Gln Lys Asp Leu Phe
        755                 760                 765
Pro Thr Glu Thr Ser Asn Gly Ser Pro Gly His Leu Asp Leu Met Glu
    770                 775                 780
Glu Ile Leu Leu Gln Lys Thr Gln Gly Ala Ile Lys Trp Asn Lys Thr
785                 790                 795                 800
Asn Arg Pro Gly Lys Val Pro Phe Leu Lys Gly Ala Thr Glu Ser Ser
                805                 810                 815
Glu Lys Thr Pro Ser Lys Leu Leu Gly Pro Leu Ala Trp Asp Asn Gln
            820                 825                 830
Tyr Ala Thr Gln Ile Pro Lys Glu Glu Trp Lys Ser Gln Glu Lys Ser
        835                 840                 845
Pro Glu Asn Thr Ala Phe Lys Thr Lys Asp Thr Ile Leu Ser Leu Asn
    850                 855                 860
Pro Cys Glu Ser Asn His Ala Ile Ala Ala Ile Asn Glu Gly Gln Asp
865                 870                 875                 880
Arg Pro Gln Arg Glu Ala Thr Trp Ala Lys Gly Gly Thr Gly Arg
                885                 890                 895
Leu Cys Ser Gln Asn Pro Pro Val Leu Lys Arg His Gln Arg
            900                 905                 910

<210> SEQ ID NO 16
<211> LENGTH: 41
<212> TYPE: PRT
<213> ORGANISM: artificial sequence
<220> FEATURE:
<223> OTHER INFORMATION: ancestral
```

<400> SEQUENCE: 16

Glu Ile Thr Leu Thr Thr Leu Gln Ser Asp Gln Glu Glu Ile Asp Tyr
1               5                   10                  15

Asp Asp Thr Ile Ser Ile Glu Thr Lys Arg Glu Asp Phe Asp Ile Tyr
            20                  25                  30

Gly Glu Asp Glu Asn Gln Ser Pro Arg
        35                  40

<210> SEQ ID NO 17
<211> LENGTH: 330
<212> TYPE: PRT
<213> ORGANISM: artificial sequence
<220> FEATURE:
<223> OTHER INFORMATION: ancestral

<400> SEQUENCE: 17

Ser Phe Gln Lys Lys Thr Arg His Tyr Phe Ile Ala Ala Val Glu Arg
1               5                   10                  15

Leu Trp Asp Tyr Gly Met Ser Arg Ser Pro His Val Leu Arg Asn Arg
            20                  25                  30

Ala Gln Ser Gly Ser Val Pro Gln Phe Lys Lys Val Val Phe Gln Glu
        35                  40                  45

Phe Thr Asp Gly Ser Phe Thr Gln Pro Leu Tyr Arg Gly Glu Leu Asn
50                  55                  60

Glu His Leu Gly Leu Leu Gly Pro Tyr Ile Arg Ala Glu Val Glu Asp
65                  70                  75                  80

Asn Ile Met Val Thr Phe Lys Asn Gln Ala Ser Arg Pro Tyr Ser Phe
                85                  90                  95

Tyr Ser Ser Leu Ile Ser Tyr Glu Glu Asp Gln Arg Gln Gly Ala Glu
            100                 105                 110

Pro Arg Lys Asn Phe Val Lys Pro Asn Glu Thr Lys Thr Tyr Phe Trp
        115                 120                 125

Lys Val Gln His His Met Ala Pro Thr Lys Asp Glu Phe Asp Cys Lys
130                 135                 140

Ala Trp Ala Tyr Phe Ser Asp Val Asp Leu Glu Lys Asp Met His Ser
145                 150                 155                 160

Gly Leu Ile Gly Pro Leu Leu Ile Cys His Thr Asn Thr Leu Asn Pro
                165                 170                 175

Ala His Gly Arg Gln Val Thr Val Gln Glu Phe Ala Leu Phe Phe Thr
            180                 185                 190

Ile Phe Asp Glu Thr Lys Ser Trp Tyr Phe Thr Glu Asn Met Glu Arg
        195                 200                 205

Asn Cys Arg Ala Pro Cys Asn Ile Gln Met Glu Asp Pro Thr Phe Lys
210                 215                 220

Glu Asn Tyr Arg Phe His Ala Ile Asn Gly Tyr Val Met Asp Thr Leu
225                 230                 235                 240

Pro Gly Leu Val Met Ala Gln Asp Gln Arg Ile Arg Trp Tyr Leu Leu
                245                 250                 255

Ser Met Gly Ser Asn Glu Asn Ile His Ser Ile His Phe Ser Gly His
            260                 265                 270

Val Phe Thr Val Arg Lys Lys Glu Glu Tyr Lys Met Ala Val Tyr Asn
        275                 280                 285

Leu Tyr Pro Gly Val Phe Glu Thr Val Glu Met Leu Pro Ser Lys Ala
        290                 295                 300

```
Gly Ile Trp Arg Val Glu Cys Leu Ile Gly Glu His Leu His Ala Gly
305                 310                 315                 320

Met Ser Thr Leu Phe Leu Val Tyr Ser Lys
                325                 330

<210> SEQ ID NO 18
<211> LENGTH: 153
<212> TYPE: PRT
<213> ORGANISM: artificial sequence
<220> FEATURE:
<223> OTHER INFORMATION: ancestral

<400> SEQUENCE: 18

Gln Cys Gln Thr Pro Leu Gly Met Ala Ser Gly His Ile Arg Asp Phe
1               5                   10                  15

Gln Ile Thr Ala Ser Gly Gln Tyr Gly Gln Trp Ala Pro Lys Leu Ala
            20                  25                  30

Arg Leu His Tyr Ser Gly Ser Ile Asn Ala Trp Ser Thr Lys Glu Pro
        35                  40                  45

Phe Ser Trp Ile Lys Val Asp Leu Leu Ala Pro Met Ile Ile His Gly
    50                  55                  60

Ile Lys Thr Gln Gly Ala Arg Gln Lys Phe Ser Ser Leu Tyr Ile Ser
65                  70                  75                  80

Gln Phe Ile Ile Met Tyr Ser Leu Asp Gly Lys Lys Trp Gln Thr Tyr
                85                  90                  95

Arg Gly Asn Ser Thr Gly Thr Leu Met Val Phe Phe Gly Asn Val Asp
            100                 105                 110

Ser Ser Gly Ile Lys His Asn Ile Phe Asn Pro Pro Ile Ile Ala Arg
        115                 120                 125

Tyr Ile Arg Leu His Pro Thr His Tyr Ser Ile Arg Ser Thr Leu Arg
    130                 135                 140

Met Glu Leu Met Gly Cys Asp Leu Asn
145                 150

<210> SEQ ID NO 19
<211> LENGTH: 160
<212> TYPE: PRT
<213> ORGANISM: artificial sequence
<220> FEATURE:
<223> OTHER INFORMATION: ancestral

<400> SEQUENCE: 19

Ser Cys Ser Met Pro Leu Gly Met Glu Ser Lys Ala Ile Ser Asp Ala
1               5                   10                  15

Gln Ile Thr Ala Ser Ser Tyr Phe Thr Asn Met Phe Ala Thr Trp Ser
            20                  25                  30

Pro Ser Gln Ala Arg Leu His Leu Gln Gly Arg Thr Asn Ala Trp Arg
        35                  40                  45

Pro Gln Val Asn Asn Pro Lys Glu Trp Leu Gln Val Asp Phe Gln Lys
    50                  55                  60

Thr Met Lys Val Thr Gly Ile Thr Thr Gln Gly Val Lys Ser Leu Leu
65                  70                  75                  80

Thr Ser Met Tyr Val Lys Glu Phe Leu Ile Ser Ser Ser Gln Asp Gly
                85                  90                  95

His His Trp Thr Leu Phe Phe Gln Asn Gly Lys Val Lys Val Phe Gln
            100                 105                 110

Gly Asn Gln Asp Ser Phe Thr Pro Val Val Asn Ser Leu Asp Pro Pro
        115                 120                 125
```

```
Leu Leu Thr Arg Tyr Leu Arg Ile His Pro Gln Ser Trp Val His Gln
    130                 135                 140

Ile Ala Leu Arg Leu Glu Val Leu Gly Cys Glu Ala Gln Gln Leu Tyr
145                 150                 155                 160
```

<210> SEQ ID NO 20
<211> LENGTH: 2359
<212> TYPE: PRT
<213> ORGANISM: artificial sequence
<220> FEATURE:
<223> OTHER INFORMATION: ancestral

<400> SEQUENCE: 20

```
Met Gln Ile Glu Leu Ser Thr Cys Phe Phe Leu Cys Leu Leu Gln Phe
1               5                   10                  15

Ser Phe Ser Ala Thr Arg Arg Tyr Tyr Leu Gly Ala Val Glu Leu Ser
                20                  25                  30

Trp Asp Tyr Met Gln Ser Asp Leu Leu Ser Glu Leu His Val Asp Thr
            35                  40                  45

Arg Phe Pro Pro Arg Val Pro Arg Ser Phe Pro Phe Asn Thr Ser Val
    50                  55                  60

Met Tyr Lys Lys Thr Val Phe Val Glu Phe Thr Asp His Leu Phe Asn
65                  70                  75                  80

Ile Ala Lys Pro Arg Pro Pro Trp Met Gly Leu Leu Gly Pro Thr Ile
                85                  90                  95

Arg Ala Glu Val Tyr Asp Thr Val Val Ile Thr Leu Lys Asn Met Ala
            100                 105                 110

Ser His Pro Val Ser Leu His Ala Val Gly Val Ser Tyr Trp Lys Ala
        115                 120                 125

Ser Glu Gly Ala Glu Tyr Asp Asp Gln Thr Ser Gln Arg Glu Lys Glu
    130                 135                 140

Asp Asp Lys Val Phe Pro Gly Glu Ser His Thr Tyr Val Trp Gln Val
145                 150                 155                 160

Leu Lys Glu Asn Gly Pro Met Ala Ser Asp Pro Pro Cys Leu Thr Tyr
                165                 170                 175

Ser Tyr Leu Ser His Val Asp Leu Val Lys Asp Leu Asn Ser Gly Leu
            180                 185                 190

Ile Gly Ala Leu Leu Val Cys Arg Glu Gly Ser Leu Ala Lys Glu Arg
        195                 200                 205

Thr Gln Thr Leu His Gln Phe Val Leu Leu Phe Ala Val Phe Asp Glu
    210                 215                 220

Gly Lys Ser Trp His Ser Glu Thr Lys Asp Ser Leu Thr Gln Ala Met
225                 230                 235                 240

Asp Ser Ala Ser Ala Arg Ala Trp Pro Lys Met His Thr Val Asn Gly
                245                 250                 255

Tyr Val Asn Arg Ser Leu Pro Gly Leu Ile Gly Cys His Arg Lys Ser
            260                 265                 270

Val Tyr Trp His Val Ile Gly Met Gly Thr Thr Pro Glu Val His Ser
        275                 280                 285

Ile Phe Leu Glu Gly His Thr Phe Leu Val Arg Asn His Arg Gln Ala
    290                 295                 300

Ser Leu Glu Ile Ser Pro Ile Thr Phe Leu Thr Ala Gln Thr Leu Leu
305                 310                 315                 320

Met Asp Leu Gly Gln Phe Leu Leu Phe Cys His Ile Ser Ser His Gln
                325                 330                 335
```

```
His Asp Gly Met Glu Ala Tyr Val Lys Val Asp Ser Cys Pro Glu
            340                 345                 350
Pro Gln Leu Arg Met Lys Asn Asn Glu Glu Glu Asp Tyr Asp Asp
            355                 360                 365
Asp Leu Tyr Asp Ser Glu Met Asp Val Val Arg Phe Asp Asp Asn
            370                 375                 380
Ser Pro Pro Phe Ile Gln Ile Arg Ser Val Ala Lys Lys His Pro Lys
385                 390                 395                 400
Thr Trp Val His Tyr Ile Ala Ala Glu Glu Asp Trp Asp Tyr Ala
            405                 410                 415
Pro Ser Val Leu Thr Pro Asp Asp Arg Ser Tyr Lys Ser Gln Tyr Leu
            420                 425                 430
Asn Asn Gly Pro Gln Arg Ile Gly Arg Lys Tyr Lys Val Arg Phe
            435                 440                 445
Met Ala Tyr Thr Asp Glu Thr Phe Lys Thr Arg Glu Ala Ile Gln Tyr
            450                 455                 460
Glu Ser Gly Ile Leu Gly Pro Leu Leu Tyr Gly Glu Val Gly Asp Thr
465                 470                 475                 480
Leu Leu Ile Ile Phe Lys Asn Gln Ala Ser Arg Pro Tyr Asn Ile Tyr
            485                 490                 495
Pro His Gly Ile Thr Asp Val Ser Pro Leu His Ser Gly Arg Leu Pro
            500                 505                 510
Lys Gly Val Lys His Leu Lys Asp Leu Pro Ile Leu Pro Gly Glu Ile
            515                 520                 525
Phe Lys Tyr Lys Trp Thr Val Thr Val Glu Asp Gly Pro Thr Lys Ser
            530                 535                 540
Asp Pro Arg Cys Leu Thr Arg Tyr Tyr Ser Ser Phe Ile Asn Leu Glu
545                 550                 555                 560
Arg Asp Leu Ala Ser Gly Leu Ile Gly Pro Leu Leu Ile Cys Tyr Lys
            565                 570                 575
Glu Ser Val Asp Gln Arg Gly Asn Gln Met Met Ser Asp Lys Arg Asn
            580                 585                 590
Val Ile Leu Phe Ser Val Phe Asp Glu Asn Arg Ser Trp Tyr Leu Thr
            595                 600                 605
Glu Asn Met Gln Arg Phe Leu Pro Asn Ala Ala Gly Val Gln Pro Gln
            610                 615                 620
Asp Pro Glu Phe Gln Ala Ser Asn Ile Met His Ser Ile Asn Gly Tyr
625                 630                 635                 640
Val Phe Asp Ser Leu Gln Leu Ser Val Cys Leu His Glu Val Ala Tyr
            645                 650                 655
Trp Tyr Ile Leu Ser Val Gly Ala Gln Thr Asp Phe Leu Ser Val Phe
            660                 665                 670
Phe Ser Gly Tyr Thr Phe Lys His Lys Met Val Tyr Glu Asp Thr Leu
            675                 680                 685
Thr Leu Phe Pro Phe Ser Gly Glu Thr Val Phe Met Ser Met Glu Asn
            690                 695                 700
Pro Gly Leu Trp Val Leu Gly Cys His Asn Ser Asp Phe Arg Asn Arg
705                 710                 715                 720
Gly Met Thr Ala Leu Leu Lys Val Ser Ser Cys Asp Arg Asn Thr Gly
            725                 730                 735
Asp Tyr Tyr Glu Asp Thr Tyr Glu Asp Ile Pro Thr Tyr Leu Leu Ser
            740                 745                 750
```

-continued

Glu Asn Asn Val Ile Glu Pro Arg Ser Phe Ser Gln Asn Ser Arg His
            755                 760                 765

Pro Ser Thr Arg Gln Lys Gln Phe Lys Ala Thr Thr Ile Pro Glu Asn
        770                 775                 780

Asp Ile Glu Lys Ile Asp Pro Gln Phe Gly Glu Arg Thr Gln Met Leu
785                 790                 795                 800

Lys Val Gln Ser Val Ser Ser Asp Leu Leu Met Leu Leu Gly Gln
                805                 810                 815

Ser Pro Thr Pro His Gly Leu Ser Leu Ser Asp Leu Gln Glu Ala Thr
            820                 825                 830

Tyr Glu Ala Ile Pro Asp Asp His Ser Pro Gly Ala Ile Asp Ser Asn
            835                 840                 845

Glu Gly Pro Ser Glu Val Ala His Leu Arg Pro Glu Leu His His Ser
850                 855                 860

Gly Asp Met Val Phe Thr Pro Glu Pro Gly Leu Gln Leu Arg Leu Asn
865                 870                 875                 880

Glu Asn Leu Gly Thr Thr Ile Ala Val Glu Leu Lys Lys Leu Asp Leu
                885                 890                 895

Lys Val Ser Ser Ser Asn Asn Leu Met Thr Ser Pro Thr Ile Pro
            900                 905                 910

Ser Asp Asn Leu Ala Ala Gly Thr Glu Lys Thr Gly Ser Leu Gly Pro
        915                 920                 925

Pro Asn Met Pro Val His Phe Ser Ser Gln Leu Gly Thr Thr Val Phe
    930                 935                 940

Gly Lys Lys Ser Ser Pro Leu Ile Gly Ser Gly Val Pro Leu Asn Leu
945                 950                 955                 960

Ser Glu Arg Asn Asn Asp Ser Lys Leu Leu Glu Ala Ala Leu Met Asn
            965                 970                 975

Ser Gln Glu Ser Ser Leu Gly Lys Asn Val Ser Ser Met Glu Ser Asp
        980                 985                 990

Arg Leu Phe Lys Glu Lys Arg Val His Gly Pro Ala Leu Leu Thr Lys
    995                 1000                1005

Asp Asn Ala Leu Phe Lys Val Asn Ile Ser Leu Val Lys Thr Asn
    1010                1015                1020

Lys Thr Ser Asn Asn Ser Thr Thr Asn Arg Lys Thr His Ile Asp
    1025                1030                1035

Gly Pro Thr Leu Leu Ile Glu Asn Ser Thr Ser Val Trp Gln Asp
    1040                1045                1050

Ile Ile Leu Glu Ser Asp Thr Glu Phe Gln Glu Val Thr Ser Leu
    1055                1060                1065

Ile His Asp Glu Met Leu Met Asp Lys Asn Thr Thr Ala Leu Arg
    1070                1075                1080

Leu Asn His Val Ser Asn Lys Thr Thr Ser Ser Lys Asn Met Glu
    1085                1090                1095

Met Val His Gln Lys Lys Glu Gly Pro Val Pro Pro Asp Ala Glu
    1100                1105                1110

Asn Pro Asp Met Ser Phe Phe Lys Met Leu Phe Leu Pro Glu Ser
    1115                1120                1125

Ala Asn Trp Ile Lys Arg Thr His Gly Lys Asn Ser Leu Asn Ser
    1130                1135                1140

Gly Gln Gly Pro Ser Pro Lys Gln Leu Ile Ser Leu Gly Ser Glu
    1145                1150                1155

Lys Ser Val Lys Asp Gln Asn Phe Leu Ser Glu Lys Asn Lys Val

-continued

|  | 1160 |  |  | 1165 |  |  |  | 1170 |  |  |
|---|---|---|---|---|---|---|---|---|---|---|

Val Val Gly Glu Asp Glu Phe Thr Lys Asp Thr Gly Leu Lys Glu
1175            1180                 1185

Met Ile Phe Pro Asn Ser Arg Ser Ile Phe Leu Thr Asn Leu Ala
1190            1195                 1200

Asn Val Gln Glu Asn Asp Thr His Asn Gln Glu Lys Lys Phe Gln
1205            1210                 1215

Glu Glu Ile Glu Arg Lys Glu Thr Leu Ile Gln Glu Asn Val Val
1220            1225                 1230

Leu Pro Gln Val Tyr Thr Val Thr Gly Thr Lys Asn Phe Leu Lys
1235            1240                 1245

Asn Leu Phe Leu Leu Ser Thr Arg Gln Asn Val Glu Gly Leu Asp
1250            1255                 1260

Glu Gly Thr Tyr Ala Pro Val Leu Gln Asp Thr Arg Ser Leu Asn
1265            1270                 1275

Asp Ser Thr Asn Arg Ala Glu Ile His Met Ala His Phe Ser Lys
1280            1285                 1290

Arg Arg Glu Glu Glu Asn Leu Glu Gly Leu Gly Asn Gln Thr Lys
1295            1300                 1305

Gln Met Val Glu Lys Tyr Pro Ser Thr Thr Arg Met Ser Pro Asn
1310            1315                 1320

Pro Ser Gln Gln Asn Val Ile Thr Gln Arg Gly Lys Arg Ala Leu
1325            1330                 1335

Lys Gln Phe Arg Leu Pro Leu Glu Glu Thr Glu Leu Glu Lys Gly
1340            1345                 1350

Leu Ile Val Asp Asp Thr Ser Thr Gln Trp Ser Lys Asn Met Lys
1355            1360                 1365

Tyr Leu Thr Gln Ser Thr Leu Thr Gln Ile Asp Tyr Asn Glu Lys
1370            1375                 1380

Glu Lys Lys Ala Ile Thr Gln Ser Pro Leu Ser Asp Cys Ser Met
1385            1390                 1395

Arg Asn His Ser Ile Thr Gln Thr Asn Ser Ser Ala Leu Pro Ile
1400            1405                 1410

Ala Lys Val Ser Ala Phe Pro Ser Ile Arg Pro Thr Asp Leu Thr
1415            1420                 1425

Lys Ile Pro Ser Gln Asp Asn Ser Ser His Leu Leu Ala Ser Ala
1430            1435                 1440

Tyr Ser Tyr Thr Phe Arg Glu Lys Ser Ser Gly Val Gln Glu Ser
1445            1450                 1455

Ser His Phe Leu Gln Gly Ala Lys Arg Asn Asn Leu Ser Leu Ala
1460            1465                 1470

Ile Leu Thr Leu Glu Met Ile Arg Asn Gln Glu Lys Val Gly Ser
1475            1480                 1485

Leu Gly Thr Ser Ala Thr Asn Ser Val Met Tyr Lys Lys Leu Glu
1490            1495                 1500

Asn Thr Val Leu Leu Lys Pro Gly Leu Pro Glu Ala Ser Gly Lys
1505            1510                 1515

Val Glu Leu Leu Pro Lys Val His Ile His Gln Glu Asp Leu Phe
1520            1525                 1530

Pro Thr Glu Thr Ser Asn Gly Ser Pro Gly His Leu Asp Leu Met
1535            1540                 1545

Glu Glu Ile Leu Leu Gln Lys Thr Gln Gly Ala Ile Lys Trp Asn
1550            1555                 1560

-continued

```
Lys Thr Asn Arg Pro Gly Lys Val Pro Phe Leu Lys Gly Ala Thr
1565                1570                1575

Glu Ser Ser Glu Lys Thr Pro Ser Lys Leu Leu Gly Pro Leu Ala
1580                1585                1590

Trp Asp Asn Gln Tyr Ala Thr Gln Ile Pro Lys Glu Glu Trp Lys
1595                1600                1605

Ser Gln Glu Lys Ser Pro Lys Asn Thr Ala Phe Lys Thr Lys Asp
1610                1615                1620

Thr Ile Leu Ser Leu Asn Pro Cys Glu Asn Asn His Ala Ile Ala
1625                1630                1635

Ala Ile Asn Glu Gly Gln Asp Arg Pro Gln Arg Glu Ala Thr Trp
1640                1645                1650

Ala Lys Gln Gly Gly Thr Gly Arg Leu Cys Ser Gln Asn Pro Pro
1655                1660                1665

Val Leu Lys Arg His Gln Arg Glu Ile Thr Leu Thr Thr Leu Gln
1670                1675                1680

Ser Glu Gln Glu Glu Ile Asp Tyr Asp Asp Thr Ile Ser Ile Glu
1685                1690                1695

Thr Lys Arg Glu Asp Phe Asp Ile Tyr Gly Glu Asp Glu Asn Gln
1700                1705                1710

Gly Pro Arg Ser Phe Gln Lys Arg Thr Arg His Tyr Phe Ile Ala
1715                1720                1725

Ala Val Glu Arg Leu Trp Asp Tyr Gly Met Ser Arg Ser Pro His
1730                1735                1740

Val Leu Arg Asn Arg Ala Gln Ser Gly Ser Val Pro Gln Phe Lys
1745                1750                1755

Lys Val Val Phe Gln Glu Phe Thr Asp Gly Ser Phe Thr Gln Pro
1760                1765                1770

Leu Tyr Arg Gly Glu Leu Asn Glu His Leu Gly Leu Leu Gly Pro
1775                1780                1785

Tyr Ile Arg Ala Glu Val Glu Asp Asn Ile Met Val Thr Phe Lys
1790                1795                1800

Asn Gln Ala Ser Arg Pro Tyr Ser Phe Tyr Ser Ser Leu Ile Ser
1805                1810                1815

Tyr Glu Glu Asp Gln Arg Gln Gly Ala Glu Pro Arg Lys Asn Phe
1820                1825                1830

Val Lys Pro Asn Glu Thr Lys Thr Tyr Phe Trp Lys Val Gln His
1835                1840                1845

His Met Ala Pro Thr Lys Asp Glu Phe Asp Cys Lys Ala Trp Ala
1850                1855                1860

Tyr Phe Ser Asp Val Asp Leu Glu Lys Asp Met His Ser Gly Leu
1865                1870                1875

Ile Gly Pro Leu Leu Ile Cys His Thr Asn Thr Leu Asn Pro Ala
1880                1885                1890

His Gly Arg Gln Val Thr Val Gln Glu Phe Ala Leu Phe Phe Thr
1895                1900                1905

Ile Phe Asp Glu Thr Lys Ser Trp Tyr Phe Thr Glu Asn Met Glu
1910                1915                1920

Arg Asn Cys Arg Ala Pro Cys Asn Ile Gln Met Glu Asp Pro Thr
1925                1930                1935

Phe Lys Glu Asn Tyr Arg Phe His Ala Ile Asn Gly Tyr Val Met
1940                1945                1950
```

```
Asp Thr Leu Pro Gly Leu Val Met Ala Gln Asp Gln Arg Ile Arg
1955                1960                1965

Trp Tyr Leu Leu Ser Met Gly Ser Asn Glu Asn Ile His Ser Ile
1970                1975                1980

His Phe Ser Gly His Val Phe Thr Val Arg Lys Lys Glu Glu Tyr
1985                1990                1995

Lys Met Ala Val Tyr Asn Leu Tyr Pro Gly Val Phe Glu Thr Val
2000                2005                2010

Glu Met Leu Pro Ser Lys Ala Gly Ile Trp Arg Val Glu Cys Leu
2015                2020                2025

Ile Gly Glu His Leu His Ala Gly Met Ser Thr Leu Phe Leu Val
2030                2035                2040

Tyr Ser Lys Gln Cys Gln Thr Pro Leu Gly Met Ala Ser Gly His
2045                2050                2055

Ile Arg Asp Phe Gln Ile Thr Ala Ser Gly Gln Tyr Gly Gln Trp
2060                2065                2070

Ala Pro Lys Leu Ala Arg Leu His Tyr Ser Gly Ser Ile Asn Ala
2075                2080                2085

Trp Ser Thr Lys Glu Pro Phe Ser Trp Ile Lys Val Asp Leu Leu
2090                2095                2100

Ala Pro Met Ile Ile His Gly Ile Lys Thr Gln Gly Ala Arg Gln
2105                2110                2115

Lys Phe Ser Ser Leu Tyr Ile Ser Gln Phe Ile Ile Met Tyr Ser
2120                2125                2130

Leu Asp Gly Lys Lys Trp Gln Thr Tyr Arg Gly Asn Ser Thr Gly
2135                2140                2145

Thr Leu Met Val Phe Phe Gly Asn Val Asp Ser Ser Gly Ile Lys
2150                2155                2160

His Asn Ile Phe Asn Pro Pro Ile Ile Ala Arg Tyr Ile Arg Leu
2165                2170                2175

His Pro Thr His Tyr Ser Ile Arg Ser Thr Leu Arg Met Glu Leu
2180                2185                2190

Met Gly Cys Asp Leu Asn Ser Cys Ser Met Pro Leu Gly Met Glu
2195                2200                2205

Ser Lys Ala Ile Ser Asp Ala Gln Ile Thr Ala Ser Ser Tyr Phe
2210                2215                2220

Thr Asn Met Phe Ala Thr Trp Ser Pro Ser Gln Ala Arg Leu His
2225                2230                2235

Leu Gln Gly Arg Thr Asn Ala Trp Arg Pro Gln Val Asn Asn Pro
2240                2245                2250

Lys Glu Trp Leu Gln Val Asp Phe Gln Lys Thr Met Lys Val Thr
2255                2260                2265

Gly Ile Thr Thr Gln Gly Val Lys Ser Leu Leu Thr Ser Met Tyr
2270                2275                2280

Val Lys Glu Phe Leu Ile Ser Ser Ser Gln Asp Gly His His Trp
2285                2290                2295

Thr Leu Phe Leu Gln Asn Gly Lys Val Lys Val Phe Gln Gly Asn
2300                2305                2310

Gln Asp Ser Phe Thr Pro Val Val Asn Ser Leu Asp Pro Pro Leu
2315                2320                2325

Leu Thr Arg Tyr Leu Arg Ile His Pro Gln Ser Trp Val His Gln
2330                2335                2340

Ile Ala Leu Arg Leu Glu Val Leu Gly Cys Glu Ala Gln Gln Leu
```

Tyr

<210> SEQ ID NO 21
<211> LENGTH: 19
<212> TYPE: PRT
<213> ORGANISM: artificial sequence
<220> FEATURE:
<223> OTHER INFORMATION: ancestral

<400> SEQUENCE: 21

Met Gln Ile Glu Leu Ser Thr Cys Phe Phe Leu Cys Leu Leu Gln Phe
 1               5                  10                  15

Ser Phe Ser

<210> SEQ ID NO 22
<211> LENGTH: 374
<212> TYPE: PRT
<213> ORGANISM: artificial sequence
<220> FEATURE:
<223> OTHER INFORMATION: ancestral

<400> SEQUENCE: 22

Ala Thr Arg Arg Tyr Tyr Leu Gly Ala Val Glu Leu Ser Trp Asp Tyr
 1               5                  10                  15

Met Gln Ser Asp Leu Leu Ser Glu Leu His Val Asp Thr Arg Phe Pro
                20                  25                  30

Pro Arg Val Pro Arg Ser Phe Pro Phe Asn Thr Ser Val Met Tyr Lys
            35                  40                  45

Lys Thr Val Phe Val Glu Phe Thr Asp His Leu Phe Asn Ile Ala Lys
        50                  55                  60

Pro Arg Pro Pro Trp Met Gly Leu Leu Gly Pro Thr Ile Arg Ala Glu
 65                 70                  75                  80

Val Tyr Asp Thr Val Val Ile Thr Leu Lys Asn Met Ala Ser His Pro
                85                  90                  95

Val Ser Leu His Ala Val Gly Val Ser Tyr Trp Lys Ala Ser Glu Gly
            100                 105                 110

Ala Glu Tyr Asp Asp Gln Thr Ser Gln Arg Glu Lys Glu Asp Asp Lys
        115                 120                 125

Val Phe Pro Gly Glu Ser His Thr Tyr Val Trp Gln Val Leu Lys Glu
130                 135                 140

Asn Gly Pro Met Ala Ser Asp Pro Pro Cys Leu Thr Tyr Ser Tyr Leu
145                 150                 155                 160

Ser His Val Asp Leu Val Lys Asp Leu Asn Ser Gly Leu Ile Gly Ala
                165                 170                 175

Leu Leu Val Cys Arg Glu Gly Ser Leu Ala Lys Glu Arg Thr Gln Thr
            180                 185                 190

Leu His Gln Phe Val Leu Leu Phe Ala Val Phe Asp Glu Gly Lys Ser
        195                 200                 205

Trp His Ser Glu Thr Lys Asp Ser Leu Thr Gln Ala Met Asp Ser Ala
    210                 215                 220

Ser Ala Arg Ala Trp Pro Lys Met His Thr Val Asn Gly Tyr Val Asn
225                 230                 235                 240

Arg Ser Leu Pro Gly Leu Ile Gly Cys His Arg Lys Ser Val Tyr Trp
                245                 250                 255

His Val Ile Gly Met Gly Thr Thr Pro Glu Val His Ser Ile Phe Leu
            260                 265                 270

```
Glu Gly His Thr Phe Leu Val Arg Asn His Arg Gln Ala Ser Leu Glu
            275                 280                 285

Ile Ser Pro Ile Thr Phe Leu Thr Ala Gln Thr Leu Leu Met Asp Leu
    290                 295                 300

Gly Gln Phe Leu Leu Phe Cys His Ile Ser Ser His Gln His Asp Gly
305                 310                 315                 320

Met Glu Ala Tyr Val Lys Val Asp Ser Cys Pro Glu Glu Pro Gln Leu
                325                 330                 335

Arg Met Lys Asn Asn Glu Glu Glu Asp Tyr Asp Asp Leu Tyr
                340                 345                 350

Asp Ser Glu Met Asp Val Val Arg Phe Asp Asp Asn Ser Pro Pro
                355                 360                 365

Phe Ile Gln Ile Arg Ser
    370
```

<210> SEQ ID NO 23
<211> LENGTH: 367
<212> TYPE: PRT
<213> ORGANISM: artificial sequence
<220> FEATURE:
<223> OTHER INFORMATION: ancestral

<400> SEQUENCE: 23

```
Val Ala Lys Lys His Pro Lys Thr Trp Val His Tyr Ile Ala Ala Glu
1               5                   10                  15

Glu Glu Asp Trp Asp Tyr Ala Pro Ser Val Leu Thr Pro Asp Asp Arg
                20                  25                  30

Ser Tyr Lys Ser Gln Tyr Leu Asn Asn Gly Pro Gln Arg Ile Gly Arg
            35                  40                  45

Lys Tyr Lys Lys Val Arg Phe Met Ala Tyr Thr Asp Glu Thr Phe Lys
50                  55                  60

Thr Arg Glu Ala Ile Gln Tyr Glu Ser Gly Ile Leu Gly Pro Leu Leu
65                  70                  75                  80

Tyr Gly Glu Val Gly Asp Thr Leu Leu Ile Ile Phe Lys Asn Gln Ala
                85                  90                  95

Ser Arg Pro Tyr Asn Ile Tyr Pro His Gly Ile Thr Asp Val Ser Pro
            100                 105                 110

Leu His Ser Gly Arg Leu Pro Lys Gly Val Lys His Leu Lys Asp Leu
        115                 120                 125

Pro Ile Leu Pro Gly Glu Ile Phe Lys Tyr Lys Trp Thr Val Thr Val
    130                 135                 140

Glu Asp Gly Pro Thr Lys Ser Asp Pro Arg Cys Leu Thr Arg Tyr Tyr
145                 150                 155                 160

Ser Ser Phe Ile Asn Leu Glu Arg Asp Leu Ala Ser Gly Leu Ile Gly
                165                 170                 175

Pro Leu Leu Ile Cys Tyr Lys Glu Ser Val Asp Gln Arg Gly Asn Gln
            180                 185                 190

Met Met Ser Asp Lys Arg Asn Val Ile Leu Phe Ser Val Phe Asp Glu
        195                 200                 205

Asn Arg Ser Trp Tyr Leu Thr Glu Asn Met Gln Arg Phe Leu Pro Asn
    210                 215                 220

Ala Ala Gly Val Gln Pro Gln Asp Pro Glu Phe Gln Ala Ser Asn Ile
225                 230                 235                 240

Met His Ser Ile Asn Gly Tyr Val Phe Asp Ser Leu Gln Leu Ser Val
                245                 250                 255
```

```
Cys Leu His Glu Val Ala Tyr Trp Tyr Ile Leu Ser Val Gly Ala Gln
            260                 265                 270

Thr Asp Phe Leu Ser Val Phe Phe Ser Gly Tyr Thr Phe Lys His Lys
        275                 280                 285

Met Val Tyr Glu Asp Thr Leu Thr Leu Phe Pro Phe Ser Gly Glu Thr
290                 295                 300

Val Phe Met Ser Met Glu Asn Pro Gly Leu Trp Val Leu Gly Cys His
305                 310                 315                 320

Asn Ser Asp Phe Arg Asn Arg Gly Met Thr Ala Leu Leu Lys Val Ser
                325                 330                 335

Ser Cys Asp Arg Asn Thr Gly Asp Tyr Tyr Glu Asp Thr Tyr Glu Asp
            340                 345                 350

Ile Pro Thr Tyr Leu Leu Ser Glu Asn Asn Val Ile Glu Pro Arg
                355                 360                 365

<210> SEQ ID NO 24
<211> LENGTH: 915
<212> TYPE: PRT
<213> ORGANISM: artificial sequence
<220> FEATURE:
<223> OTHER INFORMATION: ancestral

<400> SEQUENCE: 24

Ser Phe Ser Gln Asn Ser Arg His Pro Ser Thr Arg Gln Lys Gln Phe
1               5                   10                  15

Lys Ala Thr Thr Ile Pro Glu Asn Asp Ile Glu Lys Ile Asp Pro Gln
            20                  25                  30

Phe Gly Glu Arg Thr Gln Met Leu Lys Val Gln Ser Val Ser Ser Ser
        35                  40                  45

Asp Leu Leu Met Leu Leu Gly Gln Ser Pro Thr Pro His Gly Leu Ser
    50                  55                  60

Leu Ser Asp Leu Gln Glu Ala Thr Tyr Glu Ala Ile Pro Asp Asp His
65                  70                  75                  80

Ser Pro Gly Ala Ile Asp Ser Asn Glu Gly Pro Ser Glu Val Ala His
                85                  90                  95

Leu Arg Pro Glu Leu His His Ser Gly Asp Met Val Phe Thr Pro Glu
            100                 105                 110

Pro Gly Leu Gln Leu Arg Leu Asn Glu Asn Leu Gly Thr Thr Ile Ala
        115                 120                 125

Val Glu Leu Lys Lys Leu Asp Leu Lys Val Ser Ser Ser Ser Asn Asn
130                 135                 140

Leu Met Thr Ser Pro Thr Ile Pro Ser Asp Asn Leu Ala Ala Gly Thr
145                 150                 155                 160

Glu Lys Thr Gly Ser Leu Gly Pro Pro Asn Met Pro Val His Phe Ser
                165                 170                 175

Ser Gln Leu Gly Thr Thr Val Phe Gly Lys Lys Ser Ser Pro Leu Ile
            180                 185                 190

Gly Ser Gly Val Pro Leu Asn Leu Ser Glu Arg Asn Asn Asp Ser Lys
        195                 200                 205

Leu Leu Glu Ala Ala Leu Met Asn Ser Gln Glu Ser Ser Leu Gly Lys
    210                 215                 220

Asn Val Ser Ser Met Glu Ser Asp Arg Leu Phe Lys Glu Lys Arg Val
225                 230                 235                 240

His Gly Pro Ala Leu Leu Thr Lys Asp Asn Ala Leu Phe Lys Val Asn
                245                 250                 255
```

```
Ile Ser Leu Val Lys Thr Asn Lys Thr Ser Asn Asn Ser Thr Thr Asn
            260                 265                 270

Arg Lys Thr His Ile Asp Gly Pro Thr Leu Leu Ile Glu Asn Ser Thr
            275                 280                 285

Ser Val Trp Gln Asp Ile Ile Leu Glu Ser Asp Thr Glu Phe Gln Glu
            290                 295                 300

Val Thr Ser Leu Ile His Asp Glu Met Leu Met Asp Lys Asn Thr Thr
305                 310                 315                 320

Ala Leu Arg Leu Asn His Val Ser Asn Lys Thr Thr Ser Ser Lys Asn
            325                 330                 335

Met Glu Met Val His Gln Lys Lys Glu Gly Pro Val Pro Pro Asp Ala
            340                 345                 350

Glu Asn Pro Asp Met Ser Phe Phe Lys Met Leu Phe Leu Pro Glu Ser
            355                 360                 365

Ala Asn Trp Ile Lys Arg Thr His Gly Lys Asn Ser Leu Asn Ser Gly
            370                 375                 380

Gln Gly Pro Ser Pro Lys Gln Leu Ile Ser Leu Gly Ser Glu Lys Ser
385                 390                 395                 400

Val Lys Asp Gln Asn Phe Leu Ser Glu Lys Asn Lys Val Val Val Gly
            405                 410                 415

Glu Asp Glu Phe Thr Lys Asp Thr Gly Leu Lys Glu Met Ile Phe Pro
            420                 425                 430

Asn Ser Arg Ser Ile Phe Leu Thr Asn Leu Ala Asn Val Gln Glu Asn
            435                 440                 445

Asp Thr His Asn Gln Glu Lys Lys Phe Gln Glu Ile Glu Arg Lys
            450                 455                 460

Glu Thr Leu Ile Gln Glu Asn Val Val Leu Pro Gln Val Tyr Thr Val
465                 470                 475                 480

Thr Gly Thr Lys Asn Phe Leu Lys Asn Leu Phe Leu Leu Ser Thr Arg
            485                 490                 495

Gln Asn Val Glu Gly Leu Asp Glu Gly Thr Tyr Ala Pro Val Leu Gln
            500                 505                 510

Asp Thr Arg Ser Leu Asn Asp Ser Thr Asn Arg Ala Glu Ile His Met
            515                 520                 525

Ala His Phe Ser Lys Arg Arg Glu Glu Glu Asn Leu Glu Gly Leu Gly
            530                 535                 540

Asn Gln Thr Lys Gln Met Val Glu Lys Tyr Pro Ser Thr Thr Arg Met
545                 550                 555                 560

Ser Pro Asn Pro Ser Gln Gln Asn Val Ile Thr Gln Arg Gly Lys Arg
            565                 570                 575

Ala Leu Lys Gln Phe Arg Leu Pro Leu Glu Glu Thr Glu Leu Glu Lys
            580                 585                 590

Gly Leu Ile Val Asp Asp Thr Ser Thr Gln Trp Ser Lys Asn Met Lys
            595                 600                 605

Tyr Leu Thr Gln Ser Thr Leu Thr Gln Ile Asp Tyr Asn Glu Lys Glu
            610                 615                 620

Lys Lys Ala Ile Thr Gln Ser Pro Leu Ser Asp Cys Ser Met Arg Asn
625                 630                 635                 640

His Ser Ile Thr Gln Thr Asn Ser Ser Ala Leu Pro Ile Ala Lys Val
            645                 650                 655

Ser Ala Phe Pro Ser Ile Arg Pro Thr Asp Leu Thr Lys Ile Pro Ser
            660                 665                 670
```

```
Gln Asp Asn Ser Ser His Leu Leu Ala Ser Ala Tyr Ser Tyr Thr Phe
            675                 680                 685

Arg Glu Lys Ser Ser Gly Val Gln Glu Ser Ser His Phe Leu Gln Gly
690                 695                 700

Ala Lys Arg Asn Asn Leu Ser Leu Ala Ile Leu Thr Leu Glu Met Ile
705                 710                 715                 720

Arg Asn Gln Glu Lys Val Gly Ser Leu Gly Thr Ser Ala Thr Asn Ser
                725                 730                 735

Val Met Tyr Lys Lys Leu Glu Asn Thr Val Leu Leu Lys Pro Gly Leu
            740                 745                 750

Pro Glu Ala Ser Gly Lys Val Glu Leu Leu Pro Lys Val His Ile His
            755                 760                 765

Gln Glu Asp Leu Phe Pro Thr Glu Thr Ser Asn Gly Ser Pro Gly His
            770                 775                 780

Leu Asp Leu Met Glu Glu Ile Leu Leu Gln Lys Thr Gln Gly Ala Ile
785                 790                 795                 800

Lys Trp Asn Lys Thr Asn Arg Pro Gly Lys Val Pro Phe Leu Lys Gly
                805                 810                 815

Ala Thr Glu Ser Ser Glu Lys Thr Pro Ser Lys Leu Leu Gly Pro Leu
            820                 825                 830

Ala Trp Asp Asn Gln Tyr Ala Thr Gln Ile Pro Lys Glu Glu Trp Lys
            835                 840                 845

Ser Gln Glu Lys Ser Pro Lys Asn Thr Ala Phe Lys Thr Lys Asp Thr
850                 855                 860

Ile Leu Ser Leu Asn Pro Cys Glu Asn His Ala Ile Ala Ala Ile
865                 870                 875                 880

Asn Glu Gly Gln Asp Arg Pro Gln Arg Glu Ala Thr Trp Ala Lys Gln
                885                 890                 895

Gly Gly Thr Gly Arg Leu Cys Ser Gln Asn Pro Val Leu Lys Arg
            900                 905                 910

His Gln Arg
        915

<210> SEQ ID NO 25
<211> LENGTH: 41
<212> TYPE: PRT
<213> ORGANISM: artificial sequence
<220> FEATURE:
<223> OTHER INFORMATION: ancestral

<400> SEQUENCE: 25

Glu Ile Thr Leu Thr Thr Leu Gln Ser Glu Gln Glu Glu Ile Asp Tyr
1               5                   10                  15

Asp Asp Thr Ile Ser Ile Glu Thr Lys Arg Glu Asp Phe Asp Ile Tyr
            20                  25                  30

Gly Glu Asp Glu Asn Gln Gly Pro Arg
        35                  40

<210> SEQ ID NO 26
<211> LENGTH: 330
<212> TYPE: PRT
<213> ORGANISM: artificial sequence
<220> FEATURE:
<223> OTHER INFORMATION: ancestral

<400> SEQUENCE: 26

Ser Phe Gln Lys Arg Thr Arg His Tyr Phe Ile Ala Ala Val Glu Arg
1               5                   10                  15
```

```
Leu Trp Asp Tyr Gly Met Ser Arg Ser Pro His Val Leu Arg Asn Arg
            20                  25                  30

Ala Gln Ser Gly Ser Val Pro Gln Phe Lys Val Phe Gln Glu
        35                  40                  45

Phe Thr Asp Gly Ser Phe Thr Gln Pro Leu Tyr Arg Gly Glu Leu Asn
 50                  55                  60

Glu His Leu Gly Leu Leu Gly Pro Tyr Ile Arg Ala Glu Val Glu Asp
 65                  70                  75                  80

Asn Ile Met Val Thr Phe Lys Asn Gln Ala Ser Arg Pro Tyr Ser Phe
                 85                  90                  95

Tyr Ser Ser Leu Ile Ser Tyr Glu Glu Asp Gln Arg Gln Gly Ala Glu
                100                 105                 110

Pro Arg Lys Asn Phe Val Lys Pro Asn Glu Thr Lys Thr Tyr Phe Trp
            115                 120                 125

Lys Val Gln His His Met Ala Pro Thr Lys Asp Glu Phe Asp Cys Lys
130                 135                 140

Ala Trp Ala Tyr Phe Ser Asp Val Asp Leu Glu Lys Asp Met His Ser
145                 150                 155                 160

Gly Leu Ile Gly Pro Leu Leu Ile Cys His Thr Asn Thr Leu Asn Pro
                165                 170                 175

Ala His Gly Arg Gln Val Thr Val Gln Glu Phe Ala Leu Phe Phe Thr
            180                 185                 190

Ile Phe Asp Glu Thr Lys Ser Trp Tyr Phe Thr Glu Asn Met Glu Arg
        195                 200                 205

Asn Cys Arg Ala Pro Cys Asn Ile Gln Met Glu Asp Pro Thr Phe Lys
    210                 215                 220

Glu Asn Tyr Arg Phe His Ala Ile Asn Gly Tyr Val Met Asp Thr Leu
225                 230                 235                 240

Pro Gly Leu Val Met Ala Gln Asp Gln Arg Ile Arg Trp Tyr Leu Leu
                245                 250                 255

Ser Met Gly Ser Asn Glu Asn Ile His Ser Ile His Phe Ser Gly His
            260                 265                 270

Val Phe Thr Val Arg Lys Lys Glu Glu Tyr Lys Met Ala Val Tyr Asn
        275                 280                 285

Leu Tyr Pro Gly Val Phe Glu Thr Val Glu Met Leu Pro Ser Lys Ala
    290                 295                 300

Gly Ile Trp Arg Val Glu Cys Leu Ile Gly Glu His Leu His Ala Gly
305                 310                 315                 320

Met Ser Thr Leu Phe Leu Val Tyr Ser Lys
                325                 330

<210> SEQ ID NO 27
<211> LENGTH: 153
<212> TYPE: PRT
<213> ORGANISM: artificial sequence
<220> FEATURE:
<223> OTHER INFORMATION: ancestral

<400> SEQUENCE: 27

Gln Cys Gln Thr Pro Leu Gly Met Ala Ser Gly His Ile Arg Asp Phe
1               5                   10                  15

Gln Ile Thr Ala Ser Gly Gln Tyr Gly Gln Trp Ala Pro Lys Leu Ala
            20                  25                  30

Arg Leu His Tyr Ser Gly Ser Ile Asn Ala Trp Ser Thr Lys Glu Pro
        35                  40                  45
```

```
Phe Ser Trp Ile Lys Val Asp Leu Leu Ala Pro Met Ile His Gly
    50                  55                  60
Ile Lys Thr Gln Gly Ala Arg Gln Lys Phe Ser Leu Tyr Ile Ser
65                  70                  75                  80
Gln Phe Ile Ile Met Tyr Ser Leu Asp Gly Lys Lys Trp Gln Thr Tyr
                85                  90                  95
Arg Gly Asn Ser Thr Gly Thr Leu Met Val Phe Phe Gly Asn Val Asp
                100                 105                 110
Ser Ser Gly Ile Lys His Asn Ile Phe Asn Pro Pro Ile Ile Ala Arg
        115                 120                 125
Tyr Ile Arg Leu His Pro Thr His Tyr Ser Ile Arg Ser Thr Leu Arg
130                 135                 140
Met Glu Leu Met Gly Cys Asp Leu Asn
145                 150
```

<210> SEQ ID NO 28
<211> LENGTH: 160
<212> TYPE: PRT
<213> ORGANISM: artificial sequence
<220> FEATURE:
<223> OTHER INFORMATION: ancestral

<400> SEQUENCE: 28

```
Ser Cys Ser Met Pro Leu Gly Met Glu Ser Lys Ala Ile Ser Asp Ala
1               5                   10                  15
Gln Ile Thr Ala Ser Ser Tyr Phe Thr Asn Met Phe Ala Thr Trp Ser
                20                  25                  30
Pro Ser Gln Ala Arg Leu His Leu Gln Gly Arg Thr Asn Ala Trp Arg
            35                  40                  45
Pro Gln Val Asn Asn Pro Lys Glu Trp Leu Gln Val Asp Phe Gln Lys
        50                  55                  60
Thr Met Lys Val Thr Gly Ile Thr Thr Gln Gly Val Lys Ser Leu Leu
65                  70                  75                  80
Thr Ser Met Tyr Val Lys Glu Phe Leu Ile Ser Ser Ser Gln Asp Gly
                85                  90                  95
His His Trp Thr Leu Phe Leu Gln Asn Gly Lys Val Lys Val Phe Gln
                100                 105                 110
Gly Asn Gln Asp Ser Phe Thr Pro Val Val Asn Ser Leu Asp Pro Pro
            115                 120                 125
Leu Leu Thr Arg Tyr Leu Arg Ile His Pro Gln Ser Trp Val His Gln
        130                 135                 140
Ile Ala Leu Arg Leu Glu Val Leu Gly Cys Glu Ala Gln Gln Leu Tyr
145                 150                 155                 160
```

<210> SEQ ID NO 29
<211> LENGTH: 2360
<212> TYPE: PRT
<213> ORGANISM: artificial sequence
<220> FEATURE:
<223> OTHER INFORMATION: ancestral

<400> SEQUENCE: 29

```
Met Arg Ile Glu Leu Pro Cys Cys Phe Phe Leu Cys Leu Leu Pro Phe
1               5                   10                  15
Ser Phe Gly Ala Thr Arg Arg Tyr Tyr Leu Gly Ala Val Glu Leu Ser
                20                  25                  30
Trp Asp Tyr Val His Ser Asp Leu Leu Ser Val Leu His Val Pro Thr
```

-continued

```
                35                  40                  45
Gly Phe Pro Gly Arg Val Gly Arg Lys Phe Pro Phe Ser Thr Ser Val
 50                  55                  60
Arg Tyr Lys Lys Thr Val Phe Val Glu Phe Thr Asp His Leu Phe Thr
 65                  70                  75                  80
Ile Ala Lys Pro Arg Pro Pro Trp Met Gly Leu Leu Gly Pro Thr Ile
                 85                  90                  95
Arg Ala Glu Val Tyr Asp Thr Val Val Thr Leu Lys Asn Leu Ala
                100                 105                 110
Ser His Pro Phe Ser Leu His Ala Val Gly Val Thr Tyr Trp Lys Ala
            115                 120                 125
Ser Glu Gly Ala Gly Tyr Asp Asp Glu Thr Ser Gln Arg Glu Lys Glu
        130                 135                 140
Asp Lys Val Asp Pro Gly Lys Thr His Thr Tyr Val Trp Glu Val
145                 150                 155                 160
Leu Lys Asp Asn Gly Pro Thr Ala Ser Asp Pro Pro Cys Leu Thr Tyr
                165                 170                 175
Ser Tyr Leu Ser Tyr Val Asp Leu Val Lys Asp Leu Asn Ser Gly Leu
            180                 185                 190
Ile Gly Ala Leu Leu Val Cys Arg Pro Gly Ala Leu Ala Lys Asp Gly
        195                 200                 205
Thr Gln Thr Leu His Glu Phe Val Leu Leu Phe Ala Val Phe Asp Glu
210                 215                 220
Gly Lys Ser Trp Tyr Pro Glu Pro Asn Glu Ser Leu Thr Gln Ala Leu
225                 230                 235                 240
Asp Thr Gly Thr Pro Arg Pro Trp Pro Lys Leu His Thr Val Asn Gly
                245                 250                 255
Tyr Val Asn Gly Ser Leu Pro Gly Leu Ile Gly Cys His Lys Arg Pro
            260                 265                 270
Val Tyr Trp His Val Ile Gly Leu Gly Thr Thr Pro Glu Val His Ser
        275                 280                 285
Ile Phe Leu Glu Gly His Thr Phe Leu Val Arg Asn His Arg His Ala
290                 295                 300
Thr Leu Glu Ile Ser Pro Ile Thr Phe Leu Thr Ala Gln Thr Leu Leu
305                 310                 315                 320
Thr Asp Leu Gly Arg Phe Leu Leu Phe Cys His Ile Pro Ala His Gln
                325                 330                 335
His Asp Gly Met Glu Ala Tyr Val Lys Val Asp Val Cys Pro Glu Glu
            340                 345                 350
Pro Lys Leu Arg Met Arg Ala Asp Ala Pro Glu Glu Asp Tyr Tyr Asp
        355                 360                 365
Asp Leu Tyr Asp Leu Asp Met Asp Val Ile Arg Phe Asp Asp Asp
370                 375                 380
Ser Pro Pro Phe Ile Gly Val Arg Ala Phe Ala Lys Lys His Pro Lys
385                 390                 395                 400
Thr Trp Ile His Tyr Ile Ala Ala Glu Glu Val Asp Trp Asp Tyr Ala
                405                 410                 415
Pro Ile Val Pro Thr Tyr Leu Asp Arg Ser Tyr Lys Ser Gln Tyr Leu
            420                 425                 430
Glu Ala Gly Pro Gln Arg Ile Gly Arg Lys Tyr Lys Lys Val Arg Phe
        435                 440                 445
Val Ala Tyr Thr Asp Gly Thr Phe Lys Thr Arg Lys Val Ile Gln Tyr
450                 455                 460
```

-continued

```
Asp Thr Gly Ile Leu Gly Pro Leu Leu Tyr Gly Glu Val Gly Asp Thr
465                 470                 475                 480

Leu Leu Ile Val Phe Lys Asn Leu Ala Ser Arg Pro Tyr Asn Ile Tyr
                485                 490                 495

Pro His Gly Leu Thr Ser Val Ser Pro Leu His Pro Gly Arg Leu Pro
            500                 505                 510

Lys Gly Val Lys His Leu Lys Asp Leu Pro Ile Leu Pro Gly Glu Ile
            515                 520                 525

Phe Lys Tyr Lys Trp Thr Val Thr Val Glu Asp Gly Pro Thr Gly Ser
530                 535                 540

Asp Pro Arg Cys Leu Thr Arg Tyr Tyr Ser Phe Ile Asn Pro Val
545                 550                 555                 560

Arg Asp Leu Ala Ser Gly Leu Ile Gly Pro Leu Leu Ile Cys Tyr Lys
                565                 570                 575

Glu Ser Val Asp Gln Arg Gly Asn Gln Met Met Ser Asp Lys Arg Arg
            580                 585                 590

Phe Ile Leu Phe Ser Val Phe Asp Glu Asn Arg Ser Trp Tyr Leu Thr
            595                 600                 605

Glu Asn Ile Gln Arg Phe Cys Pro Asp Ala Ala Gly Val Gln Pro Gln
610                 615                 620

Asp Pro Glu Phe Tyr Ala Ser Asn Val Met His Ser Ile Asn Gly Tyr
625                 630                 635                 640

Val Phe Asp Asn Leu His Leu Lys Leu Cys Leu His Glu Val Ala Tyr
                645                 650                 655

Trp Tyr Val Leu Ser Val Gly Ala Gln Thr Asp Phe Leu Ser Val Phe
            660                 665                 670

Phe Ser Gly Tyr Thr Phe Lys His Lys Met Val Phe Glu Asp Thr Leu
            675                 680                 685

Thr Leu Phe Pro Phe Ser Gly Glu Thr Val Phe Met Ser Met Glu Lys
690                 695                 700

Pro Gly Leu Trp Val Leu Gly Cys Leu Asn Pro Asp Phe Arg Asp Arg
705                 710                 715                 720

Gly Met Trp Ala Leu Leu Lys Val Ser Ser Cys Asp Arg Asp Pro Gly
                725                 730                 735

Leu Tyr Tyr Gly Asp Asp Tyr Asp Leu Ile Pro Thr Tyr Leu Leu Asn
            740                 745                 750

Glu Asn Asn Val Leu Glu Pro Arg Gly Phe Pro Lys Asn Lys Arg Trp
            755                 760                 765

Pro Arg Leu Cys Leu Arg Lys Phe Lys Ala Val Thr Ser Pro Glu Lys
770                 775                 780

Asp Ile Glu Lys Leu Asp Pro Gln Phe Gly Glu Arg Thr Gln Cys Leu
785                 790                 795                 800

Arg Ala Gln Pro Leu Lys Phe Ser Asp Leu Leu Met Leu Leu Gly Gln
                805                 810                 815

Asn Pro Asp Pro His Gly Leu Ser Leu Ser Asp Leu Thr Glu Ala Thr
            820                 825                 830

Tyr Glu Pro Ile Pro Tyr Asp Ser Phe Pro Gly Pro Val Gly Asn Ser
            835                 840                 845

Thr Gly Pro Ser Glu Val Val His Leu Arg Pro Glu Leu His His Ala
850                 855                 860

Gly Asp Ala Gly Phe Tyr Pro Glu Gly Gly Leu Leu Leu Phe Gly Lys
865                 870                 875                 880
```

```
Glu Arg Leu Gly Pro Thr Val Ala Val Glu Leu Lys Lys Leu Asp Leu
                885                 890                 895
Lys Leu His Lys Ser Val Asp Asn Val Met Phe Ser Pro Thr Ala Pro
        900                 905                 910
Leu Asp Asn Leu Glu Lys Gly Leu Lys Gly Thr Gly Thr Leu Gly Pro
            915                 920                 925
Leu Lys Glu Pro Val Arg Phe Ser Gly His Leu Gly Pro Thr Val Phe
930                 935                 940
Gly Lys Lys Glu Thr Gly Leu Ile Gly Ser Gly Val Pro Leu Gln Leu
945                 950                 955                 960
Ser Asp Arg Asp His Asp Ser Arg Leu Leu Glu Arg Val Leu Leu Asn
                965                 970                 975
Asp Glu Glu Ser Pro Leu Gly Leu Asn Val Thr Ser Leu Lys Pro Asp
            980                 985                 990
Arg Pro Phe Lys Asp Lys Arg Val His Gly Pro Ala Ser Leu Thr Lys
        995                 1000                1005
Asp Asn Ala Leu Phe Lys Gly Asn Ile Thr Leu Val Lys Leu Asp
    1010                1015                1020
Lys Thr Pro Asp Asn Thr Thr Asn Arg Lys Thr Tyr Val Asp
    1025                1030                1035
Gly Pro Ala Leu Leu Lys Glu Asn Gly Thr Pro Val Trp Leu Asp
    1040                1045                1050
Ile Leu Glu Asn Asp Thr Arg Phe Gln Glu Val Ala Ser Leu Gly
    1055                1060                1065
Phe Tyr Glu Thr Phe Gln Asp Gly Lys Leu Thr Ala Pro Gly Leu
    1070                1075                1080
Asp His Val Leu Asn Lys Thr Ser Ser Lys Asn Gly Glu Val
    1085                1090                1095
Phe Phe Glu Lys Lys Val Glu Pro Val Pro Leu Asp Ala Glu Arg
    1100                1105                1110
Pro Pro Ala Pro Phe Lys Asp Leu Phe Leu Pro Arg Thr Ala
    1115                1120                1125
Asn Trp Leu Leu Asp Thr His Gly Lys Ala Asp Leu Arg Ala Gly
    1130                1135                1140
Gln Gly Pro Ser Pro Lys Gln Leu Ile Ser Leu Gly Ser Asp Lys
    1145                1150                1155
Ser Gly Asp Gly Glu His Phe Leu Ser Ala Lys Ser Lys Val Arg
    1160                1165                1170
Leu Gly Pro Asp Lys Phe Thr Lys Gly Thr Gly Leu Leu Glu Met
    1175                1180                1185
Ile Phe Pro Gly Arg Lys Asp Ile Phe Leu Thr Ser Leu Val Thr
    1190                1195                1200
Val Gln Glu Asn Asp Thr Leu Ile Leu Gly Lys Lys Phe Gln Glu
    1205                1210                1215
Ala Ile Glu Arg Lys Glu Thr Leu Ile Gln Glu Asn Val Asp Leu
    1220                1225                1230
Pro Lys Leu Tyr Val Val Ala Gly Thr Arg Asn Phe Leu Lys Asp
    1235                1240                1245
Leu Phe Leu Leu His Thr Arg Thr Asn Leu Thr Leu Asp Gly Pro
    1250                1255                1260
Asp Glu Gly Asp Tyr Ala Pro Leu Leu Gln Asp Thr Arg Tyr Leu
    1265                1270                1275
Asn Gly Lys Val Pro Pro Ala Gly Val His Leu Val His Gly Ser
```

-continued

```
            1280                1285                1290

Lys Leu Leu Glu Ala Ala Asp Leu Glu Gly Leu His Lys Thr
        1295                1300                1305

Lys Arg Met Val Leu Asp Tyr Pro Ser Thr Thr Arg Thr Ala Pro
        1310                1315                1320

Lys Pro Cys Asp Gln Asn Cys Ile Thr His Arg Gly Lys Arg Ala
        1325                1330                1335

Leu Lys Gln Phe Gly Leu Pro Leu Glu Glu Thr Glu Leu Glu Arg
        1340                1345                1350

Gly Leu Val Asp Lys Asp Arg Ala Leu Lys Gly Arg Lys Asn Met
        1355                1360                1365

Gly Tyr Leu Thr Gly Gly Thr Leu Thr Lys Ile Asp Tyr Asn Asp
        1370                1375                1380

Arg Ala Lys Arg Leu Val Ala Arg Pro Pro Leu Val Asp Cys Thr
        1385                1390                1395

Ala Arg Asp His Gly Val Thr Gly Thr Asp Gly Pro Ala Gly Pro
        1400                1405                1410

Ile Arg Gly Val Ser Ala Phe Pro Pro Ile Arg Pro Thr Asp Leu
        1415                1420                1425

Thr Lys Leu Pro Ser His Asp Asn Ser Ser His Leu Pro Ala Ala
        1430                1435                1440

Ala Cys Gly Tyr Thr Phe Arg Glu Lys Ser Ser Gly Val Arg Gly
        1445                1450                1455

Gly Ser His Phe Leu Gln Gly Ala Lys Arg Thr Ser Leu Thr Ser
        1460                1465                1470

Ala Tyr Leu Thr Leu Lys Thr Ile Arg Gly Glu Glu Lys Val Ser
        1475                1480                1485

Ser Leu Gly Thr Ser Ala Asp Thr Pro Pro Thr Tyr Lys Lys Leu
        1490                1495                1500

Glu Asn Thr Val Leu Leu Lys Pro Gly Leu Pro Glu Val Val Gly
        1505                1510                1515

Lys Val Glu Gly Leu Pro Lys Pro His Val Trp Glu Ala Asp Leu
        1520                1525                1530

Phe Pro Thr Pro Thr Gly Asn Gly Thr Pro Gly His Leu Asp Leu
        1535                1540                1545

Lys Glu Glu Trp Leu Leu Gln Lys Leu Gln Gly Ala Ile Lys Leu
        1550                1555                1560

Ser Lys Val Lys Arg Pro Gly Asp Phe Pro Phe Leu Lys Gly Ala
        1565                1570                1575

Thr Glu Ile Leu Glu Lys Arg Pro Ser Lys Leu Leu Gly Pro Leu
        1580                1585                1590

Pro Trp Asp Gly Gln Tyr Leu Thr Gln Ile Leu Arg Asp Glu Trp
        1595                1600                1605

Lys Leu Lys His Lys Ser Pro Lys Asn Thr Val Phe Lys Thr Lys
        1610                1615                1620

Asp Ala Ile Leu Pro Leu Ser Gly Cys Glu Asn Val His Gly Val
        1625                1630                1635

Asp Gly Ile Asn Glu Gly Arg Asp Arg Leu Gln Lys Ala Ala Thr
        1640                1645                1650

Trp Ala Lys Gln Gly Gly Thr Glu Arg Leu Cys Ser Arg Glu Pro
        1655                1660                1665

Pro Val Leu Lys Asn His Lys Arg Glu Ile Thr Leu Thr Thr Leu
        1670                1675                1680
```

```
Gln Pro Glu Lys Glu Lys Ile Asp Tyr Asp Asp Tyr Leu Lys Pro
    1685            1690                1695

Glu Thr Asp Arg Asp Asp Phe Asp Ile Tyr Gly Glu Asp Glu Asn
    1700            1705                1710

Gln Gly Pro Arg Thr Phe Thr Gly Arg Thr Arg His Tyr Phe Ile
    1715            1720                1725

Ala Ala Val Glu Arg Leu Trp Asp Tyr Gly Met Ser Arg Pro Pro
    1730            1735                1740

His Phe Leu Arg Asn Arg Ala Arg Gly Gly Arg Val Pro Phe Phe
    1745            1750                1755

Lys Lys Val Val Phe Arg Gly Phe Leu Asp Gly Ser Phe Thr Gln
    1760            1765                1770

Pro Leu Tyr Arg Gly Glu Leu Asp Glu His Leu Gly Leu Leu Gly
    1775            1780                1785

Pro Tyr Ile Arg Ala Glu Val Asp Val Ile Met Val Thr Phe
    1790            1795                1800

Lys Asn Leu Ala Ser Arg Pro Tyr Ser Phe Tyr Ser Ser Leu Leu
    1805            1810                1815

Pro Tyr Glu Gly Gly Leu Gly Gln Gly Ser Glu Pro Arg Lys Glu
    1820            1825                1830

Val Val Lys Pro Gly Glu Leu Arg Thr Tyr Phe Trp Lys Val Leu
    1835            1840                1845

Pro His Met Ala Pro Thr Val Asp Glu Phe Asp Cys Lys Ala Trp
    1850            1855                1860

Ala Tyr Phe Ser Asp Val Asp Leu Glu Lys Asp Leu His Ser Gly
    1865            1870                1875

Leu Val Gly Pro Leu Leu Ile Cys Arg Pro Gly Thr Leu Ser Pro
    1880            1885                1890

Ala Phe Gly Arg Gln Leu Thr Val Gln Glu Phe Ala Leu Leu Phe
    1895            1900                1905

Thr Ile Phe Asp Glu Thr Lys Ser Trp Tyr Phe Thr Glu Asn Met
    1910            1915                1920

Glu Arg Asn Cys Pro Pro Cys Gln Ile Gln Pro Asp Asp Pro
    1925            1930                1935

Asp Phe Arg Arg Ser Tyr Arg Phe His Ala Ile Asn Gly Tyr Val
    1940            1945                1950

Met Asp Thr Leu Pro Gly Leu Val Met Ala Gln Asp Gln Arg Val
    1955            1960                1965

Arg Trp Tyr Leu Leu Ser Val Gly Gly Thr Glu Asp Ile His Ser
    1970            1975                1980

Val Tyr Phe His Gly His Val Phe Thr Val Arg Lys Lys His Glu
    1985            1990                1995

Tyr Arg Met Gly Val Tyr Asn Leu Tyr Pro Gly Val Phe Gly Thr
    2000            2005                2010

Val Glu Met Leu Pro Ser Lys Pro Gly Ile Trp Arg Val Glu Cys
    2015            2020                2025

Leu Val Gly Glu His Leu Gln Ala Gly Met Ser Thr Leu Phe Leu
    2030            2035                2040

Val Tyr Asp Pro Lys Cys Gln Thr Pro Leu Gly Leu Ala Ser Gly
    2045            2050                2055

His Ile Arg Asp Ala Gln Ile Thr Ala Ser Gly Gln Tyr Gly Gln
    2060            2065                2070
```

```
Trp Ala Pro Arg Leu Ala Arg Leu His Tyr Ser Gly Ser Val Asn
    2075                2080                2085

Ala Trp Ser Thr Lys Asp Pro Phe Ser Trp Ile Lys Val Asp Leu
    2090                2095                2100

Leu Arg Pro Met Ile Leu His Gly Ile Lys Thr Gln Gly Ala Arg
    2105                2110                2115

Gln Lys Phe Ser Ser Leu Tyr Ile Ser Gln Phe Ile Ile Phe Tyr
    2120                2125                2130

Gly Leu Asp Gly Lys Arg Trp Lys Arg Tyr Arg Gly Asn Ala Thr
    2135                2140                2145

Gly Thr Leu Met Val Phe Phe Gly Asn Val Asp Ala Thr Gly Val
    2150                2155                2160

Lys His Asn Arg Phe Asn Pro Pro Ile Ile Ala Arg Tyr Ile Arg
    2165                2170                2175

Leu His Pro Thr His Tyr Ser Ile Arg Thr Thr Leu Arg Met Glu
    2180                2185                2190

Leu Ile Gly Cys Asp Leu Asn Ser Cys Ser Met Pro Leu Gly Met
    2195                2200                2205

Glu Asn Lys Ala Ile Ser Asp Ala Gln Ile Thr Ala Ser Ser Tyr
    2210                2215                2220

Phe Thr Asn Met Phe Ala Thr Trp Ala Pro Ser Gln Ala Arg Leu
    2225                2230                2235

His Leu Gln Gly Arg Thr Asn Ala Trp Arg Pro Lys Val Asn Ser
    2240                2245                2250

Pro Lys Glu Trp Leu Gln Val Asp Phe Glu Lys Thr Met Arg Val
    2255                2260                2265

Thr Gly Ile Val Thr Gln Gly Ala Lys Ser Leu Leu Thr Ser Met
    2270                2275                2280

Tyr Val Lys Glu Phe Leu Val Ser Ser Ser Gln Asp Gly His Arg
    2285                2290                2295

Trp Thr Pro Phe Leu Gln Asp Gly Lys Val Lys Val Phe Lys Gly
    2300                2305                2310

Asn Gln Asp His Phe Thr Pro Val Val Asn Ser Leu Asp Pro Pro
    2315                2320                2325

Leu Leu Thr Arg Tyr Leu Arg Ile His Pro Arg Arg Trp Val His
    2330                2335                2340

His Ile Ala Leu Arg Leu Glu Phe Leu Gly Cys Asp Ala Gln Gln
    2345                2350                2355

Leu Tyr
    2360

<210> SEQ ID NO 30
<211> LENGTH: 2362
<212> TYPE: PRT
<213> ORGANISM: artificial sequence
<220> FEATURE:
<223> OTHER INFORMATION: ancestral

<400> SEQUENCE: 30

Met Gln Ile Glu Leu Ser Thr Cys Phe Phe Leu Cys Leu Leu Pro Phe
1               5                   10                  15

Ser Phe Ser Ala Thr Arg Arg Tyr Tyr Leu Gly Ala Val Glu Leu Ser
                20                  25                  30

Trp Asp Tyr Met Gln Ser Asp Leu Leu Ser Glu Leu His Val Asp Thr
            35                  40                  45
```

```
Arg Phe Pro Pro Arg Val Pro Arg Ser Phe Pro Phe Asn Thr Ser Val
    50                  55                  60

Met Tyr Lys Lys Thr Val Phe Val Glu Phe Thr Asp His Leu Phe Asn
 65                  70                  75                  80

Ile Ala Lys Pro Arg Pro Pro Trp Met Gly Leu Leu Gly Pro Thr Ile
                 85                  90                  95

Arg Ala Glu Val Tyr Asp Thr Val Val Ile Thr Leu Lys Asn Met Ala
                100                 105                 110

Ser His Pro Val Ser Leu His Ala Val Gly Val Ser Tyr Trp Lys Ala
            115                 120                 125

Ser Glu Gly Ala Glu Tyr Asp Asp Gln Thr Ser Gln Arg Glu Lys Glu
130                 135                 140

Asp Asp Lys Val Ile Pro Gly Glu Ser His Thr Tyr Val Trp Gln Val
145                 150                 155                 160

Leu Lys Glu Asn Gly Pro Met Ala Ser Asp Pro Pro Cys Leu Thr Tyr
                165                 170                 175

Ser Tyr Leu Ser His Val Asp Leu Val Lys Asp Leu Asn Ser Gly Leu
            180                 185                 190

Ile Gly Ala Leu Leu Val Cys Arg Glu Gly Ser Leu Ala Lys Glu Arg
            195                 200                 205

Thr Gln Thr Leu His Glu Phe Val Leu Leu Phe Ala Val Phe Asp Glu
            210                 215                 220

Gly Lys Ser Trp His Ser Glu Thr Asn Glu Ser Leu Thr Gln Ala Met
225                 230                 235                 240

Asp Ser Ala Ser Ala Arg Ala Trp Pro Lys Met His Thr Val Asn Gly
                245                 250                 255

Tyr Val Asn Arg Ser Leu Pro Gly Leu Ile Gly Cys His Arg Lys Ser
            260                 265                 270

Val Tyr Trp His Val Ile Gly Met Gly Thr Thr Pro Glu Val His Ser
            275                 280                 285

Ile Phe Leu Glu Gly His Thr Phe Leu Val Arg Asn His Arg Gln Ala
            290                 295                 300

Ser Leu Glu Ile Ser Pro Ile Thr Phe Leu Thr Ala Gln Thr Leu Leu
305                 310                 315                 320

Met Asp Leu Gly Gln Phe Leu Leu Phe Cys His Ile Ser Ser His Gln
                325                 330                 335

His Asp Gly Met Glu Ala Tyr Val Lys Val Asp Ser Cys Pro Glu Glu
                340                 345                 350

Pro Gln Leu Arg Met Lys Asn Asn Glu Glu Glu Asp Tyr Asp Asp
            355                 360                 365

Asp Leu Tyr Asp Ser Asp Met Asp Val Val Arg Phe Asp Asp Asp Asn
            370                 375                 380

Ser Pro Pro Phe Ile Gln Ile Arg Ser Val Ala Lys Lys His Pro Lys
385                 390                 395                 400

Thr Trp Val His Tyr Ile Ala Ala Glu Glu Asp Trp Asp Tyr Ala
                405                 410                 415

Pro Ser Val Leu Thr Pro Asn Asp Arg Ser Tyr Lys Ser Gln Tyr Leu
            420                 425                 430

Asn Asn Gly Pro Gln Arg Ile Gly Arg Lys Tyr Lys Lys Val Arg Phe
            435                 440                 445

Met Ala Tyr Thr Asp Glu Thr Phe Lys Thr Arg Glu Ala Ile Gln Tyr
450                 455                 460

Glu Ser Gly Ile Leu Gly Pro Leu Leu Tyr Gly Glu Val Gly Asp Thr
```

```
                465                 470                 475                 480
Leu Leu Ile Ile Phe Lys Asn Gln Ala Ser Arg Pro Tyr Asn Ile Tyr
                    485                 490                 495

Pro His Gly Ile Thr Asp Val Ser Pro Leu His Ser Gly Arg Leu Pro
                    500                 505                 510

Lys Gly Val Lys His Leu Lys Asp Leu Pro Ile Leu Pro Gly Glu Ile
                    515                 520                 525

Phe Lys Tyr Lys Trp Thr Val Thr Val Glu Asp Gly Pro Thr Lys Ser
530                 535                 540

Asp Pro Arg Cys Leu Thr Arg Tyr Tyr Ser Ser Phe Ile Asn Leu Glu
545                 550                 555                 560

Arg Asp Leu Ala Ser Gly Leu Ile Gly Pro Leu Leu Ile Cys Tyr Lys
                    565                 570                 575

Glu Ser Val Asp Gln Arg Gly Asn Gln Met Met Ser Asp Lys Arg Asn
                    580                 585                 590

Val Ile Leu Phe Ser Val Phe Asp Glu Asn Arg Ser Trp Tyr Leu Thr
                    595                 600                 605

Glu Asn Met Gln Arg Phe Leu Pro Asn Ala Ala Gly Val Gln Pro Gln
                    610                 615                 620

Asp Pro Glu Phe Gln Ala Ser Asn Ile Met His Ser Ile Asn Gly Tyr
625                 630                 635                 640

Val Phe Asp Ser Leu Gln Leu Ser Val Cys Leu His Glu Val Ala Tyr
                    645                 650                 655

Trp Tyr Ile Leu Ser Val Gly Ala Gln Thr Asp Phe Leu Ser Val Phe
                    660                 665                 670

Phe Ser Gly Tyr Thr Phe Lys His Lys Met Val Tyr Glu Asp Thr Leu
                    675                 680                 685

Thr Leu Phe Pro Phe Ser Gly Glu Thr Val Phe Met Ser Met Glu Asn
                    690                 695                 700

Pro Gly Leu Trp Val Leu Gly Cys His Asn Ser Asp Phe Arg Asn Arg
705                 710                 715                 720

Gly Met Thr Ala Leu Leu Lys Val Ser Ser Cys Asp Arg Asn Thr Gly
                    725                 730                 735

Asp Tyr Tyr Glu Asp Thr Tyr Glu Asp Ile Pro Thr Tyr Leu Leu Asn
                    740                 745                 750

Glu Asn Asn Val Ile Glu Pro Arg Ser Phe Ser Gln Asn Ser Arg His
                    755                 760                 765

Pro Ser Thr Arg Gln Lys Gln Phe Lys Ala Thr Thr Thr Pro Glu Asn
770                 775                 780

Asp Ile Glu Lys Ile Asp Pro Gln Phe Gly Glu Arg Thr Gln Leu Leu
785                 790                 795                 800

Lys Val Gln Ser Val Ser Ser Ser Asp Leu Leu Met Leu Leu Gly Gln
                    805                 810                 815

Ser Pro Thr Pro His Gly Leu Ser Leu Ser Asp Leu Gln Glu Ala Thr
                    820                 825                 830

Tyr Glu Ala Ile Pro Asp Asp His Ser Pro Gly Ala Ile Glu Ser Asn
                    835                 840                 845

Glu Gly Pro Ser Glu Val Ala His Leu Arg Pro Glu Leu His His Ser
                    850                 855                 860

Gly Asp Met Val Phe Thr Pro Glu Pro Gly Leu Gln Leu Arg Leu Asn
865                 870                 875                 880

Glu Asn Leu Gly Thr Thr Ile Thr Val Glu Leu Lys Lys Leu Asp Leu
                    885                 890                 895
```

```
Lys Val Ser Ser Ser Asn Leu Met Thr Ser Pro Thr Ile Pro
         900                 905                 910

Ser Asp Asn Leu Ala Ala Gly Thr Glu Lys Thr Gly Ser Leu Gly Pro
         915                 920                 925

Pro Asn Met Pro Val His Phe Ser Ser Gln Leu Gly Thr Ile Val Phe
         930                 935                 940

Gly Lys Lys Ser Ser Pro Leu Ile Gly Ser Gly Val Pro Leu Asn Leu
945                 950                 955                 960

Ser Glu Arg Asp Asn Asp Ser Lys Leu Leu Glu Ala Ala Leu Met Asn
         965                 970                 975

Ser Gln Glu Ser Ser Leu Gly Lys Asn Val Ser Met Glu Ser Asp
         980                 985                 990

Arg Leu Phe Lys Glu Lys Arg Val  His Gly Pro Ala Ser  Leu Thr Lys
         995                1000                1005

Asp Asn  Ala Leu Phe Lys Val  Asn Ile Ser Leu Val  Lys Thr Asn
        1010                1015                1020

Lys Thr  Pro Asn Asn Ser Thr  Thr Asn Arg Lys Thr  His Ile Asp
        1025                1030                1035

Gly Pro  Thr Leu Leu Ile Glu  Asn Ser Thr Ser Val  Trp Gln Asp
        1040                1045                1050

Ile Leu  Glu Asn Asp Thr Glu  Phe Gln Glu Val Thr  Ser Leu Ile
        1055                1060                1065

His Asp  Glu Met Phe Met Asp  Lys Asn Thr Thr Ala  Leu Gly Leu
        1070                1075                1080

Asn His  Val Ser Asn Lys Thr  Thr Ser Ser Lys Asn  Met Glu Met
        1085                1090                1095

Val His  Gln Lys Lys Glu Gly  Pro Val Pro Leu Asp  Ala Glu Asn
        1100                1105                1110

Pro Asp  Met Ser Phe Phe Lys  Met Leu Phe Leu Pro  Asp Ser Ala
        1115                1120                1125

Asn Trp  Ile Lys Arg Thr His  Gly Lys Asn Ser Leu  Ser Ser Gly
        1130                1135                1140

Gln Gly  Pro Ser Pro Lys Gln  Leu Ile Ser Leu Gly  Ser Glu Lys
        1145                1150                1155

Ser Val  Lys Asp Gln Asn Phe  Leu Ser Glu Lys Asn  Lys Val Val
        1160                1165                1170

Val Gly  Glu Asp Glu Phe Thr  Lys Asp Thr Gly Leu  Lys Glu Met
        1175                1180                1185

Ile Phe  Pro Asn Ser Lys Ser  Ile Phe Leu Thr Asn  Leu Ala Asn
        1190                1195                1200

Val Gln  Glu Asn Asp Thr His  Asn Gln Glu Lys Lys  Phe Gln Glu
        1205                1210                1215

Glu Ile  Glu Arg Lys Glu Thr  Leu Ile Gln Glu Asn  Val Val Leu
        1220                1225                1230

Pro Gln  Val Tyr Thr Val Thr  Gly Thr Lys Asn Phe  Leu Lys Asn
        1235                1240                1245

Leu Phe  Leu Leu Ser Thr Arg  Gln Asn Val Thr Val  Glu Gly Leu
        1250                1255                1260

Asp Glu  Gly Thr Tyr Ala Pro  Val Leu Gln Asp Thr  Arg Ser Leu
        1265                1270                1275

Asn Asp  Ser Ala Asn Arg Ala  Gly Ile His Met Ala  His Phe Ser
        1280                1285                1290
```

```
Lys Arg Arg Glu Glu Ala Glu Thr Asn Leu Glu Gly Leu Gly Asn
    1295                1300                1305

Gln Thr Lys Gln Met Val Glu Lys Tyr Pro Ser Thr Thr Arg Met
    1310                1315                1320

Ser Pro Asn Pro Ser Gln Gln Asn Val Ile Thr Gln Arg Gly Lys
    1325                1330                1335

Arg Ala Leu Lys Gln Phe Arg Leu Pro Leu Glu Glu Ile Glu Leu
    1340                1345                1350

Glu Arg Gly Leu Ile Val Asn Asp Thr Ser Thr Gln Trp Ser Lys
    1355                1360                1365

Asn Met Lys Tyr Leu Thr Gln Gly Thr Leu Thr Gln Ile Asp Tyr
    1370                1375                1380

Asn Glu Lys Glu Lys Arg Ala Ile Thr Gln Ser Pro Leu Ser Asp
    1385                1390                1395

Cys Ser Met Arg Asn His Ser Ile Thr Gln Thr Asn Gly Ser Ala
    1400                1405                1410

Leu Pro Ile Ala Lys Val Ser Ala Phe Pro Ser Ile Arg Pro Thr
    1415                1420                1425

Asp Leu Thr Lys Ile Pro Ser Gln Asp Asn Ser Ser His Leu Leu
    1430                1435                1440

Ala Ser Ala Cys Ser Tyr Thr Phe Arg Glu Lys Ser Ser Gly Val
    1445                1450                1455

Gln Glu Ser Ser His Phe Leu Gln Gly Ala Lys Arg Asn Asn Leu
    1460                1465                1470

Ser Leu Ala Ile Leu Thr Leu Glu Met Ile Arg Gly Gln Glu Lys
    1475                1480                1485

Val Ser Ser Leu Gly Thr Ser Ala Thr Asn Pro Leu Met Tyr Lys
    1490                1495                1500

Lys Leu Glu Asn Thr Val Leu Leu Lys Pro Gly Leu Pro Glu Ala
    1505                1510                1515

Ser Gly Lys Val Glu Leu Leu Pro Lys Val His Val His Gln Glu
    1520                1525                1530

Asp Leu Phe Pro Thr Glu Thr Ser Asn Gly Ser Pro Gly His Leu
    1535                1540                1545

Asp Leu Met Glu Glu Ile Leu Leu Gln Lys Thr Gln Gly Ala Ile
    1550                1555                1560

Lys Leu Asn Lys Val Asn Arg Pro Gly Lys Val Pro Phe Leu Lys
    1565                1570                1575

Gly Ala Thr Glu Ser Ser Glu Lys Thr Pro Ser Lys Leu Leu Gly
    1580                1585                1590

Pro Leu Ala Trp Asp Asn Gln Tyr Ala Thr Gln Ile Pro Arg Glu
    1595                1600                1605

Glu Trp Lys Ser Gln Glu Lys Ser Pro Lys Asn Thr Ala Phe Lys
    1610                1615                1620

Thr Lys Asp Thr Ile Leu Pro Leu Asn Pro Cys Glu Asn Asn His
    1625                1630                1635

Ala Ile Ala Ala Ile Asn Glu Gly Gln Asp Arg Pro Gln Arg Glu
    1640                1645                1650

Ala Thr Trp Ala Lys Gln Gly Gly Thr Gly Arg Leu Cys Ser Gln
    1655                1660                1665

Asn Pro Pro Val Leu Lys Arg His Gln Arg Glu Ile Thr Leu Thr
    1670                1675                1680

Thr Leu Gln Pro Glu Gln Glu Lys Ile Asp Tyr Asp Asp Thr Ile
```

```
                1685                1690                1695

Ser Ile Glu Thr Lys Arg Glu Asp Phe Asp Ile Tyr Gly Glu Asp
    1700                1705                1710

Glu Asn Gln Gly Pro Arg Ser Phe Gln Lys Arg Thr Arg His Tyr
    1715                1720                1725

Phe Ile Ala Ala Val Glu Arg Leu Trp Asp Tyr Gly Met Ser Arg
    1730                1735                1740

Ser Pro His Ala Leu Arg Asn Arg Ala Gln Ser Gly Ser Val Pro
    1745                1750                1755

Gln Phe Lys Lys Val Val Phe Gln Glu Phe Thr Asp Gly Ser Phe
    1760                1765                1770

Thr Gln Pro Leu Tyr Arg Gly Glu Leu Asn Glu His Leu Gly Leu
    1775                1780                1785

Leu Gly Pro Tyr Ile Arg Ala Glu Val Glu Asp Asn Ile Met Val
    1790                1795                1800

Thr Phe Lys Asn Gln Ala Ser Arg Pro Tyr Ser Phe Tyr Ser Ser
    1805                1810                1815

Leu Ile Ser Tyr Glu Glu Asp Gln Arg Gln Gly Ala Glu Pro Arg
    1820                1825                1830

Lys Asn Phe Val Lys Pro Asn Glu Thr Lys Thr Tyr Phe Trp Lys
    1835                1840                1845

Val Gln His His Met Ala Pro Thr Lys Asp Glu Phe Asp Cys Lys
    1850                1855                1860

Ala Trp Ala Tyr Phe Ser Asp Val Asp Leu Glu Lys Asp Met His
    1865                1870                1875

Ser Gly Leu Ile Gly Pro Leu Leu Ile Cys Arg Thr Asn Thr Leu
    1880                1885                1890

Asn Pro Ala His Gly Arg Gln Val Thr Val Gln Glu Phe Ala Leu
    1895                1900                1905

Phe Phe Thr Ile Phe Asp Glu Thr Lys Ser Trp Tyr Phe Thr Glu
    1910                1915                1920

Asn Met Glu Arg Asn Cys Arg Ala Pro Cys Asn Ile Gln Met Glu
    1925                1930                1935

Asp Pro Thr Phe Lys Glu Asn Tyr Arg Phe His Ala Ile Asn Gly
    1940                1945                1950

Tyr Val Met Asp Thr Leu Pro Gly Leu Val Met Ala Gln Asp Gln
    1955                1960                1965

Arg Ile Arg Trp Tyr Leu Leu Ser Met Gly Ser Asn Glu Asn Ile
    1970                1975                1980

His Ser Ile His Phe Ser Gly His Val Phe Thr Val Arg Lys Lys
    1985                1990                1995

Glu Glu Tyr Lys Met Ala Val Tyr Asn Leu Tyr Pro Gly Val Phe
    2000                2005                2010

Glu Thr Val Glu Met Leu Pro Ser Lys Ala Gly Ile Trp Arg Val
    2015                2020                2025

Glu Cys Leu Ile Gly Glu His Leu Gln Ala Gly Met Ser Thr Leu
    2030                2035                2040

Phe Leu Val Tyr Ser Lys Cys Gln Thr Pro Leu Gly Met Ala
    2045                2050                2055

Ser Gly Arg Ile Arg Asp Phe Gln Ile Thr Ala Ser Gly Gln Tyr
    2060                2065                2070

Gly Gln Trp Ala Pro Lys Leu Ala Arg Leu His Tyr Ser Gly Ser
    2075                2080                2085
```

```
Ile Asn Ala Trp Ser Thr Lys Asp Pro Phe Ser Trp Ile Lys Val
    2090                2095                2100

Asp Leu Leu Ala Pro Met Ile Ile His Gly Ile Lys Thr Gln Gly
    2105                2110                2115

Ala Arg Gln Lys Phe Ser Ser Leu Tyr Ile Ser Gln Phe Ile Ile
    2120                2125                2130

Met Tyr Ser Leu Asp Gly Lys Lys Trp Gln Ser Tyr Arg Gly Asn
    2135                2140                2145

Ser Thr Gly Thr Leu Met Val Phe Phe Gly Asn Val Asp Ser Ser
    2150                2155                2160

Gly Ile Lys His Asn Ile Phe Asn Pro Pro Ile Ile Ala Arg Tyr
    2165                2170                2175

Ile Arg Leu His Pro Thr His Tyr Ser Ile Arg Ser Thr Leu Arg
    2180                2185                2190

Met Glu Leu Met Gly Cys Asp Leu Asn Ser Cys Ser Met Pro Leu
    2195                2200                2205

Gly Met Glu Ser Lys Ala Ile Ser Asp Ala Gln Ile Thr Ala Ser
    2210                2215                2220

Ser Tyr Phe Thr Asn Met Phe Ala Thr Trp Ser Pro Ser Gln Ala
    2225                2230                2235

Arg Leu His Leu Gln Gly Arg Thr Asn Ala Trp Arg Pro Gln Val
    2240                2245                2250

Asn Asn Pro Lys Glu Trp Leu Gln Val Asp Phe Gln Lys Thr Met
    2255                2260                2265

Lys Val Thr Gly Ile Thr Thr Gln Gly Val Lys Ser Leu Leu Thr
    2270                2275                2280

Ser Met Tyr Val Lys Glu Phe Leu Ile Ser Ser Ser Gln Asp Gly
    2285                2290                2295

His His Trp Thr Leu Phe Leu Gln Asn Gly Lys Val Lys Val Phe
    2300                2305                2310

Gln Gly Asn Gln Asp Ser Phe Thr Pro Val Val Asn Ser Leu Asp
    2315                2320                2325

Pro Pro Leu Leu Thr Arg Tyr Leu Arg Ile His Pro Gln Ser Trp
    2330                2335                2340

Val His Gln Ile Ala Leu Arg Leu Glu Val Leu Gly Cys Glu Ala
    2345                2350                2355

Gln Gln Leu Tyr
    2360

<210> SEQ ID NO 31
<211> LENGTH: 2351
<212> TYPE: PRT
<213> ORGANISM: artificial sequence
<220> FEATURE:
<223> OTHER INFORMATION: ancestral

<400> SEQUENCE: 31

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Thr Arg
        35                  40                  45

Phe Pro Pro Arg Val Pro Arg Ser Phe Pro Phe Asn Thr Ser Val Val
    50                  55                  60
```

-continued

```
Tyr Lys Lys Thr Val Phe Val Glu Phe Thr Asp His Leu Phe Asn Ile
 65                  70                  75                  80

Ala Lys Pro Arg Pro Pro Trp Met Gly Leu Leu Gly Pro Thr Ile Gln
                 85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Val Leu Leu Phe Ala Val Phe Asp Glu Gly
210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
                405                 410                 415

Ser Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
450                 455                 460

Ser Gly Ile Leu Gly Pro Leu Leu Tyr Gly Glu Val Gly Asp Thr Leu
465                 470                 475                 480
```

```
Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Ile Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Thr Tyr Leu Leu Ser Lys
            740                 745                 750

Asn Asn Ala Ile Glu Pro Arg Ser Phe Ser Gln Asn Ser Arg His Pro
        755                 760                 765

Ser Thr Arg Gln Lys Gln Phe Asn Ala Thr Thr Ile Pro Glu Asn Asp
    770                 775                 780

Ile Glu Lys Thr Asp Pro Trp Phe Ala His Arg Thr Pro Met Pro Lys
785                 790                 795                 800

Val Gln Asn Val Ser Ser Ser Asp Leu Leu Met Leu Leu Arg Gln Ser
                805                 810                 815

Pro Thr Pro His Gly Leu Ser Leu Ser Asp Leu Gln Glu Ala Lys Tyr
            820                 825                 830

Glu Thr Phe Ser Asp Asp Pro Ser Pro Gly Ala Ile Asp Ser Asn Asn
        835                 840                 845

Ser Leu Ser Glu Met Thr His Phe Arg Pro Gln Leu His His Ser Gly
    850                 855                 860

Asp Met Val Phe Thr Pro Glu Pro Gly Leu Gln Leu Arg Leu Asn Glu
865                 870                 875                 880

Lys Leu Gly Thr Thr Ala Ala Thr Glu Leu Lys Lys Leu Asp Phe Lys
                885                 890                 895

Val Ser Ser Thr Ser Asn Asn Leu Ile Ser Thr Ile Pro Ser Asp Asn
```

```
                900             905             910
Leu Ala Ala Gly Thr Asp Asn Thr Ser Ser Leu Gly Pro Pro Asn Met
            915             920             925

Pro Val His Tyr Asp Ser Gln Leu Asp Thr Thr Leu Phe Gly Lys Lys
            930             935             940

Ser Ser Pro Leu Ile Glu Ser Gly Gly Pro Leu Ser Leu Ser Glu Glu
945             950             955             960

Asn Asn Asp Ser Lys Leu Leu Glu Ser Gly Leu Met Asn Ser Gln Glu
            965             970             975

Ser Ser Trp Gly Lys Asn Val Ser Ser Thr Glu Ser Gly Arg Leu Phe
            980             985             990

Lys Glu Lys Arg Ala His Gly Pro Ala Leu Leu Thr Lys Asp Asn Ala
            995            1000            1005

Leu Phe Lys Val Ser Ile Ser Leu Leu Lys Thr Asn Lys Thr Ser
        1010            1015            1020

Asn Asn Ser Ala Thr Asn Arg Lys Thr His Ile Asp Gly Pro Ser
        1025            1030            1035

Leu Leu Ile Glu Asn Ser Pro Ser Val Trp Gln Asn Ile Leu Glu
        1040            1045            1050

Ser Asp Thr Glu Phe Gln Lys Val Thr Pro Leu Ile His Asp Arg
        1055            1060            1065

Met Leu Met Asp Lys Asn Ala Thr Ala Leu Arg Leu Asn His Met
        1070            1075            1080

Ser Asn Lys Thr Thr Ser Ser Lys Asn Met Glu Met Val Gln Gln
        1085            1090            1095

Lys Lys Glu Gly Pro Ile Pro Pro Asp Ala Glu Asn Pro Asp Met
        1100            1105            1110

Ser Phe Phe Lys Met Leu Phe Leu Pro Glu Ser Ala Asn Trp Ile
        1115            1120            1125

Gln Arg Thr His Gly Lys Asn Ser Leu Asn Ser Gly Gln Gly Pro
        1130            1135            1140

Ser Pro Lys Gln Leu Val Ser Leu Gly Pro Glu Lys Ser Val Glu
        1145            1150            1155

Gly Gln Asn Phe Leu Ser Glu Lys Asn Lys Val Val Val Gly Lys
        1160            1165            1170

Gly Glu Phe Thr Lys Asp Val Gly Leu Lys Glu Met Val Phe Pro
        1175            1180            1185

Ser Ser Arg Asn Leu Phe Leu Thr Asn Leu Asp Asn Leu His Glu
        1190            1195            1200

Asn Asn Thr His Asn Gln Glu Lys Lys Ile Gln Glu Glu Ile Glu
        1205            1210            1215

Arg Lys Glu Thr Leu Ile Gln Glu Asn Val Val Leu Pro Gln Ile
        1220            1225            1230

His Thr Val Thr Gly Thr Lys Asn Phe Met Lys Asn Leu Phe Leu
        1235            1240            1245

Leu Ser Thr Arg Gln Asn Val Glu Gly Ser Tyr Glu Gly Ala Tyr
        1250            1255            1260

Ala Pro Val Leu Gln Asp Phe Arg Ser Leu Asn Asp Ser Thr Asn
        1265            1270            1275

Arg Thr Lys Lys His Thr Ala His Phe Ser Lys Lys Gly Glu Glu
        1280            1285            1290

Glu Asn Leu Glu Gly Leu Gly Asn Gln Thr Lys Gln Ile Val Glu
        1295            1300            1305
```

```
Lys Tyr Pro Arg Thr Thr Arg Ile Ser Pro Asn Pro Ser Gln Gln
    1310                1315                1320

Asn Phe Val Thr Gln Arg Gly Lys Arg Ala Leu Lys Gln Phe Arg
    1325                1330                1335

Leu Pro Leu Glu Glu Thr Glu Leu Glu Lys Arg Ile Ile Val Asp
    1340                1345                1350

Asp Thr Ser Thr Gln Trp Ser Lys Asn Met Lys His Leu Thr Pro
    1355                1360                1365

Ser Thr Leu Thr Gln Ile Asp Tyr Asn Glu Lys Glu Lys Gly Ala
    1370                1375                1380

Ile Thr Gln Ser Pro Leu Ser Asp Cys Leu Thr Arg Ser His Ser
    1385                1390                1395

Ile Thr Gln Ala Asn Arg Ser Pro Leu Pro Ile Ala Lys Val Ser
    1400                1405                1410

Ser Phe Pro Ser Ile Arg Pro Ile Asp Leu Thr Arg Val Leu Phe
    1415                1420                1425

Gln Asp Asn Ser Ser His Leu Pro Ala Pro Ser Tyr Arg Lys Lys
    1430                1435                1440

Asp Ser Gly Val Gln Glu Ser Ser His Phe Leu Gln Gly Ala Lys
    1445                1450                1455

Lys Asn Asn Leu Ser Leu Ala Ile Leu Thr Leu Glu Met Thr Gly
    1460                1465                1470

Asp Gln Arg Glu Val Gly Ser Leu Gly Thr Ser Ala Thr Asn Ser
    1475                1480                1485

Val Thr Tyr Lys Lys Val Glu Asn Thr Val Leu Leu Lys Pro Gly
    1490                1495                1500

Leu Pro Lys Thr Ser Gly Lys Val Glu Leu Leu Pro Lys Val His
    1505                1510                1515

Ile Tyr Gln Lys Asp Leu Phe Pro Thr Glu Thr Ser Asn Gly Ser
    1520                1525                1530

Pro Gly His Leu Asp Leu Val Glu Gly Ser Leu Leu Gln Glu Thr
    1535                1540                1545

Glu Gly Ala Ile Lys Trp Asn Glu Ala Asn Arg Pro Gly Lys Ile
    1550                1555                1560

Pro Phe Leu Arg Val Ala Thr Glu Ser Ser Ala Lys Thr Pro Ser
    1565                1570                1575

Lys Leu Leu Gly Pro Leu Ala Trp Asp Asn His Tyr Gly Thr Gln
    1580                1585                1590

Ile Pro Lys Glu Glu Trp Lys Ser Gln Glu Lys Ser Pro Glu Lys
    1595                1600                1605

Thr Ala Phe Lys Lys Lys Asp Thr Ile Leu Ser Leu Asn Ala Cys
    1610                1615                1620

Glu Ser Asn His Ala Ile Ala Ala Ile Asn Glu Gly Gln Asn Lys
    1625                1630                1635

Pro Glu Ile Glu Val Thr Trp Ala Lys Gln Gly Gly Thr Glu Arg
    1640                1645                1650

Leu Cys Ser Gln Asn Pro Pro Val Leu Lys Arg His Gln Arg Glu
    1655                1660                1665

Ile Thr Leu Thr Thr Leu Gln Ser Asp Gln Glu Glu Ile Asp Tyr
    1670                1675                1680

Asp Asp Thr Ile Ser Val Glu Met Lys Lys Glu Asp Phe Asp Ile
    1685                1690                1695
```

-continued

```
Tyr Asp Glu Asp Glu Asn Gln Ser Pro Arg Ser Phe Gln Lys Lys
    1700                1705                1710

Thr Arg His Tyr Phe Ile Ala Ala Val Glu Arg Leu Trp Asp Tyr
    1715                1720                1725

Gly Met Ser Ser Ser Pro His Val Leu Arg Asn Arg Ala Gln Ser
    1730                1735                1740

Gly Ser Val Pro Gln Phe Lys Lys Val Val Phe Gln Glu Phe Thr
    1745                1750                1755

Asp Gly Ser Phe Thr Gln Pro Leu Tyr Arg Gly Glu Leu Asn Glu
    1760                1765                1770

His Leu Gly Leu Leu Gly Pro Tyr Ile Arg Ala Glu Val Glu Asp
    1775                1780                1785

Asn Ile Met Val Thr Phe Lys Asn Gln Ala Ser Arg Pro Tyr Ser
    1790                1795                1800

Phe Tyr Ser Ser Leu Ile Ser Tyr Glu Glu Asp Gln Arg Gln Gly
    1805                1810                1815

Ala Glu Pro Arg Lys Asn Phe Val Lys Pro Asn Glu Thr Lys Thr
    1820                1825                1830

Tyr Phe Trp Lys Val Gln His His Met Ala Pro Thr Lys Asp Glu
    1835                1840                1845

Phe Asp Cys Lys Ala Trp Ala Tyr Phe Ser Asp Val Asp Leu Glu
    1850                1855                1860

Lys Asp Val His Ser Gly Leu Ile Gly Pro Leu Leu Val Cys His
    1865                1870                1875

Thr Asn Thr Leu Asn Pro Ala His Gly Arg Gln Val Thr Val Gln
    1880                1885                1890

Glu Phe Ala Leu Phe Phe Thr Ile Phe Asp Glu Thr Lys Ser Trp
    1895                1900                1905

Tyr Phe Thr Glu Asn Met Glu Arg Asn Cys Arg Ala Pro Cys Asn
    1910                1915                1920

Ile Gln Met Glu Asp Pro Thr Phe Lys Glu Asn Tyr Arg Phe His
    1925                1930                1935

Ala Ile Asn Gly Tyr Ile Met Asp Thr Leu Pro Gly Leu Val Met
    1940                1945                1950

Ala Gln Asp Gln Arg Ile Arg Trp Tyr Leu Leu Ser Met Gly Ser
    1955                1960                1965

Asn Glu Asn Ile His Ser Ile His Phe Ser Gly His Val Phe Thr
    1970                1975                1980

Val Arg Lys Lys Glu Glu Tyr Lys Met Ala Val Tyr Asn Leu Tyr
    1985                1990                1995

Pro Gly Val Phe Glu Thr Val Glu Met Leu Pro Ser Lys Ala Gly
    2000                2005                2010

Ile Trp Arg Val Glu Cys Leu Ile Gly Glu His Leu His Ala Gly
    2015                2020                2025

Met Ser Thr Leu Phe Leu Val Tyr Ser Asn Lys Cys Gln Thr Pro
    2030                2035                2040

Leu Gly Met Ala Ser Gly His Ile Arg Asp Phe Gln Ile Thr Ala
    2045                2050                2055

Ser Gly Gln Tyr Gly Gln Trp Ala Pro Lys Leu Ala Arg Leu His
    2060                2065                2070

Tyr Ser Gly Ser Ile Asn Ala Trp Ser Thr Lys Glu Pro Phe Ser
    2075                2080                2085

Trp Ile Lys Val Asp Leu Leu Ala Pro Met Ile Ile His Gly Ile
```

```
                2090                2095                2100
Lys Thr Gln Gly Ala Arg Gln Lys Phe Ser Ser Leu Tyr Ile Ser
        2105                2110                2115

Gln Phe Ile Ile Met Tyr Ser Leu Asp Gly Lys Lys Trp Gln Thr
        2120                2125                2130

Tyr Arg Gly Asn Ser Thr Gly Thr Leu Met Val Phe Phe Gly Asn
        2135                2140                2145

Val Asp Ser Ser Gly Ile Lys His Asn Ile Phe Asn Pro Pro Ile
        2150                2155                2160

Ile Ala Arg Tyr Ile Arg Leu His Pro Thr His Tyr Ser Ile Arg
        2165                2170                2175

Ser Thr Leu Arg Met Glu Leu Met Gly Cys Asp Leu Asn Ser Cys
        2180                2185                2190

Ser Met Pro Leu Gly Met Glu Ser Lys Ala Ile Ser Asp Ala Gln
        2195                2200                2205

Ile Thr Ala Ser Ser Tyr Phe Thr Asn Met Phe Ala Thr Trp Ser
        2210                2215                2220

Pro Ser Lys Ala Arg Leu His Leu Gln Gly Arg Ser Asn Ala Trp
        2225                2230                2235

Arg Pro Gln Val Asn Asn Pro Lys Glu Trp Leu Gln Val Asp Phe
        2240                2245                2250

Gln Lys Thr Met Lys Val Thr Gly Ile Thr Thr Gln Gly Val Lys
        2255                2260                2265

Ser Leu Leu Thr Ser Met Tyr Val Lys Glu Phe Leu Ile Ser Ser
        2270                2275                2280

Ser Gln Asp Gly His His Trp Thr Leu Phe Phe Gln Asn Gly Lys
        2285                2290                2295

Val Lys Val Phe Gln Gly Asn Gln Asp Ser Phe Thr Pro Val Val
        2300                2305                2310

Asn Ser Leu Asp Pro Pro Leu Leu Thr Arg Tyr Leu Arg Ile His
        2315                2320                2325

Pro Gln Ser Trp Val His Gln Ile Ala Leu Arg Met Glu Val Leu
        2330                2335                2340

Gly Cys Glu Ala Gln Glu Leu Tyr
        2345                2350

<210> SEQ ID NO 32
<211> LENGTH: 2351
<212> TYPE: PRT
<213> ORGANISM: artificial sequence
<220> FEATURE:
<223> OTHER INFORMATION: ancestral

<400> SEQUENCE: 32

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Val Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
```

```
                    85                  90                  95
Ala Glu Val Tyr Asp Thr Val Val Ile Thr Leu Lys Asn Met Ala Ser
                100                 105                 110
His Pro Val Ser Leu His Ala Val Gly Val Ser Tyr Trp Lys Ala Ser
                115                 120                 125
Glu Gly Ala Glu Tyr Asp Asp Gln Thr Ser Gln Arg Glu Lys Glu Asp
                130                 135                 140
Asp Lys Val Phe Pro Gly Gly Ser His Thr Tyr Val Trp Gln Val Leu
145                 150                 155                 160
Lys Glu Asn Gly Pro Met Ala Ser Asp Pro Leu Cys Leu Thr Tyr Ser
                165                 170                 175
Tyr Leu Ser His Val Asp Leu Val Lys Asp Leu Asn Ser Gly Leu Ile
                180                 185                 190
Gly Ala Leu Leu Val Cys Arg Glu Gly Ser Leu Ala Lys Glu Lys Thr
                195                 200                 205
Gln Thr Leu His Lys Phe Ile Leu Leu Phe Ala Val Phe Asp Glu Gly
                210                 215                 220
Lys Ser Trp His Ser Glu Thr Lys Asn Ser Leu Met Gln Asp Arg Asp
225                 230                 235                 240
Ala Ala Ser Ala Arg Ala Trp Pro Lys Met His Thr Val Asn Gly Tyr
                245                 250                 255
Val Asn Arg Ser Leu Pro Gly Leu Ile Gly Cys His Arg Lys Ser Val
                260                 265                 270
Tyr Trp His Val Ile Gly Met Gly Thr Thr Pro Glu Val His Ser Ile
                275                 280                 285
Phe Leu Glu Gly His Thr Phe Leu Val Arg Asn His Arg Gln Ala Ser
290                 295                 300
Leu Glu Ile Ser Pro Ile Thr Phe Leu Thr Ala Gln Thr Leu Leu Met
305                 310                 315                 320
Asp Leu Gly Gln Phe Leu Leu Phe Cys His Ile Ser Ser His Gln His
                325                 330                 335
Asp Gly Met Glu Ala Tyr Val Lys Val Asp Ser Cys Pro Glu Glu Pro
                340                 345                 350
Gln Leu Arg Met Lys Asn Asn Glu Glu Ala Glu Asp Tyr Asp Asp Asp
                355                 360                 365
Leu Thr Asp Ser Glu Met Asp Val Val Arg Phe Asp Asp Asp Asn Ser
                370                 375                 380
Pro Ser Phe Ile Gln Ile Arg Ser Val Ala Lys Lys His Pro Lys Thr
385                 390                 395                 400
Trp Val His Tyr Ile Ala Ala Glu Glu Glu Asp Trp Asp Tyr Ala Pro
                405                 410                 415
Leu Val Leu Ala Pro Asp Asp Arg Ser Tyr Lys Ser Gln Tyr Leu Asn
                420                 425                 430
Asn Gly Pro Gln Arg Ile Gly Arg Lys Tyr Lys Lys Val Arg Phe Met
                435                 440                 445
Ala Tyr Thr Asp Glu Thr Phe Lys Thr Arg Glu Ala Ile Gln His Glu
                450                 455                 460
Ser Gly Ile Leu Gly Pro Leu Leu Tyr Gly Glu Val Gly Asp Thr Leu
465                 470                 475                 480
Leu Ile Ile Phe Lys Asn Gln Ala Ser Arg Pro Tyr Asn Ile Tyr Pro
                485                 490                 495
His Gly Ile Thr Asp Val Arg Pro Leu Tyr Ser Arg Arg Leu Pro Lys
                500                 505                 510
```

```
Gly Val Lys His Leu Lys Asp Phe Pro Ile Leu Pro Gly Glu Ile Phe
            515                 520                 525
Lys Tyr Lys Trp Thr Val Thr Val Glu Asp Gly Pro Thr Lys Ser Asp
        530                 535                 540
Pro Arg Cys Leu Thr Arg Tyr Tyr Ser Ser Phe Ile Asn Met Glu Arg
545                 550                 555                 560
Asp Leu Ala Ser Gly Leu Ile Gly Pro Leu Leu Ile Cys Tyr Lys Glu
                565                 570                 575
Ser Val Asp Gln Arg Gly Asn Gln Ile Met Ser Asp Lys Arg Asn Val
            580                 585                 590
Ile Leu Phe Ser Val Phe Asp Glu Asn Arg Ser Trp Tyr Leu Thr Glu
        595                 600                 605
Asn Ile Gln Arg Phe Leu Pro Asn Pro Ala Gly Val Gln Leu Glu Asp
    610                 615                 620
Pro Glu Phe Gln Ala Ser Asn Ile Met His Ser Ile Asn Gly Tyr Val
625                 630                 635                 640
Phe Asp Ser Leu Gln Leu Ser Val Cys Leu His Glu Val Ala Tyr Trp
                645                 650                 655
Tyr Ile Leu Ser Ile Gly Ala Gln Thr Asp Phe Leu Ser Val Phe Phe
            660                 665                 670
Ser Gly Tyr Thr Phe Lys His Lys Met Val Tyr Glu Asp Thr Leu Thr
        675                 680                 685
Leu Phe Pro Phe Ser Gly Glu Thr Val Phe Met Ser Met Glu Asn Pro
    690                 695                 700
Gly Leu Trp Ile Leu Gly Cys His Asn Ser Asp Phe Arg Asn Arg Gly
705                 710                 715                 720
Met Thr Ala Leu Leu Lys Val Ser Ser Cys Asp Lys Asn Thr Gly Asp
                725                 730                 735
Tyr Tyr Glu Asp Ser Tyr Glu Asp Ile Ser Ala Tyr Leu Leu Ser Lys
            740                 745                 750
Asn Asn Ala Ile Glu Pro Arg Ser Phe Ser Gln Asn Ser Arg His Pro
        755                 760                 765
Ser Thr Arg Gln Lys Gln Phe Asn Ala Thr Thr Ile Pro Glu Asn Asp
    770                 775                 780
Ile Glu Lys Thr Asp Pro Trp Phe Ala His Arg Thr Pro Met Pro Lys
785                 790                 795                 800
Val Gln Asn Val Ser Ser Ser Asp Leu Leu Met Leu Leu Arg Gln Ser
                805                 810                 815
Pro Thr Pro His Gly Leu Ser Leu Ser Asp Leu Gln Glu Ala Lys Tyr
            820                 825                 830
Glu Thr Phe Ser Asp Asp Pro Ser Pro Gly Ala Ile Asp Ser Asn Asn
        835                 840                 845
Ser Leu Ser Glu Met Thr His Phe Arg Pro Gln Leu His His Ser Gly
    850                 855                 860
Asp Met Val Phe Thr Pro Glu Ser Gly Leu Gln Leu Arg Leu Asn Glu
865                 870                 875                 880
Lys Leu Gly Thr Thr Ala Ala Thr Glu Leu Lys Lys Leu Asp Phe Lys
                885                 890                 895
Val Ser Ser Thr Ser Asn Asn Leu Ile Ser Thr Ile Pro Ser Asp Asn
            900                 905                 910
Leu Ala Ala Gly Thr Asp Asn Thr Ser Ser Leu Gly Pro Pro Ser Met
        915                 920                 925
```

-continued

```
Pro Val His Tyr Asp Ser Gln Leu Asp Thr Thr Leu Phe Gly Lys Lys
    930             935                 940

Ser Ser Pro Leu Thr Glu Ser Gly Gly Pro Leu Ser Leu Ser Glu Glu
945             950                 955                 960

Asn Asn Asp Ser Lys Leu Leu Glu Ser Gly Leu Met Asn Ser Gln Glu
            965                 970                 975

Ser Ser Trp Gly Lys Asn Val Ser Ser Thr Glu Ser Gly Arg Leu Phe
        980                 985                 990

Lys Gly Lys Arg Ala His Gly Pro Ala Leu Leu Thr Lys Asp Asn Ala
    995                 1000                1005

Leu Phe Lys Val Ser Ile Ser Leu Leu Lys Thr Asn Lys Thr Ser
    1010                1015                1020

Asn Asn Ser Ala Thr Asn Arg Lys Thr His Ile Asp Gly Pro Ser
    1025                1030                1035

Leu Leu Ile Glu Asn Ser Pro Ser Val Trp Gln Asn Ile Leu Glu
    1040                1045                1050

Ser Asp Thr Glu Phe Gln Lys Val Thr Pro Leu Ile His Asp Arg
    1055                1060                1065

Met Leu Met Asp Lys Asn Ala Thr Ala Leu Arg Leu Asn His Met
    1070                1075                1080

Ser Asn Lys Thr Thr Ser Ser Lys Asn Met Glu Met Val Gln Gln
    1085                1090                1095

Lys Lys Glu Gly Pro Ile Pro Pro Asp Ala Glu Asn Pro Asp Met
    1100                1105                1110

Ser Phe Phe Lys Met Leu Phe Leu Pro Glu Ser Ala Ser Trp Ile
    1115                1120                1125

Gln Arg Thr His Gly Lys Asn Ser Leu Asn Ser Gly Gln Gly Pro
    1130                1135                1140

Ser Pro Lys Gln Leu Val Ser Leu Gly Pro Glu Lys Ser Val Glu
    1145                1150                1155

Gly Gln Asn Phe Leu Ser Glu Lys Asn Lys Val Val Val Gly Lys
    1160                1165                1170

Gly Glu Phe Thr Lys Asp Val Gly Leu Lys Glu Met Val Phe Pro
    1175                1180                1185

Ser Ser Arg Asn Leu Phe Leu Thr Asn Leu Asp Asn Leu His Glu
    1190                1195                1200

Asn Asn Thr His Asn Gln Glu Lys Lys Ile Gln Glu Glu Ile Glu
    1205                1210                1215

Arg Lys Glu Thr Leu Ile Gln Glu Asn Val Val Leu Pro Gln Ile
    1220                1225                1230

His Thr Val Thr Gly Thr Lys Asn Phe Met Lys Asn Leu Phe Leu
    1235                1240                1245

Leu Ser Thr Arg Gln Asn Val Glu Gly Ser Tyr Glu Gly Ala Tyr
    1250                1255                1260

Ala Pro Val Leu Gln Asp Phe Arg Ser Leu Asn Asp Ser Thr Asn
    1265                1270                1275

Arg Thr Lys Lys His Thr Ala His Phe Ser Lys Lys Gly Glu Glu
    1280                1285                1290

Glu Asn Leu Glu Gly Leu Gly Asn Gln Thr Lys Gln Ile Val Glu
    1295                1300                1305

Lys Tyr Ala Cys Thr Thr Arg Ile Ser Pro Asn Thr Ser Gln Gln
    1310                1315                1320

Asn Phe Val Thr Gln Arg Ser Lys Arg Ala Leu Lys Gln Phe Arg
```

-continued

```
            1325               1330                1335

Leu Pro Leu Glu Glu Thr Glu Leu Glu Lys Arg Ile Ile Val Asp
    1340                1345                1350

Asp Thr Ser Thr Gln Trp Ser Lys Asn Met Lys His Leu Thr Pro
    1355                1360                1365

Ser Thr Leu Thr Gln Ile Asp Tyr Asn Glu Lys Glu Lys Gly Ala
    1370                1375                1380

Ile Thr Gln Ser Pro Leu Ser Asp Cys Leu Thr Arg Ser His Ser
    1385                1390                1395

Ile Pro Gln Ala Asn Arg Ser Pro Leu Pro Ile Ala Lys Val Ser
    1400                1405                1410

Ser Phe Pro Ser Ile Arg Pro Ile Tyr Leu Thr Arg Val Leu Phe
    1415                1420                1425

Gln Asp Asn Ser Ser His Leu Pro Ala Ala Ser Tyr Arg Lys Lys
    1430                1435                1440

Asp Ser Gly Val Gln Glu Ser Ser His Phe Leu Gln Gly Ala Lys
    1445                1450                1455

Lys Asn Asn Leu Ser Leu Ala Ile Leu Thr Leu Glu Met Thr Gly
    1460                1465                1470

Asp Gln Arg Glu Val Gly Ser Leu Gly Thr Ser Ala Thr Asn Ser
    1475                1480                1485

Val Thr Tyr Lys Lys Val Glu Asn Thr Val Leu Pro Lys Pro Gly
    1490                1495                1500

Leu Pro Lys Thr Ser Gly Lys Val Glu Leu Leu Pro Lys Val His
    1505                1510                1515

Ile Tyr Gln Lys Asp Leu Phe Pro Thr Glu Thr Ser Asn Gly Ser
    1520                1525                1530

Pro Gly His Leu Asp Leu Val Glu Gly Ser Leu Leu Gln Glu Thr
    1535                1540                1545

Glu Gly Ala Ile Lys Trp Asn Glu Ala Asn Arg Pro Gly Lys Ile
    1550                1555                1560

Pro Phe Leu Arg Val Ala Thr Glu Ser Ser Ala Lys Thr Pro Ser
    1565                1570                1575

Lys Leu Leu Gly Pro Leu Ala Trp Asp Asn His Tyr Gly Thr Gln
    1580                1585                1590

Ile Pro Lys Glu Glu Trp Lys Ser Gln Glu Lys Ser Pro Glu Lys
    1595                1600                1605

Thr Ala Phe Lys Lys Lys Asp Thr Ile Leu Ser Leu Asn Ala Cys
    1610                1615                1620

Glu Ser Asn His Ala Ile Ala Ala Ile Asn Glu Gly Gln Asn Lys
    1625                1630                1635

Pro Glu Ile Glu Val Thr Trp Ala Lys Gln Gly Arg Thr Glu Arg
    1640                1645                1650

Leu Cys Ser Gln Asn Pro Pro Val Leu Lys Arg His Gln Arg Glu
    1655                1660                1665

Ile Thr Arg Thr Thr Leu Gln Ser Asp Gln Glu Glu Ile Asp Tyr
    1670                1675                1680

Asp Asp Thr Ile Ser Val Glu Met Lys Lys Glu Asp Phe Asp Ile
    1685                1690                1695

Tyr Asp Glu Asp Glu Asn Gln Ser Pro Arg Ser Phe Gln Lys Lys
    1700                1705                1710

Thr Arg His Tyr Phe Ile Ala Ala Val Glu Arg Leu Trp Asp Tyr
    1715                1720                1725
```

```
Gly Met Ser Ser Ser Pro His Val Leu Arg Asn Arg Ala Gln Ser
    1730                1735                1740

Gly Ser Val Pro Gln Phe Lys Lys Val Val Phe Gln Glu Phe Thr
    1745                1750                1755

Asp Gly Ser Phe Thr Gln Pro Leu Tyr Arg Gly Glu Leu Asn Glu
    1760                1765                1770

His Leu Gly Leu Leu Gly Pro Tyr Ile Arg Ala Glu Val Glu Asp
    1775                1780                1785

Asn Ile Met Val Thr Phe Lys Asn Gln Ala Ser Arg Pro Tyr Ser
    1790                1795                1800

Phe Tyr Ser Ser Leu Ile Ser Tyr Glu Glu Asp Gln Arg Gln Gly
    1805                1810                1815

Ala Glu Pro Arg Lys Asn Phe Val Lys Pro Asn Glu Thr Lys Thr
    1820                1825                1830

Tyr Phe Trp Lys Val Gln His His Met Ala Pro Thr Lys Asp Glu
    1835                1840                1845

Phe Asp Cys Lys Ala Trp Ala Tyr Phe Ser Asp Val Asp Leu Glu
    1850                1855                1860

Lys Asp Val His Ser Gly Leu Ile Gly Pro Leu Leu Val Cys His
    1865                1870                1875

Thr Asn Thr Leu Asn Pro Ala His Gly Arg Gln Val Thr Val Gln
    1880                1885                1890

Glu Phe Ala Leu Phe Phe Thr Ile Phe Asp Glu Thr Lys Ser Trp
    1895                1900                1905

Tyr Phe Thr Glu Asn Met Glu Arg Asn Cys Arg Ala Pro Cys Asn
    1910                1915                1920

Ile Gln Met Glu Asp Pro Thr Phe Lys Glu Asn Tyr Arg Phe His
    1925                1930                1935

Ala Ile Asn Gly Tyr Ile Met Asp Thr Leu Pro Gly Leu Val Met
    1940                1945                1950

Ala Gln Asp Gln Arg Ile Arg Trp Tyr Leu Leu Ser Met Gly Ser
    1955                1960                1965

Asn Glu Asn Ile His Ser Ile His Phe Ser Gly His Val Phe Thr
    1970                1975                1980

Val Arg Lys Lys Glu Glu Tyr Lys Met Ala Leu Tyr Asn Leu Tyr
    1985                1990                1995

Pro Gly Val Phe Glu Thr Val Glu Met Leu Pro Ser Lys Ala Gly
    2000                2005                2010

Ile Trp Arg Val Glu Cys Leu Ile Gly Glu His Leu His Ala Gly
    2015                2020                2025

Met Ser Thr Leu Phe Leu Val Tyr Ser Asn Lys Cys Gln Thr Pro
    2030                2035                2040

Leu Gly Met Ala Ser Gly His Ile Arg Asp Phe Gln Ile Thr Ala
    2045                2050                2055

Ser Gly Gln Tyr Gly Gln Trp Ala Pro Lys Leu Ala Arg Leu His
    2060                2065                2070

Tyr Ser Gly Ser Ile Asn Ala Trp Ser Thr Lys Glu Pro Phe Ser
    2075                2080                2085

Trp Ile Lys Val Asp Leu Leu Ala Pro Met Ile Ile His Gly Ile
    2090                2095                2100

Lys Thr Gln Gly Ala Arg Gln Lys Phe Ser Ser Leu Tyr Ile Ser
    2105                2110                2115
```

-continued

```
Gln Phe Ile Ile Met Tyr Ser Leu Asp Gly Lys Lys Trp Gln Thr
    2120                2125                2130

Tyr Arg Gly Asn Ser Thr Gly Thr Leu Met Val Phe Phe Gly Asn
    2135                2140                2145

Val Asp Ser Ser Gly Ile Lys His Asn Ile Phe Asn Pro Pro Ile
    2150                2155                2160

Ile Ala Arg Tyr Ile Arg Leu His Pro Thr His Tyr Ser Ile Arg
    2165                2170                2175

Ser Thr Leu Arg Met Glu Leu Met Gly Cys Asp Leu Asn Ser Cys
    2180                2185                2190

Ser Met Pro Leu Gly Met Glu Ser Lys Ala Ile Ser Asp Ala Gln
    2195                2200                2205

Ile Thr Ala Ser Ser Tyr Phe Thr Asn Met Phe Ala Thr Trp Ser
    2210                2215                2220

Pro Ser Lys Ala Arg Leu His Leu Gln Gly Arg Ser Asn Ala Trp
    2225                2230                2235

Arg Pro Gln Val Asn Asn Pro Lys Glu Trp Leu Gln Val Asp Phe
    2240                2245                2250

Gln Lys Thr Met Lys Val Thr Gly Ile Thr Thr Gln Gly Val Lys
    2255                2260                2265

Ser Leu Leu Thr Ser Met Tyr Val Lys Glu Phe Leu Ile Ser Ser
    2270                2275                2280

Ser Gln Asp Gly His His Trp Thr Leu Phe Phe Gln Asn Gly Lys
    2285                2290                2295

Val Lys Val Phe Gln Gly Asn Gln Asp Ser Phe Thr Pro Val Val
    2300                2305                2310

Asn Ser Leu Asp Pro Pro Leu Leu Thr Arg Tyr Leu Arg Ile His
    2315                2320                2325

Pro Gln Ser Trp Val His Gln Ile Ala Leu Arg Met Glu Val Leu
    2330                2335                2340

Gly Cys Glu Ala Gln Asp Leu Tyr
    2345                2350
```

<210> SEQ ID NO 33
<211> LENGTH: 2360
<212> TYPE: PRT
<213> ORGANISM: artificial sequence
<220> FEATURE:
<223> OTHER INFORMATION: ancestral

<400> SEQUENCE: 33

```
Met Gln Ile Glu Leu Ser Thr Cys Phe Phe Leu Cys Leu Leu Gln Phe
1               5                   10                  15

Ser Phe Ser Ala Thr Arg Arg Tyr Tyr Leu Gly Ala Val Glu Leu Ser
            20                  25                  30

Trp Asp Tyr Met Gln Ser Asp Leu Leu Ser Glu Leu His Val Asp Thr
        35                  40                  45

Arg Phe Pro Pro Arg Met Pro Arg Ser Phe Pro Phe Asn Thr Ser Val
    50                  55                  60

Met Tyr Lys Lys Thr Val Phe Val Glu Phe Thr Asp His Leu Phe Asn
65                  70                  75                  80

Ile Ala Lys Pro Arg Pro Pro Trp Met Gly Leu Leu Gly Pro Thr Ile
                85                  90                  95

Trp Ala Glu Val Tyr Asp Thr Val Val Ile Thr Leu Lys Asn Met Ala
            100                 105                 110
```

```
Ser His Pro Val Ser Leu His Ala Val Gly Val Ser Tyr Trp Lys Ala
        115                 120                 125
Ser Glu Gly Ala Glu Tyr Asp Asp Gln Thr Ser Gln Arg Gly Lys Glu
130                 135                 140
Asp Asp Lys Val Phe Pro Gly Glu Ser His Thr Tyr Val Trp Gln Val
145                 150                 155                 160
Leu Lys Glu Asn Gly Pro Met Ala Ser Asp Pro Pro Cys Leu Thr Tyr
                165                 170                 175
Ser Tyr Leu Ser His Val Asp Leu Val Lys Asp Leu Asn Ser Gly Leu
            180                 185                 190
Ile Gly Ala Leu Leu Val Cys Arg Glu Gly Ser Leu Ala Lys Glu Arg
        195                 200                 205
Thr Gln Met Leu His Gln Phe Val Leu Leu Phe Ala Val Phe Asp Glu
    210                 215                 220
Gly Lys Ser Trp His Ser Glu Thr Lys Gly Ser Leu Thr Gln Ala Met
225                 230                 235                 240
Asp Ser Ala Ser Ala Arg Ala Trp Pro Lys Met His Thr Val Asn Gly
                245                 250                 255
Tyr Val Asn Arg Ser Leu Pro Gly Leu Ile Gly Cys His Arg Lys Ser
            260                 265                 270
Val Tyr Trp His Val Ile Gly Met Gly Thr Thr Pro Glu Val His Ser
        275                 280                 285
Ile Phe Leu Glu Gly His Thr Phe Leu Val Arg Asn His Arg Gln Ala
    290                 295                 300
Ser Leu Glu Ile Ser Pro Ile Thr Phe Leu Thr Ala Gln Thr Leu Leu
305                 310                 315                 320
Met Asp Leu Gly Gln Phe Leu Leu Phe Cys His Ile Ser Ser His Gln
                325                 330                 335
His Asp Gly Met Glu Ala Tyr Val Lys Val Asp Ser Cys Pro Glu Glu
            340                 345                 350
Pro Gln Leu Arg Met Lys Asn Asn Glu Glu Glu Asp Tyr Asp Asp
        355                 360                 365
Asp Leu Leu Asp Ser Glu Met Asp Val Phe Arg Phe Asp Asp Asp Asn
    370                 375                 380
Ser Pro Pro Phe Ile Gln Ile Arg Ser Val Ala Lys Lys His Pro Lys
385                 390                 395                 400
Thr Trp Ile His Tyr Ile Ala Ala Glu Glu Asp Trp Asp Tyr Ala
                405                 410                 415
Pro Ser Val Leu Thr Ser Asp Asp Arg Ser Tyr Lys Ser Gln Tyr Leu
            420                 425                 430
Asn Asn Gly Pro Gln Arg Ile Gly Arg Lys Tyr Lys Lys Val Arg Phe
        435                 440                 445
Met Ala Tyr Thr Asp Glu Thr Phe Lys Thr Arg Glu Thr Ile Gln Tyr
    450                 455                 460
Glu Ser Gly Ile Leu Gly Pro Leu Leu Tyr Gly Glu Val Gly Asp Thr
465                 470                 475                 480
Leu Leu Ile Ile Phe Lys Asn Gln Ala Ser Arg Pro Tyr Asn Ile Tyr
                485                 490                 495
Pro His Gly Ile Thr Asp Val Ser Pro Leu His Ser Gly Arg Leu Pro
            500                 505                 510
Lys Gly Val Lys His Leu Lys Asp Leu Pro Ile Leu Pro Gly Glu Ile
        515                 520                 525
Phe Lys Tyr Lys Trp Thr Val Thr Val Glu Asp Gly Pro Thr Lys Ser
```

-continued

```
              530                 535                 540
Asp Pro Arg Cys Leu Thr Arg Tyr Tyr Ser Ser Phe Ile Asn Leu Glu
545                 550                 555                 560

Arg Asp Leu Ala Ser Gly Leu Ile Gly Pro Leu Leu Ile Cys Tyr Lys
                    565                 570                 575

Glu Ser Val Asp Gln Arg Gly Asn Gln Met Met Ser Asp Lys Arg Asn
                580                 585                 590

Val Ile Leu Phe Ser Val Phe Asp Glu Asn Arg Ser Trp Tyr Leu Thr
                595                 600                 605

Glu Asn Met Gln Arg Phe Leu Pro Asn Ala Ala Gly Val Gln Pro Gln
            610                 615                 620

Asp Pro Glu Phe Gln Ala Ser Asn Ile Met His Ser Ile Asn Gly Tyr
625                 630                 635                 640

Val Phe Asp Ser Leu Gln Leu Ser Val Cys Leu His Glu Val Ala Tyr
                    645                 650                 655

Trp Tyr Ile Leu Ser Val Gly Ala Gln Thr Asp Phe Leu Ser Val Phe
                    660                 665                 670

Phe Ser Gly Tyr Thr Phe Lys His Lys Met Val Tyr Glu Asp Thr Leu
                675                 680                 685

Thr Leu Phe Pro Phe Ser Gly Glu Thr Val Phe Met Ser Met Glu Asn
            690                 695                 700

Pro Gly Leu Trp Val Leu Gly Cys His Asn Ser Asp Phe Arg Asn Arg
705                 710                 715                 720

Gly Met Thr Ala Leu Leu Lys Val Ser Ser Cys Asp Arg Asn Thr Gly
                    725                 730                 735

Asp Tyr Tyr Glu Asp Thr Tyr Glu Asp Ile Pro Thr Tyr Leu Leu Ser
                740                 745                 750

Glu Asn Asn Val Ile Glu Pro Arg Ser Phe Ser Gln Asn Ser Arg His
                755                 760                 765

Pro Ser Thr Arg Gln Lys Gln Phe Lys Ala Thr Thr Ile Pro Glu Asn
770                 775                 780

Asp Ile Glu Lys Ile Asp Pro Gln Phe Gly Glu Arg Thr Gln Met Leu
785                 790                 795                 800

Lys Val Gln Ser Val Ser Ser Asp Leu Leu Met Leu Leu Gly Gln
                    805                 810                 815

Ser Pro Thr Pro His Gly Leu Ser Leu Ser Asp Leu Gln Glu Ala Thr
                820                 825                 830

Tyr Glu Ala Ile Pro Asp Asp His Ser Pro Gly Ala Ile Asp Ser Asn
                835                 840                 845

Glu Gly Pro Ser Glu Val Ala His Leu Arg Pro Glu Leu His His Ser
850                 855                 860

Gly Asp Ile Val Phe Thr Pro Glu Pro Gly Leu Gln Leu Arg Leu Asn
865                 870                 875                 880

Glu Asn Leu Gly Thr Thr Ile Ala Val Glu Leu Lys Lys Leu Asp Leu
                    885                 890                 895

Lys Val Ser Ser Ser Pro Asn Asn Leu Met Thr Ser Pro Thr Ile Pro
                900                 905                 910

Ser Asp Asn Leu Ala Ala Gly Thr Glu Lys Thr Gly Ser Leu Gly Pro
                915                 920                 925

Pro Asn Met Pro Val His Phe Ser Ser Gln Leu Ser Thr Thr Val Phe
            930                 935                 940

Gly Lys Lys Ser Ser Pro Leu Ile Gly Ser Gly Val Pro Leu Asn Leu
945                 950                 955                 960
```

```
Ser Glu Arg Asn Asn Asp Ser Lys Leu Leu Glu Ala Ala Leu Met Asn
                965                 970                 975

Ser Gln Glu Ser Ser Leu Gly Lys Asn Val Ser Ser Met Glu Ser Asp
            980                 985                 990

Arg Leu Phe Lys Glu Lys Arg Val His Gly Pro Ala Leu Leu Thr Lys
        995                1000                1005

Asp Asn Ala Leu Phe Lys Val Asn Ile Ser Leu Ile Lys Thr Asn
   1010                1015                1020

Lys Thr Ser Asn Asn Ser Thr Thr Asn Arg Lys Thr His Ile Asp
   1025                1030                1035

Gly Pro Thr Leu Leu Ile Glu Asn Ser Thr Ser Val Trp Gln Asp
   1040                1045                1050

Thr Ile Leu Glu Ser Asp Glu Phe Gln Glu Val Thr Ser Leu
   1055                1060                1065

Ile His Asp Glu Met Leu Met Asp Lys Asn Thr Thr Ala Leu Arg
   1070                1075                1080

Leu Asn His Val Ser Asn Lys Thr Thr Ser Ser Lys Asn Met Glu
   1085                1090                1095

Met Val His Gln Lys Lys Glu Gly Pro Val Pro Pro Asp Ala Glu
   1100                1105                1110

Asn Pro Asp Met Ser Phe Phe Lys Met Leu Phe Leu Pro Glu Ser
   1115                1120                1125

Ala Asn Trp Ile Lys Arg Thr His Gly Lys Asn Ser Leu Asn Ser
   1130                1135                1140

Gly Gln Gly Pro Ser Pro Lys Gln Leu Ile Ser Leu Gly Ser Glu
   1145                1150                1155

Lys Ser Val Lys Asp Gln Asn Phe Leu Ser Glu Lys Asn Lys Val
   1160                1165                1170

Val Val Gly Glu Asp Glu Phe Thr Lys Asp Thr Gly Leu Lys Glu
   1175                1180                1185

Met Ile Phe Pro Asn Asn Arg Ser Ile Phe Leu Thr Asn Leu Ala
   1190                1195                1200

Asn Val Gln Glu Asn Asp Thr His Asn Gln Glu Lys Lys Phe Gln
   1205                1210                1215

Glu Glu Ile Glu Arg Lys Glu Ala Leu Ile Gln Glu Asn Val Val
   1220                1225                1230

Leu Pro Gln Val Tyr Thr Val Thr Gly Thr Lys Asn Phe Leu Lys
   1235                1240                1245

Asn Leu Phe Leu Leu Ser Thr Arg Gln Asn Ile Gly Leu Asp Glu
   1250                1255                1260

Gly Thr Tyr Ala Pro Val Leu Gln Asp Thr Arg Ser Leu Asn Asp
   1265                1270                1275

Ser Thr Asn Arg Ala Glu Ile His Met Ala His Phe Ser Lys Arg
   1280                1285                1290

Arg Glu Glu Glu Thr Asn Leu Glu Gly Leu Gly Asn Gln Thr
   1295                1300                1305

Lys Gln Met Val Glu Lys Tyr Pro Ser Thr Thr Arg Met Ser Pro
   1310                1315                1320

Asn Pro Ser Gln Gln Asn Val Ile Thr Gln Arg Gly Lys Arg Ala
   1325                1330                1335

Leu Lys Gln Phe Arg Leu Pro Leu Glu Glu Thr Glu Leu Glu Lys
   1340                1345                1350
```

```
Gly Leu Ile Val Asp Asp Thr Ser Thr Gln Trp Ser Lys Asn Met
    1355                1360                1365

Lys Tyr Leu Thr Gln Ser Thr Leu Thr Gln Ile Asp Tyr Asn Glu
    1370                1375                1380

Lys Glu Lys Lys Ala Ile Thr Gln Ser Pro Leu Ser Asp Ser Pro
    1385                1390                1395

Met Arg Asn His Ser Ile Thr Gln Met Asn Ser Ser Ala Leu Pro
    1400                1405                1410

Ile Ala Lys Ile Ser Ala Phe Pro Ser Ile Arg Pro Thr Asp Leu
    1415                1420                1425

Thr Lys Ile Pro Ser Gln Asp Asn Ser Ser His Phe Leu Ala Ser
    1430                1435                1440

Ala Tyr Asn Tyr Thr Phe Arg Glu Lys Ser Ser Gly Val Gln Glu
    1445                1450                1455

Ser Ser His Phe Leu Gln Gly Ala Lys Arg Asn Asn Leu Ser Leu
    1460                1465                1470

Ala Ile Leu Pro Leu Glu Met Ile Arg Asn Gln Glu Lys Val Gly
    1475                1480                1485

Ser Leu Gly Thr Ser Ala Thr Asn Ser Val Met Tyr Lys Lys Leu
    1490                1495                1500

Glu Asn Thr Val Leu Leu Lys Pro Gly Leu Pro Glu Ala Ser Gly
    1505                1510                1515

Lys Val Glu Leu Leu Pro Lys Val Pro Ile His Gln Glu Asp Leu
    1520                1525                1530

Phe Pro Thr Glu Thr Ser His Gly Ser Pro Gly His Leu Asp Leu
    1535                1540                1545

Met Glu Glu Ile Leu Leu Gln Lys Thr Gln Gly Ala Ile Lys Trp
    1550                1555                1560

Asn Lys Thr Asn Arg Pro Gly Lys Val Pro Phe Leu Lys Gly Ala
    1565                1570                1575

Thr Glu Ser Ser Glu Lys Thr Pro Ser Lys Leu Leu Gly Pro Leu
    1580                1585                1590

Ala Trp Asp Asn Gln Tyr Ala Thr Gln Ile Pro Lys Glu Glu Trp
    1595                1600                1605

Lys Ser Gln Glu Lys Ser Pro Lys Asn Thr Ala Phe Lys Thr Lys
    1610                1615                1620

Asp Thr Ile Leu Ser Leu Asn Pro Cys Glu Asn Asn His Ala Ile
    1625                1630                1635

Ala Ala Ile Asn Glu Gly Gln Asp Arg Pro Gln Arg Glu Ala Thr
    1640                1645                1650

Trp Ala Lys Gln Gly Gly Thr Gly Arg Leu Cys Ser Gln Asn Pro
    1655                1660                1665

Pro Val Leu Lys Arg His Gln Arg Glu Ile Thr Leu Thr Thr Leu
    1670                1675                1680

Gln Ser Glu Gln Glu Glu Ile Asp Tyr Asp Asp Thr Ile Ser Ile
    1685                1690                1695

Glu Thr Lys Arg Glu Asp Phe Asp Ile Tyr Gly Glu Asp Glu Asn
    1700                1705                1710

Gln Gly Pro Arg Ser Phe Gln Lys Arg Thr Arg His Tyr Phe Ile
    1715                1720                1725

Ala Ala Val Glu Arg Leu Trp Asp Tyr Gly Met Ser Arg Ser Pro
    1730                1735                1740

His Val Leu Arg Asn Arg Asp Gln Ser Gly Ser Val Pro Gln Phe
```

```
           1745                1750                1755
Lys Lys Val Val Phe Gln Glu Phe Thr Asp Gly Ser Phe Thr Gln
       1760                1765                1770
Pro Leu Tyr Arg Gly Glu Leu Asn Glu His Leu Gly Leu Leu Gly
       1775                1780                1785
Pro Tyr Ile Arg Ala Glu Val Glu Asp Asn Ile Met Val Thr Phe
       1790                1795                1800
Lys Asn Gln Ala Ser Arg Pro Tyr Ser Phe Tyr Ser Ser Leu Ile
       1805                1810                1815
Ser Tyr Lys Glu Asp Gln Arg Gln Gly Ala Glu Pro Arg Lys Asn
       1820                1825                1830
Phe Val Lys Pro Asn Glu Thr Lys Thr Tyr Phe Trp Lys Val Gln
       1835                1840                1845
His His Met Ala Pro Thr Lys Asp Glu Phe Asp Cys Lys Ala Trp
       1850                1855                1860
Ala Tyr Phe Ser Asp Val Asp Leu Glu Lys Asp Met His Ser Gly
       1865                1870                1875
Leu Ile Gly Pro Leu Leu Ile Cys His Thr Asn Thr Leu Asn Pro
       1880                1885                1890
Ala His Gly Arg Gln Val Thr Val Gln Glu Phe Ala Leu Phe Phe
       1895                1900                1905
Thr Ile Phe Asp Glu Thr Lys Ser Trp Tyr Phe Thr Glu Asn Met
       1910                1915                1920
Glu Arg Asn Cys Arg Ala Pro Cys Asn Ile Gln Met Glu Asp Pro
       1925                1930                1935
Thr Phe Lys Glu Asn Tyr Arg Phe His Ala Ile Asn Gly Tyr Val
       1940                1945                1950
Met Asp Thr Leu Pro Gly Leu Val Met Ala Gln Asp Gln Arg Ile
       1955                1960                1965
Arg Trp Tyr Leu Leu Ser Met Gly Ser Asn Glu Asn Ile His Ser
       1970                1975                1980
Ile His Phe Ser Gly His Val Phe Thr Val Arg Lys Lys Glu Glu
       1985                1990                1995
Tyr Lys Met Ala Val Tyr Asn Leu Tyr Pro Gly Val Phe Glu Thr
       2000                2005                2010
Val Glu Met Leu Pro Ser Lys Ala Gly Ile Trp Arg Val Glu Cys
       2015                2020                2025
Leu Ile Gly Glu His Leu His Ala Gly Met Ser Thr Leu Phe Leu
       2030                2035                2040
Val Tyr Ser Lys Gln Cys Gln Ile Pro Leu Gly Met Ala Ser Gly
       2045                2050                2055
His Ile Arg Asp Phe Gln Ile Thr Ala Ser Gly Gln Tyr Gly Gln
       2060                2065                2070
Trp Ala Pro Lys Leu Ala Arg Leu His Tyr Ser Gly Ser Ile Asn
       2075                2080                2085
Ala Trp Ser Thr Lys Glu Pro Phe Ser Trp Ile Lys Val Asp Leu
       2090                2095                2100
Leu Ala Pro Met Ile Ile His Gly Ile Lys Thr Gln Gly Ala Arg
       2105                2110                2115
Gln Lys Phe Ser Ser Leu Tyr Ile Ser Gln Phe Ile Ile Met Tyr
       2120                2125                2130
Ser Leu Asp Gly Lys Lys Trp Gln Thr Tyr Arg Gly Asn Ser Thr
       2135                2140                2145
```

```
Gly Thr Leu Met Val Phe Phe Gly Asn Val Asp Ser Ser Gly Ile
    2150                2155                2160

Lys His Asn Ile Phe Asn Pro Pro Ile Ile Ala Arg Tyr Ile Arg
    2165                2170                2175

Leu His Pro Thr His Tyr Ser Ile Arg Ser Thr Leu Arg Met Glu
    2180                2185                2190

Leu Met Gly Cys Asp Leu Asn Ser Cys Ser Met Pro Leu Gly Met
    2195                2200                2205

Glu Ser Lys Ala Ile Ser Asp Ala Gln Ile Thr Ala Ser Ser Tyr
    2210                2215                2220

Phe Thr Asn Met Phe Ala Thr Trp Ser Pro Ser Gln Ala Arg Leu
    2225                2230                2235

His Leu Gln Gly Arg Thr Asn Ala Trp Arg Pro Gln Val Asn Asn
    2240                2245                2250

Pro Lys Glu Trp Leu Gln Val Asp Phe Gln Lys Thr Met Lys Val
    2255                2260                2265

Thr Gly Ile Ile Thr Gln Gly Val Lys Ser Leu Leu Thr Ser Met
    2270                2275                2280

Phe Val Lys Glu Phe Leu Ile Ser Ser Ser Gln Asp Gly His His
    2285                2290                2295

Trp Thr Leu Phe Leu Gln Asn Gly Lys Val Lys Val Phe Gln Gly
    2300                2305                2310

Asn Gln Asp Ser Phe Thr Pro Val Val Asn Ser Leu Asp Pro Pro
    2315                2320                2325

Leu Leu Thr Arg Tyr Leu Arg Ile His Pro Gln Ser Trp Val His
    2330                2335                2340

Gln Ile Ala Leu Arg Leu Glu Val Leu Gly Cys Glu Ala Gln Gln
    2345                2350                2355

Leu Tyr
    2360

<210> SEQ ID NO 34
<211> LENGTH: 2357
<212> TYPE: PRT
<213> ORGANISM: artificial sequence
<220> FEATURE:
<223> OTHER INFORMATION: ancestral

<400> SEQUENCE: 34

Met Gln Ile Glu Leu Ser Thr Cys Phe Phe Leu Cys Leu Leu Pro Phe
1               5                   10                  15

Ser Phe Ser Ala Thr Arg Arg Tyr Tyr Leu Gly Ala Val Glu Leu Ser
                20                  25                  30

Trp Asp Tyr Met Gln Ser Glu Leu Ser Glu Leu His Val Asp Thr
        35                  40                  45

Arg Phe Pro Pro Arg Val Pro Arg Ser Phe Pro Phe Asn Thr Ser Val
    50                  55                  60

Met Tyr Lys Lys Thr Val Phe Val Glu Phe Thr Asp His Leu Phe Asn
65                  70                  75                  80

Ile Ala Lys Pro Arg Pro Pro Trp Met Gly Leu Leu Gly Pro Thr Ile
                85                  90                  95

Arg Ala Glu Val Tyr Asp Thr Val Val Ile Thr Leu Lys Asn Met Ala
                100                 105                 110

Ser His Pro Val Ser Leu His Ala Val Gly Val Ser Tyr Trp Lys Ala
            115                 120                 125
```

```
Ser Glu Gly Ala Glu Tyr Glu Asp Gln Thr Ser Gln Arg Glu Lys Glu
    130                 135                 140

Asp Asp Lys Val Ile Pro Gly Glu Ser His Thr Tyr Val Trp Gln Val
145                 150                 155                 160

Leu Lys Glu Asn Gly Pro Met Ala Ser Asp Pro Pro Cys Leu Thr Tyr
                165                 170                 175

Ser Tyr Leu Ser His Val Asp Leu Val Lys Asp Leu Asn Ser Gly Leu
            180                 185                 190

Ile Gly Ala Leu Leu Val Cys Arg Glu Gly Ser Leu Ala Lys Glu Arg
        195                 200                 205

Thr Gln Thr Leu His Glu Phe Val Leu Leu Phe Ala Val Phe Asp Glu
    210                 215                 220

Gly Lys Ser Trp His Ser Glu Thr Asn Glu Ser Leu Thr Gln Ala Met
225                 230                 235                 240

Asp Pro Ala Ser Ala Arg Ala Gln Pro Glu Met His Thr Val Asn Gly
                245                 250                 255

Tyr Val Asn Arg Ser Leu Pro Gly Leu Ile Gly Cys His Lys Lys Ser
            260                 265                 270

Val Tyr Trp His Val Ile Gly Met Gly Thr Thr Pro Glu Val His Ser
        275                 280                 285

Ile Phe Leu Glu Gly His Thr Phe Leu Val Arg Asn His Arg Gln Ala
    290                 295                 300

Ser Leu Glu Ile Ser Pro Ile Thr Phe Leu Thr Ala Gln Thr Leu Leu
305                 310                 315                 320

Met Asp Leu Gly Gln Phe Leu Leu Phe Cys His Ile Ser Ser His Gln
                325                 330                 335

His Asp Gly Met Glu Ala Tyr Val Lys Val Asp Ser Cys Pro Glu Glu
            340                 345                 350

Pro Gln Leu Arg Met Lys Asn Asn Glu Glu Glu Glu Asp Tyr Asp Asp
        355                 360                 365

Asp Leu Tyr Asp Ser Asp Met Asp Val Val Arg Phe Asp Asp Asp Asn
    370                 375                 380

Ser Pro Pro Phe Ile Gln Ile Arg Ser Val Ala Lys Lys His Pro Lys
385                 390                 395                 400

Thr Trp Val His Tyr Ile Ala Ala Glu Glu Glu Asp Trp Asp Tyr Ala
                405                 410                 415

Pro Ser Val Leu Thr Pro Asn Asp Arg Ser Tyr Lys Ser Leu Tyr Leu
            420                 425                 430

Asn Asn Gly Pro Gln Arg Ile Gly Arg Lys Tyr Lys Lys Val Arg Phe
        435                 440                 445

Met Ala Tyr Thr Asp Glu Thr Phe Lys Thr Arg Glu Ala Ile Gln Tyr
    450                 455                 460

Glu Ser Gly Ile Leu Gly Pro Leu Leu Tyr Gly Glu Val Gly Asp Thr
465                 470                 475                 480

Leu Leu Ile Ile Phe Lys Asn Gln Ala Ser Arg Pro Tyr Asn Ile Tyr
                485                 490                 495

Pro His Gly Ile Thr Asp Val Ser Pro Leu His Ser Gly Arg Leu Pro
            500                 505                 510

Lys Gly Val Lys His Leu Lys Asp Met Pro Ile Leu Pro Gly Glu Ile
        515                 520                 525

Phe Lys Tyr Lys Trp Thr Val Thr Val Glu Asp Gly Pro Thr Lys Ser
    530                 535                 540
```

-continued

```
Asp Pro Arg Cys Leu Thr Arg Tyr Tyr Ser Ser Phe Val Asn Leu Glu
545                 550                 555                 560

Arg Asp Leu Ala Ser Gly Leu Ile Gly Pro Leu Leu Ile Cys Tyr Lys
                565                 570                 575

Glu Ser Val Asp Gln Arg Gly Asn Gln Met Met Ser Asp Lys Arg Asn
            580                 585                 590

Val Ile Leu Phe Ser Val Phe Asp Glu Asn Arg Ser Trp Tyr Leu Thr
        595                 600                 605

Glu Asn Met Gln Arg Phe Leu Pro Asn Ala Asp Gly Val Gln Pro Gln
    610                 615                 620

Asp Pro Glu Phe Gln Val Ser Asn Ile Met His Ser Ile Asn Gly Tyr
625                 630                 635                 640

Val Phe Asp Ser Leu Gln Leu Ser Val Cys Leu His Glu Val Ala Tyr
                645                 650                 655

Trp Tyr Ile Leu Ser Val Gly Ala Gln Thr Asp Phe Leu Ser Val Phe
                660                 665                 670

Phe Ser Gly Tyr Thr Phe Lys His Lys Met Val Tyr Glu Asp Thr Leu
            675                 680                 685

Thr Leu Phe Pro Phe Ser Gly Glu Thr Val Phe Met Ser Met Glu Asn
        690                 695                 700

Pro Gly Leu Trp Val Leu Gly Cys His Asn Ser Asp Phe Arg Asn Arg
705                 710                 715                 720

Gly Met Thr Ala Leu Leu Lys Val Ser Ser Cys Asp Arg Asn Thr Gly
                725                 730                 735

Asp Tyr Tyr Glu Asp Thr Tyr Glu Asp Ile Pro Thr Ser Leu Leu Asn
            740                 745                 750

Glu Asn Asn Val Ile Glu Pro Arg Ser Phe Ser Gln Asn Ser Arg His
        755                 760                 765

Pro Ser Thr Arg Gln Lys Gln Phe Lys Ala Thr Thr Thr Pro Glu Asn
    770                 775                 780

Asp Ile Glu Lys Ile Asp Pro Gln Ser Gly Glu Arg Thr Gln Leu Leu
785                 790                 795                 800

Lys Val Gln Ser Val Ser Ser Asp Leu Leu Met Leu Leu Gly Gln
                805                 810                 815

Asn Pro Thr Pro His Gly Leu Ser Leu Ser Asp Leu Gln Glu Ala Thr
            820                 825                 830

Tyr Glu Ala Asp Asp His Leu Pro Gly Ala Ile Glu Arg Asn Lys Gly
        835                 840                 845

Pro Ser Glu Val Ala His Leu Arg Pro Glu Leu His His Ser Gly Asp
    850                 855                 860

Arg Val Phe Thr Pro Glu Pro Glu Leu Gln Leu Arg Leu Asn Glu Asn
865                 870                 875                 880

Leu Gly Thr Thr Ile Thr Val Glu Leu Lys Lys Leu Asp Leu Lys Ile
                885                 890                 895

Ser Ser Ser Ser Asn Asn Leu Met Thr Ser Pro Thr Ile Pro Ser Asp
            900                 905                 910

Lys Leu Ala Ala Gly Thr Glu Lys Thr Gly Ser Leu Gly Pro Pro Asn
        915                 920                 925

Met Pro Val His Phe Ser Ser Gln Leu Gly Thr Ile Val Phe Gly Lys
    930                 935                 940

Asn Ser Ser His Leu Ile Gly Ser Gly Val Pro Leu Gly Leu Ser Glu
945                 950                 955                 960

Gly Asp Asn Asp Ser Lys Leu Leu Glu Ala Ala Leu Met Asn Ser Gln
```

-continued

```
                965                 970                 975
Glu Ser Ser Leu Gly Glu Asn Val Leu Ser Met Glu Ser Asp Arg Leu
                    980                 985                 990
Phe Lys Glu Glu Arg Val His Gly Pro Ala Ser Leu Thr Lys Asp Asn
        995                 1000                1005
Ala Leu Phe Lys Val Asn Ile Ser Leu Val Lys Thr Asn Lys Ala
    1010                1015                1020
Pro Ile Asn Ser Thr Thr Asn Arg Lys Thr His Ile Asp Gly Pro
    1025                1030                1035
Thr Leu Leu Ile Glu Asn Ser Thr Ser Val Trp Gln Asp Ile Ile
    1040                1045                1050
Leu Glu Ser Asn Thr Glu Phe Gln Glu Val Thr Ser Leu Ile His
    1055                1060                1065
Asp Glu Thr Phe Met Asp Lys Asn Thr Thr Ala Leu Gly Leu Asn
    1070                1075                1080
His Val Ser Asn Lys Thr Thr Ser Ser Lys Asn Met Glu Met Val
    1085                1090                1095
His Gln Lys Lys Glu Gly Pro Val Pro Leu Gly Ala Glu Asn Pro
    1100                1105                1110
Asp Thr Ser Phe Phe Lys Met Leu Phe Leu Pro Asp Ser Ala Asn
    1115                1120                1125
Trp Ile Lys Arg Thr His Gly Lys Asn Ser Leu Ser Ser Gly Gln
    1130                1135                1140
Arg Pro Ser Pro Lys Gln Leu Thr Ser Leu Gly Ser Glu Lys Ser
    1145                1150                1155
Val Lys Asp Gln Asn Phe Leu Ser Glu Lys Asn Lys Val Val Val
    1160                1165                1170
Gly Glu Asp Glu Phe Thr Lys Asp Thr Gly Leu Lys Glu Met Ile
    1175                1180                1185
Phe Pro Asn Ser Lys Ser Ile Phe Leu Thr Asn Leu Ala Asn Val
    1190                1195                1200
Gln Glu Asn Asp Thr His Asn Gln Glu Lys Lys Ser Gln Glu Glu
    1205                1210                1215
Ile Glu Arg Lys Glu Lys Leu Ile Gln Glu Asn Val Val Leu Pro
    1220                1225                1230
Gln Val Tyr Thr Val Thr Gly Thr Lys Asn Phe Leu Lys Asn Leu
    1235                1240                1245
Phe Leu Leu Ser Thr Lys Gln Asn Val Glu Gly Leu Asp Glu Gly
    1250                1255                1260
Thr Tyr Thr Pro Ile Leu Gln Asp Thr Arg Ser Leu Asn Asp Ser
    1265                1270                1275
Ala Asn Arg Ala Gly Ile His Met Ala His Phe Ser Lys Ile Arg
    1280                1285                1290
Glu Glu Ala Asn Leu Glu Gly Leu Gly Asn Gln Thr Lys Gln Met
    1295                1300                1305
Val Glu Lys Tyr Pro Ser Thr Thr Arg Met Ser Pro Asn Pro Ser
    1310                1315                1320
Gln Gln Asn Val Ile Thr Gln Arg Gly Lys Arg Ala Leu Lys Gln
    1325                1330                1335
Phe Arg Leu Pro Leu Glu Glu Ile Lys Leu Glu Arg Gly Val Ile
    1340                1345                1350
Leu Asn Asp Thr Ser Thr Gln Trp Ser Lys Asn Met Lys Tyr Leu
    1355                1360                1365
```

```
Thr Gln Gly Thr Leu Thr Gln Ile Glu Tyr Asn Glu Lys Glu Lys
    1370            1375                1380

Arg Ala Ile Thr Gln Ser Leu Leu Ser Asp Cys Ser Met Arg Ser
    1385            1390                1395

His Gly Ile Ile Gln Thr Asn Gly Ser Ala Leu Pro Ile Ala Lys
    1400            1405                1410

Val Ser Ala Phe Pro Ser Ile Arg Pro Thr Asp Leu Thr Lys Ile
    1415            1420                1425

Pro Ser Gln Asp Asn Ser Ser His Leu Leu Ala Ser Ala Cys Ser
    1430            1435                1440

Tyr Thr Phe Arg Glu Arg Ser Ser Gly Val Gln Glu Ser Ser His
    1445            1450                1455

Phe Leu Gln Gly Ala Lys Arg Asn Asn Leu Ser Leu Ala Phe Leu
    1460            1465                1470

Thr Leu Glu Met Ile Arg Gly Gln Glu Lys Ile Ser Ser Leu Gly
    1475            1480                1485

Lys Ser Ala Thr Asn Pro Leu Met Tyr Lys Lys Leu Glu Asn Thr
    1490            1495                1500

Val Leu Leu Lys Pro Gly Leu Ser Glu Ala Ser Gly Lys Val Glu
    1505            1510                1515

Leu Leu Pro Lys Val His Val His Gln Glu Asp Ser Phe Pro Thr
    1520            1525                1530

Lys Thr Ser Asn Gly Ser Pro Gly His Leu Asp Leu Met Glu Glu
    1535            1540                1545

Ile Phe Leu Gln Lys Thr Gln Gly Pro Val Lys Leu Asn Lys Val
    1550            1555                1560

Asn Arg Pro Gly Lys Val Pro Phe Leu Lys Trp Ala Thr Glu Ser
    1565            1570                1575

Ser Glu Lys Thr Pro Ser Lys Leu Leu Gly Pro Leu Ala Trp Asp
    1580            1585                1590

Asn Gln Tyr Ala Thr Gln Ile Pro Arg Glu Glu Trp Lys Ser Gln
    1595            1600                1605

Glu Lys Ser Gln Lys Asn Thr Ala Phe Lys Thr Lys Asp Thr Ile
    1610            1615                1620

Leu Pro Leu Asp Pro Cys Glu Asn Asn His Ser Ile Ala Ala Ile
    1625            1630                1635

Asn Glu Gly Gln Asp Lys Pro Gln Arg Glu Ala Thr Trp Ala Lys
    1640            1645                1650

Gln Gly Gly Thr Gly Arg Leu Cys Ser Gln Asn Pro Pro Val Leu
    1655            1660                1665

Lys Arg His Gln Arg Glu Ile Thr Leu Thr Thr Leu Gln Pro Glu
    1670            1675                1680

Glu Asp Lys Ile Asp Tyr Asp Thr Phe Ser Ile Glu Thr Lys
    1685            1690                1695

Arg Glu Asp Phe Asp Ile Tyr Gly Glu Asp Glu Asn Gln Gly Pro
    1700            1705                1710

Arg Ser Phe Gln Lys Arg Thr Arg His Tyr Phe Ile Ala Ala Val
    1715            1720                1725

Glu Arg Leu Trp Asp Tyr Gly Met Ser Arg Ser Pro His Ala Leu
    1730            1735                1740

Arg Asn Arg Ala Gln Ser Gly Ser Val Pro Gln Phe Lys Lys Val
    1745            1750                1755
```

```
Val Phe Gln Glu Phe Thr Asp Gly Ser Phe Thr Gln Pro Leu Tyr
1760                1765                1770

Arg Gly Glu Leu Asn Glu His Leu Gly Leu Leu Gly Pro Tyr Ile
1775                1780                1785

Arg Ala Glu Val Glu Asp Asn Ile Met Val Thr Phe Lys Asn Gln
1790                1795                1800

Ala Ser Arg Pro Tyr Ser Phe Tyr Ser Ser Leu Ile Ser Tyr Glu
1805                1810                1815

Glu Asp Gln Arg Gln Gly Ala Glu Pro Arg Lys Lys Phe Val Lys
1820                1825                1830

Pro Asn Glu Thr Lys Ile Tyr Phe Trp Lys Val Gln His His Met
1835                1840                1845

Ala Pro Thr Lys Asp Glu Phe Asp Cys Lys Ala Trp Ala Tyr Phe
1850                1855                1860

Ser Asp Val Asp Leu Glu Lys Asp Met His Ser Gly Leu Ile Gly
1865                1870                1875

Pro Leu Leu Ile Cys Arg Thr Asn Thr Leu Asn Pro Ala His Gly
1880                1885                1890

Arg Gln Val Thr Val Gln Glu Phe Ala Leu Phe Phe Thr Ile Phe
1895                1900                1905

Asp Glu Thr Lys Ser Trp Tyr Phe Thr Glu Asn Met Glu Arg Asn
1910                1915                1920

Cys Arg Ala Pro Cys Asn Ile Gln Met Glu Asp Pro Thr Phe Lys
1925                1930                1935

Glu Asn Tyr Arg Phe His Ala Ile Asn Gly Tyr Val Met Asp Thr
1940                1945                1950

Leu Pro Gly Leu Val Met Ala Gln Asp Gln Arg Ile Arg Trp Tyr
1955                1960                1965

Leu Leu Ser Met Gly Ser Asn Glu Asn Ile His Ser Ile His Phe
1970                1975                1980

Ser Gly His Val Phe Thr Val Arg Lys Lys Glu Glu Tyr Lys Met
1985                1990                1995

Ala Val Tyr Asn Leu Tyr Pro Gly Val Phe Glu Thr Val Glu Met
2000                2005                2010

Leu Pro Ser Lys Ala Gly Ile Trp Arg Ile Glu Cys Leu Ile Gly
2015                2020                2025

Glu His Leu Gln Ala Gly Met Ser Thr Leu Phe Leu Val Tyr Ser
2030                2035                2040

Lys Lys Cys Gln Thr Pro Leu Gly Met Ala Ser Gly Arg Ile Arg
2045                2050                2055

Asp Phe Gln Ile Thr Ala Ser Gly Gln Tyr Gly Gln Trp Ala Pro
2060                2065                2070

Lys Leu Ala Arg Leu His Tyr Ser Gly Ser Ile Asn Ala Trp Ser
2075                2080                2085

Thr Lys Asp Pro Phe Ser Trp Ile Lys Val Asp Leu Leu Ala Pro
2090                2095                2100

Met Ile Ile His Ser Ile Met Thr Gln Gly Ala Arg Gln Lys Phe
2105                2110                2115

Ser Ser Leu Tyr Ile Ser Gln Phe Ile Ile Met Tyr Ser Leu Asp
2120                2125                2130

Gly Lys Lys Trp Gln Ser Tyr Arg Gly Asn Ser Thr Gly Thr Leu
2135                2140                2145

Met Val Phe Phe Gly Asn Val Asp Ser Ser Gly Ile Lys His Asn
```

```
                   2150                2155                2160
Ile Phe Asn Pro Pro Ile Ile Ala Arg Tyr Ile Arg Leu His Pro
               2165                2170                2175

Thr His Tyr Ser Ile Arg Ser Thr Leu Arg Met Glu Leu Met Gly
           2180                2185                2190

Cys Asp Leu Asn Ser Cys Ser Met Pro Leu Gly Met Glu Asn Lys
       2195                2200                2205

Ala Ile Ser Asp Ala Gln Ile Thr Ala Ser Ser Tyr Leu Asn Asn
   2210                2215                2220

Met Phe Ala Thr Trp Ser Pro Ser Gln Ala Arg Leu His Leu Gln
2225                2230                2235

Gly Arg Thr Asn Ala Trp Arg Pro Gln Val Asn Asn Pro Lys Glu
       2240                2245                2250

Trp Leu Gln Val Asp Phe Gln Lys Thr Met Lys Val Thr Gly Ile
   2255                2260                2265

Thr Thr Gln Gly Val Lys Ser Leu Leu Thr Ser Met Tyr Val Lys
2270                2275                2280

Glu Phe Leu Ile Ser Ser Ser Gln Asp Gly His Asn Trp Thr Leu
       2285                2290                2295

Phe Leu Gln Asn Gly Lys Val Lys Val Phe Gln Gly Asn Gln Asp
   2300                2305                2310

Ser Phe Thr Pro Val Val Asn Ser Leu Asp Pro Pro Leu Leu Thr
2315                2320                2325

Arg Tyr Leu Arg Ile His Pro Gln Ser Trp Ala His Gln Ile Ala
       2330                2335                2340

Leu Arg Leu Glu Val Leu Gly Cys Glu Ala Gln Gln Leu Tyr
   2345                2350                2355

<210> SEQ ID NO 35
<211> LENGTH: 2357
<212> TYPE: PRT
<213> ORGANISM: artificial sequence
<220> FEATURE:
<223> OTHER INFORMATION: ancestral

<400> SEQUENCE: 35

Met Gln Ile Glu Leu Ser Thr Cys Phe Phe Leu Cys Leu Leu Pro Phe
1               5                   10                  15

Ser Phe Ser Ala Ile Arg Arg Tyr Tyr Leu Gly Ala Val Glu Leu Ser
            20                  25                  30

Trp Asp Tyr Met Gln Ser Glu Leu Leu Ser Glu Leu His Val Asp Thr
        35                  40                  45

Arg Phe Pro Pro Arg Val Pro Arg Ser Phe Pro Phe Asn Thr Ser Val
    50                  55                  60

Met Tyr Lys Lys Thr Val Phe Val Glu Phe Thr Asp Gln Leu Phe Asn
65                  70                  75                  80

Ile Ala Lys Pro Arg Pro Pro Trp Met Gly Leu Leu Gly Pro Thr Ile
                85                  90                  95

Gln Ala Glu Val Tyr Asp Thr Val Val Ile Thr Leu Lys Asn Met Ala
            100                 105                 110

Ser His Pro Val Ser Leu His Ala Val Gly Val Ser Tyr Trp Lys Ser
        115                 120                 125

Ser Glu Gly Ala Glu Tyr Glu Asp Gln Thr Ser Gln Arg Glu Lys Glu
    130                 135                 140

Asp Asp Lys Val Ile Pro Gly Lys Ser His Thr Tyr Val Trp Gln Val
```

```
            145                 150                 155                 160
Leu Lys Glu Asn Gly Pro Thr Ala Ser Asp Pro Pro Cys Leu Thr Tyr
            165                 170                 175

Ser Tyr Leu Ser His Val Asp Leu Val Lys Asp Leu Asn Ser Gly Leu
            180                 185                 190

Ile Gly Ala Leu Leu Val Cys Arg Glu Gly Ser Leu Thr Lys Glu Arg
            195                 200                 205

Thr Gln Thr Leu His Glu Phe Val Leu Leu Phe Ala Val Phe Asp Glu
            210                 215                 220

Gly Lys Ser Trp His Ser Gly Lys Asn Glu Ser Leu Thr Gln Ala Met
225                 230                 235                 240

Asp Pro Ala Ser Ala Arg Ala Gln Pro Ala Met His Thr Ile Asn Gly
            245                 250                 255

Tyr Ile Asn Arg Ser Leu Pro Gly Leu Ile Gly Cys His Lys Lys Ser
            260                 265                 270

Val Tyr Trp His Val Ile Gly Met Gly Thr Thr Pro Glu Val His Ser
            275                 280                 285

Ile Phe Leu Glu Gly His Thr Phe Leu Val Arg Asn His Arg Gln Ala
            290                 295                 300

Ser Leu Glu Ile Ser Pro Ile Thr Phe Leu Thr Ala Gln Thr Leu Leu
305                 310                 315                 320

Met Asp Leu Gly Gln Phe Leu Leu Phe Cys His Ile Ser Ser His Gln
            325                 330                 335

His Asp Gly Met Glu Ala Tyr Val Lys Val Asp Ser Cys Pro Glu Glu
            340                 345                 350

Pro Gln Leu Arg Met Lys Asn Asn Glu Glu Glu Asp Tyr Asp Asp
            355                 360                 365

Asp Leu Tyr Asp Ser Asp Met Asp Val Val Arg Phe Asp Gly Asp Asn
            370                 375                 380

Ala Pro Pro Phe Ile Gln Ile Arg Ser Val Ala Lys Lys His Pro Lys
385                 390                 395                 400

Thr Trp Val His Tyr Ile Ala Ala Glu Glu Glu Asp Trp Asp Tyr Ala
            405                 410                 415

Pro Ser Val Leu Thr Ser Asn Asp Arg Ser Tyr Lys Ser Leu Tyr Leu
            420                 425                 430

Asn Asn Gly Pro Gln Arg Ile Gly Arg Lys Tyr Lys Lys Val Arg Phe
            435                 440                 445

Ile Ala Tyr Thr Asp Glu Thr Phe Lys Thr Arg Glu Ala Ile Gln Tyr
            450                 455                 460

Glu Ser Gly Ile Leu Gly Pro Leu Leu Tyr Gly Glu Val Gly Asp Thr
465                 470                 475                 480

Leu Leu Ile Ile Phe Lys Asn Gln Ala Ser Arg Pro Tyr Asn Ile Tyr
            485                 490                 495

Pro His Gly Ile Thr Asp Val Ser Pro Leu His Ser Gly Arg Phe Pro
            500                 505                 510

Lys Gly Val Lys His Leu Lys Asp Met Pro Ile Leu Pro Gly Glu Ile
            515                 520                 525

Phe Lys Tyr Lys Trp Thr Val Thr Val Glu Asp Gly Pro Thr Lys Ser
            530                 535                 540

Asp Pro Arg Cys Leu Thr Arg Tyr Tyr Ser Ser Phe Val Asn Leu Glu
545                 550                 555                 560

Lys Asp Leu Ala Ser Gly Leu Ile Gly Pro Leu Leu Ile Cys Tyr Lys
            565                 570                 575
```

-continued

Glu Ser Val Asp Gln Arg Gly Asn Gln Met Met Ser Asp Lys Arg Asn
             580                 585                 590

Val Ile Leu Phe Ser Val Phe Asp Glu Asn Gln Ser Trp Tyr Leu Thr
             595                 600                 605

Glu Asn Ile Gln Arg Phe Leu Pro Asn Ala Asp Gly Val Gln Pro Gln
610                 615                 620

Asp Pro Glu Phe Gln Val Ser Asn Ile Met His Ser Ile Asn Gly Tyr
625                 630                 635                 640

Val Phe Asp Ser Leu Gln Leu Ser Val Cys Leu His Glu Val Ala Tyr
             645                 650                 655

Trp Tyr Ile Leu Ser Val Gly Ala Gln Thr Asp Phe Leu Ser Val Phe
             660                 665                 670

Phe Ser Gly Tyr Thr Phe Lys His Lys Met Val Tyr Glu Asp Thr Leu
             675                 680                 685

Thr Leu Phe Pro Phe Ser Gly Glu Thr Val Phe Met Ser Met Glu Asn
             690                 695                 700

Pro Gly Leu Trp Val Leu Gly Cys His Asn Ser Asp Phe Arg Asn Arg
705                 710                 715                 720

Gly Met Thr Ala Leu Leu Lys Val Tyr Ser Cys Asp Arg Asn Thr Gly
             725                 730                 735

Asp Tyr Tyr Glu Asp Thr Tyr Glu Asp Ile Pro Thr Phe Leu Leu Asn
             740                 745                 750

Glu Asn Asn Val Ile Glu Pro Arg Ser Phe Ser Gln Asn Ser Arg His
             755                 760                 765

Pro Ser Thr Arg Gln Lys Gln Phe Lys Ala Thr Thr Thr Pro Glu Asn
             770                 775                 780

Asp Ile Glu Lys Ile Asp Pro Gln Ser Gly Glu Arg Thr Gln Leu Leu
785                 790                 795                 800

Lys Glu Gln Ser Val Ser Ser Asp Leu Leu Met Leu Leu Gly Gln
                 805                 810                 815

Asn Pro Thr Pro His Gly Leu Ser Leu Ser Asp Leu Gln Glu Ala Arg
             820                 825                 830

Asn Glu Ala Asp Asp His Leu Pro Gly Ala Ile Glu Arg Asn Lys Gly
             835                 840                 845

Pro Ser Glu Val Ala His Leu Arg Pro Glu Leu His His Ser Gly Glu
850                 855                 860

Arg Val Phe Thr Pro Glu Pro Glu Leu Pro Leu Arg Leu Asn Glu Asn
865                 870                 875                 880

Leu Gly Thr Thr Ile Thr Val Glu Leu Lys Lys Leu Asp Phe Lys Ile
                 885                 890                 895

Ser Ser Ser Ser Asn Asn Leu Met Thr Ser Pro Thr Ile Pro Ser Asp
                 900                 905                 910

Lys Leu Ser Ala Gly Thr Glu Lys Thr Gly Ser Leu Gly Pro Pro Asn
             915                 920                 925

Met Pro Val Asn Phe Ser Ser Gln Leu Gly Thr Ile Val Phe Gly Lys
             930                 935                 940

Asn Ser Ser His Phe Ile Gly Ser Gly Val Pro Leu Gly Leu Ser Glu
945                 950                 955                 960

Glu Asp Asn Asp Ser Lys Leu Leu Glu Ala Ala Leu Met Asn Ser Gln
                 965                 970                 975

Glu Ser Ser Leu Gly Glu Asn Val Leu Ser Met Glu Ser Asp Arg Leu
             980                 985                 990

```
Phe Lys Glu Glu Arg Val His Gly Pro Ala Ser Leu Thr Lys Asp Asp
            995                 1000                1005

Ala Leu Phe Lys Val Asn Ile Ser Leu Val Lys Thr Asn Lys Ala
    1010                1015                1020

Pro Val Asn Ser Thr Thr Asn Arg Lys Thr His Ile Asp Asp Pro
    1025                1030                1035

Thr Leu Leu Ile Glu Asn Ser Thr Ser Val Trp Gln Asp Ile Ile
    1040                1045                1050

Leu Glu Ser Asn Thr Glu Phe Gln Glu Val Thr Ser Leu Ile His
    1055                1060                1065

Asp Glu Thr Phe Met Asp Lys Asn Thr Thr Ala Leu Gly Leu Asn
    1070                1075                1080

His Val Ser Asn Lys Thr Thr Ser Ser Lys Asn Met Glu Met Val
    1085                1090                1095

His Gln Lys Lys Glu Gly Pro Val Pro Leu Asp Ala Glu Tyr Pro
    1100                1105                1110

Asp Thr Ser Phe Phe Lys Thr Leu Phe Leu Pro Asp Ser Thr Asn
    1115                1120                1125

Trp Ile Lys Arg Thr His Gly Lys Asn Ser Leu Ser Ser Gly Gln
    1130                1135                1140

Arg Pro Ser Pro Lys Gln Leu Thr Ser Ser Gly Ser Glu Lys Ser
    1145                1150                1155

Val Lys Asp Gln Asn Phe Leu Ser Glu Lys Asn Lys Val Val Val
    1160                1165                1170

Gly Glu Asp Glu Phe Ser Lys Asp Thr Gly Leu Lys Glu Met Ile
    1175                1180                1185

Phe Pro Asn Ser Lys Ser Ile Phe Leu Thr Asn Leu Ala Asn Val
    1190                1195                1200

Gln Glu Asn Asp Thr His Asn Gln Glu Lys Lys Ser Gln Glu Glu
    1205                1210                1215

Ile Glu Arg Lys Glu Lys Leu Ile Gln Glu Asn Val Val Leu Pro
    1220                1225                1230

Gln Val Tyr Thr Val Thr Gly Thr Lys Asn Phe Leu Lys Asn Leu
    1235                1240                1245

Phe Leu Leu Ser Thr Lys Gln Asn Val Glu Gly Leu Asp Glu Gly
    1250                1255                1260

Thr Tyr Thr Pro Val Leu Gln Asp Thr Arg Ser Leu Asn Asp Ser
    1265                1270                1275

Ala Lys Arg Ala Gly Ile His Met Ala His Phe Ser Lys Ile Arg
    1280                1285                1290

Glu Glu Ala Asn Leu Glu Gly Leu Gly Asn Gln Thr Lys Gln Met
    1295                1300                1305

Val Glu Lys Tyr Pro Ser Thr Thr Arg Met Ser Pro Asn Pro Ser
    1310                1315                1320

Gln Gln Asn Val Ile Pro Gln Arg Gly Lys Arg Asp Leu Lys Gln
    1325                1330                1335

Phe Arg Leu Pro Leu Glu Glu Ile Lys Leu Glu Arg Gly Val Ile
    1340                1345                1350

Leu Asn Asp Thr Ser Thr Gln Trp Ser Lys Asn Met Lys Tyr Leu
    1355                1360                1365

Thr Gln Gly Thr Phe Thr Gln Ile Glu Tyr Asn Lys Lys Glu Lys
    1370                1375                1380

Arg Ala Ile Thr Gln Ser Phe Leu Ser Asp Cys Ser Met Arg Ser
```

```
            1385                1390                1395

His Gly Ile Ile Gln Thr Asn Gly Ser Ala Leu Pro Ile Ala Lys
        1400                1405                1410

Val Ser Ala Phe Pro Ser Ile Arg Pro Thr Asp Leu Thr Lys Ile
        1415                1420                1425

Pro Ser Gln Asp Asn Ser Ser His Leu Pro Ala Ser Ala Cys Ser
        1430                1435                1440

Tyr Thr Phe Gly Glu Arg Ser Ser Gly Val Gln Glu Ser Ser His
        1445                1450                1455

Phe Leu Gln Gly Ala Lys Arg Asn Asn Leu Ser Leu Ala Phe Leu
        1460                1465                1470

Thr Leu Glu Met Ile Arg Gly Gln Gly Lys Ile Ser Thr Leu Gly
        1475                1480                1485

Lys Ser Ala Thr Asn Pro Leu Met Tyr Lys Lys Leu Glu Asn Thr
        1490                1495                1500

Val Leu Leu Lys Pro Gly Leu Ser Glu Ala Ser Gly Lys Val Glu
        1505                1510                1515

Phe Leu Pro Lys Val His Val His Gln Glu Asp Phe Phe Pro Thr
        1520                1525                1530

Lys Thr Ser Asn Gly Ser Pro Ala His Leu Asp Leu Arg Glu Glu
        1535                1540                1545

Ile Phe Leu Gln Lys Thr Gln Gly Leu Val Lys Leu Asn Lys Val
        1550                1555                1560

Asn Arg Pro Gly Lys Val Pro Phe Leu Lys Trp Ala Thr Glu Ser
        1565                1570                1575

Ser Glu Lys Thr Pro Ser Lys Leu Leu Gly Pro Leu Ala Trp Asp
        1580                1585                1590

Asn Gln Tyr Ala Thr Leu Ile Pro Arg Glu Glu Trp Lys Ser Leu
        1595                1600                1605

Glu Lys Ser Gln Lys Asn Thr Ala Phe Lys Thr Lys Asp Thr Ile
        1610                1615                1620

Leu Pro Leu Asp Pro Cys Glu Asn Asn His Ser Ile Ala Ala Ile
        1625                1630                1635

Asn Glu Gly Gln Asp Lys Pro Gln Arg Glu Ala Thr Trp Val Lys
        1640                1645                1650

Gln Gly Gly Thr Gly Arg Leu Cys Ser Gln Asn Pro Pro Val Leu
        1655                1660                1665

Lys Arg His Gln Arg Glu Ile Thr Leu Thr Thr Phe Gln Pro Glu
        1670                1675                1680

Glu Asp Lys Ile Asp Tyr Asp Asp Thr Phe Ser Ile Glu Thr Lys
        1685                1690                1695

Arg Glu Asp Phe Asp Ile Tyr Gly Glu Asp Glu Asn Gln Gly Pro
        1700                1705                1710

Arg Ser Phe Gln Lys Arg Thr Arg His Tyr Phe Ile Ala Ala Val
        1715                1720                1725

Glu Arg Leu Trp Asp Tyr Gly Met Ser Arg Ser Pro His Ala Leu
        1730                1735                1740

Arg Asn Arg Ala Gln Asn Gly Asp Val Pro Gln Phe Lys Lys Val
        1745                1750                1755

Val Phe Gln Glu Phe Thr Asp Gly Ser Phe Thr Gln Pro Leu Tyr
        1760                1765                1770

Arg Gly Glu Leu Asn Glu His Leu Gly Leu Leu Gly Pro Tyr Ile
        1775                1780                1785
```

-continued

```
Arg Ala Glu Val Glu Asp Asn Ile Met Val Thr Phe Lys Asn Gln
1790                1795                1800

Ala Ser Arg Pro Tyr Ser Phe Tyr Ser Ser Leu Ile Ser Tyr Glu
1805                1810                1815

Glu Asp Gln Arg Gln Gly Ala Glu Pro Arg Lys Lys Phe Val Lys
1820                1825                1830

Pro Asn Glu Thr Lys Ile Tyr Phe Trp Lys Val Gln His His Met
1835                1840                1845

Ala Pro Thr Lys Asp Glu Phe Asp Cys Lys Ala Trp Ala Tyr Phe
1850                1855                1860

Ser Asp Val Asp Leu Glu Lys Asp Val His Ser Gly Leu Ile Gly
1865                1870                1875

Pro Leu Leu Ile Cys Arg Thr Asn Thr Leu Asn Ala Ala His Gly
1880                1885                1890

Arg Gln Val Thr Val Gln Glu Phe Ala Leu Phe Phe Thr Ile Phe
1895                1900                1905

Asp Glu Thr Lys Ser Trp Tyr Phe Thr Glu Asn Met Glu Arg Asn
1910                1915                1920

Cys Arg Ala Pro Cys Asn Ile Gln Met Glu Asp Pro Thr Phe Lys
1925                1930                1935

Glu Asn Tyr Arg Phe His Ala Ile Asn Gly Tyr Val Met Asp Thr
1940                1945                1950

Leu Pro Gly Leu Val Met Ala Gln Asp Gln Arg Ile Arg Trp Tyr
1955                1960                1965

Leu Leu Ser Met Gly Ser Asn Glu Asn Ile His Ser Ile His Phe
1970                1975                1980

Ser Gly His Val Phe Thr Val Arg Lys Lys Glu Glu Tyr Lys Met
1985                1990                1995

Ala Val Tyr Asn Leu Tyr Pro Gly Val Phe Glu Thr Val Glu Met
2000                2005                2010

Leu Pro Ser Lys Val Gly Ile Trp Arg Ile Glu Cys Leu Ile Gly
2015                2020                2025

Glu His Leu Gln Ala Gly Met Ser Thr Leu Phe Leu Val Tyr Ser
2030                2035                2040

Lys Lys Cys Gln Thr Pro Leu Gly Met Ala Ser Gly Arg Ile Arg
2045                2050                2055

Asp Phe Gln Ile Thr Ala Ser Gly Gln Tyr Gly Gln Trp Ala Pro
2060                2065                2070

Lys Leu Ala Arg Leu His Tyr Ser Gly Ser Ile Asn Ala Trp Ser
2075                2080                2085

Thr Lys Asp Pro Phe Ser Trp Ile Lys Val Asp Leu Leu Ala Pro
2090                2095                2100

Met Ile Ile His Ser Ile Met Thr Gln Gly Ala Arg Gln Lys Phe
2105                2110                2115

Ser Ser Leu Tyr Ile Ser Gln Phe Ile Ile Met Tyr Ser Leu Asp
2120                2125                2130

Gly Lys Lys Trp Gln Ser Tyr Arg Gly Asn Ser Thr Gly Thr Leu
2135                2140                2145

Met Val Phe Phe Gly Asn Val Asp Ser Ser Gly Ile Lys His Asn
2150                2155                2160

Ile Phe Asn Pro Pro Ile Ile Ala Arg Tyr Ile Arg Leu His Pro
2165                2170                2175
```

Thr His Tyr Ser Ile Arg Ser Thr Leu Arg Met Glu Leu Met Gly
     2180                2185                2190

Cys Asp Leu Asn Ser Cys Ser Met Pro Leu Gly Met Glu Asn Lys
     2195                2200                2205

Ala Ile Ser Asp Ala Gln Ile Thr Ala Ser Ser His Leu Ser Asn
     2210                2215                2220

Met Phe Ala Thr Trp Ser Pro Ser Gln Ala Arg Leu His Leu Gln
     2225                2230                2235

Gly Arg Thr Asn Ala Trp Arg Pro Gln Val Asn Asn Pro Lys Glu
     2240                2245                2250

Trp Leu Gln Val Asp Phe Gln Lys Thr Met Lys Val Thr Gly Ile
     2255                2260                2265

Thr Thr Gln Gly Val Lys Ser Leu Leu Thr Ser Met Tyr Val Lys
     2270                2275                2280

Glu Phe Leu Ile Ser Ser Ser Gln Asp Gly His Asn Trp Thr Leu
     2285                2290                2295

Phe Leu Gln Asn Gly Lys Val Lys Val Phe Gln Gly Asn Gln Asp
     2300                2305                2310

Ser Phe Thr Pro Val Val Asn Ala Leu Asp Pro Pro Leu Phe Thr
     2315                2320                2325

Arg Tyr Leu Arg Ile His Pro Gln Ser Trp Ala His His Ile Ala
     2330                2335                2340

Leu Arg Leu Glu Val Leu Gly Cys Glu Ala Gln Gln Leu Tyr
     2345                2350                2355

<210> SEQ ID NO 36
<211> LENGTH: 2351
<212> TYPE: PRT
<213> ORGANISM: artificial sequence
<220> FEATURE:
<223> OTHER INFORMATION: ancestral

<400> SEQUENCE: 36

Met Gln Ile Glu Leu Ser Thr Cys Phe Phe Leu Cys Leu Leu Pro Phe
1               5                   10                  15

Ser Phe Ser Ala Thr Arg Arg Tyr Tyr Leu Gly Ala Val Glu Leu Ser
                20                  25                  30

Trp Asp Tyr Met Gln Ser Glu Leu Leu Ser Glu Leu His Val Asp Thr
            35                  40                  45

Arg Phe Ser Pro Arg Val Pro Arg Ser Leu Pro Phe Asn Thr Ser Val
        50                  55                  60

Met Tyr Lys Lys Thr Val Phe Val Glu Phe Thr Asp His Leu Phe Asn
65                  70                  75                  80

Ile Ala Lys Pro Arg Pro Pro Trp Met Gly Leu Leu Gly Pro Thr Ile
                85                  90                  95

Arg Ala Glu Val Tyr Asp Thr Val Val Ile Thr Leu Lys Asn Met Ala
            100                 105                 110

Ser His Pro Val Ser Leu His Ala Val Gly Val Ser Tyr Trp Lys Ala
        115                 120                 125

Ser Glu Gly Ala Glu Tyr Glu Asp Gln Thr Ser Gln Lys Glu Lys Glu
    130                 135                 140

Asp Asp Lys Val Ile Pro Gly Glu Ser His Thr Tyr Val Trp Gln Val
145                 150                 155                 160

Leu Lys Glu Asn Gly Pro Met Ala Ser Asp Pro Pro Cys Leu Thr Tyr
                165                 170                 175

```
Ser Tyr Phe Ser His Val Asp Leu Val Lys Asp Leu Asn Ser Gly Leu
            180                 185                 190

Ile Gly Ala Leu Leu Val Cys Lys Glu Gly Ser Leu Ala Lys Glu Arg
        195                 200                 205

Thr Gln Thr Leu His Glu Phe Val Leu Leu Phe Ala Val Phe Asp Glu
    210                 215                 220

Gly Lys Ser Trp His Ser Glu Thr Asn Glu Ser Leu Thr Gln Ser Ala
225                 230                 235                 240

Gln Ala Gln His Glu Met His Thr Val Asn Gly Tyr Val Asn Arg Ser
                245                 250                 255

Leu Pro Gly Leu Thr Gly Cys His Lys Lys Ser Val Tyr Trp His Val
            260                 265                 270

Ile Gly Met Gly Thr Thr Pro Glu Val His Ser Ile Phe Leu Glu Gly
        275                 280                 285

His Thr Phe Leu Val Arg Asn His Arg Gln Ala Ser Leu Glu Ile Ser
    290                 295                 300

Pro Ile Thr Phe Leu Thr Ala Gln Thr Phe Leu Met Asp Leu Gly Gln
305                 310                 315                 320

Phe Leu Leu Phe Cys His Ile Ser Ser His Gln His Asp Gly Met Glu
                325                 330                 335

Ala Tyr Val Lys Val Asp Ser Cys Pro Glu Glu Pro Gln Leu Arg Met
            340                 345                 350

Lys Asn Asn Glu Glu Glu Asp Tyr Asp Asp Leu Tyr Asp Ser
        355                 360                 365

Asp Met Asp Val Val Arg Phe Asp Gly Asp Asn Ser Ser Pro Phe Ile
    370                 375                 380

Gln Ile Arg Ser Val Ala Lys Lys His Pro Lys Thr Trp Val His Tyr
385                 390                 395                 400

Ile Ala Ala Glu Glu Glu Asp Trp Asp Tyr Ala Pro Ser Ala Pro Thr
                405                 410                 415

Pro Asn Asp Arg Ser Tyr Lys Asn Leu Tyr Leu Asn Asn Gly Pro Gln
            420                 425                 430

Arg Ile Gly Arg Lys Tyr Lys Lys Val Arg Phe Met Ala Tyr Thr Asp
        435                 440                 445

Glu Thr Phe Lys Thr Arg Glu Ala Ile Gln Tyr Glu Ser Gly Ile Leu
    450                 455                 460

Gly Pro Leu Leu Tyr Gly Glu Val Gly Asp Thr Leu Leu Ile Ile Phe
465                 470                 475                 480

Lys Asn Gln Ala Ser Arg Pro Tyr Asn Ile Tyr Pro His Gly Ile Thr
                485                 490                 495

Asp Val Ser Pro Leu His Ser Gly Arg Leu Pro Lys Gly Val Lys His
            500                 505                 510

Leu Lys Asp Met Pro Ile Leu Pro Gly Glu Ile Phe Lys Tyr Lys Trp
        515                 520                 525

Thr Val Thr Val Glu Asp Gly Pro Thr Lys Ser Asp Pro Arg Cys Leu
    530                 535                 540

Thr Arg Tyr Tyr Ser Ser Phe Ile Asn Leu Glu Arg Asp Leu Ala Ser
545                 550                 555                 560

Gly Leu Ile Gly Pro Leu Leu Ile Cys Tyr Lys Glu Ser Val Asp Gln
                565                 570                 575

Arg Gly Asn Gln Met Met Ser Asp Lys Arg Asn Val Ile Leu Phe Ser
            580                 585                 590

Val Phe Asp Glu Asn Arg Ser Trp Tyr Leu Thr Glu Asn Met Gln Arg
```

-continued

```
                595                 600                 605

Phe Leu Pro Asn Ala Asp Ala Val Gln Pro His Asp Pro Glu Phe Gln
610                 615                 620

Val Ser Asn Ile Met His Ser Ile Asn Gly Tyr Val Phe Asp Asn Leu
625                 630                 635                 640

Gln Leu Ser Val Cys Leu His Glu Val Ala Tyr Trp Tyr Ile Leu Ser
                645                 650                 655

Val Gly Ala Gln Thr Asp Phe Leu Ser Val Phe Phe Ser Gly Tyr Thr
                660                 665                 670

Phe Lys His Lys Met Val Tyr Glu Asp Thr Leu Thr Leu Phe Pro Phe
                675                 680                 685

Ser Gly Glu Thr Val Phe Met Ser Met Glu Asn Pro Gly Leu Trp Val
                690                 695                 700

Leu Gly Cys His Asn Ser Asp Phe Arg Asn Arg Gly Met Thr Ala Leu
705                 710                 715                 720

Leu Lys Val Ser Ser Cys Asn Arg Asn Thr Gly Asp Tyr Tyr Glu Asp
                725                 730                 735

Thr Tyr Glu Asp Ile Pro Thr Ser Leu Leu Asn Glu Asn Asn Val Ile
                740                 745                 750

Glu Pro Arg Ser Phe Ser Gln Asn Ser Arg His Pro Ser Thr Arg Gln
                755                 760                 765

Lys Gln Phe Lys Ala Thr Thr Thr Pro Glu Asn Asp Ile Glu Lys Ile
770                 775                 780

Asp Pro Gln Ser Gly Glu Arg Thr Gln Leu Leu Lys Val Gln Ser Val
785                 790                 795                 800

Ser Ser Ser Asp Leu Leu Met Leu Leu Gly Gln Asn Pro Thr Pro His
                805                 810                 815

Gly Leu Phe Leu Ser Asp Leu Gln Glu Ala Thr His Glu Ala Asp Asp
                820                 825                 830

His Leu Leu Gly Ala Ile Glu Arg Asn Lys Gly Pro Ser Glu Val Ala
                835                 840                 845

Ser Leu Arg Pro Glu Leu His His Ser Gly Asp Arg Val Phe Thr Pro
850                 855                 860

Glu Pro Glu Leu Gln Leu Arg Leu Asn Glu Asn Leu Gly Thr Thr Val
865                 870                 875                 880

Thr Val Glu Leu Lys Lys Leu Asp Leu Lys Ile Ser Ser Ser Ser Asp
                885                 890                 895

Asn Leu Met Thr Ser Pro Thr Ile Pro Ser Asp Lys Leu Ala Ala Gly
                900                 905                 910

Thr Glu Lys Thr Gly Ser Leu Gly Pro Pro Asn Met Ser Val His Phe
                915                 920                 925

Asn Ser His Leu Gly Thr Ile Val Phe Gly Lys Asn Ser Ser His Leu
                930                 935                 940

Ile Glu Ser Gly Val Pro Leu Gly Leu Ser Glu Gly Asp Asn Asp Ser
945                 950                 955                 960

Lys Leu Leu Glu Ala Ala Leu Met Asn Ser Gln Glu Ser Ser Leu Gly
                965                 970                 975

Glu Asn Val Leu Ser Met Glu Ser Asn Arg Leu Phe Lys Glu Glu Arg
                980                 985                 990

Val His Gly Pro Ala Ser Leu Ile  Lys Asp Asn Ala Leu  Phe Lys Val
                995                 1000                1005

Asn Ile  Ser Leu Val Lys Thr  Asn Lys Ala Pro Ile  Asn Ser Thr
        1010                1015                1020
```

```
Thr Asn Arg Lys Thr His Val Asp Val Pro Thr Leu Leu Ile Glu
1025                1030                1035

Asn Ser Thr Ser Val Trp Gln Asp Ile Ile Leu Glu Ser Asn Thr
    1040                1045                1050

Glu Phe Gln Glu Val Thr Ser Leu Ile His Asn Glu Thr Phe Met
1055                1060                1065

Asp Arg Asn Thr Thr Ala Leu Gly Leu Asn His Val Ser Asn Lys
1070                1075                1080

Thr Thr Ser Ser Lys Asn Val Glu Met Val His Gln Lys Lys Glu
1085                1090                1095

Gly Pro Val Pro Leu Gly Ala Glu Asn Pro Asp Leu Ser Phe Phe
1100                1105                1110

Lys Ile Leu Phe Leu Pro Asp Ser Ala Asn Trp Ile Lys Arg Thr
1115                1120                1125

His Gly Lys Asn Ser Leu Ser Ser Gly Gln Arg Pro Ser Pro Lys
1130                1135                1140

Gln Leu Thr Ser Leu Gly Ser Glu Lys Ser Val Lys Asp Gln Asn
1145                1150                1155

Phe Leu Ser Glu Lys Lys Val Val Val Gly Glu Asp Glu Phe Thr
1160                1165                1170

Lys Asp Thr Gly Leu Lys Glu Met Ile Phe Pro Asn Ser Lys Ser
1175                1180                1185

Ile Phe Phe Thr Asn Leu Ala Asn Val Gln Glu Asn Asp Thr Tyr
1190                1195                1200

Asn Gln Glu Lys Lys Ser Gln Glu Glu Ile Glu Arg Lys Glu Lys
1205                1210                1215

Leu Thr Gln Glu Asn Val Val Leu Pro Gln Val Tyr Thr Val Thr
1220                1225                1230

Gly Thr Lys Asn Phe Leu Lys Asn Leu Phe Leu Thr Lys Gln Asn
1235                1240                1245

Val Thr Val Glu Gly Leu Asp Glu Gly Pro Tyr Thr Pro Ile Leu
1250                1255                1260

Gln Asp Thr Arg Ser Leu Asn Asp Ser Ala His Arg Ala Gly Ile
1265                1270                1275

His Met Ala His Phe Ser Lys Ile Arg Glu Glu Ala Asn Leu Glu
1280                1285                1290

Gly Leu Gly Asn Gln Thr Lys Gln Met Val Glu Arg Phe Pro Ser
1295                1300                1305

Thr Thr Arg Met Ser Pro Asn Pro Ser Gln His Asn Val Ile Thr
1310                1315                1320

Gln Arg Gly Lys Arg Ala Leu Lys Gln Pro Arg Leu Ser Leu Glu
1325                1330                1335

Glu Ile Lys Phe Glu Arg Gly Val Ile Leu Asn Asp Thr Ser Thr
1340                1345                1350

Gln Trp Ser Lys Asn Met Asn Tyr Leu Thr Gln Gly Thr Leu Thr
1355                1360                1365

Gln Ile Glu Tyr Asn Glu Lys Glu Lys Arg Ala Ile Thr Gln Ser
1370                1375                1380

Leu Leu Ser Asp Cys Ser Met Arg Asn His Gly Thr Ile Gln Met
1385                1390                1395

Asn Asp Ser Ala Leu Pro Ile Ala Lys Val Ser Ala Phe Pro Ser
1400                1405                1410
```

```
Ile Arg His Thr Asp Leu Thr Lys Ile Pro Ser Gln Asp Asn Ser
1415                1420                1425

Ser His Leu Pro Ala Ser Ala Cys Ser Tyr Thr Phe Arg Glu Arg
1430                1435                1440

Ser Ser Gly Val Gln Glu Ser Ser His Phe Leu Gln Gly Ala Lys
1445                1450                1455

Arg Asn Asn Leu Ser Leu Ala Phe Leu Thr Leu Glu Met Ile Arg
1460                1465                1470

Gly Gln Gly Lys Phe Ser Ser Leu Gly Lys Ser Ala Thr Asn Gln
1475                1480                1485

Pro Met Tyr Lys Lys Leu Glu Asn Thr Val Leu Leu Lys Pro Gly
1490                1495                1500

Leu Ser Glu Ala Ser Gly Lys Val Glu Leu Leu Pro Lys Val His
1505                1510                1515

Val His Gln Glu Asp Ser Phe Pro Thr Lys Thr Ser Asn Asp Ser
1520                1525                1530

Pro Gly His Leu Asp Leu Met Glu Lys Ile Phe Leu Gln Lys Thr
1535                1540                1545

Gln Gly Pro Val Lys Leu Asn Lys Val Asn Arg Pro Gly Lys Val
1550                1555                1560

Pro Phe Leu Lys Trp Ala Thr Glu Ser Ser Glu Lys Ile Pro Ser
1565                1570                1575

Lys Leu Leu Gly Pro Leu Ala Trp Asp Asn His Tyr Ala Thr Gln
1580                1585                1590

Ile Pro Arg Glu Glu Trp Lys Ser Gln Lys Lys Ser Gln Lys Asn
1595                1600                1605

Thr Ala Phe Lys Thr Lys Asp Thr Ile Leu Pro Leu Gly Pro Cys
1610                1615                1620

Glu Asn Asn His Ser Ile Ala Ala Ile Asn Glu Gly Gln Asp Lys
1625                1630                1635

Pro Gln Arg Glu Ala Thr Trp Ala Lys Gln Gly Glu Thr Gly Arg
1640                1645                1650

Leu Cys Ser Gln Asn Pro Pro Val Ser Lys Arg His Gln Arg Glu
1655                1660                1665

Ile Thr Leu Thr Thr Leu Gln Pro Glu Glu Asp Lys Ile Glu Tyr
1670                1675                1680

Asp Asp Thr Phe Ser Ile Glu Met Lys Arg Glu Asp Phe Asp Ile
1685                1690                1695

Tyr Gly Glu Asp Glu Asn Gln Gly Leu Arg Ser Phe Gln Lys Arg
1700                1705                1710

Thr Arg His Tyr Phe Ile Ala Ala Val Glu Arg Leu Trp Asp Tyr
1715                1720                1725

Gly Met Ser Arg Ser Pro His Ala Leu Arg Asn Arg Ala Gln Ser
1730                1735                1740

Gly Asp Val Pro Gln Phe Lys Lys Val Val Phe Gln Glu Phe Thr
1745                1750                1755

Asp Gly Ser Phe Thr Gln Pro Leu Tyr Arg Gly Glu Leu Asn Glu
1760                1765                1770

His Leu Gly Leu Leu Gly Pro Tyr Ile Arg Ala Glu Val Glu Asp
1775                1780                1785

Asn Ile Met Val Thr Phe Lys Asn Gln Ala Ser Arg Pro Tyr Ser
1790                1795                1800

Phe Tyr Ser Ser Leu Ile Ser Tyr Glu Glu Asp Gln Arg Gln Gly
```

```
            1805                1810                1815

Ala Glu Pro Arg Lys Lys Phe Val Asn Pro Asn Glu Thr Lys Ile
    1820                1825                1830

Tyr Phe Trp Lys Val Gln His His Met Ala Pro Thr Lys Asp Glu
    1835                1840                1845

Phe Asp Cys Lys Ala Trp Ala Tyr Phe Ser Asp Val Asp Leu Glu
    1850                1855                1860

Lys Asp Val His Ser Gly Leu Ile Gly Pro Leu Leu Ile Cys Arg
    1865                1870                1875

Ser Asn Thr Leu Asn Pro Ala His Gly Arg Gln Val Thr Val Gln
    1880                1885                1890

Glu Phe Ala Leu Phe Phe Thr Ile Phe Asp Glu Thr Lys Ser Trp
    1895                1900                1905

Tyr Phe Thr Glu Asn Met Glu Arg Asn Cys Arg Ala Pro Cys Asn
    1910                1915                1920

Ile Gln Lys Glu Asp Pro Thr Phe Lys Glu Asn Tyr Arg Phe His
    1925                1930                1935

Ala Ile Asn Gly Tyr Val Met Asp Thr Leu Pro Gly Leu Val Met
    1940                1945                1950

Ala Gln Asp Gln Lys Ile Arg Trp Tyr Leu Leu Ser Met Gly Ser
    1955                1960                1965

Asn Glu Asn Ile His Ser Ile His Phe Ser Gly His Val Phe Thr
    1970                1975                1980

Val Arg Lys Lys Glu Glu Tyr Lys Met Ala Val Tyr Asn Leu Tyr
    1985                1990                1995

Pro Gly Val Phe Glu Thr Val Glu Met Leu Pro Ser Lys Val Gly
    2000                2005                2010

Ile Trp Arg Ile Glu Cys Leu Ile Gly Glu His Leu Gln Ala Gly
    2015                2020                2025

Met Ser Thr Leu Phe Leu Val Tyr Ser Lys Lys Cys Gln Thr Pro
    2030                2035                2040

Leu Gly Met Ala Ser Gly His Ile Arg Asp Phe Gln Ile Thr Ala
    2045                2050                2055

Ser Gly Gln Tyr Gly Gln Trp Ala Pro Lys Leu Ala Arg Leu His
    2060                2065                2070

Tyr Ser Gly Ser Ile Asn Ala Trp Ser Thr Lys Asp Pro Phe Ser
    2075                2080                2085

Trp Ile Lys Val Asp Leu Leu Ala Pro Met Ile Ile His Ser Ile
    2090                2095                2100

Met Thr Gln Gly Ala Arg Gln Lys Phe Ser Ser Leu Tyr Ile Ser
    2105                2110                2115

Gln Phe Ile Ile Met Tyr Ser Leu Asp Gly Lys Lys Trp Gln Ser
    2120                2125                2130

Tyr Arg Gly Asn Ser Thr Gly Thr Leu Met Val Phe Phe Gly Asn
    2135                2140                2145

Val Asp Ser Ser Gly Ile Lys His Asn Ile Phe Asn Pro Pro Ile
    2150                2155                2160

Ile Ala Arg Tyr Ile Arg Leu His Pro Thr His Tyr Ser Ile Arg
    2165                2170                2175

Ser Thr Leu Arg Met Glu Leu Met Gly Cys Asp Leu Asn Ser Cys
    2180                2185                2190

Ser Met Pro Leu Gly Met Glu Asn Lys Ala Ile Ser Asp Ala Gln
    2195                2200                2205
```

-continued

Ile Thr Ala Ser Ser Tyr Leu Asn Ser Met Phe Ala Thr Trp Ser
2210                2215                2220

Pro Ser Gln Ala Arg Leu His Leu Gln Gly Arg Thr Asn Ala Trp
2225                2230                2235

Arg Pro Gln Ala Asn Asn Pro Lys Glu Trp Leu Gln Val Asp Phe
2240                2245                2250

Gln Lys Thr Met Lys Val Thr Gly Ile Thr Thr Gln Gly Val Lys
2255                2260                2265

Ser Leu Leu Thr Ser Met Tyr Val Lys Glu Phe Leu Ile Ser Ser
2270                2275                2280

Ser Gln Asp Gly His Asn Trp Thr Leu Phe Leu Gln Asn Gly Lys
2285                2290                2295

Val Lys Val Phe Gln Gly Asn Gln Asp Ser Phe Thr Pro Val Val
2300                2305                2310

Asn Ser Leu Asp Pro Pro Leu Leu Thr Arg Tyr Leu Arg Ile His
2315                2320                2325

Pro Gln Ser Trp Ala His Gln Ile Ala Leu Arg Leu Glu Val Leu
2330                2335                2340

Gly Cys Glu Ala Gln Gln Leu Tyr
2345                2350

<210> SEQ ID NO 37
<211> LENGTH: 2331
<212> TYPE: PRT
<213> ORGANISM: artificial sequence
<220> FEATURE:
<223> OTHER INFORMATION: ancestral

<400> SEQUENCE: 37

Met Gln Ile Glu Leu Ser Thr Cys Phe Phe Leu Cys Leu Leu Pro Phe
1               5                   10                  15

Ser Phe Ser Ala Thr Arg Arg Tyr Tyr Leu Gly Thr Val Glu Leu Ser
                20                  25                  30

Trp Asp Tyr Met Gln Ser Glu Leu Leu Ser Glu Leu His Val Asp Thr
            35                  40                  45

Arg Phe Pro Pro Arg Val Pro Arg Ser Phe Pro Phe Asn Pro Ser Val
        50                  55                  60

Met Tyr Lys Lys Thr Val Phe Val Glu Phe Thr Asp His Leu Phe Asn
65                  70                  75                  80

Ile Ala Lys Pro Arg Pro Pro Trp Met Gly Leu Leu Gly Pro Thr Ile
                85                  90                  95

Arg Ala Glu Val Tyr Asp Thr Val Val Ile Thr Leu Lys Asn Met Ala
            100                 105                 110

Ser His Pro Val Ser Leu His Ala Val Gly Val Ser Tyr Trp Lys Ala
        115                 120                 125

Ser Glu Gly Ala Glu Tyr Glu Asp Gln Thr Ser Gln Arg Glu Lys Glu
    130                 135                 140

Asp Asp Lys Val Ile Pro Gly Glu Ser Tyr Thr Tyr Val Trp Gln Val
145                 150                 155                 160

Leu Lys Glu Asn Gly Pro Met Ala Ser Asp Pro Pro Cys Leu Thr Tyr
                165                 170                 175

Ser Tyr Leu Ser His Val Asp Leu Val Lys Asp Leu Asn Ser Gly Leu
            180                 185                 190

Ile Gly Ala Leu Leu Val Cys Arg Glu Gly Ser Leu Ala Lys Glu Arg
        195                 200                 205

```
Thr Gln Thr Leu His Glu Phe Val Leu Leu Phe Ala Val Phe Asp Glu
    210             215                 220
Gly Lys Ser Trp His Ser Glu Thr Asn Glu Ser Leu Thr Gln Ala Met
225             230                 235                 240
Asp Pro Ala Ser Ala Arg Ala Gln Pro Glu Met His Thr Val Asn Gly
                245                 250                 255
Tyr Val Asn Arg Ser Leu Pro Gly Leu Ile Gly Cys His Lys Lys Ser
            260                 265                 270
Val Tyr Trp His Val Ile Gly Met Gly Thr Thr Pro Glu Val His Ser
        275                 280                 285
Ile Phe Leu Glu Gly His Thr Phe Leu Val Arg Asn His Arg Gln Ala
    290                 295                 300
Ser Leu Glu Ile Ser Pro Ile Ser Phe Leu Thr Ala Gln Thr Leu Leu
305                 310                 315                 320
Met Asp Leu Gly Gln Phe Leu Leu Phe Cys His Ile Ser Ser His Gln
                325                 330                 335
His Asp Gly Met Glu Ala Tyr Val Lys Val Asp Ser Cys Pro Glu Glu
            340                 345                 350
Pro Gln Leu Arg Met Lys Asn Asn Glu Glu Glu Asp Tyr Asp Asp
                355                 360                 365
Asp Leu Tyr Asp Ser Asp Met Asp Val Val Arg Phe Asp Gly Asp Asn
    370                 375                 380
Ser Pro Pro Phe Ile Gln Ile Arg Ser Val Ala Lys Lys His Pro Lys
385                 390                 395                 400
Thr Trp Val His Tyr Ile Ala Ala Glu Glu Asp Trp Asp Tyr Ala
                405                 410                 415
Pro Ser Val Leu Thr Pro Asn Asp Arg Ser Tyr Lys Ser Leu Tyr Leu
                420                 425                 430
Asn Asn Gly Pro Gln Gln Ile Gly Arg Lys Tyr Lys Lys Ala Arg Phe
            435                 440                 445
Met Ala Tyr Thr Asp Glu Thr Phe Lys Thr Arg Glu Ala Ile Gln Tyr
    450                 455                 460
Glu Ser Gly Ile Leu Gly Pro Leu Leu Tyr Gly Glu Val Gly Asp Thr
465                 470                 475                 480
Leu Leu Ile Ile Phe Lys Asn Gln Ala Ser Arg Pro Tyr Asn Ile Tyr
                485                 490                 495
Pro His Gly Ile Thr Asp Val Ser Pro Leu His Ser Gly Arg Leu Pro
            500                 505                 510
Lys Gly Val Lys His Leu Lys Asp Met Pro Ile Leu Pro Gly Glu Ile
        515                 520                 525
Phe Lys Tyr Lys Trp Thr Val Thr Val Glu Asp Gly Pro Thr Lys Ser
    530                 535                 540
Asp Pro Arg Cys Leu Thr Arg Tyr Tyr Ser Ser Phe Val Asn Leu Glu
545                 550                 555                 560
Arg Asp Leu Ala Ser Gly Leu Ile Gly Pro Leu Leu Ile Cys Tyr Lys
                565                 570                 575
Glu Ser Val Asp Gln Arg Gly Asn Gln Met Met Ser Asp Lys Arg Asn
            580                 585                 590
Val Ile Leu Phe Ser Val Phe Asp Glu Asn Arg Ser Trp Tyr Leu Thr
        595                 600                 605
Glu Asn Met Gln Arg Phe Leu Pro Asn Ala Asp Gly Val Gln Pro Gln
    610                 615                 620
```

```
Asp Pro Glu Phe Gln Val Ser Asn Ile Met His Ser Ile Asn Gly Tyr
625                 630                 635                 640

Val Phe Asp Ser Leu Gln Leu Ser Val Cys Leu His Glu Val Ala Tyr
            645                 650                 655

Trp Tyr Ile Leu Ser Val Gly Ala Gln Thr Asp Phe Leu Ser Val Phe
                660                 665                 670

Phe Ser Gly Tyr Thr Phe Lys His Lys Met Val Tyr Glu Asp Thr Leu
        675                 680                 685

Thr Leu Phe Pro Phe Ser Gly Glu Thr Val Phe Met Ser Met Glu Asn
    690                 695                 700

Pro Gly Leu Trp Val Leu Gly Cys His Asn Ser Asp Phe Arg Asn Arg
705                 710                 715                 720

Gly Met Thr Ala Leu Leu Lys Val Ser Ser Cys Asn Arg Asn Thr Gly
                725                 730                 735

Asp Tyr Tyr Glu Asp Thr Tyr Glu Asp Ile Pro Thr Ser Leu Leu Asn
            740                 745                 750

Glu Asn Asn Val Ile Glu Pro Arg Ser Phe Ser Gln Asn Ser Arg His
        755                 760                 765

Pro Ser Thr Arg Gln Lys Gln Phe Lys Ala Thr Thr Pro Glu Asn
    770                 775                 780

Asp Val Glu Lys Ile Asp Leu Arg Ser Gly Glu Arg Thr Gln Leu Leu
785                 790                 795                 800

Lys Val Gln Ser Val Ser Ser Ser Asp Leu Met Leu Leu Gly Gln
                805                 810                 815

Asn Pro Thr Pro His Ala Leu Ser Leu Ser Asp Leu Gln Glu Val Thr
            820                 825                 830

Tyr Glu Ala Asp Asp His Leu Pro Gly Thr Ile Glu Arg Asn Lys Gly
        835                 840                 845

Pro Ser Glu Val Ala His Leu Arg Pro Glu Leu His His Ser Gly Asp
    850                 855                 860

Arg Val Phe Thr Pro Glu Pro Glu Leu Gln Leu Arg Leu Asn Glu Asn
865                 870                 875                 880

Leu Gly Thr Thr Ile Thr Val Glu Leu Lys Lys Leu Asp Leu Lys Ile
                885                 890                 895

Ser Ser Ser Ser Asn Asn Leu Met Ile Ser Pro Thr Ile Pro Ser Asp
            900                 905                 910

Lys Leu Ala Ala Gly Thr Glu Lys Thr Gly Ser Leu Gly Pro Pro Asn
        915                 920                 925

Met Pro Val His Phe Ser Ser Gln Leu Gly Thr Ile Val Phe Gly Lys
    930                 935                 940

Asn Ser Ser His Leu Ile Glu Ser Ala Val Pro Leu Gly Leu Ser Glu
945                 950                 955                 960

Gly Asp Asn Asp Ser Lys Leu Ile Glu Ala Ala Leu Met Asn Ser Gln
                965                 970                 975

Glu Ser Ser Leu Glu Glu Asn Val Leu Ser Met Glu Ser Asp Arg Leu
            980                 985                 990

Phe Lys Glu Glu Arg Val His Gly Pro Val Ser Leu Thr Lys Asp Asn
        995                 1000                1005

Ala Leu Phe Lys Val Asn Phe Ser Leu Val Lys Thr Asn Lys Ala
    1010                1015                1020

Pro Ile Asn Ser Thr Thr Asn Arg Lys Thr His Ile Asp Gly Pro
    1025                1030                1035

Thr Leu Leu Ile Glu Asn Ser Thr Ser Val Trp Gln Asp Ile Ile
```

-continued

```
                    1040                1045                1050
Leu Glu Ser Asn Ser Gly Phe Gln Glu Val Thr Ser Leu Ile His
        1055                1060                1065
Asp Glu Thr Phe Met Asp Lys Asn Thr Thr Ala Leu Gly Leu Asn
        1070                1075                1080
His Val Ser Asn Lys Thr Thr Ser Ser Lys Asn Met Glu Met Val
        1085                1090                1095
His Gln Lys Lys Glu Asp Pro Ala Pro Leu Gly Ala Glu Asn Pro
        1100                1105                1110
Asp Ile Ser Phe Phe Lys Met Leu Phe Leu Pro Asp Ser Ala Asn
        1115                1120                1125
Trp Ile Lys Arg Thr His Cys Lys Asn Ser Leu Ser Ser Gly Gln
        1130                1135                1140
Arg Pro Ser Pro Lys Gln Leu Thr Ser Leu Gly Ser Glu Lys Ser
        1145                1150                1155
Val Lys Asp Gln Asn Phe Leu Ser Glu Lys Asn Lys Val Val Val
        1160                1165                1170
Gly Glu Asp Glu Phe Thr Lys Asp Thr Gly Leu Lys Glu Met Ile
        1175                1180                1185
Phe Pro Asn Ser Lys Ser Ile Phe Leu Thr Asn Leu Ala Asn Val
        1190                1195                1200
Gln Glu Asn Asp Thr His Asn Gln Glu Lys Asn Ser Gln Glu Glu
        1205                1210                1215
Ile Glu Arg Lys Glu Lys Leu Ile Gln Lys Asn Val Val Leu Pro
        1220                1225                1230
Gln Val Tyr Thr Val Thr Gly Thr Lys Asn Phe Leu Lys Asn Leu
        1235                1240                1245
Phe Leu Leu Ser Thr Lys Gln Asn Val Glu Gly Leu Asp Glu Gly
        1250                1255                1260
Thr Tyr Thr Pro Ile Leu Gln Asp Thr Arg Ser Leu Asn Glu Ser
        1265                1270                1275
Ala Asn Arg Ala Arg Ile His Met Ala His Phe Ser Lys Ile Arg
        1280                1285                1290
Glu Glu Ala Asn Leu Glu Gly Leu Gly Asn Gln Thr Lys Gln Met
        1295                1300                1305
Val Glu Lys Tyr Pro Ser Thr Thr Arg Met Ser Pro Asn Pro Arg
        1310                1315                1320
Gln Gln Asn Val Ile Thr His His Gly Lys Arg Ala Leu Lys Gln
        1325                1330                1335
Phe Arg Leu Pro Gln Glu Glu Ile Lys Leu Glu Arg Gly Val Ile
        1340                1345                1350
Leu Asn Asp Thr Ser Thr Gln Trp Ser Lys Asn Met Lys Tyr Leu
        1355                1360                1365
Thr Gln Gly Thr Leu Thr Gln Ile Glu Tyr Asn Glu Lys Glu Lys
        1370                1375                1380
Arg Ala Ile Thr Gln Ser Leu Leu Ser Asp Cys Ser Val Arg Ser
        1385                1390                1395
His Gly Ile Ile Gln Thr Asn Gly Ser Ala Leu Pro Ile Ala Lys
        1400                1405                1410
Val Ser Ala Phe Pro Ser Ile Arg Pro Thr Asp Leu Thr Lys Ile
        1415                1420                1425
Pro Ser Gln Asp Asn Ser Ser His Leu Leu Ala Ser Ala Cys Ser
        1430                1435                1440
```

-continued

Tyr Thr Phe Arg Glu Lys Ser Ser Gly Ile Gln Glu Ser Ser His
1445                    1450                1455

Phe Leu Gln Gly Ala Lys Arg Asn Asn Leu Ser Leu Ala Phe Leu
1460                    1465                1470

Thr Leu Glu Met Ile Arg Gly Gln Gly Lys Ile Ser Ser Leu Gly
1475                    1480                1485

Lys Leu Ser Glu Ala Ser Gly Lys Val Glu Leu Leu Pro Lys Val
1490                    1495                1500

His Val His Gln Glu Asp Ser Phe Pro Thr Lys Thr Ser Asn Gly
1505                    1510                1515

Ser Pro Gly His Leu Asp Leu Met Glu Glu Ile Phe Leu Gln Lys
1520                    1525                1530

Thr Gln Gly Pro Val Lys Leu Asn Lys Val Asn Arg Pro Gly Lys
1535                    1540                1545

Ile Pro Phe Leu Lys Trp Ala Ala Glu Ser Ser Glu Lys Thr Pro
1550                    1555                1560

Ser Lys Leu Leu Gly Pro Leu Ala Thr Gln Ile Pro Arg Glu Glu
1565                    1570                1575

Trp Asn Ser Gln Glu Lys Ser Gln Lys Asn Lys Ala Phe Lys Thr
1580                    1585                1590

Lys Asp Thr Ile Ser Pro Leu Asp Pro Cys Glu Asn Asn His Ser
1595                    1600                1605

Ile Ala Ala Ile Asn Lys Gly Gln Asp Lys Pro Gln Arg Glu Ala
1610                    1615                1620

Thr Trp Ala Lys Gln Glu Glu Thr Gly Arg Leu Cys Ser Gln Asn
1625                    1630                1635

Pro Pro Val Leu Lys Arg His Gln Arg Gln Ile Thr Leu Thr Thr
1640                    1645                1650

Val Gln Pro Glu Glu Asp Lys Ile Asp Tyr Asp Asp Thr Phe Ser
1655                    1660                1665

Thr Glu Thr Lys Arg Glu Asp Phe Asp Ile Tyr Gly Glu Asp Glu
1670                    1675                1680

Asn Gln Asp Pro Arg Ser Phe Gln Lys Arg Thr Arg His Tyr Phe
1685                    1690                1695

Ile Ala Ala Val Glu Arg Leu Trp Asp Tyr Gly Met Ser Arg Ser
1700                    1705                1710

Pro His Ala Leu Arg Asn Arg Ala Gln Ser Gly Asp Val Pro Gln
1715                    1720                1725

Phe Lys Lys Val Val Phe Gln Glu Phe Thr Asp Gly Ser Phe Thr
1730                    1735                1740

Gln Pro Leu Tyr Arg Gly Glu Leu Asn Glu His Leu Gly Leu Leu
1745                    1750                1755

Gly Pro Tyr Ile Arg Ala Glu Val Glu Asp Asn Ile Met Val Thr
1760                    1765                1770

Phe Lys Asn Gln Ala Ser Arg Pro Tyr Ser Phe Tyr Ser Ser Leu
1775                    1780                1785

Ile Ser Tyr Glu Asp Asp Gln Arg Gln Gly Ala Glu Pro Arg Lys
1790                    1795                1800

Lys Phe Val Lys Pro Asn Glu Thr Glu Val Tyr Phe Trp Lys Val
1805                    1810                1815

Gln His His Met Ala Pro Thr Lys Asp Glu Phe Asp Cys Lys Ala
1820                    1825                1830

```
Trp Ala Tyr Phe Ser Asp Val Asp Leu Asp Lys Asp Val His Ser
1835                1840                1845

Gly Leu Val Gly Pro Leu Leu Ile Cys Arg Ala Asn Thr Leu Asn
1850                1855                1860

Pro Ala His Gly Arg Gln Val Thr Val Gln Glu Phe Ala Leu Phe
1865                1870                1875

Phe Thr Ile Phe Asp Glu Thr Lys Ser Trp Tyr Phe Thr Glu Asn
1880                1885                1890

Met Glu Arg Asn Cys Arg Ala Pro Cys Asn Ile Gln Met Glu Asp
1895                1900                1905

Pro Thr Phe Lys Glu Asn Tyr Arg Phe His Ala Ile Asn Gly Tyr
1910                1915                1920

Val Met Asp Thr Leu Pro Gly Leu Val Met Ala Gln Asp Gln Arg
1925                1930                1935

Ile Arg Trp Tyr Leu Leu Ser Met Gly Ser Asn Glu Asn Ile His
1940                1945                1950

Ser Ile His Phe Ser Gly His Val Phe Thr Val Arg Lys Lys Glu
1955                1960                1965

Glu Tyr Lys Met Ala Val Tyr Asn Leu Tyr Pro Gly Val Phe Glu
1970                1975                1980

Thr Val Glu Met Leu Pro Ser Lys Val Gly Ile Trp Arg Ile Glu
1985                1990                1995

Cys Leu Ile Gly Glu His Leu Gln Ala Gly Met Ser Thr Leu Phe
2000                2005                2010

Leu Val Tyr Ser Lys Lys Cys Gln Thr Pro Leu Gly Met Ala Ser
2015                2020                2025

Gly His Ile Arg Asp Phe Gln Ile Thr Ala Ser Gly Gln Tyr Gly
2030                2035                2040

Gln Trp Ala Pro Lys Leu Ala Arg Leu His Tyr Ser Gly Ser Ile
2045                2050                2055

Asn Ala Trp Ser Thr Lys Asp Pro Phe Ser Trp Ile Lys Val Asp
2060                2065                2070

Leu Leu Ala Pro Met Ile Ile His Ser Ile Met Thr Gln Gly Ala
2075                2080                2085

Arg Gln Lys Phe Ser Ser Leu Tyr Ile Ser Gln Phe Ile Ile Met
2090                2095                2100

Tyr Ser Leu Asp Gly Lys Lys Trp Gln Ser Tyr Arg Gly Asn Ser
2105                2110                2115

Thr Gly Thr Leu Met Val Phe Phe Gly Asn Val Asp Ser Ser Gly
2120                2125                2130

Ile Lys His Asn Ile Phe Asn Pro Pro Ile Ile Ala Arg Tyr Ile
2135                2140                2145

Arg Leu His Pro Thr His Tyr Ser Ile Arg Ser Thr Leu Arg Met
2150                2155                2160

Glu Leu Met Gly Cys Asp Leu Asn Ser Cys Ser Met Pro Leu Gly
2165                2170                2175

Met Glu Asn Lys Ala Ile Ala Asp Ala Gln Ile Thr Ala Ser Ser
2180                2185                2190

Tyr Leu Asn Asn Met Phe Ala Thr Trp Ser Pro Ser Gln Ala Arg
2195                2200                2205

Leu His Leu Gln Gly Arg Thr Asn Ala Trp Arg Pro Arg Val Asn
2210                2215                2220

Asn Pro Lys Glu Trp Leu Gln Val Asp Phe Gln Lys Thr Met Lys
```

```
                      2225                2230                 2235
Val Thr Gly Ile Thr Thr Gln Gly Val Lys Ser Leu Leu Thr Ser
    2240                2245                 2250
Met Tyr Val Lys Glu Phe Leu Ile Ser Ser Ser Gln Asp Gly His
    2255                2260                 2265
Asn Trp Thr Leu Phe Leu Gln Asn Gly Lys Val Lys Val Phe Gln
    2270                2275                 2280
Gly Asn Gln Asp Ser Phe Thr Pro Val Val Asn Ser Leu Asp Pro
    2285                2290                 2295
Pro Leu Leu Thr Arg Tyr Leu Arg Ile His Pro Gln Ser Trp Gly
    2300                2305                 2310
His Gln Ile Ala Leu Arg Leu Glu Val Leu Gly Cys Glu Ala Gln
    2315                2320                 2325
Gln Leu Tyr
    2330

<210> SEQ ID NO 38
<211> LENGTH: 2358
<212> TYPE: PRT
<213> ORGANISM: artificial sequence
<220> FEATURE:
<223> OTHER INFORMATION: ancestral

<400> SEQUENCE: 38

Met Gln Ile Glu Leu Ser Val Cys Phe Phe Leu Cys Leu Leu Pro Phe
1               5                   10                  15
Ser Phe Ser Ala Thr Arg Arg Tyr Tyr Leu Gly Ala Val Glu Leu Ser
            20                  25                  30
Trp Asp Tyr Met Gln Ser Asp Leu Leu Ser Glu Leu His Val Asp Thr
        35                  40                  45
Arg Leu Leu Pro Arg Val Pro Arg Ser Phe Pro Phe Asn Thr Ser Val
    50                  55                  60
Met Phe Lys Lys Thr Val Phe Val Glu Phe Thr Asp His Leu Phe Asn
65                  70                  75                  80
Ile Ala Lys Pro Arg Pro Pro Trp Met Gly Leu Leu Gly Pro Thr Ile
                85                  90                  95
Arg Ala Glu Val Tyr Asp Thr Val Ile Ile Thr Leu Lys Asn Met Ala
            100                 105                 110
Ser His Pro Val Ser Leu His Ala Val Gly Val Ser Tyr Trp Lys Ala
        115                 120                 125
Ser Glu Gly Ala Glu Tyr Asp Asp Lys Thr Ser Gln Arg Glu Lys Glu
    130                 135                 140
Asp Asp Lys Val Ile Pro Gly Glu Ser His Thr Tyr Ile Trp Gln Val
145                 150                 155                 160
Leu Lys Glu Asn Gly Pro Met Ala Ser Asp Pro Pro Cys Leu Thr Tyr
                165                 170                 175
Ser Tyr Leu Ser His Val Asp Leu Val Lys Asp Leu Asn Ser Gly Leu
            180                 185                 190
Ile Gly Ala Leu Leu Val Cys Arg Glu Gly Ser Leu Ala Lys Glu Arg
        195                 200                 205
Thr Gln Thr Leu His Glu Phe Val Leu Leu Phe Ala Val Phe Asp Glu
    210                 215                 220
Gly Lys Ser Trp His Ser Glu Ala Asn Glu Ser Leu Ala Gln Gly Val
225                 230                 235                 240
Asp Ser Ala Ser Thr Arg Pro Trp Pro Lys Met Tyr Thr Val Asn Gly
```

```
                245                 250                 255
Tyr Val Asn Arg Ser Leu Pro Gly Leu Ile Gly Cys His Arg Lys Ser
                260                 265                 270

Val Tyr Trp His Val Ile Gly Met Gly Thr Thr Pro Glu Val His Ser
            275                 280                 285

Ile Phe Leu Glu Gly His Thr Phe Leu Val Arg Asn His Arg Gln Ala
        290                 295                 300

Ser Leu Glu Ile Ser Pro Ile Thr Phe Leu Thr Ala Gln Thr Leu Leu
305                 310                 315                 320

Met Asp Leu Gly Gln Phe Leu Leu Phe Cys His Ile Pro Ser His Gln
                325                 330                 335

His Asp Gly Met Glu Ala Tyr Val Lys Val Asp Ser Cys Pro Glu Glu
            340                 345                 350

Pro Gln Leu Arg Lys Lys Asn Asn Glu Glu Glu Asp Tyr Glu Asp
        355                 360                 365

Asp Leu Tyr Asp Ser Asp Met Asp Val Leu Arg Phe Asp Asp Asp Asn
    370                 375                 380

Ser Pro Pro Phe Ile Gln Ile Arg Ser Val Ala Lys Lys His Pro Lys
385                 390                 395                 400

Thr Trp Ile His Tyr Ile Ala Ala Glu Glu Asp Trp Asp Tyr Ala
                405                 410                 415

Pro Ala Val Leu Pro Ser Thr Asp Arg Ser Tyr Lys Ser Gln Tyr Leu
            420                 425                 430

Asn Asn Gly Thr Gln Arg Ile Gly Arg Lys Tyr Lys Lys Val Arg Phe
        435                 440                 445

Ile Ala Tyr Thr Asp Glu Thr Phe Gln Thr Arg Glu Ala Ile Gln Tyr
    450                 455                 460

Glu Ser Gly Ile Leu Gly Pro Leu Leu Tyr Gly Glu Val Gly Asp Thr
465                 470                 475                 480

Leu Leu Ile Ile Phe Lys Asn Gln Ala Ser Arg Pro Tyr Asn Ile Tyr
                485                 490                 495

Pro His Gly Ile Thr Asn Val Ser Pro Leu His Ser Gly Arg Leu Pro
            500                 505                 510

Lys Gly Val Lys His Leu Lys Asp Leu Gln Ile Met Pro Gly Glu Ile
        515                 520                 525

Phe Lys Tyr Lys Trp Thr Val Thr Val Glu Asp Gly Pro Thr Lys Ser
    530                 535                 540

Asp Pro Arg Cys Leu Thr Arg Tyr Tyr Ser Ser Phe Ile Asn Leu Glu
545                 550                 555                 560

Arg Asp Leu Ala Ser Gly Leu Ile Gly Pro Leu Leu Ile Cys Tyr Lys
                565                 570                 575

Glu Ser Val Asp Gln Arg Gly Asn Gln Met Met Ser Asp Lys Arg Asn
            580                 585                 590

Val Ile Leu Phe Ser Val Phe Asp Glu Asn Arg Ser Trp Tyr Leu Thr
        595                 600                 605

Glu Asn Met Gln Arg Phe Leu Pro Asn Ala Ala Gly Val Gln Pro Gln
    610                 615                 620

Asp Pro Glu Phe Gln Ala Ser Asn Met Met Tyr Ser Ile Asn Gly Tyr
625                 630                 635                 640

Val Phe Asp Asn Leu Gln Leu Ser Val Cys Leu His Glu Val Ala Tyr
                645                 650                 655

Trp Tyr Ile Leu Ser Val Gly Ala Gln Thr Asp Phe Leu Ser Val Phe
            660                 665                 670
```

-continued

```
Phe Ser Gly Tyr Thr Phe Lys His Lys Met Val Phe Glu Asp Thr Leu
            675                 680                 685

Thr Leu Phe Pro Phe Ser Gly Glu Thr Val Phe Met Ser Met Glu Asn
        690                 695                 700

Pro Gly Leu Trp Val Leu Gly Cys His Asn Ser Asp Phe Arg Asn Arg
705                 710                 715                 720

Gly Met Thr Ala Leu Leu Lys Val Ser Ser Cys Asp Arg Asn Thr Asp
                725                 730                 735

Asp Tyr Tyr Glu Asp Thr Tyr Glu Asp Ile Pro Thr Tyr Leu Leu Asn
            740                 745                 750

Glu Asn Ser Val Ile Glu Pro Arg Ser Phe Ser Gln Asn Ser Arg His
            755                 760                 765

Pro Ser Pro Arg Gln Lys Gln Phe Lys Ala Thr Thr Ala Pro Glu Asn
770                 775                 780

Asp Ile Glu Lys Met Asp Pro Arg Phe Gly Glu Arg Thr Gln Leu Leu
785                 790                 795                 800

Lys Ala Gln Ser Val Ser Ser Ser Asp Leu Leu Met Leu Leu Gly Gln
                805                 810                 815

Ser Pro Thr Pro His Gly Leu Ser Leu Ser Asp Leu Gln Glu Ala Lys
            820                 825                 830

Tyr Glu Ala Ile Pro Asp Asp Pro Ser Pro Gly Ala Ile Glu Asn Lys
            835                 840                 845

Glu Gly Pro Ser Glu Val Ala His Leu Arg Pro Glu Leu His His Ser
850                 855                 860

Glu Asp Met Val Phe Thr Pro Glu Pro Gly Leu Gln Leu Arg Leu Asn
865                 870                 875                 880

Glu Asn Leu Glu Thr Thr Ile Thr Glu Asp Leu Lys Lys Leu Asp Leu
                885                 890                 895

Lys Val Ser Ser Ser Asn Asn Val Met Thr Ser Pro Ile Ser Ser
            900                 905                 910

Ser Asp Asn Leu Pro Ala Asp Thr Glu Lys Thr Asp Ser Leu Gly Pro
            915                 920                 925

Leu Asn Thr Pro Val His Phe Ser Ser Gln Leu Gly Thr Ile Leu Phe
        930                 935                 940

Gly Lys Lys Ser Ser Pro Leu Ile Gly Ser Gly Val Pro Leu Asn Leu
945                 950                 955                 960

Ser Glu Arg Asp Asn Asp Ser Thr Leu Leu Glu Ala Ala Leu Met Ser
                965                 970                 975

Ser Gln Glu Ser Ser Leu Gly Lys Lys Val Ser Ser Met Glu Ser Asp
            980                 985                 990

Arg Leu Phe Lys Glu Lys Lys Val His Gly Pro Ala Ser Leu Thr Lys
            995                1000                1005

Asp Asn Ala Leu Phe Lys Val Asn Ile Ser Leu Val Lys Thr Asn
        1010                1015                1020

Lys Thr Pro Asn Asn Ser Thr Thr Asn Arg Lys Thr His Ile Asp
        1025                1030                1035

Gly Pro Thr Leu Leu Asn Glu Asn Ser Thr Ser Gly Trp Gln Asp
        1040                1045                1050

Ile Leu Lys Asn Asp Thr Glu Phe Gln Glu Val Thr Ser Leu Ile
        1055                1060                1065

His Asn Glu Met Phe Met Asp Lys Asn Thr Thr Ala Leu Gly Leu
        1070                1075                1080
```

```
Asn His Val Ser Asn Lys Thr Thr Ser Ser Lys Asp Met Glu Met
    1085            1090                1095

Val His Gln Lys Lys Glu Asp Pro Val Ser Leu Asp Ala Glu Asn
    1100            1105                1110

Pro Asp Met Ser Phe Phe Lys Met Leu Phe Leu Pro Asp Ser Ala
    1115            1120                1125

Asn Trp Ile Lys Arg Thr His Gly Lys Asn Ser Leu Ser Ser Glu
    1130            1135                1140

Gln Gly Pro Ser Pro Lys Gln Leu Ile Ser Leu Gly Ser Glu Asn
    1145            1150                1155

Ser Val Lys Asp Gln Asn Phe Leu Ser Glu Lys Asn Lys Val Ala
    1160            1165                1170

Val Gly Glu Asp Glu Phe Thr Lys Asp Thr Gly Phe Lys Glu Met
    1175            1180                1185

Ile Phe Pro Asn Ser Lys Ser Ile Phe Leu Thr Asn Leu Ala Asn
    1190            1195                1200

Val Gln Glu Asn Asp Thr Gln Asn Gln Glu Lys Lys Phe Gln Glu
    1205            1210                1215

Glu Ile Glu Arg Lys Glu Thr Leu Ile Gln Glu Asn Val Gly Leu
    1220            1225                1230

Pro Gln Val Phe Pro Val Thr Gly Thr Lys Asn Phe Leu Lys Thr
    1235            1240                1245

Leu Phe Leu Leu Ser Thr Arg Gln Asn Val Thr Val Glu Gly Leu
    1250            1255                1260

Asp Glu Gly Thr Tyr Ala Pro Val Leu Gln Asp Thr Arg Ser Leu
    1265            1270                1275

Asn Asp Ser Ala Asn Arg Leu Gly Leu His Met Ala His Phe Ser
    1280            1285                1290

Lys Arg Arg Glu Glu Ala Asn Leu Glu Gly Leu Arg Asn Gln Thr
    1295            1300                1305

Lys Gln Met Val Glu Lys Tyr Pro Ser Pro Thr Arg Met Ser Pro
    1310            1315                1320

Asn Pro Ser Gln Gln Asn Ala Ile Thr Gln Arg Ser Lys Arg Ala
    1325            1330                1335

Leu Lys Gln Phe Gly Pro Pro Leu Glu Glu Ile Glu Leu Glu Arg
    1340            1345                1350

Gly Leu Ile Val Asn Asp Thr Ser Thr Leu Gln Ser Arg Asn Met
    1355            1360                1365

Lys Tyr Leu Thr Gln Gly Thr Leu Thr Gln Ile Asp Tyr Asn Glu
    1370            1375                1380

Lys Glu Lys Arg Ala Ile Thr Gln Ser Pro Leu Ser Asp Cys Ser
    1385            1390                1395

Met Arg Asn His Val Ile Thr Gln Thr Asn Gly Ser Ala Leu Pro
    1400            1405                1410

Ile Ala Lys Thr Ser Ala Phe Pro Ser Ile Arg Pro Thr Asp Leu
    1415            1420                1425

Thr Lys Ile Pro Ser Gln Asp Asn Ser Ser His Leu Leu Ser Ser
    1430            1435                1440

Ala Cys Asn Tyr Thr Phe Arg Glu Lys Ser Ser Gly Val Gln Glu
    1445            1450                1455

Ser Ser His Phe Leu Gln Gly Ala Lys Arg Asn Asn Leu Ser Ser
    1460            1465                1470

Ala Ile Leu Thr Leu Asp Met Ile Arg Gly Gln Glu Lys Val Ile
```

```
            1475                1480                1485

Ser Leu Ser Ala Thr Asp Pro Leu Met Tyr Lys Lys Leu Glu Asn
        1490                1495                1500

Thr Val Leu Leu Lys Pro Gly Leu Pro Glu Ala Ser Gly Lys Val
        1505                1510                1515

Glu Leu Leu Pro Lys Ile His Val His Gln Glu Asp Pro Phe Pro
        1520                1525                1530

Thr Glu Thr Ser Asn Gly Ser Pro Gly His Leu Asp Leu Met Glu
        1535                1540                1545

Glu Ile Leu Leu Gln Lys Thr Gln Gly Ala Ile Lys Leu Asn Lys
        1550                1555                1560

Val Asn Arg Pro Gly Lys Val Pro Phe Leu Lys Gly Ala Thr Glu
        1565                1570                1575

Ser Ser Glu Lys Thr Leu Pro Lys Leu Leu Gly Pro Leu Ala Trp
        1580                1585                1590

Asp Asn Gln Tyr Ala Thr Gln Ile Ser Arg Glu Glu Trp Gln Ser
        1595                1600                1605

Gln Glu Lys Ser Pro Lys Asn Thr Ala Phe Asn Thr Lys Asp Thr
        1610                1615                1620

Ile Ser Pro Leu Asn Pro Cys Glu Asn Asn His Ala Ile Ala Ala
        1625                1630                1635

Ile Asn Glu Gly Gln Asp Arg Leu Gln Lys Glu Ala Thr Trp Ala
        1640                1645                1650

Lys Gln Gly Glu Thr Glu Arg Leu Cys Ser Glu Asn Pro Pro Val
        1655                1660                1665

Leu Lys His His Pro Arg Glu Ile Thr Leu Thr Ala Leu Gln Gln
        1670                1675                1680

Glu Gln Glu Lys Ile Asp Tyr Asp Asp Ala Leu Ser Ile Glu Thr
        1685                1690                1695

Lys Arg Glu Asp Phe Asp Ile Tyr Gly Glu Asp Glu Asn Gln Gly
        1700                1705                1710

Pro Arg Ser Phe Gln Lys Lys Thr Arg His Tyr Phe Ile Ala Ala
        1715                1720                1725

Val Glu Arg Leu Trp Asp Tyr Gly Met Ser Lys Ser Pro His Ala
        1730                1735                1740

Leu Arg Asn Arg Ala Gln Ser Gly Ser Val Pro Gln Phe Lys Lys
        1745                1750                1755

Val Val Phe Gln Glu Phe Thr Asp Gly Ser Phe Thr Gln Pro Leu
        1760                1765                1770

Tyr Arg Gly Glu Leu Asn Glu His Leu Gly Leu Leu Gly Pro Tyr
        1775                1780                1785

Ile Arg Ala Glu Val Glu Asp Asn Ile Met Val Thr Phe Lys Asn
        1790                1795                1800

Gln Ala Ser Arg Pro Tyr Ser Phe Tyr Ser Ser Leu Ile Ser Tyr
        1805                1810                1815

Glu Glu Asp Gln Arg Gln Gly Thr Glu Pro Arg Lys Asn Leu Val
        1820                1825                1830

Lys Pro Asn Glu Thr Lys Thr Tyr Phe Trp Lys Val Gln His His
        1835                1840                1845

Met Ala Pro Thr Lys Asp Glu Phe Asp Cys Lys Ala Trp Ala Tyr
        1850                1855                1860

Phe Ser Asp Val Asp Leu Glu Lys Asp Leu His Ser Gly Leu Ile
        1865                1870                1875
```

```
Gly Pro Leu Leu Ile Cys Arg Thr Asn Thr Leu Asn Pro Ala His
    1880            1885                1890

Gly Arg Gln Leu Thr Val Gln Glu Phe Ala Leu Phe Phe Thr Ile
    1895            1900                1905

Phe Asp Glu Thr Lys Ser Trp Tyr Phe Thr Glu Asn Met Glu Arg
    1910            1915                1920

Asn Cys Lys Ala Pro Cys Asn Ile Gln Met Glu Asp Pro Thr Phe
    1925            1930                1935

Lys Lys Asn Tyr Arg Phe His Ala Ile Asn Gly Tyr Val Met Asp
    1940            1945                1950

Thr Leu Pro Gly Leu Val Met Ala Gln Asp Gln Arg Ile Arg Trp
    1955            1960                1965

Tyr Leu Leu Ser Met Gly Ser Asn Glu Asn Ile His Ser Ile His
    1970            1975                1980

Phe Ser Gly His Val Phe Thr Val Arg Lys Lys Glu Glu Tyr Lys
    1985            1990                1995

Met Ala Val Tyr Asn Leu Tyr Pro Gly Val Phe Glu Thr Val Glu
    2000            2005                2010

Met Leu Pro Ser Lys Ala Gly Ile Trp Arg Val Glu Cys Leu Ile
    2015            2020                2025

Gly Glu His Leu Gln Ala Gly Met Ser Thr Leu Phe Leu Val Tyr
    2030            2035                2040

Ser Lys Glu Cys Gln Thr Pro Leu Gly Met Ala Ser Gly Arg Ile
    2045            2050                2055

Arg Asp Ser Gln Ile Thr Ala Ser Gly His Tyr Gly Gln Trp Ala
    2060            2065                2070

Pro Lys Leu Ala Arg Leu His Tyr Thr Gly Ser Ile Asn Ala Trp
    2075            2080                2085

Ser Thr Lys Asp Pro Phe Ser Trp Ile Lys Val Asp Leu Leu Ala
    2090            2095                2100

Pro Met Ile Ile His Gly Ile Lys Thr Gln Gly Ala Arg Gln Lys
    2105            2110                2115

Leu Ser Ser Leu Tyr Ile Ser Gln Phe Ile Ile Met Tyr Ser Leu
    2120            2125                2130

Asp Gly Lys Lys Trp Gln Ser Tyr Arg Gly Asn Ser Thr Gly Thr
    2135            2140                2145

Leu Met Val Phe Phe Gly Asn Val Asp Ser Ser Gly Ile Lys His
    2150            2155                2160

Asn Ile Phe Asn Pro Pro Ile Ile Ala Gln Tyr Ile Arg Leu His
    2165            2170                2175

Pro Thr His His Ser Ile Arg Ser Thr Leu Arg Met Glu Leu Met
    2180            2185                2190

Gly Cys Asp Leu Asn Ser Cys Ser Met Pro Leu Gly Met Glu Ser
    2195            2200                2205

Lys Ala Ile Ser Asp Ala Gln Ile Thr Ala Ser Ser Tyr Phe Thr
    2210            2215                2220

Asn Met Phe Ala Thr Trp Ser Pro Ser Gln Ala Arg Leu His Leu
    2225            2230                2235

Gln Gly Arg Thr Asn Ala Trp Arg Pro Gln Val Asn Asn Pro Lys
    2240            2245                2250

Glu Trp Leu Gln Val Asp Phe Gln Lys Thr Met Lys Val Thr Gly
    2255            2260                2265
```

```
Ile Thr Thr Gln Gly Ala Lys Ser Leu Leu Thr Ser Met Tyr Val
    2270                2275                2280

Lys Glu Phe Leu Ile Ser Ser Gln Asp Gly His His Trp Thr
2285                2290                2295

Leu Phe Leu Gln Asn Gly Lys Val Lys Val Phe Gln Gly Asn Gln
    2300                2305                2310

Asp Ser Phe Thr Pro Val Val Asn Ser Leu Asp Pro Pro Leu Leu
    2315                2320                2325

Thr Arg Tyr Leu Arg Ile Tyr Pro Gln Ser Trp Val His Gln Ile
    2330                2335                2340

Ala Leu Arg Leu Glu Val Leu Gly Cys Gln Ser Gln Gln His Tyr
    2345                2350                2355

<210> SEQ ID NO 39
<211> LENGTH: 1453
<212> TYPE: PRT
<213> ORGANISM: artificial sequence
<220> FEATURE:
<223> OTHER INFORMATION: ancestral

<400> SEQUENCE: 39

Met Gln Ile Ala Leu Phe Thr Cys Phe Phe Leu Ser Leu Phe Asn
1               5                   10                  15

Cys Ser Ser Ala Thr Arg Arg Tyr Tyr Leu Gly Ala Val Glu Leu Ser
            20                  25                  30

Trp Asn Tyr Met Gln Ser Asp Leu Leu Ser Val Leu His Thr Asp Thr
                35                  40                  45

Arg Phe Leu Pro Arg Met Pro Thr Ser Phe Pro Phe Asn Thr Ser Ile
50                  55                  60

Met Tyr Lys Lys Thr Val Phe Val Glu Tyr Met Asp His Leu Phe Asn
65                  70                  75                  80

Ile Ala Lys Pro Arg Pro Pro Trp Met Gly Leu Leu Gly Pro Thr Ile
                85                  90                  95

Trp Thr Glu Val His Asp Thr Val Val Ile Thr Leu Lys Asn Met Ala
            100                 105                 110

Ser His Pro Val Ser Leu His Ala Val Gly Val Ser Tyr Trp Lys Ala
        115                 120                 125

Ser Glu Gly Ala Glu Tyr Glu Asp Gln Thr Ser Gln Arg Glu Lys Glu
    130                 135                 140

Asp Asp Lys Val Phe Pro Gly Glu Ser His Thr Tyr Val Trp Gln Val
145                 150                 155                 160

Leu Lys Glu Asn Gly Pro Met Ala Ser Asp Pro Pro Cys Leu Thr Tyr
                165                 170                 175

Ser Tyr Leu Ser His Val Asp Leu Val Lys Asp Leu Asn Ser Gly Leu
            180                 185                 190

Ile Gly Ala Leu Leu Val Cys Lys Glu Gly Ser Leu Ser Lys Glu Arg
        195                 200                 205

Thr Gln Met Leu His Gln Phe Val Leu Leu Phe Ala Val Phe Asp Glu
    210                 215                 220

Gly Lys Ser Trp His Ser Glu Thr Lys Asp Ser Phe Thr Gln Ala Met
225                 230                 235                 240

Asp Ser Ala Ser Thr Arg Ala Trp Pro Lys Met His Thr Val Asn Gly
                245                 250                 255

Tyr Val Asn Arg Ser Leu Pro Gly Leu Ile Gly Cys His Arg Lys Ser
            260                 265                 270
```

-continued

```
Val Tyr Trp His Val Ile Gly Met Gly Thr Thr Pro Glu Val His Ser
            275                 280                 285
Ile Phe Leu Glu Gly His Thr Phe Leu Val Arg Asn His Arg Gln Ala
290                 295                 300
Ser Leu Glu Ile Ser Pro Ile Thr Phe Leu Thr Ala Gln Thr Leu Leu
305                 310                 315                 320
Ile Asp Leu Gly Gln Phe Leu Leu Phe Cys His Ile Ser Ser His Lys
            325                 330                 335
His Asp Gly Met Glu Ala Tyr Val Lys Val Asp Ser Cys Pro Glu Glu
            340                 345                 350
Pro Gln Trp Gln Lys Lys Asn Asn Glu Glu Met Glu Asp Tyr Asp Asp
            355                 360                 365
Asp Leu Asp Ser Glu Met Asp Met Phe Thr Leu Asp Asp Asp Asn Ser
            370                 375                 380
Pro Phe Ile Gln Ile Arg Ser Val Ala Lys Lys Tyr Pro Lys Thr Trp
385                 390                 395                 400
Ile His Tyr Ile Ser Ala Glu Glu Asp Trp Asp Tyr Ala Pro Ser
            405                 410                 415
Val Leu Thr Ser Asp Asp Gly Ser Tyr Lys Ser Gln Tyr Leu Ser Asn
            420                 425                 430
Gly Pro His Arg Ile Gly Arg Lys Tyr Lys Val Arg Phe Ile Ala
            435                 440                 445
Tyr Thr Asp Val Thr Phe Lys Thr Arg Glu Thr Ile Gln His Glu Ser
            450                 455                 460
Gly Ile Leu Gly Pro Leu Leu Tyr Gly Glu Val Gly Asp Thr Leu Leu
465                 470                 475                 480
Ile Ile Phe Lys Asn Gln Ala Ser Arg Pro Tyr Asn Ile Tyr Pro His
            485                 490                 495
Gly Ile Thr Asp Val Ser Pro Leu His Ser Arg Arg Leu Pro Arg Gly
            500                 505                 510
Ile Lys His Val Lys Asp Leu Pro Ile Arg Pro Gly Glu Ile Phe Lys
            515                 520                 525
Tyr Lys Trp Thr Val Thr Val Glu Asp Gly Pro Thr Lys Ser Asp Pro
            530                 535                 540
Arg Cys Leu Thr Arg Tyr Tyr Ser Ser Phe Ile Asn Pro Glu Arg Asp
545                 550                 555                 560
Leu Ala Ser Gly Leu Ile Gly Pro Leu Leu Ile Cys Tyr Lys Glu Ser
            565                 570                 575
Val Asp Gln Arg Gly Asn Gln Met Met Ser Asp Lys Arg Asn Val Ile
            580                 585                 590
Leu Phe Ser Val Phe Asp Glu Asn Gln Ser Trp Tyr Ile Thr Glu Asn
            595                 600                 605
Met Gln Arg Phe Leu Pro Asn Ala Ala Asp Thr Gln Pro Gln Asp Pro
610                 615                 620
Glu Phe Gln Ala Ser Asn Ile Met His Ser Ile Asn Gly Tyr Val Phe
625                 630                 635                 640
Asp Ser Leu Gln Leu Thr Val Cys Leu His Glu Val Ala Tyr Trp Tyr
            645                 650                 655
Ile Leu Ser Val Gly Ala Gln Thr Asp Phe Leu Ser Ile Phe Phe Ser
            660                 665                 670
Gly Tyr Thr Phe Lys His Lys Met Val Tyr Glu Asp Thr Leu Thr Leu
            675                 680                 685
Phe Pro Phe Ser Gly Glu Thr Val Phe Met Ser Met Glu Asn Pro Gly
```

```
                690             695             700
Leu Trp Val Leu Gly Cys His Asn Ser Asp Phe Arg Lys Arg Gly Met
705             710             715             720

Thr Ala Leu Leu Lys Val Ser Ser Cys Asp Lys Ser Thr Ser Asp Tyr
            725             730             735

Tyr Glu Glu Ile Tyr Glu Asp Ile Pro Thr Gln Leu Val Asn Asp Asn
                740             745             750

Asn Val Ile Glu Pro Arg Ser Phe Gln Asn Pro Pro Val Leu Lys
        755             760             765

Arg His Gln Arg Glu Leu Ser Ala Leu Gln Ser Glu Gln Glu Ala Thr
    770             775             780

Asp Tyr Asp Asp Ser Ile Thr Ile Glu Thr Asn Glu Asp Phe Asp Ile
785             790             795             800

Tyr Gly Glu Asp Ile Lys Gln Gly Pro Arg Ser Phe Gln Lys Thr
                805             810             815

Arg His Tyr Phe Ile Ala Ala Val Glu Arg Leu Trp Asp Tyr Gly Met
            820             825             830

Ser Thr Ser Pro His Val Leu Arg Asn Arg Asp Gln Ser Gly Asn Ala
        835             840             845

Pro Gln Phe Lys Lys Val Val Phe Gln Glu Phe Thr Asp Gly Ser Phe
    850             855             860

Ser Gln Pro Leu Tyr Arg Gly Glu Leu Asn Glu His Leu Gly Leu Leu
865             870             875             880

Gly Pro Tyr Ile Arg Ala Glu Val Glu Asp Asn Ile Met Val Thr Phe
                885             890             895

Lys Asn Gln Ala Ser Arg Pro Tyr Ser Phe Tyr Ser Ser Leu Ile Ser
            900             905             910

Tyr Lys Glu Asp Gln Arg Gln Gly Glu Glu Pro Arg Arg Asn Phe Val
        915             920             925

Lys Pro Asn Glu Thr Lys Ile Tyr Phe Trp Lys Val Gln His His Met
    930             935             940

Ala Pro Thr Glu Asp Glu Phe Asp Cys Lys Ala Trp Ala Tyr Phe Ser
945             950             955             960

Asp Val Asp Leu Glu Arg Asp Met His Ser Gly Leu Ile Gly Pro Leu
                965             970             975

Leu Ile Cys His Thr Asn Thr Leu Asn Pro Ala His Gly Arg Gln Val
            980             985             990

Ala Val Gln Glu Phe Ala Leu Phe Phe Thr Ile Phe Asp Glu Thr Lys
        995             1000            1005

Ser Trp Tyr Phe Thr Glu Asn Val Glu Arg Asn Cys Lys Thr Pro
    1010            1015            1020

Cys Asn Ile Gln Met Glu Asp Pro Thr Leu Lys Glu Asn Tyr Arg
    1025            1030            1035

Phe His Ala Ile Asn Gly Tyr Val Met Asp Thr Leu Pro Gly Leu
    1040            1045            1050

Val Met Ala Gln Asp Gln Arg Ile Arg Trp Tyr Leu Leu Ser Met
    1055            1060            1065

Gly Ser Asn Glu Asn Ile Gln Ser Ile His Phe Ser Gly His Val
    1070            1075            1080

Phe Thr Val Arg Lys Lys Glu Glu Tyr Lys Met Ala Val Tyr Asn
    1085            1090            1095

Leu Tyr Pro Gly Val Phe Glu Thr Val Glu Met Leu Pro Ser Arg
    1100            1105            1110
```

Ala Gly Ile Trp Arg Val Glu Cys Leu Ile Gly Glu His Leu Gln
1115                1120                1125

Ala Gly Met Ser Thr Leu Phe Leu Val Tyr Ser Lys Gln Cys Gln
1130                1135                1140

Ile Pro Leu Gly Met Ala Ser Gly Ser Ile Arg Asp Phe Gln Ile
1145                1150                1155

Thr Ala Ser Gly His Tyr Gly Gln Trp Ala Pro Asn Leu Ala Arg
1160                1165                1170

Leu His His Ser Gly Ser Ile Asn Ala Trp Ser Thr Lys Glu Pro
1175                1180                1185

Phe Ser Trp Ile Lys Val Asp Leu Leu Thr Pro Met Ile Ile His
1190                1195                1200

Gly Ile Lys Thr Gln Gly Ala Arg Gln Lys Phe Ser Ser Leu Tyr
1205                1210                1215

Ile Ser Gln Phe Ile Ile Met Tyr Ser Leu Asp Gly Lys Lys Trp
1220                1225                1230

Leu Ser Tyr Arg Gly Asn Ser Thr Gly Thr Leu Met Val Phe Phe
1235                1240                1245

Gly Asn Val Asp Ser Ser Gly Ile Lys His Asn Ser Phe Asn Pro
1250                1255                1260

Pro Ile Ile Ala Arg Tyr Ile Arg Leu His Pro Thr His Ser Ser
1265                1270                1275

Ile Arg Ser Thr Leu Arg Met Glu Leu Met Gly Cys Asp Leu Asn
1280                1285                1290

Ser Cys Ser Ile Pro Leu Gly Met Glu Asn Lys Val Ile Ser Asp
1295                1300                1305

Thr Gln Ile Thr Ala Ser Ser Tyr Phe Thr Asn Met Phe Ala Thr
1310                1315                1320

Trp Ser Pro Ser Gln Ala Arg Leu His Leu Gln Gly Arg Thr Asn
1325                1330                1335

Ala Trp Arg Pro Gln Val Asn Asp Pro Lys Glu Trp Leu Gln Val
1340                1345                1350

Asp Leu Gln Lys Thr Met Lys Val Thr Gly Ile Ile Thr Gln Gly
1355                1360                1365

Val Lys Ser Leu Phe Thr Ser Met Phe Val Lys Glu Phe Leu Ile
1370                1375                1380

Ser Ser Ser Gln Asp Gly His His Trp Thr His Ile Leu His Asn
1385                1390                1395

Gly Lys Val Lys Val Phe Gln Gly Asn Gln Asp Ser Ser Thr Pro
1400                1405                1410

Met Val Asn Ser Leu Asp Pro Pro Leu Leu Thr Arg Tyr Leu Arg
1415                1420                1425

Ile His Pro Gln Ile Trp Glu His Gln Ile Ala Leu Arg Leu Glu
1430                1435                1440

Ile Leu Gly Cys Glu Ala Gln Gln Leu Tyr
1445                1450

<210> SEQ ID NO 40
<211> LENGTH: 1458
<212> TYPE: PRT
<213> ORGANISM: artificial sequence
<220> FEATURE:
<223> OTHER INFORMATION: ancestral

<400> SEQUENCE: 40

```
Met Gln Ile Glu Leu Ser Thr Cys Phe Phe Leu Cys Leu Leu Gln Phe
1               5                   10                  15

Ser Phe Ser Ala Thr Arg Arg Tyr Tyr Leu Gly Ala Val Glu Leu Ser
            20                  25                  30

Trp Asp Tyr Met Gln Ser Asp Leu Leu Ser Glu Leu His Val Asp Thr
            35                  40                  45

Arg Phe Pro Pro Arg Val Pro Arg Ser Phe Pro Phe Asn Thr Ser Val
        50                  55                  60

Met Tyr Lys Lys Thr Val Phe Val Glu Phe Thr Asp His Leu Phe Asn
65                  70                  75                  80

Ile Ala Lys Pro Arg Pro Pro Trp Met Gly Leu Leu Gly Pro Thr Ile
                85                  90                  95

Arg Ala Glu Val Tyr Asp Thr Val Val Ile Thr Leu Lys Asn Met Ala
                100                 105                 110

Ser His Pro Val Ser Leu His Ala Val Gly Val Ser Tyr Trp Lys Ala
            115                 120                 125

Ser Glu Gly Ala Glu Tyr Asp Asp Gln Thr Ser Gln Arg Glu Lys Glu
            130                 135                 140

Asp Asp Lys Val Phe Pro Gly Glu Ser His Thr Tyr Val Trp Gln Val
145                 150                 155                 160

Leu Lys Glu Asn Gly Pro Met Ala Ser Asp Pro Pro Cys Leu Thr Tyr
                165                 170                 175

Ser Tyr Leu Ser His Val Asp Leu Val Lys Asp Leu Asn Ser Gly Leu
            180                 185                 190

Ile Gly Ala Leu Leu Val Cys Arg Glu Gly Ser Leu Ala Lys Glu Arg
            195                 200                 205

Thr Gln Thr Leu His Gln Phe Val Leu Leu Phe Ala Val Phe Asp Glu
            210                 215                 220

Gly Lys Ser Trp His Ser Glu Thr Lys Asp Ser Leu Thr Gln Ala Met
225                 230                 235                 240

Asp Ser Ala Ser Ala Arg Ala Trp Pro Lys Met His Thr Val Asn Gly
                245                 250                 255

Tyr Val Asn Arg Ser Leu Pro Gly Leu Ile Gly Cys His Arg Lys Ser
            260                 265                 270

Val Tyr Trp His Val Ile Gly Met Gly Thr Thr Pro Glu Val His Ser
            275                 280                 285

Ile Phe Leu Glu Gly His Thr Phe Leu Val Arg Asn His Arg Gln Ala
            290                 295                 300

Ser Leu Glu Ile Ser Pro Ile Thr Phe Leu Thr Ala Gln Thr Leu Leu
305                 310                 315                 320

Met Asp Leu Gly Gln Phe Leu Leu Phe Cys His Ile Ser Ser His Gln
            325                 330                 335

His Asp Gly Met Glu Ala Tyr Val Lys Val Asp Ser Cys Pro Glu Glu
            340                 345                 350

Pro Gln Leu Arg Met Lys Asn Asn Glu Glu Glu Glu Asp Tyr Asp Asp
            355                 360                 365

Asp Leu Tyr Asp Ser Glu Met Asp Val Val Arg Phe Asp Asp Asp Asn
            370                 375                 380

Ser Pro Pro Phe Ile Gln Ile Arg Ser Val Ala Lys Lys His Pro Lys
385                 390                 395                 400

Thr Trp Val His Tyr Ile Ala Ala Glu Glu Glu Asp Trp Asp Tyr Ala
                405                 410                 415
```

```
Pro Ser Val Leu Thr Pro Asp Asp Arg Ser Tyr Lys Ser Gln Tyr Leu
            420                 425                 430
Asn Asn Gly Pro Gln Arg Ile Gly Arg Lys Tyr Lys Val Arg Phe
        435                 440                 445
Met Ala Tyr Thr Asp Val Thr Phe Lys Thr Arg Glu Ala Ile Gln Tyr
450                 455                 460
Glu Ser Gly Ile Leu Gly Pro Leu Leu Tyr Gly Glu Val Gly Asp Thr
465                 470                 475                 480
Leu Leu Ile Ile Phe Lys Asn Gln Ala Ser Arg Pro Tyr Asn Ile Tyr
                485                 490                 495
Pro His Gly Ile Thr Asp Val Ser Pro Leu His Ser Gly Arg Leu Pro
            500                 505                 510
Lys Gly Val Lys His Leu Lys Asp Leu Pro Ile Leu Pro Gly Glu Ile
            515                 520                 525
Phe Lys Tyr Lys Trp Thr Val Thr Val Glu Asp Gly Pro Thr Lys Ser
            530                 535                 540
Asp Pro Arg Cys Leu Thr Arg Tyr Tyr Ser Ser Phe Ile Asn Leu Glu
545                 550                 555                 560
Arg Asp Leu Ala Ser Gly Leu Ile Gly Pro Leu Leu Ile Cys Tyr Lys
                565                 570                 575
Glu Ser Val Asp Gln Arg Gly Asn Gln Met Met Ser Asp Lys Arg Asn
            580                 585                 590
Val Ile Leu Phe Ser Val Phe Asp Glu Asn Arg Ser Trp Tyr Leu Thr
                595                 600                 605
Glu Asn Met Gln Arg Phe Leu Pro Asn Ala Ala Gly Val Gln Pro Gln
610                 615                 620
Asp Pro Glu Phe Gln Ala Ser Asn Ile Met His Ser Ile Asn Gly Tyr
625                 630                 635                 640
Val Phe Asp Ser Leu Gln Leu Ser Val Cys Leu His Glu Val Ala Tyr
                645                 650                 655
Trp Tyr Ile Leu Ser Val Gly Ala Gln Thr Asp Phe Leu Ser Val Phe
            660                 665                 670
Phe Ser Gly Tyr Thr Phe Lys His Lys Met Val Tyr Glu Asp Thr Leu
            675                 680                 685
Thr Leu Phe Pro Phe Ser Gly Glu Thr Val Phe Met Ser Met Glu Asn
            690                 695                 700
Pro Gly Leu Trp Val Leu Gly Cys His Asn Ser Asp Phe Arg Asn Arg
705                 710                 715                 720
Gly Met Thr Ala Leu Leu Lys Val Ser Ser Cys Asp Arg Asn Thr Gly
                725                 730                 735
Asp Tyr Tyr Glu Asp Thr Tyr Glu Asp Ile Pro Thr Tyr Leu Leu Ser
            740                 745                 750
Glu Asn Asn Val Ile Glu Pro Arg Ser Phe Ser Gln Asn Pro Pro Val
            755                 760                 765
Leu Lys Arg His Gln Arg Glu Ile Thr Leu Thr Thr Leu Gln Ser Glu
            770                 775                 780
Gln Glu Glu Ile Asp Tyr Asp Asp Thr Ile Ser Ile Glu Thr Lys Arg
785                 790                 795                 800
Glu Asp Phe Asp Ile Tyr Gly Glu Asp Glu Asn Gln Gly Pro Arg Ser
                805                 810                 815
Phe Gln Lys Arg Thr Arg His Tyr Phe Ile Ala Ala Val Glu Arg Leu
            820                 825                 830
Trp Asp Tyr Gly Met Ser Arg Ser Pro His Val Leu Arg Asn Arg Ala
```

-continued

```
            835                 840                 845
Gln Ser Gly Ser Val Pro Gln Phe Lys Lys Val Val Phe Gln Glu Phe
            850                 855                 860

Thr Asp Gly Ser Phe Thr Gln Pro Leu Tyr Arg Gly Glu Leu Asn Glu
865                 870                 875                 880

His Leu Gly Leu Leu Gly Pro Tyr Ile Arg Ala Glu Val Glu Asp Asn
                        885                 890                 895

Ile Met Val Thr Phe Lys Asn Gln Ala Ser Arg Pro Tyr Ser Phe Tyr
                900                 905                 910

Ser Ser Leu Ile Ser Tyr Glu Glu Asp Gln Arg Gln Gly Ala Glu Pro
            915                 920                 925

Arg Lys Asn Phe Val Lys Pro Asn Glu Thr Lys Thr Tyr Phe Trp Lys
        930                 935                 940

Val Gln His His Met Ala Pro Thr Lys Asp Glu Phe Asp Cys Lys Ala
945                 950                 955                 960

Trp Ala Tyr Phe Ser Asp Val Asp Leu Glu Lys Asp Met His Ser Gly
                    965                 970                 975

Leu Ile Gly Pro Leu Leu Ile Cys His Thr Asn Thr Leu Asn Pro Ala
                980                 985                 990

His Gly Arg Gln Val Thr Val Gln Glu Phe Ala Leu Phe Phe Thr Ile
                    995                 1000                1005

Phe Asp Glu Thr Lys Ser Trp Tyr Phe Thr Glu Asn Met Glu Arg
    1010                1015                1020

Asn Cys Arg Ala Pro Cys Asn Ile Gln Met Glu Asp Pro Thr Phe
    1025                1030                1035

Lys Glu Asn Tyr Arg Phe His Ala Ile Asn Gly Tyr Val Met Asp
    1040                1045                1050

Thr Leu Pro Gly Leu Val Met Ala Gln Asp Gln Arg Ile Arg Trp
    1055                1060                1065

Tyr Leu Leu Ser Met Gly Ser Asn Glu Asn Ile His Ser Ile His
    1070                1075                1080

Phe Ser Gly His Val Phe Thr Val Arg Lys Lys Glu Glu Tyr Lys
    1085                1090                1095

Met Ala Val Tyr Asn Leu Tyr Pro Gly Val Phe Glu Thr Val Glu
    1100                1105                1110

Met Leu Pro Ser Lys Ala Gly Ile Trp Arg Val Glu Cys Leu Ile
    1115                1120                1125

Gly Glu His Leu His Ala Gly Met Ser Thr Leu Phe Leu Val Tyr
    1130                1135                1140

Ser Lys Gln Cys Gln Thr Pro Leu Gly Met Ala Ser Gly His Ile
    1145                1150                1155

Arg Asp Phe Gln Ile Thr Ala Ser Gly Gln Tyr Gly Gln Trp Ala
    1160                1165                1170

Pro Lys Leu Ala Arg Leu His Tyr Ser Gly Ser Ile Asn Ala Trp
    1175                1180                1185

Ser Thr Lys Glu Pro Phe Ser Trp Ile Lys Val Asp Leu Leu Ala
    1190                1195                1200

Pro Met Ile Ile His Gly Ile Lys Thr Gln Gly Ala Arg Gln Lys
    1205                1210                1215

Phe Ser Ser Leu Tyr Ile Ser Gln Phe Ile Ile Met Tyr Ser Leu
    1220                1225                1230

Asp Gly Lys Lys Trp Gln Thr Tyr Arg Gly Asn Ser Thr Gly Thr
    1235                1240                1245
```

Leu Met Val Phe Phe Gly Asn Val Asp Ser Ser Gly Ile Lys His
    1250            1255             1260

Asn Ile Phe Asn Pro Pro Ile Ala Arg Tyr Ile Arg Leu His
    1265            1270             1275

Pro Thr His Tyr Ser Ile Arg Ser Thr Leu Arg Met Glu Leu Met
    1280            1285             1290

Gly Cys Asp Leu Asn Ser Cys Ser Met Pro Leu Gly Met Glu Ser
    1295            1300             1305

Lys Ala Ile Ser Asp Ala Gln Ile Thr Ala Ser Ser Tyr Phe Thr
    1310            1315             1320

Asn Met Phe Ala Thr Trp Ser Pro Ser Gln Ala Arg Leu His Leu
    1325            1330             1335

Gln Gly Arg Thr Asn Ala Trp Arg Pro Gln Val Asn Asn Pro Lys
    1340            1345             1350

Glu Trp Leu Gln Val Asp Phe Gln Lys Thr Met Lys Val Thr Gly
    1355            1360             1365

Ile Thr Thr Gln Gly Val Lys Ser Leu Leu Thr Ser Met Tyr Val
    1370            1375             1380

Lys Glu Phe Leu Ile Ser Ser Gln Asp Gly His His Trp Thr
    1385            1390             1395

Leu Phe Leu Gln Asn Gly Lys Val Lys Val Phe Gln Gly Asn Gln
    1400            1405             1410

Asp Ser Phe Thr Pro Val Val Asn Ser Leu Asp Pro Pro Leu Leu
    1415            1420             1425

Thr Arg Tyr Leu Arg Ile His Pro Gln Ser Trp Val His Gln Ile
    1430            1435             1440

Ala Leu Arg Leu Glu Val Leu Gly Cys Glu Ala Gln Gln Leu Tyr
    1445            1450             1455

<210> SEQ ID NO 41
<211> LENGTH: 10
<212> TYPE: PRT
<213> ORGANISM: artificial sequence
<220> FEATURE:
<223> OTHER INFORMATION: ancestral

<400> SEQUENCE: 41

Ser Arg Pro Pro Ser Ala Ser Ala Pro Lys
1               5                   10

<210> SEQ ID NO 42
<211> LENGTH: 1463
<212> TYPE: PRT
<213> ORGANISM: artificial sequence
<220> FEATURE:
<223> OTHER INFORMATION: ancestral

<400> SEQUENCE: 42

Met Gln Ile Ala Leu Phe Thr Cys Phe Leu Ser Leu Phe Asn Phe
1               5                   10                  15

Cys Ser Ser Ala Thr Arg Arg Tyr Tyr Leu Gly Ala Val Glu Leu Ser
                20                  25                  30

Trp Asn Tyr Met Gln Ser Asp Leu Leu Ser Val Leu His Thr Asp Thr
                35                  40                  45

Arg Phe Leu Pro Arg Met Pro Thr Ser Phe Pro Phe Asn Thr Ser Ile
            50                  55                  60

Met Tyr Lys Lys Thr Val Phe Val Glu Tyr Met Asp His Leu Phe Asn

```
                65                  70                  75                  80
Ile Ala Lys Pro Arg Pro Pro Trp Met Gly Leu Leu Gly Pro Thr Ile
                    85                  90                  95
Trp Thr Glu Val His Asp Thr Val Val Ile Thr Leu Lys Asn Met Ala
                    100                 105                 110
Ser His Pro Val Ser Leu His Ala Val Gly Val Ser Tyr Trp Lys Ala
                    115                 120                 125
Ser Glu Gly Ala Glu Tyr Glu Asp Gln Thr Ser Gln Arg Glu Lys Glu
                    130                 135                 140
Asp Asp Lys Val Phe Pro Gly Glu Ser His Thr Tyr Val Trp Gln Val
145                 150                 155                 160
Leu Lys Glu Asn Gly Pro Met Ala Ser Asp Pro Pro Cys Leu Thr Tyr
                    165                 170                 175
Ser Tyr Leu Ser His Val Asp Leu Val Lys Asp Leu Asn Ser Gly Leu
                    180                 185                 190
Ile Gly Ala Leu Leu Val Cys Lys Glu Gly Ser Leu Ser Lys Glu Arg
                    195                 200                 205
Thr Gln Met Leu His Gln Phe Val Leu Phe Ala Val Phe Asp Glu
                    210                 215                 220
Gly Lys Ser Trp His Ser Glu Thr Lys Asp Ser Phe Thr Gln Ala Met
225                 230                 235                 240
Asp Ser Ala Ser Thr Arg Ala Trp Pro Lys Met His Thr Val Asn Gly
                    245                 250                 255
Tyr Val Asn Arg Ser Leu Pro Gly Leu Ile Gly Cys His Arg Lys Ser
                    260                 265                 270
Val Tyr Trp His Val Ile Gly Met Gly Thr Thr Pro Glu Val His Ser
                    275                 280                 285
Ile Phe Leu Glu Gly His Thr Phe Leu Val Arg Asn His Arg Gln Ala
                    290                 295                 300
Ser Leu Glu Ile Ser Pro Ile Thr Phe Leu Thr Ala Gln Thr Leu Leu
305                 310                 315                 320
Ile Asp Leu Gly Gln Phe Leu Leu Phe Cys His Ile Ser Ser His Lys
                    325                 330                 335
His Asp Gly Met Glu Ala Tyr Val Lys Val Asp Ser Cys Pro Glu Glu
                    340                 345                 350
Pro Gln Trp Gln Lys Lys Asn Asn Glu Glu Met Glu Asp Tyr Asp Asp
                    355                 360                 365
Asp Leu Asp Ser Glu Met Asp Met Phe Thr Leu Asp Asp Asn Ser
                    370                 375                 380
Pro Phe Ile Gln Ile Arg Ser Val Ala Lys Lys His Pro Lys Thr Trp
385                 390                 395                 400
Val His Tyr Ile Ala Ala Glu Glu Glu Asp Trp Asp Tyr Ala Pro Leu
                    405                 410                 415
Val Leu Ala Pro Asp Asp Arg Ser Tyr Lys Ser Gln Tyr Leu Asn Asn
                    420                 425                 430
Gly Pro Gln Arg Ile Gly Arg Lys Tyr Lys Lys Val Arg Phe Met Ala
                    435                 440                 445
Tyr Thr Asp Val Thr Phe Lys Thr Arg Glu Ala Ile Gln His Glu Ser
                    450                 455                 460
Gly Ile Leu Gly Pro Leu Leu Tyr Gly Glu Val Gly Asp Thr Leu Leu
465                 470                 475                 480
Ile Ile Phe Lys Asn Gln Ala Ser Arg Pro Tyr Asn Ile Tyr Pro His
                    485                 490                 495
```

-continued

```
Gly Ile Thr Asp Val Arg Pro Leu Tyr Ser Arg Arg Leu Pro Lys Gly
            500                 505                 510
Val Lys His Leu Lys Asp Phe Pro Ile Leu Pro Gly Glu Ile Phe Lys
        515                 520                 525
Tyr Lys Trp Thr Val Thr Val Glu Asp Gly Pro Thr Lys Ser Asp Pro
    530                 535                 540
Arg Cys Leu Thr Arg Tyr Tyr Ser Ser Phe Val Asn Met Glu Arg Asp
545                 550                 555                 560
Leu Ala Ser Gly Leu Ile Gly Pro Leu Leu Ile Cys Tyr Lys Glu Ser
                565                 570                 575
Val Asp Gln Arg Gly Asn Gln Ile Met Ser Asp Lys Arg Asn Val Ile
            580                 585                 590
Leu Phe Ser Val Phe Asp Glu Asn Arg Ser Trp Tyr Leu Thr Glu Asn
        595                 600                 605
Ile Gln Arg Phe Leu Pro Asn Pro Ala Gly Val Gln Leu Glu Asp Pro
    610                 615                 620
Glu Phe Gln Ala Ser Asn Ile Met His Ser Ile Asn Gly Tyr Val Phe
625                 630                 635                 640
Asp Ser Leu Gln Leu Ser Val Cys Leu His Glu Val Ala Tyr Trp Tyr
                645                 650                 655
Ile Leu Ser Ile Gly Ala Gln Thr Asp Phe Leu Ser Val Phe Phe Ser
            660                 665                 670
Gly Tyr Thr Phe Lys His Lys Met Val Tyr Glu Asp Thr Leu Thr Leu
        675                 680                 685
Phe Pro Phe Ser Gly Glu Thr Val Phe Met Ser Met Glu Asn Pro Gly
    690                 695                 700
Leu Trp Ile Leu Gly Cys His Asn Ser Asp Phe Arg Asn Arg Gly Met
705                 710                 715                 720
Thr Ala Leu Leu Lys Val Ser Ser Cys Asp Lys Asn Thr Gly Asp Tyr
                725                 730                 735
Tyr Glu Asp Ser Tyr Glu Asp Ile Ser Ala Tyr Leu Leu Ser Lys Asn
            740                 745                 750
Asn Ala Ile Glu Pro Arg Ser Phe Ala Gln Asn Ser Arg Pro Pro Ser
        755                 760                 765
Ala Ser Ala Pro Lys Pro Pro Val Leu Lys Arg His Gln Arg Glu Leu
    770                 775                 780
Ser Ala Leu Gln Ser Glu Gln Glu Ala Thr Asp Tyr Asp Asp Ser Ile
785                 790                 795                 800
Thr Ile Glu Thr Asn Glu Asp Phe Asp Ile Tyr Gly Glu Asp Ile Lys
                805                 810                 815
Gln Gly Pro Arg Ser Phe Gln Lys Thr Arg His Tyr Phe Ile Ala
            820                 825                 830
Ala Val Glu Arg Leu Trp Asp Tyr Gly Met Ser Thr Ser Pro His Val
        835                 840                 845
Leu Arg Asn Arg Asp Gln Ser Gly Asn Ala Pro Gln Phe Lys Lys Val
    850                 855                 860
Val Phe Gln Glu Phe Thr Asp Gly Ser Phe Ser Gln Pro Leu Tyr Arg
865                 870                 875                 880
Gly Glu Leu Asn Glu His Leu Gly Leu Leu Gly Pro Tyr Ile Arg Ala
                885                 890                 895
Glu Val Glu Asp Asn Ile Met Val Thr Phe Lys Asn Gln Ala Ser Arg
            900                 905                 910
```

```
Pro Tyr Ser Phe Tyr Ser Ser Leu Ile Ser Tyr Lys Glu Asp Gln Arg
            915                 920                 925

Gln Gly Glu Glu Pro Arg Arg Asn Phe Val Lys Pro Asn Glu Thr Lys
        930                 935                 940

Ile Tyr Phe Trp Lys Val Gln His His Met Ala Pro Thr Glu Asp Glu
945                 950                 955                 960

Phe Asp Cys Lys Ala Trp Ala Tyr Phe Ser Asp Val Asp Leu Glu Arg
                965                 970                 975

Asp Met His Ser Gly Leu Ile Gly Pro Leu Leu Ile Cys His Thr Asn
            980                 985                 990

Thr Leu Asn Pro Ala His Gly Arg Gln Val Ala Val Gln Glu Phe Ala
            995                 1000                1005

Leu Phe Phe Thr Ile Phe Asp Glu Thr Lys Ser Trp Tyr Phe Thr
    1010                1015                1020

Glu Asn Val Glu Arg Asn Cys Lys Thr Pro Cys Asn Ile Gln Met
    1025                1030                1035

Glu Asp Pro Thr Leu Lys Glu Asn Tyr Arg Phe His Ala Ile Asn
    1040                1045                1050

Gly Tyr Val Met Asp Thr Leu Pro Gly Leu Val Met Ala Gln Asp
    1055                1060                1065

Gln Arg Ile Arg Trp Tyr Leu Leu Ser Met Gly Ser Asn Glu Asn
    1070                1075                1080

Ile Gln Ser Ile His Phe Ser Gly His Val Phe Thr Val Arg Lys
    1085                1090                1095

Lys Glu Glu Tyr Lys Met Ala Val Tyr Asn Leu Tyr Pro Gly Val
    1100                1105                1110

Phe Glu Thr Val Glu Met Leu Pro Ser Arg Ala Gly Ile Trp Arg
    1115                1120                1125

Val Glu Cys Leu Ile Gly Glu His Leu Gln Ala Gly Met Ser Thr
    1130                1135                1140

Leu Phe Leu Val Tyr Ser Lys Lys Cys Gln Thr Pro Leu Gly Met
    1145                1150                1155

Ala Ser Gly His Ile Arg Asp Phe Gln Ile Thr Ala Ser Gly Gln
    1160                1165                1170

Tyr Gly Gln Trp Ala Pro Lys Leu Ala Arg Leu His Tyr Ser Gly
    1175                1180                1185

Ser Ile Asn Ala Trp Ser Thr Lys Glu Pro Phe Ser Trp Ile Lys
    1190                1195                1200

Val Asp Leu Leu Ala Pro Met Ile Ile His Gly Ile Lys Thr Gln
    1205                1210                1215

Gly Ala Arg Gln Lys Phe Ser Ser Leu Tyr Ile Ser Gln Phe Ile
    1220                1225                1230

Ile Met Tyr Ser Leu Asp Gly Lys Lys Trp Gln Thr Tyr Arg Gly
    1235                1240                1245

Asn Ser Thr Gly Thr Leu Met Val Phe Phe Gly Asn Val Asp Ser
    1250                1255                1260

Ser Gly Ile Lys His Asn Ile Phe Asn Pro Pro Ile Ile Ala Arg
    1265                1270                1275

Tyr Ile Arg Leu His Pro Thr His Tyr Ser Ile Arg Ser Thr Leu
    1280                1285                1290

Arg Met Glu Leu Met Gly Cys Asp Leu Asn Ser Cys Ser Met Pro
    1295                1300                1305

Leu Gly Met Glu Ser Lys Ala Ile Ser Asp Ala Gln Ile Thr Ala
```

```
                    1310                1315                1320

Ser  Ser  Tyr  Phe  Thr  Asn  Met  Phe  Ala  Thr  Trp  Ser  Pro  Ser  Lys
     1325                1330                1335

Ala  Arg  Leu  His  Leu  Gln  Gly  Arg  Ser  Asn  Ala  Trp  Arg  Pro  Gln
     1340                1345                1350

Val  Asn  Asn  Pro  Lys  Glu  Trp  Leu  Gln  Val  Asp  Phe  Gln  Lys  Thr
     1355                1360                1365

Met  Lys  Val  Thr  Gly  Val  Thr  Thr  Gln  Gly  Val  Lys  Ser  Leu  Leu
     1370                1375                1380

Thr  Ser  Met  Tyr  Val  Lys  Glu  Phe  Leu  Ile  Ser  Ser  Ser  Gln  Asp
     1385                1390                1395

Gly  His  Gln  Trp  Thr  Leu  Phe  Phe  Gln  Asn  Gly  Lys  Val  Lys  Val
     1400                1405                1410

Phe  Gln  Gly  Asn  Gln  Asp  Ser  Phe  Thr  Pro  Val  Val  Asn  Ser  Leu
     1415                1420                1425

Asp  Pro  Pro  Leu  Leu  Thr  Arg  Tyr  Leu  Arg  Ile  His  Pro  Gln  Ser
     1430                1435                1440

Trp  Val  His  Gln  Ile  Ala  Leu  Arg  Met  Glu  Val  Leu  Gly  Cys  Glu
     1445                1450                1455

Ala  Gln  Asp  Leu  Tyr
     1460

<210> SEQ ID NO 43
<211> LENGTH: 5
<212> TYPE: PRT
<213> ORGANISM: artificial sequence
<220> FEATURE:
<223> OTHER INFORMATION: ancestral

<400> SEQUENCE: 43

Thr  Asp  Val  Thr  Phe
1                  5

<210> SEQ ID NO 44
<211> LENGTH: 4
<212> TYPE: PRT
<213> ORGANISM: artificial sequence
<220> FEATURE:
<223> OTHER INFORMATION: ancestral

<400> SEQUENCE: 44

Ile  Ala  Leu  Phe
1

<210> SEQ ID NO 45
<211> LENGTH: 4
<212> TYPE: PRT
<213> ORGANISM: artificial sequence
<220> FEATURE:
<223> OTHER INFORMATION: ancestral

<400> SEQUENCE: 45

Phe  Phe  Leu  Ser
1

<210> SEQ ID NO 46
<211> LENGTH: 4
<212> TYPE: PRT
<213> ORGANISM: artificial sequence
<220> FEATURE:
<223> OTHER INFORMATION: ancestral
```

```
<400> SEQUENCE: 46

Phe Leu Ser Leu
1

<210> SEQ ID NO 47
<211> LENGTH: 4
<212> TYPE: PRT
<213> ORGANISM: artificial sequence
<220> FEATURE:
<223> OTHER INFORMATION: ancestral

<400> SEQUENCE: 47

Leu Ser Leu Phe
1

<210> SEQ ID NO 48
<211> LENGTH: 4
<212> TYPE: PRT
<213> ORGANISM: artificial sequence
<220> FEATURE:
<223> OTHER INFORMATION: ancestral

<400> SEQUENCE: 48

Ser Leu Phe Asn
1

<210> SEQ ID NO 49
<211> LENGTH: 4
<212> TYPE: PRT
<213> ORGANISM: artificial sequence
<220> FEATURE:
<223> OTHER INFORMATION: ancestral

<400> SEQUENCE: 49

Leu Phe Asn Phe
1

<210> SEQ ID NO 50
<211> LENGTH: 4
<212> TYPE: PRT
<213> ORGANISM: artificial sequence
<220> FEATURE:
<223> OTHER INFORMATION: ancestral

<400> SEQUENCE: 50

Phe Asn Phe Cys
1

<210> SEQ ID NO 51
<211> LENGTH: 4
<212> TYPE: PRT
<213> ORGANISM: artificial sequence
<220> FEATURE:
<223> OTHER INFORMATION: ancestral

<400> SEQUENCE: 51

Asn Phe Cys Ser
1

<210> SEQ ID NO 52
<211> LENGTH: 4
<212> TYPE: PRT
<213> ORGANISM: artificial sequence
<220> FEATURE:
<223> OTHER INFORMATION: ancestral

<400> SEQUENCE: 52
```

```
Phe Cys Ser Ser
1

<210> SEQ ID NO 53
<211> LENGTH: 4
<212> TYPE: PRT
<213> ORGANISM: artificial sequence
<220> FEATURE:
<223> OTHER INFORMATION: ancestral

<400> SEQUENCE: 53

Cys Ser Ser Ala
1

<210> SEQ ID NO 54
<211> LENGTH: 4
<212> TYPE: PRT
<213> ORGANISM: artificial sequence
<220> FEATURE:
<223> OTHER INFORMATION: ancestral

<400> SEQUENCE: 54

Ser Ser Ala Thr
1

<210> SEQ ID NO 55
<211> LENGTH: 4
<212> TYPE: PRT
<213> ORGANISM: artificial sequence
<220> FEATURE:
<223> OTHER INFORMATION: ancestral

<400> SEQUENCE: 55

Leu Ser Trp Asn
1

<210> SEQ ID NO 56
<211> LENGTH: 4
<212> TYPE: PRT
<213> ORGANISM: artificial sequence
<220> FEATURE:
<223> OTHER INFORMATION: ancestral

<400> SEQUENCE: 56

Trp Asn Tyr Met
1

<210> SEQ ID NO 57
<211> LENGTH: 4
<212> TYPE: PRT
<213> ORGANISM: artificial sequence
<220> FEATURE:
<223> OTHER INFORMATION: ancestral

<400> SEQUENCE: 57

Asn Tyr Met Gln
1

<210> SEQ ID NO 58
<211> LENGTH: 4
<212> TYPE: PRT
<213> ORGANISM: artificial sequence
<220> FEATURE:
<223> OTHER INFORMATION: ancestral

<400> SEQUENCE: 58
```

Asp Leu Leu Ser
1

<210> SEQ ID NO 59
<211> LENGTH: 4
<212> TYPE: PRT
<213> ORGANISM: artificial sequence
<220> FEATURE:
<223> OTHER INFORMATION: ancestral

<400> SEQUENCE: 59

Leu Leu Ser Val
1

<210> SEQ ID NO 60
<211> LENGTH: 4
<212> TYPE: PRT
<213> ORGANISM: artificial sequence
<220> FEATURE:
<223> OTHER INFORMATION: ancestral

<400> SEQUENCE: 60

Leu Ser Val Leu
1

<210> SEQ ID NO 61
<211> LENGTH: 4
<212> TYPE: PRT
<213> ORGANISM: artificial sequence
<220> FEATURE:
<223> OTHER INFORMATION: ancestral

<400> SEQUENCE: 61

Ser Val Leu His
1

<210> SEQ ID NO 62
<211> LENGTH: 4
<212> TYPE: PRT
<213> ORGANISM: artificial sequence
<220> FEATURE:
<223> OTHER INFORMATION: ancestral

<400> SEQUENCE: 62

Val Leu His Thr
1

<210> SEQ ID NO 63
<211> LENGTH: 4
<212> TYPE: PRT
<213> ORGANISM: artificial sequence
<220> FEATURE:
<223> OTHER INFORMATION: ancestral

<400> SEQUENCE: 63

Leu His Thr Asp
1

<210> SEQ ID NO 64
<211> LENGTH: 4
<212> TYPE: PRT
<213> ORGANISM: artificial sequence
<220> FEATURE:
<223> OTHER INFORMATION: ancestral

<400> SEQUENCE: 64

His Thr Asp Thr

```
<210> SEQ ID NO 65
<211> LENGTH: 4
<212> TYPE: PRT
<213> ORGANISM: artificial sequence
<220> FEATURE:
<223> OTHER INFORMATION: ancestral

<400> SEQUENCE: 65

Thr Asp Thr Arg
1

<210> SEQ ID NO 66
<211> LENGTH: 4
<212> TYPE: PRT
<213> ORGANISM: artificial sequence
<220> FEATURE:
<223> OTHER INFORMATION: ancestral

<400> SEQUENCE: 66

Thr Arg Phe Leu
1

<210> SEQ ID NO 67
<211> LENGTH: 4
<212> TYPE: PRT
<213> ORGANISM: artificial sequence
<220> FEATURE:
<223> OTHER INFORMATION: ancestral

<400> SEQUENCE: 67

Arg Phe Leu Pro
1

<210> SEQ ID NO 68
<211> LENGTH: 4
<212> TYPE: PRT
<213> ORGANISM: artificial sequence
<220> FEATURE:
<223> OTHER INFORMATION: ancestral

<400> SEQUENCE: 68

Phe Leu Pro Arg
1

<210> SEQ ID NO 69
<211> LENGTH: 4
<212> TYPE: PRT
<213> ORGANISM: artificial sequence
<220> FEATURE:
<223> OTHER INFORMATION: ancestral

<400> SEQUENCE: 69

Leu Pro Arg Met
1

<210> SEQ ID NO 70
<211> LENGTH: 4
<212> TYPE: PRT
<213> ORGANISM: artificial sequence
<220> FEATURE:
<223> OTHER INFORMATION: ancestral

<400> SEQUENCE: 70

Pro Arg Met Pro
1
```

```
<210> SEQ ID NO 71
<211> LENGTH: 4
<212> TYPE: PRT
<213> ORGANISM: artificial sequence
<220> FEATURE:
<223> OTHER INFORMATION: ancestral

<400> SEQUENCE: 71

Arg Met Pro Thr
1

<210> SEQ ID NO 72
<211> LENGTH: 4
<212> TYPE: PRT
<213> ORGANISM: artificial sequence
<220> FEATURE:
<223> OTHER INFORMATION: ancestral

<400> SEQUENCE: 72

Pro Thr Ser Phe
1

<210> SEQ ID NO 73
<211> LENGTH: 4
<212> TYPE: PRT
<213> ORGANISM: artificial sequence
<220> FEATURE:
<223> OTHER INFORMATION: ancestral

<400> SEQUENCE: 73

Thr Ser Phe Pro
1

<210> SEQ ID NO 74
<211> LENGTH: 4
<212> TYPE: PRT
<213> ORGANISM: artificial sequence
<220> FEATURE:
<223> OTHER INFORMATION: ancestral

<400> SEQUENCE: 74

Asn Thr Ser Ile
1

<210> SEQ ID NO 75
<211> LENGTH: 4
<212> TYPE: PRT
<213> ORGANISM: artificial sequence
<220> FEATURE:
<223> OTHER INFORMATION: ancestral

<400> SEQUENCE: 75

Thr Ser Ile Met
1

<210> SEQ ID NO 76
<211> LENGTH: 4
<212> TYPE: PRT
<213> ORGANISM: artificial sequence
<220> FEATURE:
<223> OTHER INFORMATION: ancestral

<400> SEQUENCE: 76

Ser Ile Met Tyr
1
```

<210> SEQ ID NO 77
<211> LENGTH: 4
<212> TYPE: PRT
<213> ORGANISM: artificial sequence
<220> FEATURE:
<223> OTHER INFORMATION: ancestral

<400> SEQUENCE: 77

Ile Met Tyr Lys
1

<210> SEQ ID NO 78
<211> LENGTH: 4
<212> TYPE: PRT
<213> ORGANISM: artificial sequence
<220> FEATURE:
<223> OTHER INFORMATION: ancestral

<400> SEQUENCE: 78

Met Tyr Lys Lys
1

<210> SEQ ID NO 79
<211> LENGTH: 4
<212> TYPE: PRT
<213> ORGANISM: artificial sequence
<220> FEATURE:
<223> OTHER INFORMATION: ancestral

<400> SEQUENCE: 79

Phe Val Glu Tyr
1

<210> SEQ ID NO 80
<211> LENGTH: 4
<212> TYPE: PRT
<213> ORGANISM: artificial sequence
<220> FEATURE:
<223> OTHER INFORMATION: ancestral

<400> SEQUENCE: 80

Val Glu Tyr Met
1

<210> SEQ ID NO 81
<211> LENGTH: 4
<212> TYPE: PRT
<213> ORGANISM: artificial sequence
<220> FEATURE:
<223> OTHER INFORMATION: ancestral

<400> SEQUENCE: 81

Glu Tyr Met Asp
1

<210> SEQ ID NO 82
<211> LENGTH: 4
<212> TYPE: PRT
<213> ORGANISM: artificial sequence
<220> FEATURE:
<223> OTHER INFORMATION: ancestral

<400> SEQUENCE: 82

Tyr Met Asp His
1

-continued

```
<210> SEQ ID NO 83
<211> LENGTH: 4
<212> TYPE: PRT
<213> ORGANISM: artificial sequence
<220> FEATURE:
<223> OTHER INFORMATION: ancestral

<400> SEQUENCE: 83

Met Asp His Leu
1

<210> SEQ ID NO 84
<211> LENGTH: 4
<212> TYPE: PRT
<213> ORGANISM: artificial sequence
<220> FEATURE:
<223> OTHER INFORMATION: ancestral

<400> SEQUENCE: 84

Asp His Leu Phe
1

<210> SEQ ID NO 85
<211> LENGTH: 4
<212> TYPE: PRT
<213> ORGANISM: artificial sequence
<220> FEATURE:
<223> OTHER INFORMATION: ancestral

<400> SEQUENCE: 85

Pro Thr Ile Trp
1

<210> SEQ ID NO 86
<211> LENGTH: 4
<212> TYPE: PRT
<213> ORGANISM: artificial sequence
<220> FEATURE:
<223> OTHER INFORMATION: ancestral

<400> SEQUENCE: 86

Thr Ile Trp Thr
1

<210> SEQ ID NO 87
<211> LENGTH: 4
<212> TYPE: PRT
<213> ORGANISM: artificial sequence
<220> FEATURE:
<223> OTHER INFORMATION: ancestral

<400> SEQUENCE: 87

Ile Trp Thr Glu
1

<210> SEQ ID NO 88
<211> LENGTH: 4
<212> TYPE: PRT
<213> ORGANISM: artificial sequence
<220> FEATURE:
<223> OTHER INFORMATION: ancestral

<400> SEQUENCE: 88

Trp Thr Glu Val
1

<210> SEQ ID NO 89
```

```
<211> LENGTH: 4
<212> TYPE: PRT
<213> ORGANISM: artificial sequence
<220> FEATURE:
<223> OTHER INFORMATION: ancestral

<400> SEQUENCE: 89

Thr Glu Val His
1

<210> SEQ ID NO 90
<211> LENGTH: 4
<212> TYPE: PRT
<213> ORGANISM: artificial sequence
<220> FEATURE:
<223> OTHER INFORMATION: ancestral

<400> SEQUENCE: 90

Glu Val His Asp
1

<210> SEQ ID NO 91
<211> LENGTH: 4
<212> TYPE: PRT
<213> ORGANISM: artificial sequence
<220> FEATURE:
<223> OTHER INFORMATION: ancestral

<400> SEQUENCE: 91

Val His Asp Thr
1

<210> SEQ ID NO 92
<211> LENGTH: 4
<212> TYPE: PRT
<213> ORGANISM: artificial sequence
<220> FEATURE:
<223> OTHER INFORMATION: ancestral

<400> SEQUENCE: 92

His Asp Thr Val
1

<210> SEQ ID NO 93
<211> LENGTH: 4
<212> TYPE: PRT
<213> ORGANISM: artificial sequence
<220> FEATURE:
<223> OTHER INFORMATION: ancestral

<400> SEQUENCE: 93

Phe Pro Gly Glu
1

<210> SEQ ID NO 94
<211> LENGTH: 4
<212> TYPE: PRT
<213> ORGANISM: artificial sequence
<220> FEATURE:
<223> OTHER INFORMATION: ancestral

<400> SEQUENCE: 94

Pro Gly Glu Ser
1

<210> SEQ ID NO 95
<211> LENGTH: 4
```

```
<212> TYPE: PRT
<213> ORGANISM: artificial sequence
<220> FEATURE:
<223> OTHER INFORMATION: ancestral

<400> SEQUENCE: 95

Gly Glu Ser His
1

<210> SEQ ID NO 96
<211> LENGTH: 4
<212> TYPE: PRT
<213> ORGANISM: artificial sequence
<220> FEATURE:
<223> OTHER INFORMATION: ancestral

<400> SEQUENCE: 96

Glu Ser His Thr
1

<210> SEQ ID NO 97
<211> LENGTH: 4
<212> TYPE: PRT
<213> ORGANISM: artificial sequence
<220> FEATURE:
<223> OTHER INFORMATION: ancestral

<400> SEQUENCE: 97

Leu Val Cys Lys
1

<210> SEQ ID NO 98
<211> LENGTH: 4
<212> TYPE: PRT
<213> ORGANISM: artificial sequence
<220> FEATURE:
<223> OTHER INFORMATION: ancestral

<400> SEQUENCE: 98

Val Cys Lys Glu
1

<210> SEQ ID NO 99
<211> LENGTH: 4
<212> TYPE: PRT
<213> ORGANISM: artificial sequence
<220> FEATURE:
<223> OTHER INFORMATION: ancestral

<400> SEQUENCE: 99

Cys Lys Glu Gly
1

<210> SEQ ID NO 100
<211> LENGTH: 4
<212> TYPE: PRT
<213> ORGANISM: artificial sequence
<220> FEATURE:
<223> OTHER INFORMATION: ancestral

<400> SEQUENCE: 100

Gly Ser Leu Ser
1

<210> SEQ ID NO 101
<211> LENGTH: 4
<212> TYPE: PRT
```

```
<213> ORGANISM: artificial sequence
<220> FEATURE:
<223> OTHER INFORMATION: ancestral

<400> SEQUENCE: 101

Ser Leu Ser Lys
1

<210> SEQ ID NO 102
<211> LENGTH: 4
<212> TYPE: PRT
<213> ORGANISM: artificial sequence
<220> FEATURE:
<223> OTHER INFORMATION: ancestral

<400> SEQUENCE: 102

Leu Ser Lys Glu
1

<210> SEQ ID NO 103
<211> LENGTH: 4
<212> TYPE: PRT
<213> ORGANISM: artificial sequence
<220> FEATURE:
<223> OTHER INFORMATION: ancestral

<400> SEQUENCE: 103

Ser Lys Glu Arg
1

<210> SEQ ID NO 104
<211> LENGTH: 4
<212> TYPE: PRT
<213> ORGANISM: artificial sequence
<220> FEATURE:
<223> OTHER INFORMATION: ancestral

<400> SEQUENCE: 104

Arg Thr Gln Met
1

<210> SEQ ID NO 105
<211> LENGTH: 4
<212> TYPE: PRT
<213> ORGANISM: artificial sequence
<220> FEATURE:
<223> OTHER INFORMATION: ancestral

<400> SEQUENCE: 105

Thr Gln Met Leu
1

<210> SEQ ID NO 106
<211> LENGTH: 4
<212> TYPE: PRT
<213> ORGANISM: artificial sequence
<220> FEATURE:
<223> OTHER INFORMATION: ancestral

<400> SEQUENCE: 106

Gln Met Leu His
1

<210> SEQ ID NO 107
<211> LENGTH: 4
<212> TYPE: PRT
<213> ORGANISM: artificial sequence
```

```
<220> FEATURE:
<223> OTHER INFORMATION: ancestral

<400> SEQUENCE: 107

Met Leu His Gln
1

<210> SEQ ID NO 108
<211> LENGTH: 4
<212> TYPE: PRT
<213> ORGANISM: artificial sequence
<220> FEATURE:
<223> OTHER INFORMATION: ancestral

<400> SEQUENCE: 108

Leu His Gln Phe
1

<210> SEQ ID NO 109
<211> LENGTH: 4
<212> TYPE: PRT
<213> ORGANISM: artificial sequence
<220> FEATURE:
<223> OTHER INFORMATION: ancestral

<400> SEQUENCE: 109

His Gln Phe Val
1

<210> SEQ ID NO 110
<211> LENGTH: 4
<212> TYPE: PRT
<213> ORGANISM: artificial sequence
<220> FEATURE:
<223> OTHER INFORMATION: ancestral

<400> SEQUENCE: 110

Gln Phe Val Leu
1

<210> SEQ ID NO 111
<211> LENGTH: 4
<212> TYPE: PRT
<213> ORGANISM: artificial sequence
<220> FEATURE:
<223> OTHER INFORMATION: ancestral

<400> SEQUENCE: 111

Lys Asp Ser Phe
1

<210> SEQ ID NO 112
<211> LENGTH: 4
<212> TYPE: PRT
<213> ORGANISM: artificial sequence
<220> FEATURE:
<223> OTHER INFORMATION: ancestral

<400> SEQUENCE: 112

Asp Ser Phe Thr
1

<210> SEQ ID NO 113
<211> LENGTH: 4
<212> TYPE: PRT
<213> ORGANISM: artificial sequence
<220> FEATURE:
```

```
<223> OTHER INFORMATION: ancestral

<400> SEQUENCE: 113

Ser Phe Thr Gln
1

<210> SEQ ID NO 114
<211> LENGTH: 4
<212> TYPE: PRT
<213> ORGANISM: artificial sequence
<220> FEATURE:
<223> OTHER INFORMATION: ancestral

<400> SEQUENCE: 114

Phe Thr Gln Ala
1

<210> SEQ ID NO 115
<211> LENGTH: 4
<212> TYPE: PRT
<213> ORGANISM: artificial sequence
<220> FEATURE:
<223> OTHER INFORMATION: ancestral

<400> SEQUENCE: 115

Thr Gln Ala Met
1

<210> SEQ ID NO 116
<211> LENGTH: 4
<212> TYPE: PRT
<213> ORGANISM: artificial sequence
<220> FEATURE:
<223> OTHER INFORMATION: ancestral

<400> SEQUENCE: 116

Gln Ala Met Asp
1

<210> SEQ ID NO 117
<211> LENGTH: 4
<212> TYPE: PRT
<213> ORGANISM: artificial sequence
<220> FEATURE:
<223> OTHER INFORMATION: ancestral

<400> SEQUENCE: 117

Ala Met Asp Ser
1

<210> SEQ ID NO 118
<211> LENGTH: 4
<212> TYPE: PRT
<213> ORGANISM: artificial sequence
<220> FEATURE:
<223> OTHER INFORMATION: ancestral

<400> SEQUENCE: 118

Met Asp Ser Ala
1

<210> SEQ ID NO 119
<211> LENGTH: 4
<212> TYPE: PRT
<213> ORGANISM: artificial sequence
<220> FEATURE:
<223> OTHER INFORMATION: ancestral
```

<400> SEQUENCE: 119

Asp Ser Ala Ser
1

<210> SEQ ID NO 120
<211> LENGTH: 4
<212> TYPE: PRT
<213> ORGANISM: artificial sequence
<220> FEATURE:
<223> OTHER INFORMATION: ancestral

<400> SEQUENCE: 120

Ser Ala Ser Thr
1

<210> SEQ ID NO 121
<211> LENGTH: 4
<212> TYPE: PRT
<213> ORGANISM: artificial sequence
<220> FEATURE:
<223> OTHER INFORMATION: ancestral

<400> SEQUENCE: 121

Ala Ser Thr Arg
1

<210> SEQ ID NO 122
<211> LENGTH: 4
<212> TYPE: PRT
<213> ORGANISM: artificial sequence
<220> FEATURE:
<223> OTHER INFORMATION: ancestral

<400> SEQUENCE: 122

Ser Thr Arg Ala
1

<210> SEQ ID NO 123
<211> LENGTH: 4
<212> TYPE: PRT
<213> ORGANISM: artificial sequence
<220> FEATURE:
<223> OTHER INFORMATION: ancestral

<400> SEQUENCE: 123

Thr Arg Ala Trp
1

<210> SEQ ID NO 124
<211> LENGTH: 4
<212> TYPE: PRT
<213> ORGANISM: artificial sequence
<220> FEATURE:
<223> OTHER INFORMATION: ancestral

<400> SEQUENCE: 124

Leu Leu Ile Asp
1

<210> SEQ ID NO 125
<211> LENGTH: 4
<212> TYPE: PRT
<213> ORGANISM: artificial sequence
<220> FEATURE:
<223> OTHER INFORMATION: ancestral

```
<400> SEQUENCE: 125

Leu Ile Asp Leu
1

<210> SEQ ID NO 126
<211> LENGTH: 4
<212> TYPE: PRT
<213> ORGANISM: artificial sequence
<220> FEATURE:
<223> OTHER INFORMATION: ancestral

<400> SEQUENCE: 126

Ile Asp Leu Gly
1

<210> SEQ ID NO 127
<211> LENGTH: 4
<212> TYPE: PRT
<213> ORGANISM: artificial sequence
<220> FEATURE:
<223> OTHER INFORMATION: ancestral

<400> SEQUENCE: 127

Ser Ser His Lys
1

<210> SEQ ID NO 128
<211> LENGTH: 4
<212> TYPE: PRT
<213> ORGANISM: artificial sequence
<220> FEATURE:
<223> OTHER INFORMATION: ancestral

<400> SEQUENCE: 128

Ser His Lys His
1

<210> SEQ ID NO 129
<211> LENGTH: 4
<212> TYPE: PRT
<213> ORGANISM: artificial sequence
<220> FEATURE:
<223> OTHER INFORMATION: ancestral

<400> SEQUENCE: 129

His Lys His Asp
1

<210> SEQ ID NO 130
<211> LENGTH: 4
<212> TYPE: PRT
<213> ORGANISM: artificial sequence
<220> FEATURE:
<223> OTHER INFORMATION: ancestral

<400> SEQUENCE: 130

Lys His Asp Gly
1

<210> SEQ ID NO 131
<211> LENGTH: 4
<212> TYPE: PRT
<213> ORGANISM: artificial sequence
<220> FEATURE:
<223> OTHER INFORMATION: ancestral

<400> SEQUENCE: 131
```

```
Glu Pro Gln Trp
1

<210> SEQ ID NO 132
<211> LENGTH: 4
<212> TYPE: PRT
<213> ORGANISM: artificial sequence
<220> FEATURE:
<223> OTHER INFORMATION: ancestral

<400> SEQUENCE: 132

Pro Gln Trp Gln
1

<210> SEQ ID NO 133
<211> LENGTH: 4
<212> TYPE: PRT
<213> ORGANISM: artificial sequence
<220> FEATURE:
<223> OTHER INFORMATION: ancestral

<400> SEQUENCE: 133

Gln Trp Gln Lys
1

<210> SEQ ID NO 134
<211> LENGTH: 4
<212> TYPE: PRT
<213> ORGANISM: artificial sequence
<220> FEATURE:
<223> OTHER INFORMATION: ancestral

<400> SEQUENCE: 134

Trp Gln Lys Lys
1

<210> SEQ ID NO 135
<211> LENGTH: 4
<212> TYPE: PRT
<213> ORGANISM: artificial sequence
<220> FEATURE:
<223> OTHER INFORMATION: ancestral

<400> SEQUENCE: 135

Gln Lys Lys Asn
1

<210> SEQ ID NO 136
<211> LENGTH: 4
<212> TYPE: PRT
<213> ORGANISM: artificial sequence
<220> FEATURE:
<223> OTHER INFORMATION: ancestral

<400> SEQUENCE: 136

Lys Lys Asn Asn
1

<210> SEQ ID NO 137
<211> LENGTH: 4
<212> TYPE: PRT
<213> ORGANISM: artificial sequence
<220> FEATURE:
<223> OTHER INFORMATION: ancestral

<400> SEQUENCE: 137
```

Asn Glu Glu Met
1

<210> SEQ ID NO 138
<211> LENGTH: 4
<212> TYPE: PRT
<213> ORGANISM: artificial sequence
<220> FEATURE:
<223> OTHER INFORMATION: ancestral

<400> SEQUENCE: 138

Glu Glu Met Glu
1

<210> SEQ ID NO 139
<211> LENGTH: 4
<212> TYPE: PRT
<213> ORGANISM: artificial sequence
<220> FEATURE:
<223> OTHER INFORMATION: ancestral

<400> SEQUENCE: 139

Glu Met Glu Asp
1

<210> SEQ ID NO 140
<211> LENGTH: 4
<212> TYPE: PRT
<213> ORGANISM: artificial sequence
<220> FEATURE:
<223> OTHER INFORMATION: ancestral

<400> SEQUENCE: 140

Met Glu Asp Tyr
1

<210> SEQ ID NO 141
<211> LENGTH: 4
<212> TYPE: PRT
<213> ORGANISM: artificial sequence
<220> FEATURE:
<223> OTHER INFORMATION: ancestral

<400> SEQUENCE: 141

Asp Asp Leu Asp
1

<210> SEQ ID NO 142
<211> LENGTH: 4
<212> TYPE: PRT
<213> ORGANISM: artificial sequence
<220> FEATURE:
<223> OTHER INFORMATION: ancestral

<400> SEQUENCE: 142

Asp Leu Asp Ser
1

<210> SEQ ID NO 143
<211> LENGTH: 4
<212> TYPE: PRT
<213> ORGANISM: artificial sequence
<220> FEATURE:
<223> OTHER INFORMATION: ancestral

<400> SEQUENCE: 143

Leu Asp Ser Glu

```
<210> SEQ ID NO 144
<211> LENGTH: 4
<212> TYPE: PRT
<213> ORGANISM: artificial sequence
<220> FEATURE:
<223> OTHER INFORMATION: ancestral

<400> SEQUENCE: 144

Glu Met Asp Met
1

<210> SEQ ID NO 145
<211> LENGTH: 4
<212> TYPE: PRT
<213> ORGANISM: artificial sequence
<220> FEATURE:
<223> OTHER INFORMATION: ancestral

<400> SEQUENCE: 145

Met Asp Met Phe
1

<210> SEQ ID NO 146
<211> LENGTH: 4
<212> TYPE: PRT
<213> ORGANISM: artificial sequence
<220> FEATURE:
<223> OTHER INFORMATION: ancestral

<400> SEQUENCE: 146

Asp Met Phe Thr
1

<210> SEQ ID NO 147
<211> LENGTH: 4
<212> TYPE: PRT
<213> ORGANISM: artificial sequence
<220> FEATURE:
<223> OTHER INFORMATION: ancestral

<400> SEQUENCE: 147

Met Phe Thr Leu
1

<210> SEQ ID NO 148
<211> LENGTH: 4
<212> TYPE: PRT
<213> ORGANISM: artificial sequence
<220> FEATURE:
<223> OTHER INFORMATION: ancestral

<400> SEQUENCE: 148

Phe Thr Leu Asp
1

<210> SEQ ID NO 149
<211> LENGTH: 4
<212> TYPE: PRT
<213> ORGANISM: artificial sequence
<220> FEATURE:
<223> OTHER INFORMATION: ancestral

<400> SEQUENCE: 149

Thr Leu Asp Asp
1
```

```
<210> SEQ ID NO 150
<211> LENGTH: 4
<212> TYPE: PRT
<213> ORGANISM: artificial sequence
<220> FEATURE:
<223> OTHER INFORMATION: ancestral

<400> SEQUENCE: 150

Leu Asp Asp Asp
 1

<210> SEQ ID NO 151
<211> LENGTH: 4
<212> TYPE: PRT
<213> ORGANISM: artificial sequence
<220> FEATURE:
<223> OTHER INFORMATION: ancestral

<400> SEQUENCE: 151

Leu Ser Ala Leu
 1

<210> SEQ ID NO 152
<211> LENGTH: 4
<212> TYPE: PRT
<213> ORGANISM: artificial sequence
<220> FEATURE:
<223> OTHER INFORMATION: ancestral

<400> SEQUENCE: 152

Ser Ala Leu Gln
 1

<210> SEQ ID NO 153
<211> LENGTH: 4
<212> TYPE: PRT
<213> ORGANISM: artificial sequence
<220> FEATURE:
<223> OTHER INFORMATION: ancestral

<400> SEQUENCE: 153

Ala Leu Gln Ser
 1

<210> SEQ ID NO 154
<211> LENGTH: 4
<212> TYPE: PRT
<213> ORGANISM: artificial sequence
<220> FEATURE:
<223> OTHER INFORMATION: ancestral

<400> SEQUENCE: 154

Leu Gln Ser Glu
 1

<210> SEQ ID NO 155
<211> LENGTH: 4
<212> TYPE: PRT
<213> ORGANISM: artificial sequence
<220> FEATURE:
<223> OTHER INFORMATION: ancestral

<400> SEQUENCE: 155

Gln Ser Glu Gln
 1
```

```
<210> SEQ ID NO 156
<211> LENGTH: 4
<212> TYPE: PRT
<213> ORGANISM: artificial sequence
<220> FEATURE:
<223> OTHER INFORMATION: ancestral

<400> SEQUENCE: 156

Ser Glu Gln Glu
1

<210> SEQ ID NO 157
<211> LENGTH: 4
<212> TYPE: PRT
<213> ORGANISM: artificial sequence
<220> FEATURE:
<223> OTHER INFORMATION: ancestral

<400> SEQUENCE: 157

Glu Gln Glu Ala
1

<210> SEQ ID NO 158
<211> LENGTH: 4
<212> TYPE: PRT
<213> ORGANISM: artificial sequence
<220> FEATURE:
<223> OTHER INFORMATION: ancestral

<400> SEQUENCE: 158

Gln Glu Ala Thr
1

<210> SEQ ID NO 159
<211> LENGTH: 4
<212> TYPE: PRT
<213> ORGANISM: artificial sequence
<220> FEATURE:
<223> OTHER INFORMATION: ancestral

<400> SEQUENCE: 159

Glu Ala Thr Asp
1

<210> SEQ ID NO 160
<211> LENGTH: 4
<212> TYPE: PRT
<213> ORGANISM: artificial sequence
<220> FEATURE:
<223> OTHER INFORMATION: ancestral

<400> SEQUENCE: 160

Ala Thr Asp Tyr
1

<210> SEQ ID NO 161
<211> LENGTH: 4
<212> TYPE: PRT
<213> ORGANISM: artificial sequence
<220> FEATURE:
<223> OTHER INFORMATION: ancestral

<400> SEQUENCE: 161

Thr Asp Tyr Asp
1
```

```
<210> SEQ ID NO 162
<211> LENGTH: 4
<212> TYPE: PRT
<213> ORGANISM: artificial sequence
<220> FEATURE:
<223> OTHER INFORMATION: ancestral

<400> SEQUENCE: 162

Tyr Asp Asp Ser
1

<210> SEQ ID NO 163
<211> LENGTH: 4
<212> TYPE: PRT
<213> ORGANISM: artificial sequence
<220> FEATURE:
<223> OTHER INFORMATION: ancestral

<400> SEQUENCE: 163

Asp Asp Ser Ile
1

<210> SEQ ID NO 164
<211> LENGTH: 4
<212> TYPE: PRT
<213> ORGANISM: artificial sequence
<220> FEATURE:
<223> OTHER INFORMATION: ancestral

<400> SEQUENCE: 164

Asp Ser Ile Thr
1

<210> SEQ ID NO 165
<211> LENGTH: 4
<212> TYPE: PRT
<213> ORGANISM: artificial sequence
<220> FEATURE:
<223> OTHER INFORMATION: ancestral

<400> SEQUENCE: 165

Ser Ile Thr Ile
1

<210> SEQ ID NO 166
<211> LENGTH: 4
<212> TYPE: PRT
<213> ORGANISM: artificial sequence
<220> FEATURE:
<223> OTHER INFORMATION: ancestral

<400> SEQUENCE: 166

Ile Thr Ile Glu
1

<210> SEQ ID NO 167
<211> LENGTH: 4
<212> TYPE: PRT
<213> ORGANISM: artificial sequence
<220> FEATURE:
<223> OTHER INFORMATION: ancestral

<400> SEQUENCE: 167

Thr Ile Glu Thr
1

<210> SEQ ID NO 168
```

```
<211> LENGTH: 4
<212> TYPE: PRT
<213> ORGANISM: artificial sequence
<220> FEATURE:
<223> OTHER INFORMATION: ancestral

<400> SEQUENCE: 168

Ile Glu Thr Asn
1

<210> SEQ ID NO 169
<211> LENGTH: 4
<212> TYPE: PRT
<213> ORGANISM: artificial sequence
<220> FEATURE:
<223> OTHER INFORMATION: ancestral

<400> SEQUENCE: 169

Glu Thr Asn Glu
1

<210> SEQ ID NO 170
<211> LENGTH: 4
<212> TYPE: PRT
<213> ORGANISM: artificial sequence
<220> FEATURE:
<223> OTHER INFORMATION: ancestral

<400> SEQUENCE: 170

Thr Asn Glu Asp
1

<210> SEQ ID NO 171
<211> LENGTH: 4
<212> TYPE: PRT
<213> ORGANISM: artificial sequence
<220> FEATURE:
<223> OTHER INFORMATION: ancestral

<400> SEQUENCE: 171

Asn Glu Asp Phe
1

<210> SEQ ID NO 172
<211> LENGTH: 4
<212> TYPE: PRT
<213> ORGANISM: artificial sequence
<220> FEATURE:
<223> OTHER INFORMATION: ancestral

<400> SEQUENCE: 172

Asp Ile Tyr Gly
1

<210> SEQ ID NO 173
<211> LENGTH: 4
<212> TYPE: PRT
<213> ORGANISM: artificial sequence
<220> FEATURE:
<223> OTHER INFORMATION: ancestral

<400> SEQUENCE: 173

Ile Tyr Gly Glu
1

<210> SEQ ID NO 174
<211> LENGTH: 4
```

```
<212> TYPE: PRT
<213> ORGANISM: artificial sequence
<220> FEATURE:
<223> OTHER INFORMATION: ancestral

<400> SEQUENCE: 174

Tyr Gly Glu Asp
1

<210> SEQ ID NO 175
<211> LENGTH: 4
<212> TYPE: PRT
<213> ORGANISM: artificial sequence
<220> FEATURE:
<223> OTHER INFORMATION: ancestral

<400> SEQUENCE: 175

Gly Glu Asp Ile
1

<210> SEQ ID NO 176
<211> LENGTH: 4
<212> TYPE: PRT
<213> ORGANISM: artificial sequence
<220> FEATURE:
<223> OTHER INFORMATION: ancestral

<400> SEQUENCE: 176

Glu Asp Ile Lys
1

<210> SEQ ID NO 177
<211> LENGTH: 4
<212> TYPE: PRT
<213> ORGANISM: artificial sequence
<220> FEATURE:
<223> OTHER INFORMATION: ancestral

<400> SEQUENCE: 177

Asp Ile Lys Gln
1

<210> SEQ ID NO 178
<211> LENGTH: 4
<212> TYPE: PRT
<213> ORGANISM: artificial sequence
<220> FEATURE:
<223> OTHER INFORMATION: ancestral

<400> SEQUENCE: 178

Ile Lys Gln Gly
1

<210> SEQ ID NO 179
<211> LENGTH: 4
<212> TYPE: PRT
<213> ORGANISM: artificial sequence
<220> FEATURE:
<223> OTHER INFORMATION: ancestral

<400> SEQUENCE: 179

Lys Gln Gly Pro
1

<210> SEQ ID NO 180
<211> LENGTH: 4
<212> TYPE: PRT
```

```
<213> ORGANISM: artificial sequence
<220> FEATURE:
<223> OTHER INFORMATION: ancestral

<400> SEQUENCE: 180

Gln Gly Pro Arg
1

<210> SEQ ID NO 181
<211> LENGTH: 4
<212> TYPE: PRT
<213> ORGANISM: artificial sequence
<220> FEATURE:
<223> OTHER INFORMATION: ancestral

<400> SEQUENCE: 181

Met Ser Thr Ser
1

<210> SEQ ID NO 182
<211> LENGTH: 4
<212> TYPE: PRT
<213> ORGANISM: artificial sequence
<220> FEATURE:
<223> OTHER INFORMATION: ancestral

<400> SEQUENCE: 182

Ser Thr Ser Pro
1

<210> SEQ ID NO 183
<211> LENGTH: 4
<212> TYPE: PRT
<213> ORGANISM: artificial sequence
<220> FEATURE:
<223> OTHER INFORMATION: ancestral

<400> SEQUENCE: 183

Thr Ser Pro His
1

<210> SEQ ID NO 184
<211> LENGTH: 4
<212> TYPE: PRT
<213> ORGANISM: artificial sequence
<220> FEATURE:
<223> OTHER INFORMATION: ancestral

<400> SEQUENCE: 184

Arg Asn Arg Asp
1

<210> SEQ ID NO 185
<211> LENGTH: 4
<212> TYPE: PRT
<213> ORGANISM: artificial sequence
<220> FEATURE:
<223> OTHER INFORMATION: ancestral

<400> SEQUENCE: 185

Asn Arg Asp Gln
1

<210> SEQ ID NO 186
<211> LENGTH: 4
<212> TYPE: PRT
<213> ORGANISM: artificial sequence
```

```
<220> FEATURE:
<223> OTHER INFORMATION: ancestral

<400> SEQUENCE: 186

Arg Asp Gln Ser
1

<210> SEQ ID NO 187
<211> LENGTH: 4
<212> TYPE: PRT
<213> ORGANISM: artificial sequence
<220> FEATURE:
<223> OTHER INFORMATION: ancestral

<400> SEQUENCE: 187

Asp Gln Ser Gly
1

<210> SEQ ID NO 188
<211> LENGTH: 4
<212> TYPE: PRT
<213> ORGANISM: artificial sequence
<220> FEATURE:
<223> OTHER INFORMATION: ancestral

<400> SEQUENCE: 188

Gln Ser Gly Asn
1

<210> SEQ ID NO 189
<211> LENGTH: 4
<212> TYPE: PRT
<213> ORGANISM: artificial sequence
<220> FEATURE:
<223> OTHER INFORMATION: ancestral

<400> SEQUENCE: 189

Ser Gly Asn Ala
1

<210> SEQ ID NO 190
<211> LENGTH: 4
<212> TYPE: PRT
<213> ORGANISM: artificial sequence
<220> FEATURE:
<223> OTHER INFORMATION: ancestral

<400> SEQUENCE: 190

Gly Asn Ala Pro
1

<210> SEQ ID NO 191
<211> LENGTH: 4
<212> TYPE: PRT
<213> ORGANISM: artificial sequence
<220> FEATURE:
<223> OTHER INFORMATION: ancestral

<400> SEQUENCE: 191

Asn Ala Pro Gln
1

<210> SEQ ID NO 192
<211> LENGTH: 4
<212> TYPE: PRT
<213> ORGANISM: artificial sequence
<220> FEATURE:
```

<223> OTHER INFORMATION: ancestral

<400> SEQUENCE: 192

Ala Pro Gln Phe
1

<210> SEQ ID NO 193
<211> LENGTH: 4
<212> TYPE: PRT
<213> ORGANISM: artificial sequence
<220> FEATURE:
<223> OTHER INFORMATION: ancestral

<400> SEQUENCE: 193

Gly Ser Phe Ser
1

<210> SEQ ID NO 194
<211> LENGTH: 4
<212> TYPE: PRT
<213> ORGANISM: artificial sequence
<220> FEATURE:
<223> OTHER INFORMATION: ancestral

<400> SEQUENCE: 194

Ser Phe Ser Gln
1

<210> SEQ ID NO 195
<211> LENGTH: 4
<212> TYPE: PRT
<213> ORGANISM: artificial sequence
<220> FEATURE:
<223> OTHER INFORMATION: ancestral

<400> SEQUENCE: 195

Phe Ser Gln Pro
1

<210> SEQ ID NO 196
<211> LENGTH: 4
<212> TYPE: PRT
<213> ORGANISM: artificial sequence
<220> FEATURE:
<223> OTHER INFORMATION: ancestral

<400> SEQUENCE: 196

Ser Gln Pro Leu
1

<210> SEQ ID NO 197
<211> LENGTH: 4
<212> TYPE: PRT
<213> ORGANISM: artificial sequence
<220> FEATURE:
<223> OTHER INFORMATION: ancestral

<400> SEQUENCE: 197

Ile Ser Tyr Lys
1

<210> SEQ ID NO 198
<211> LENGTH: 4
<212> TYPE: PRT
<213> ORGANISM: artificial sequence
<220> FEATURE:
<223> OTHER INFORMATION: ancestral

```
<400> SEQUENCE: 198

Ser Tyr Lys Glu
1

<210> SEQ ID NO 199
<211> LENGTH: 4
<212> TYPE: PRT
<213> ORGANISM: artificial sequence
<220> FEATURE:
<223> OTHER INFORMATION: ancestral

<400> SEQUENCE: 199

Tyr Lys Glu Asp
1

<210> SEQ ID NO 200
<211> LENGTH: 4
<212> TYPE: PRT
<213> ORGANISM: artificial sequence
<220> FEATURE:
<223> OTHER INFORMATION: ancestral

<400> SEQUENCE: 200

Lys Glu Asp Gln
1

<210> SEQ ID NO 201
<211> LENGTH: 4
<212> TYPE: PRT
<213> ORGANISM: artificial sequence
<220> FEATURE:
<223> OTHER INFORMATION: ancestral

<400> SEQUENCE: 201

Arg Gln Gly Glu
1

<210> SEQ ID NO 202
<211> LENGTH: 4
<212> TYPE: PRT
<213> ORGANISM: artificial sequence
<220> FEATURE:
<223> OTHER INFORMATION: ancestral

<400> SEQUENCE: 202

Gln Gly Glu Glu
1

<210> SEQ ID NO 203
<211> LENGTH: 4
<212> TYPE: PRT
<213> ORGANISM: artificial sequence
<220> FEATURE:
<223> OTHER INFORMATION: ancestral

<400> SEQUENCE: 203

Gly Glu Glu Pro
1

<210> SEQ ID NO 204
<211> LENGTH: 4
<212> TYPE: PRT
<213> ORGANISM: artificial sequence
<220> FEATURE:
<223> OTHER INFORMATION: ancestral
```

```
<400> SEQUENCE: 204

Glu Glu Pro Arg
1

<210> SEQ ID NO 205
<211> LENGTH: 4
<212> TYPE: PRT
<213> ORGANISM: artificial sequence
<220> FEATURE:
<223> OTHER INFORMATION: ancestral

<400> SEQUENCE: 205

Glu Pro Arg Arg
1

<210> SEQ ID NO 206
<211> LENGTH: 4
<212> TYPE: PRT
<213> ORGANISM: artificial sequence
<220> FEATURE:
<223> OTHER INFORMATION: ancestral

<400> SEQUENCE: 206

Pro Arg Arg Asn
1

<210> SEQ ID NO 207
<211> LENGTH: 4
<212> TYPE: PRT
<213> ORGANISM: artificial sequence
<220> FEATURE:
<223> OTHER INFORMATION: ancestral

<400> SEQUENCE: 207

Arg Arg Asn Phe
1

<210> SEQ ID NO 208
<211> LENGTH: 4
<212> TYPE: PRT
<213> ORGANISM: artificial sequence
<220> FEATURE:
<223> OTHER INFORMATION: ancestral

<400> SEQUENCE: 208

Arg Asn Phe Val
1

<210> SEQ ID NO 209
<211> LENGTH: 4
<212> TYPE: PRT
<213> ORGANISM: artificial sequence
<220> FEATURE:
<223> OTHER INFORMATION: ancestral

<400> SEQUENCE: 209

Glu Thr Lys Ile
1

<210> SEQ ID NO 210
<211> LENGTH: 4
<212> TYPE: PRT
<213> ORGANISM: artificial sequence
<220> FEATURE:
<223> OTHER INFORMATION: ancestral

<400> SEQUENCE: 210
```

Thr Lys Ile Tyr
1

<210> SEQ ID NO 211
<211> LENGTH: 4
<212> TYPE: PRT
<213> ORGANISM: artificial sequence
<220> FEATURE:
<223> OTHER INFORMATION: ancestral

<400> SEQUENCE: 211

Lys Ile Tyr Phe
1

<210> SEQ ID NO 212
<211> LENGTH: 4
<212> TYPE: PRT
<213> ORGANISM: artificial sequence
<220> FEATURE:
<223> OTHER INFORMATION: ancestral

<400> SEQUENCE: 212

Ile Tyr Phe Trp
1

<210> SEQ ID NO 213
<211> LENGTH: 4
<212> TYPE: PRT
<213> ORGANISM: artificial sequence
<220> FEATURE:
<223> OTHER INFORMATION: ancestral

<400> SEQUENCE: 213

Asp Leu Glu Arg
1

<210> SEQ ID NO 214
<211> LENGTH: 4
<212> TYPE: PRT
<213> ORGANISM: artificial sequence
<220> FEATURE:
<223> OTHER INFORMATION: ancestral

<400> SEQUENCE: 214

Leu Glu Arg Asp
1

<210> SEQ ID NO 215
<211> LENGTH: 4
<212> TYPE: PRT
<213> ORGANISM: artificial sequence
<220> FEATURE:
<223> OTHER INFORMATION: ancestral

<400> SEQUENCE: 215

Glu Arg Asp Met
1

<210> SEQ ID NO 216
<211> LENGTH: 4
<212> TYPE: PRT
<213> ORGANISM: artificial sequence
<220> FEATURE:
<223> OTHER INFORMATION: ancestral

<400> SEQUENCE: 216

Arg Asp Met His
1

<210> SEQ ID NO 217
<211> LENGTH: 4
<212> TYPE: PRT
<213> ORGANISM: artificial sequence
<220> FEATURE:
<223> OTHER INFORMATION: ancestral

<400> SEQUENCE: 217

Asp Met His Ser
1

<210> SEQ ID NO 218
<211> LENGTH: 4
<212> TYPE: PRT
<213> ORGANISM: artificial sequence
<220> FEATURE:
<223> OTHER INFORMATION: ancestral

<400> SEQUENCE: 218

Met His Ser Gly
1

<210> SEQ ID NO 219
<211> LENGTH: 4
<212> TYPE: PRT
<213> ORGANISM: artificial sequence
<220> FEATURE:
<223> OTHER INFORMATION: ancestral

<400> SEQUENCE: 219

Leu Ile Cys His
1

<210> SEQ ID NO 220
<211> LENGTH: 4
<212> TYPE: PRT
<213> ORGANISM: artificial sequence
<220> FEATURE:
<223> OTHER INFORMATION: ancestral

<400> SEQUENCE: 220

Ile Cys His Thr
1

<210> SEQ ID NO 221
<211> LENGTH: 4
<212> TYPE: PRT
<213> ORGANISM: artificial sequence
<220> FEATURE:
<223> OTHER INFORMATION: ancestral

<400> SEQUENCE: 221

Cys His Thr Asn
1

<210> SEQ ID NO 222
<211> LENGTH: 4
<212> TYPE: PRT
<213> ORGANISM: artificial sequence
<220> FEATURE:
<223> OTHER INFORMATION: ancestral

<400> SEQUENCE: 222

His Thr Asn Thr

```
<210> SEQ ID NO 223
<211> LENGTH: 4
<212> TYPE: PRT
<213> ORGANISM: artificial sequence
<220> FEATURE:
<223> OTHER INFORMATION: ancestral

<400> SEQUENCE: 223

Thr Asn Thr Leu
1

<210> SEQ ID NO 224
<211> LENGTH: 4
<212> TYPE: PRT
<213> ORGANISM: artificial sequence
<220> FEATURE:
<223> OTHER INFORMATION: ancestral

<400> SEQUENCE: 224

Thr Leu Asn Pro
1

<210> SEQ ID NO 225
<211> LENGTH: 4
<212> TYPE: PRT
<213> ORGANISM: artificial sequence
<220> FEATURE:
<223> OTHER INFORMATION: ancestral

<400> SEQUENCE: 225

Leu Asn Pro Ala
1

<210> SEQ ID NO 226
<211> LENGTH: 4
<212> TYPE: PRT
<213> ORGANISM: artificial sequence
<220> FEATURE:
<223> OTHER INFORMATION: ancestral

<400> SEQUENCE: 226

Asn Pro Ala His
1

<210> SEQ ID NO 227
<211> LENGTH: 4
<212> TYPE: PRT
<213> ORGANISM: artificial sequence
<220> FEATURE:
<223> OTHER INFORMATION: ancestral

<400> SEQUENCE: 227

Pro Ala His Gly
1

<210> SEQ ID NO 228
<211> LENGTH: 4
<212> TYPE: PRT
<213> ORGANISM: artificial sequence
<220> FEATURE:
<223> OTHER INFORMATION: ancestral

<400> SEQUENCE: 228

Arg Gln Val Ala
1
```

```
<210> SEQ ID NO 229
<211> LENGTH: 4
<212> TYPE: PRT
<213> ORGANISM: artificial sequence
<220> FEATURE:
<223> OTHER INFORMATION: ancestral

<400> SEQUENCE: 229

Gln Val Ala Val
1

<210> SEQ ID NO 230
<211> LENGTH: 4
<212> TYPE: PRT
<213> ORGANISM: artificial sequence
<220> FEATURE:
<223> OTHER INFORMATION: ancestral

<400> SEQUENCE: 230

Val Ala Val Gln
1

<210> SEQ ID NO 231
<211> LENGTH: 4
<212> TYPE: PRT
<213> ORGANISM: artificial sequence
<220> FEATURE:
<223> OTHER INFORMATION: ancestral

<400> SEQUENCE: 231

Ala Val Gln Glu
1

<210> SEQ ID NO 232
<211> LENGTH: 4
<212> TYPE: PRT
<213> ORGANISM: artificial sequence
<220> FEATURE:
<223> OTHER INFORMATION: ancestral

<400> SEQUENCE: 232

Arg Asn Cys Lys
1

<210> SEQ ID NO 233
<211> LENGTH: 4
<212> TYPE: PRT
<213> ORGANISM: artificial sequence
<220> FEATURE:
<223> OTHER INFORMATION: ancestral

<400> SEQUENCE: 233

Asn Cys Lys Thr
1

<210> SEQ ID NO 234
<211> LENGTH: 4
<212> TYPE: PRT
<213> ORGANISM: artificial sequence
<220> FEATURE:
<223> OTHER INFORMATION: ancestral

<400> SEQUENCE: 234

Cys Lys Thr Pro
1
```

```
<210> SEQ ID NO 235
<211> LENGTH: 4
<212> TYPE: PRT
<213> ORGANISM: artificial sequence
<220> FEATURE:
<223> OTHER INFORMATION: ancestral

<400> SEQUENCE: 235

Lys Thr Pro Cys
1

<210> SEQ ID NO 236
<211> LENGTH: 4
<212> TYPE: PRT
<213> ORGANISM: artificial sequence
<220> FEATURE:
<223> OTHER INFORMATION: ancestral

<400> SEQUENCE: 236

Thr Pro Cys Asn
1

<210> SEQ ID NO 237
<211> LENGTH: 4
<212> TYPE: PRT
<213> ORGANISM: artificial sequence
<220> FEATURE:
<223> OTHER INFORMATION: ancestral

<400> SEQUENCE: 237

Glu Asn Ile Gln
1

<210> SEQ ID NO 238
<211> LENGTH: 4
<212> TYPE: PRT
<213> ORGANISM: artificial sequence
<220> FEATURE:
<223> OTHER INFORMATION: ancestral

<400> SEQUENCE: 238

Asn Ile Gln Ser
1

<210> SEQ ID NO 239
<211> LENGTH: 4
<212> TYPE: PRT
<213> ORGANISM: artificial sequence
<220> FEATURE:
<223> OTHER INFORMATION: ancestral

<400> SEQUENCE: 239

Ile Gln Ser Ile
1

<210> SEQ ID NO 240
<211> LENGTH: 4
<212> TYPE: PRT
<213> ORGANISM: artificial sequence
<220> FEATURE:
<223> OTHER INFORMATION: ancestral

<400> SEQUENCE: 240

Gln Ser Ile His
1
```

```
<210> SEQ ID NO 241
<211> LENGTH: 4
<212> TYPE: PRT
<213> ORGANISM: artificial sequence
<220> FEATURE:
<223> OTHER INFORMATION: ancestral

<400> SEQUENCE: 241

Leu Pro Ser Arg
1

<210> SEQ ID NO 242
<211> LENGTH: 4
<212> TYPE: PRT
<213> ORGANISM: artificial sequence
<220> FEATURE:
<223> OTHER INFORMATION: ancestral

<400> SEQUENCE: 242

Pro Ser Arg Ala
1

<210> SEQ ID NO 243
<211> LENGTH: 4
<212> TYPE: PRT
<213> ORGANISM: artificial sequence
<220> FEATURE:
<223> OTHER INFORMATION: ancestral

<400> SEQUENCE: 243

Ser Arg Ala Gly
1

<210> SEQ ID NO 244
<211> LENGTH: 4
<212> TYPE: PRT
<213> ORGANISM: artificial sequence
<220> FEATURE:
<223> OTHER INFORMATION: ancestral

<400> SEQUENCE: 244

Arg Ala Gly Ile
1

<210> SEQ ID NO 245
<211> LENGTH: 4
<212> TYPE: PRT
<213> ORGANISM: artificial sequence
<220> FEATURE:
<223> OTHER INFORMATION: ancestral

<400> SEQUENCE: 245

Arg His Gln Arg
1

<210> SEQ ID NO 246
<211> LENGTH: 24
<212> TYPE: PRT
<213> ORGANISM: artificial sequence
<220> FEATURE:
<223> OTHER INFORMATION: ancestral

<400> SEQUENCE: 246

Ser Phe Ala Gln Asn Ser Arg Pro Pro Ser Ala Ser Ala Pro Lys Pro
1               5                   10                  15

Pro Val Leu Arg Arg His Gln Arg
            20
```

```
<210> SEQ ID NO 247
<211> LENGTH: 4
<212> TYPE: PRT
<213> ORGANISM: artificial sequence
<220> FEATURE:
<223> OTHER INFORMATION: ancestral

<400> SEQUENCE: 247

Cys Leu Leu Gln
1

<210> SEQ ID NO 248
<211> LENGTH: 4
<212> TYPE: PRT
<213> ORGANISM: artificial sequence
<220> FEATURE:
<223> OTHER INFORMATION: ancestral

<400> SEQUENCE: 248

Leu Leu Gln Phe
1

<210> SEQ ID NO 249
<211> LENGTH: 4
<212> TYPE: PRT
<213> ORGANISM: artificial sequence
<220> FEATURE:
<223> OTHER INFORMATION: ancestral

<400> SEQUENCE: 249

Leu Gln Phe Ser
1

<210> SEQ ID NO 250
<211> LENGTH: 4
<212> TYPE: PRT
<213> ORGANISM: artificial sequence
<220> FEATURE:
<223> OTHER INFORMATION: ancestral

<400> SEQUENCE: 250

Gln Phe Ser Phe
1

<210> SEQ ID NO 251
<211> LENGTH: 4
<212> TYPE: PRT
<213> ORGANISM: artificial sequence
<220> FEATURE:
<223> OTHER INFORMATION: ancestral

<400> SEQUENCE: 251

Leu Leu Ser Glu
1

<210> SEQ ID NO 252
<211> LENGTH: 4
<212> TYPE: PRT
<213> ORGANISM: artificial sequence
<220> FEATURE:
<223> OTHER INFORMATION: ancestral

<400> SEQUENCE: 252

Leu Ser Glu Leu
1
```

```
<210> SEQ ID NO 253
<211> LENGTH: 4
<212> TYPE: PRT
<213> ORGANISM: artificial sequence
<220> FEATURE:
<223> OTHER INFORMATION: ancestral

<400> SEQUENCE: 253

Glu Leu His Val
1

<210> SEQ ID NO 254
<211> LENGTH: 4
<212> TYPE: PRT
<213> ORGANISM: artificial sequence
<220> FEATURE:
<223> OTHER INFORMATION: ancestral

<400> SEQUENCE: 254

Arg Val Pro Arg
1

<210> SEQ ID NO 255
<211> LENGTH: 4
<212> TYPE: PRT
<213> ORGANISM: artificial sequence
<220> FEATURE:
<223> OTHER INFORMATION: ancestral

<400> SEQUENCE: 255

Val Pro Arg Ser
1

<210> SEQ ID NO 256
<211> LENGTH: 4
<212> TYPE: PRT
<213> ORGANISM: artificial sequence
<220> FEATURE:
<223> OTHER INFORMATION: ancestral

<400> SEQUENCE: 256

Pro Thr Ile Arg
1

<210> SEQ ID NO 257
<211> LENGTH: 4
<212> TYPE: PRT
<213> ORGANISM: artificial sequence
<220> FEATURE:
<223> OTHER INFORMATION: ancestral

<400> SEQUENCE: 257

Thr Ile Arg Ala
1

<210> SEQ ID NO 258
<211> LENGTH: 4
<212> TYPE: PRT
<213> ORGANISM: artificial sequence
<220> FEATURE:
<223> OTHER INFORMATION: ancestral

<400> SEQUENCE: 258

Ile Arg Ala Glu
1
```

```
<210> SEQ ID NO 259
<211> LENGTH: 4
<212> TYPE: PRT
<213> ORGANISM: artificial sequence
<220> FEATURE:
<223> OTHER INFORMATION: ancestral

<400> SEQUENCE: 259

Asn Glu Glu Glu
1

<210> SEQ ID NO 260
<211> LENGTH: 4
<212> TYPE: PRT
<213> ORGANISM: artificial sequence
<220> FEATURE:
<223> OTHER INFORMATION: ancestral

<400> SEQUENCE: 260

Glu Glu Glu Asp
1

<210> SEQ ID NO 261
<211> LENGTH: 4
<212> TYPE: PRT
<213> ORGANISM: artificial sequence
<220> FEATURE:
<223> OTHER INFORMATION: ancestral

<400> SEQUENCE: 261

Cys Asp Arg Asn
1

<210> SEQ ID NO 262
<211> LENGTH: 4
<212> TYPE: PRT
<213> ORGANISM: artificial sequence
<220> FEATURE:
<223> OTHER INFORMATION: ancestral

<400> SEQUENCE: 262

Glu Asp Thr Tyr
1

<210> SEQ ID NO 263
<211> LENGTH: 4
<212> TYPE: PRT
<213> ORGANISM: artificial sequence
<220> FEATURE:
<223> OTHER INFORMATION: ancestral

<400> SEQUENCE: 263

Pro Thr Tyr Leu
1

<210> SEQ ID NO 264
<211> LENGTH: 4
<212> TYPE: PRT
<213> ORGANISM: artificial sequence
<220> FEATURE:
<223> OTHER INFORMATION: ancestral

<400> SEQUENCE: 264

Leu Ser Glu Asn
1

<210> SEQ ID NO 265
```

```
<211> LENGTH: 4
<212> TYPE: PRT
<213> ORGANISM: artificial sequence
<220> FEATURE:
<223> OTHER INFORMATION: ancestral

<400> SEQUENCE: 265

Ile Thr Leu Thr
1

<210> SEQ ID NO 266
<211> LENGTH: 4
<212> TYPE: PRT
<213> ORGANISM: artificial sequence
<220> FEATURE:
<223> OTHER INFORMATION: ancestral

<400> SEQUENCE: 266

Ser Ile Glu Thr
1

<210> SEQ ID NO 267
<211> LENGTH: 4
<212> TYPE: PRT
<213> ORGANISM: artificial sequence
<220> FEATURE:
<223> OTHER INFORMATION: ancestral

<400> SEQUENCE: 267

Ile Glu Thr Lys
1

<210> SEQ ID NO 268
<211> LENGTH: 4
<212> TYPE: PRT
<213> ORGANISM: artificial sequence
<220> FEATURE:
<223> OTHER INFORMATION: ancestral

<400> SEQUENCE: 268

Glu Thr Lys Arg
1

<210> SEQ ID NO 269
<211> LENGTH: 4
<212> TYPE: PRT
<213> ORGANISM: artificial sequence
<220> FEATURE:
<223> OTHER INFORMATION: ancestral

<400> SEQUENCE: 269

Thr Lys Arg Glu
1

<210> SEQ ID NO 270
<211> LENGTH: 4
<212> TYPE: PRT
<213> ORGANISM: artificial sequence
<220> FEATURE:
<223> OTHER INFORMATION: ancestral

<400> SEQUENCE: 270

Lys Arg Glu Asp
1

<210> SEQ ID NO 271
<211> LENGTH: 4
```

```
<212> TYPE: PRT
<213> ORGANISM: artificial sequence
<220> FEATURE:
<223> OTHER INFORMATION: ancestral

<400> SEQUENCE: 271

Arg Glu Asp Phe
1

<210> SEQ ID NO 272
<211> LENGTH: 4
<212> TYPE: PRT
<213> ORGANISM: artificial sequence
<220> FEATURE:
<223> OTHER INFORMATION: ancestral

<400> SEQUENCE: 272

Gln Lys Arg Thr
1

<210> SEQ ID NO 273
<211> LENGTH: 4
<212> TYPE: PRT
<213> ORGANISM: artificial sequence
<220> FEATURE:
<223> OTHER INFORMATION: ancestral

<400> SEQUENCE: 273

Val Glu Gln Leu
1

<210> SEQ ID NO 274
<211> LENGTH: 4
<212> TYPE: PRT
<213> ORGANISM: artificial sequence
<220> FEATURE:
<223> OTHER INFORMATION: ancestral

<400> SEQUENCE: 274

Glu Gly Leu Trp
1

<210> SEQ ID NO 275
<211> LENGTH: 4
<212> TYPE: PRT
<213> ORGANISM: artificial sequence
<220> FEATURE:
<223> OTHER INFORMATION: ancestral

<400> SEQUENCE: 275

Gly Met Ser Arg
1

<210> SEQ ID NO 276
<211> LENGTH: 4
<212> TYPE: PRT
<213> ORGANISM: artificial sequence
<220> FEATURE:
<223> OTHER INFORMATION: ancestral

<400> SEQUENCE: 276

Met Ser Arg Ser
1

<210> SEQ ID NO 277
<211> LENGTH: 4
<212> TYPE: PRT
```

```
<213> ORGANISM: artificial sequence
<220> FEATURE:
<223> OTHER INFORMATION: ancestral

<400> SEQUENCE: 277

Ser Arg Ser Pro
1

<210> SEQ ID NO 278
<211> LENGTH: 6
<212> TYPE: PRT
<213> ORGANISM: Artificial Sequence
<220> FEATURE:
<223> OTHER INFORMATION: synthetic peptide

<400> SEQUENCE: 278

Gly Gly Gly Gly Gly Gly
1               5

<210> SEQ ID NO 279
<211> LENGTH: 5
<212> TYPE: PRT
<213> ORGANISM: Artificial Sequence
<220> FEATURE:
<223> OTHER INFORMATION: synthetic peptide

<400> SEQUENCE: 279

Gly Gly Gly Gly Thr
1               5

<210> SEQ ID NO 280
<211> LENGTH: 6
<212> TYPE: PRT
<213> ORGANISM: Artificial Sequence
<220> FEATURE:
<223> OTHER INFORMATION: synthetic peptide

<400> SEQUENCE: 280

Gly Gly Gly Pro Pro Pro
1               5

<210> SEQ ID NO 281
<211> LENGTH: 7
<212> TYPE: PRT
<213> ORGANISM: Artificial Sequence
<220> FEATURE:
<223> OTHER INFORMATION: synthetic peptide

<400> SEQUENCE: 281

Gly Gly Gly Ala Pro Pro Pro
1               5
```

FACTOR VIII PROTEINS HAVING ANCESTRAL SEQUENCES, EXPRESSION VECTORS, AND USES RELATED THERETO

CROSS REFERENCE TO RELATED APPLICATIONS

This is the U.S. National Stage of International Application. No. PCT/US2016/015092, filed Jan. 27, 2016, which was published in English under PCT Article 21(2), which in turn claims the benefit of U.S. Provisional Application No. 62/109,964 filed Jan. 30, 2015. The provisional application is incorporated by reference herein in its entirety.

STATEMENT REGARDING FEDERALLY FUNDED RESEARCH

This invention was made with government support under Grants R01 HL092179 and U54 HL112309 awarded by the National Institutes of Health. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy, and is hereby incorporated by reference into the specification. The name of the text file containing the Sequence Listing is Sequence.txt. The text file is 416 KB, was created on Jul. 27, 2017, and is being submitted electronically via EFS-Web.

BACKGROUND

Mutations in the coagulation factor VIII gene result in a decreased or defective coagulation factor (FVIII) protein that gives rise to hemophilia A characterized by uncontrolled bleeding. Treatment of hemophilia A typically entails life-long, multi-weekly intravenous infusion of either human plasma-derived or recombinant FVIII products. Patients treated with FVIII replacement products often develop neutralizing antibodies that render future treatment ineffective. Thus, there is a need to identify improved therapies.

Gene therapies are typically based on genetically engineered viruses designed to deliver functional transgenes to the patient so that their own cells can biosynthesize a missing or defective protein. Clinical advancements have been made using recombinant adeno-associated viral (rAAV) vectors for the expression of blood factors in the liver. McIntosh et al. report therapeutic levels of FVIII following administration of rAAV vector encoding a human factor VIII variant. Blood. 2013, 121(17):3335-44. See also Brown et al. Molecular Therapy, Methods & Clinical Development (2014) 1, 14036; Doering et al. J. Biol. Chem. 2004, 279:6546-6552; Zakas et al., J Thromb Haemost, 2015, 13(1):72-81; and U.S. Patent Application Publication US20040197875.

References cited herein are not an admission of prior art.

SUMMARY

This disclosure relates to recombinant or chimeric FVIII proteins, variants, and vectors encoding the proteins containing one or more ancestral mutations. In certain embodiments, one or more protein domains comprise amino acid sequences that are derived from ancestrally reconstructed amino acid sequences. In certain embodiments, the disclosure relates to pharmaceutical compositions comprising the proteins or vectors and related methods of inducing blood clotting.

In certain embodiments, ancestral domain mutations are those contained in SEQ ID NO: 2, 11, 20, and 29-38. In certain embodiments, the ancestral domain is a sequence within the A1 domain, A2 domain, activation peptide(ap) domain, A3 domain, C1 domain, or C2 domain optionally having a signaling peptide (sp) domain. In certain embodiments, the FVIII variant comprises a deleted B domain.

In certain embodiments, FVIII variant comprises an A1 domain, an A2 domain, a RHQR sequence (SEQ ID NO: 245), an A3 domain, a C1 domain, and a C2 domain.

In certain embodiments, FVIII variant comprises an A1 domain, an A2 domain, an activation peptide (ap) domain, an A3 domain, a C1 domain, and a C2 domain. In certain embodiments, the FVIII variant optionally comprises a deleted B domain.

In certain embodiments, the FVIII variant comprises a linker of between two and fifty, or two and twenty five, or two and fifteen amino acids between the A2 domain and the an activation peptide (ap) domain.

In certain embodiments, the ancestral sp domain is SEQ ID NO: 3, 12, or 21 or variants thereof. In certain embodiments, the ancestral A1 domain is SEQ ID NO: 4, 13, or 22 or variants thereof.

In certain embodiments, the ancestral A2 domain is SEQ ID NO: 5, 14, or 23 or variants thereof. In certain embodiments, the ancestral B domain is SEQ ID NO: 6, 15, or 24 or variants thereof. In certain embodiments, the ancestral ap domain is SEQ ID NO: 7, 16 or 25 or variants thereof. In certain embodiments, the ancestral A3 domain is SEQ ID NO: 8, 17, or 26 or variants thereof. In certain embodiments, the ancestral C1 domain is SEQ ID NO: 9, 18, or 27 or variants thereof. In certain embodiments, the ancestral C2 domain is SEQ ID NO: 10, 19, or 28 or variants thereof. In certain embodiments, the variants are those having greater than 80, 85, 90, 95, 96, 97, 98, or 99% identity or similarity to the domains. In certain embodiments, the variants are those having one, two, or more amino acid substitutions or conservative substitutions. In certain embodiments, the variants are those having one, two, three, four, five, six seven, eight, nine, or more amino acid substitutions, deletions, or additions.

In certain embodiments, the recombinant FVIII protein has SEQ ID NO: 39, 40, or 42 or variants thereof. In certain embodiments, the variants are those having greater than 80, 85, 90, 95, 96, 97, 98, or 99% identity or similarity to the proteins including or not including the signaling peptide. In certain embodiments, the variants are those having one, two, or more amino acid substitutions or conservative substitutions. In certain embodiments, the variants are those having one, two, three, four, five, six seven, eight, nine, or more amino acid substitutions, deletions, or additions.

In certain embodiments, the disclosure relates to recombinant or chimeric FVIII protein having one or more ancestral sequences or variants thereof such as SEQ ID NOs: 44-244 and 247-277 in the corresponding domains. In certain embodiments, the disclosure relates to recombinant FVIII protein having an ancestral domain selected from a signaling peptide (sp) domain, A1 domain, activation peptide (ap) domain, and A3 domain wherein one or more amino acids in B-domain are optionally deleted or the B-domain has one or more naturally or non-naturally occurring substitutions.

In certain embodiments, the recombinant or chimeric FVIII protein has the E434V mutation as reported in FIG. 1 of US20040197875 wherein the protein has an A2 domain having TDVTF (SEQ ID NO: 43)

In certain embodiments, the disclosure relates to nucleic acids encoding a recombinant or chimeric FVIII protein disclosed herein.

In certain embodiments, the disclosure relates to vectors comprising a promotor nucleic acid sequence in operable combination with a heterologous nucleic acid sequence encoding a recombinant or chimeric FVIII protein disclosed herein. In certain embodiments, the vector comprises a liver-specific promotor and 5' and 3' AAV inverted terminal repeats (ITRs).

In certain embodiments, the disclosure contemplates lentiviral gene therapy targeting hematopoietic stem cells. In certain embodiments, the vector is a retroviral or lentiviral vector such as a self-inactivating lentiviral vector derived from HIV-1. In certain embodiments, the vector contains an internal constitutive promoter such as EF1-alpha, PGK or UbC or a cell specific promoter such as GPIb-alpha, CD68, or beta globin LCR.

In certain embodiments, the disclosure contemplates pharmaceutical compositions comprising a recombinant or chimeric FVIII protein and a pharmaceutically acceptable excipient.

In certain embodiments, the disclosure contemplates methods of inducing blood clotting comprising administering an effective amount of a pharmaceutical composition disclosed herein to a subject in need thereof. In certain embodiments, the subject is at risk for, suspected of, exhibiting symptoms of, or diagnosed with a blood clotting disorder, e.g., wherein the subject is diagnosed with hemophilia A or acquired hemophilia.

In certain embodiments, the disclosure contemplates pharmaceutical composition comprising a vector of encoding a protein disclosed herein.

In certain embodiments, the disclosure contemplates method of inducing blood clotting comprising administering an effective amount of a pharmaceutical composition comprising a vector encoding a protein disclosed herein to a subject in need thereof wherein the subject is diagnosed with hemophilia A or acquired hemophilia under conditions such that the protein is expressed inducing blood clotting. In certain embodiments, the subject is unlikely to respond to exogenous FVIII infusions.

In certain embodiments, the disclosure relates to expression systems comprising nucleic acids or vectors comprising nucleic acids disclosed herein.

In certain embodiments, the disclosure relates to methods of inducing blood clotting comprising administering an effective amount of allogenic or autologous cells transduced ex vivo with a vector to express a FVIII disclosed herein.

Figure 1:
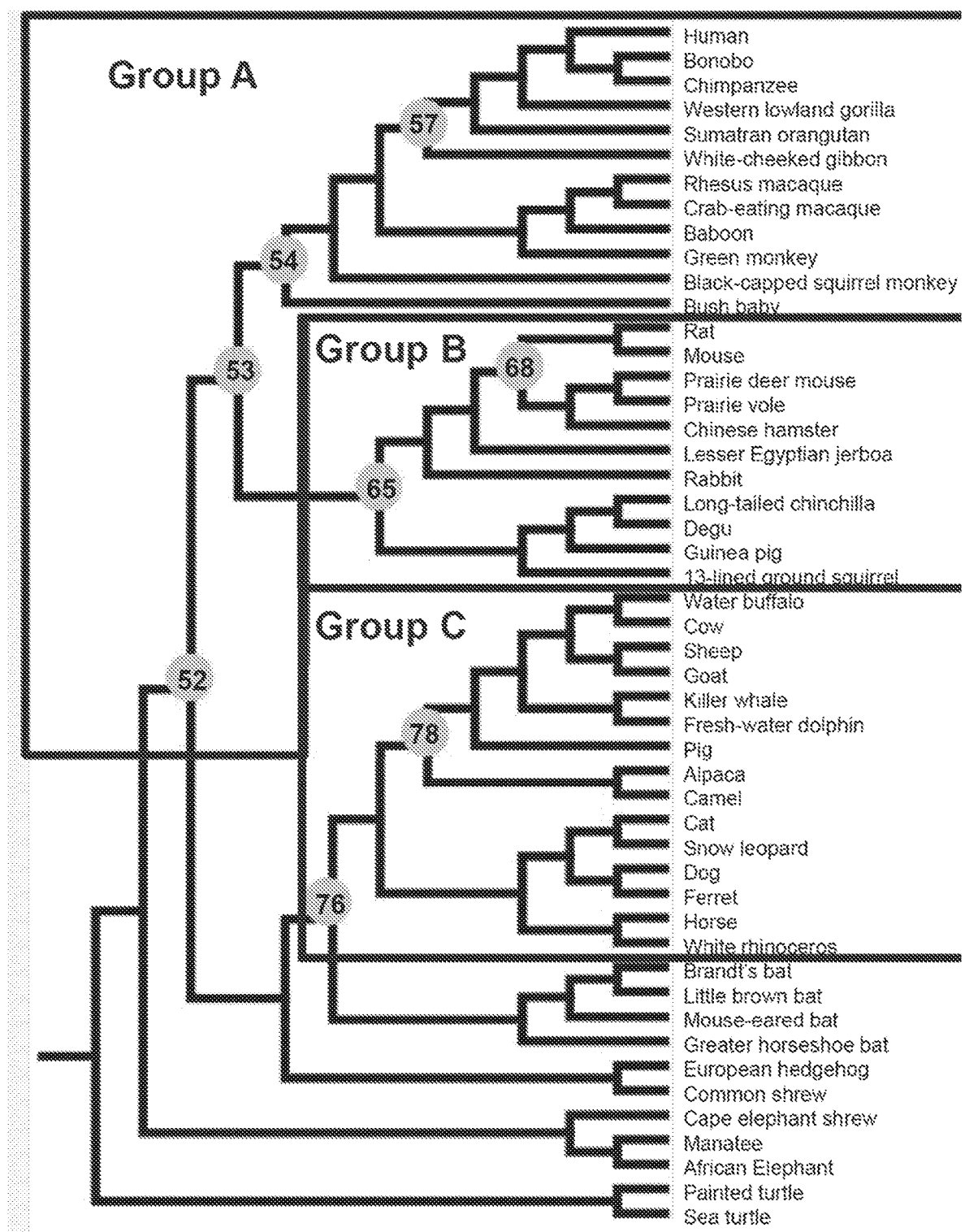
FIG. 1 shows a phylogenetic tree that was constructed for mammalian FVIII genes using known amino acid sequences. The ancestral intermediary nodes that were reconstructed through gene synthesis are numbered within the circles. These B-domain deleted genes have been codon optimized for human cell expression and have been subcloned into the mammalian expression plasmid ReNeo.
Figure 2:
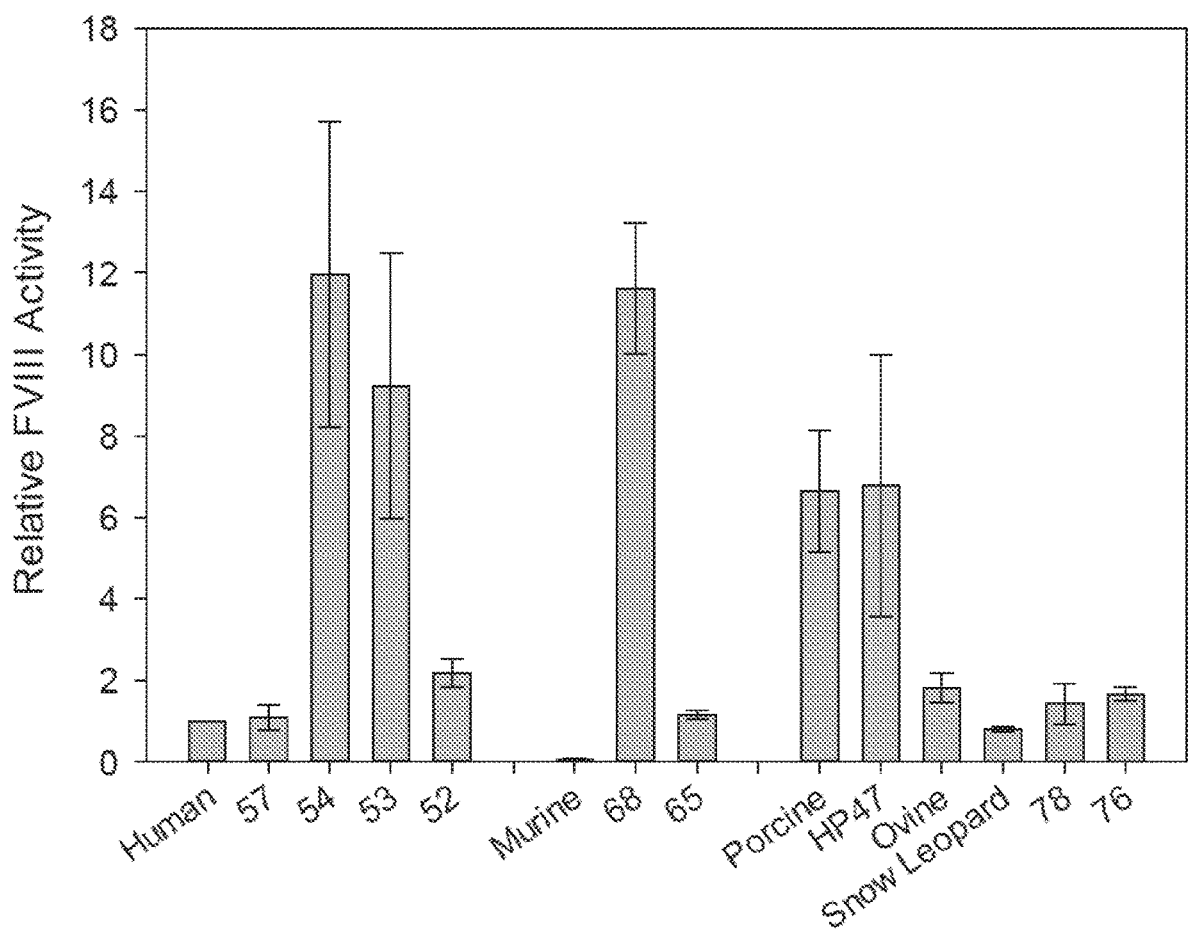
FIG. 2 shows relative FVIII activity data where HEK293T-17 cells were transiently transfected with FVIII plasmid via PEI. Twenty-four hours after replacing DMEM media with serum-free Aim-V, supernatant was assayed for FVIII activity via one-stage coagulation assay and shown as the mean fold increase over human FVIII from two separate experiments. Total activity was normalized to cell counts taken at the time of the FVIII detection and then normalized to human FVIII activity levels.
Figure 3:
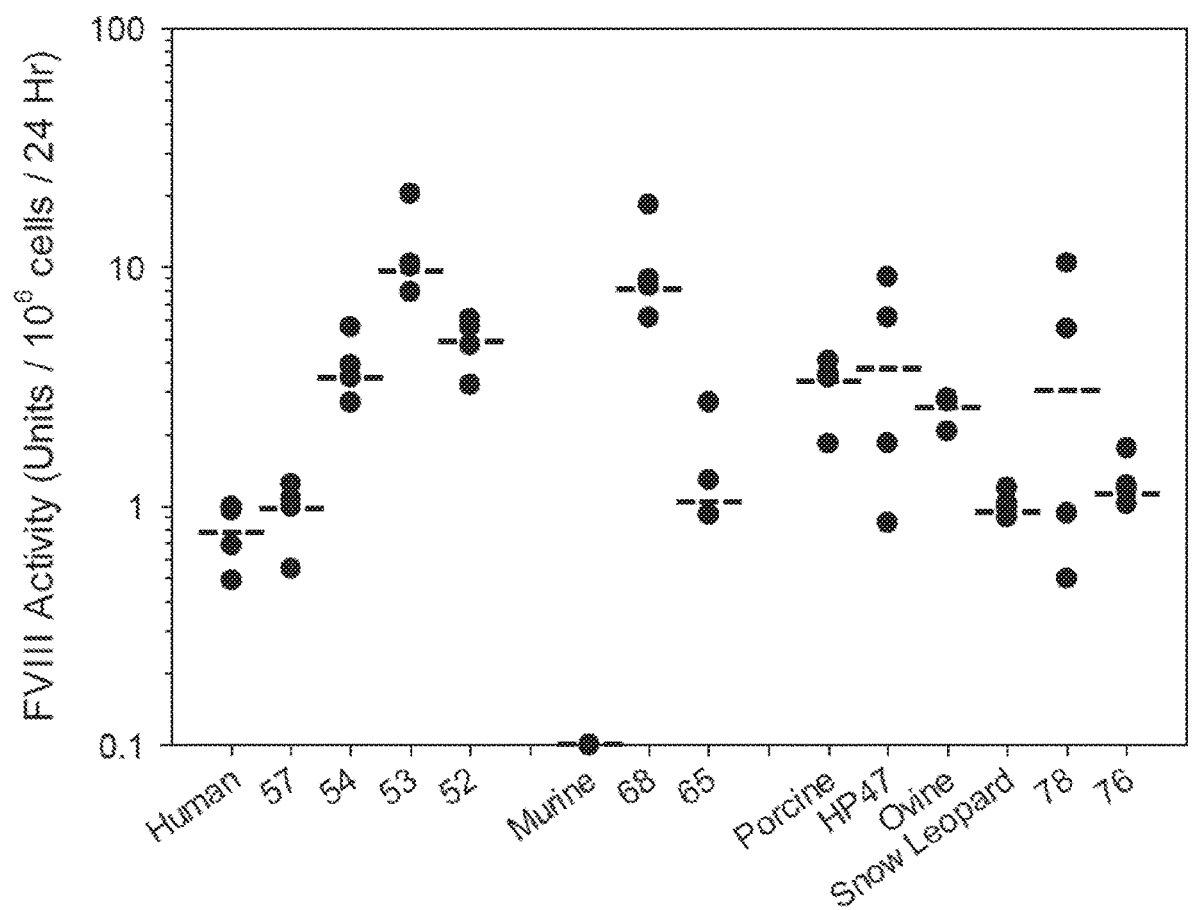
FIG. 3 shows activity data. Stable BHK-M clones were generated using G418 selection following transfection of FVIII plasmid with Lipofectamine 2000. Twenty-four clones were selected from each FVIII treatment. Shown are the FVIII activity levels of the 4 highest producing clones as determined by one-stage coagulation and normalized to cell counts. Dashed lines indicate the median value for each FVIII treatment. Of the ancestral FVIII sequences, production of nodes 52, 53, and 68 FVIII is significantly different from human FVIII. Furthermore, ancestral nodes 53 and 68 produce significantly higher concentrations of FVIII compared to porcine FVIII.
Figure 4:
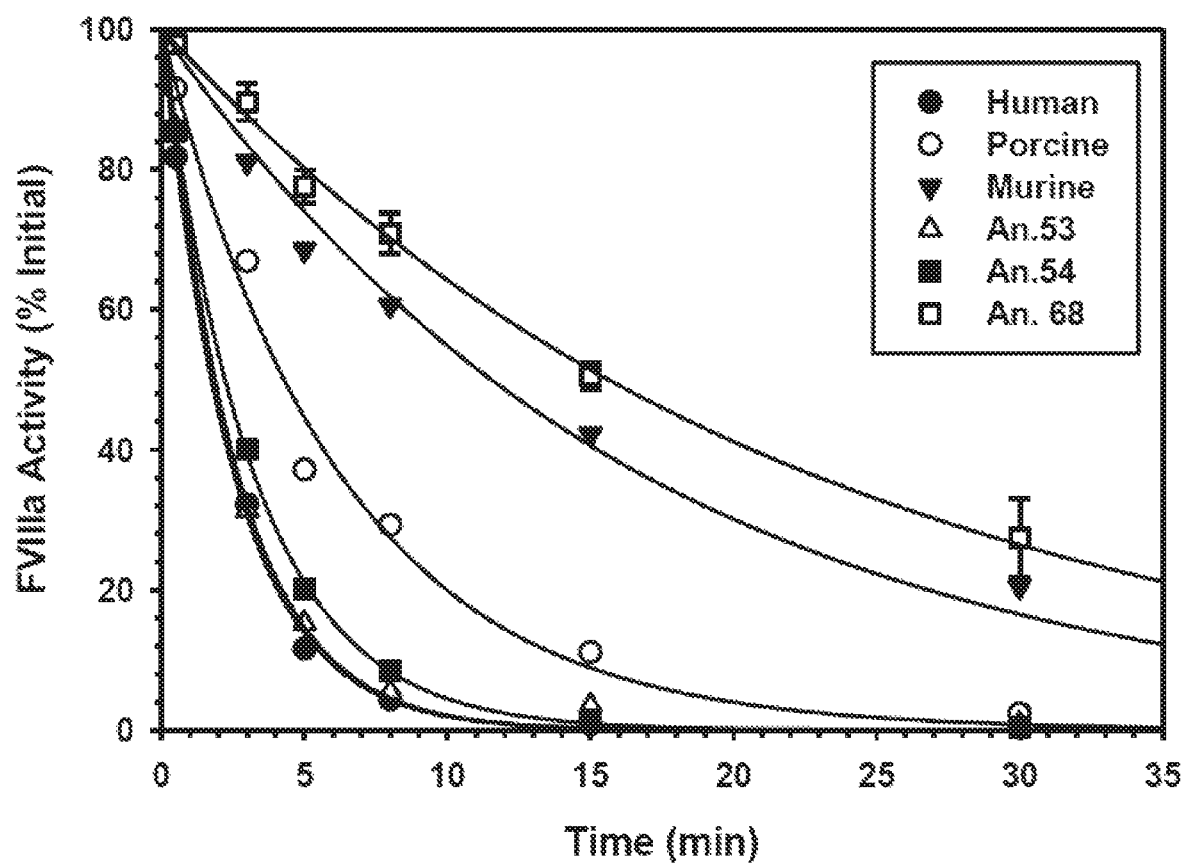
FIG. 4 shows the decay rate of 1 nM ancestral node 68 FVIIIa determined by chromogenic Xase assay. FVIII protein from the top producing BHK-M clone was collected and purified from serum-free media using one-step ion-exchange chromatography. FVIII was captured with an SPHP HiTrap column and eluted with an increasing concentration of NaCl. Compared to the human FVIII half-life of 1.8 minutes, the ancestral node 68 protein displays a 9-fold prolonged half-life of 16.2 minutes, n=1. Of note, node 68 retains 75% identity to murine FVIII and 71% identity to porcine FVIII.

FIG. 5 shows data on cross-reactivity of inhibitory mouse anti-human monoclonal antibodies (MAbs) to An-53 (black circles) and An-68 (white circles) via direct ELISA. MAbs were selected for high potency (≥1000 BU/mg) and specificity to the A2 or C2 domain. Epitope groups within the domain are listed in parentheses. Cross-reactivity to ancestral FVIII is defined as the percent absorbance compared to human FVIII.

FIG. 6 shows data on the ability to the E434 mutant in A2 to evade 4A4 inhibition.

FIG. 7 shows a schematic of a AAV-FVIII plasmid. FVIII was human codon optimized and subcloned into an AAV expression cassette under the liver-directed HLP promoter.

FIG. 8 shows data comparing An-53 (white) and ET3 (black) FVIII levels following hydrodynamic injection in mice at two doses of AAV-FVIII plasmid DNA. Circles represent 3 μg and downward triangles represent 0.75 μg per mouse. FVIII activity was measured by two-stage chromogenic assay compared to a FACT standard and error bars represent standard deviation of 4 mice.

FIG. 9 shows SDS-PAGE analysis of An-53 and An-68 following two-step ion-exchange. SC: single chain; HC: heavy chain; LC: light chain; cLC: cleaved light chain; A1 and A2: FVIII A domains

DETAILED DISCUSSION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.
Figure 5:
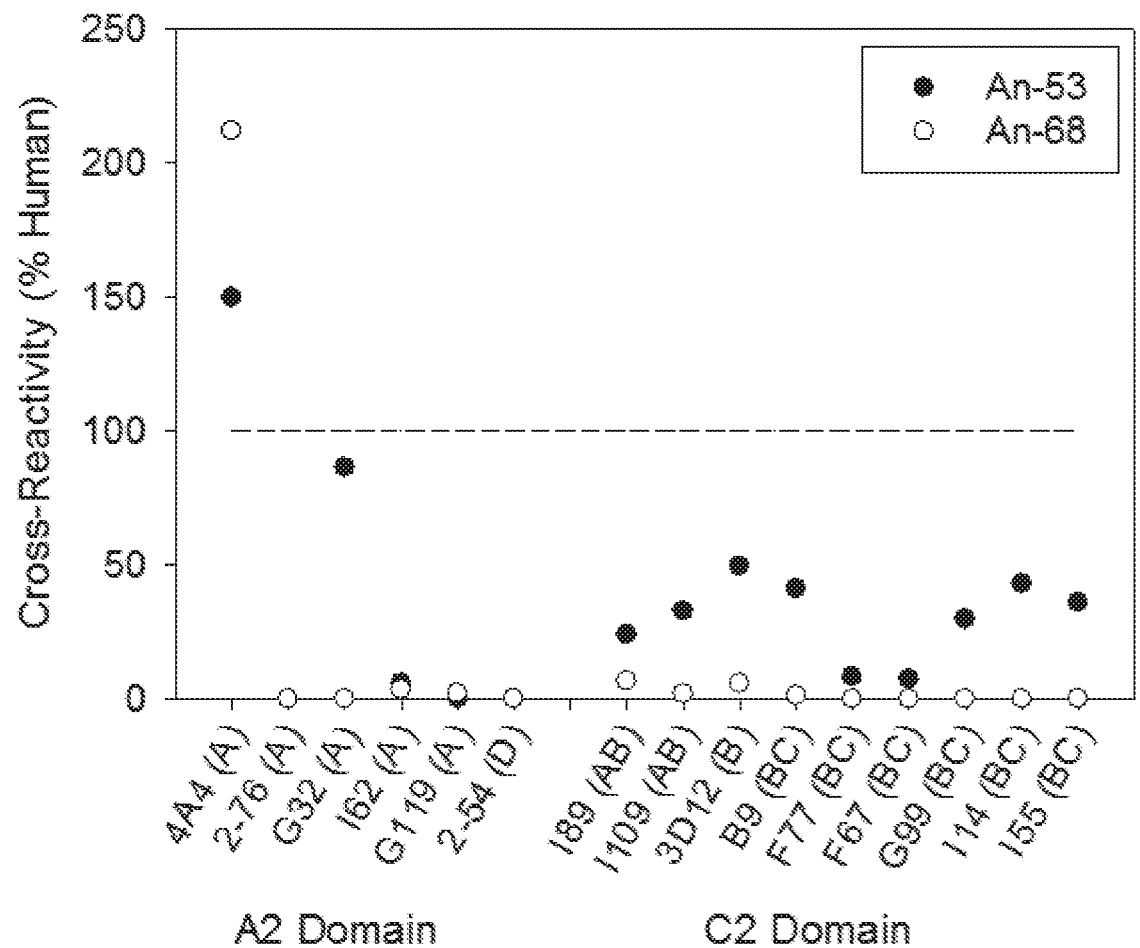
Figure 6:
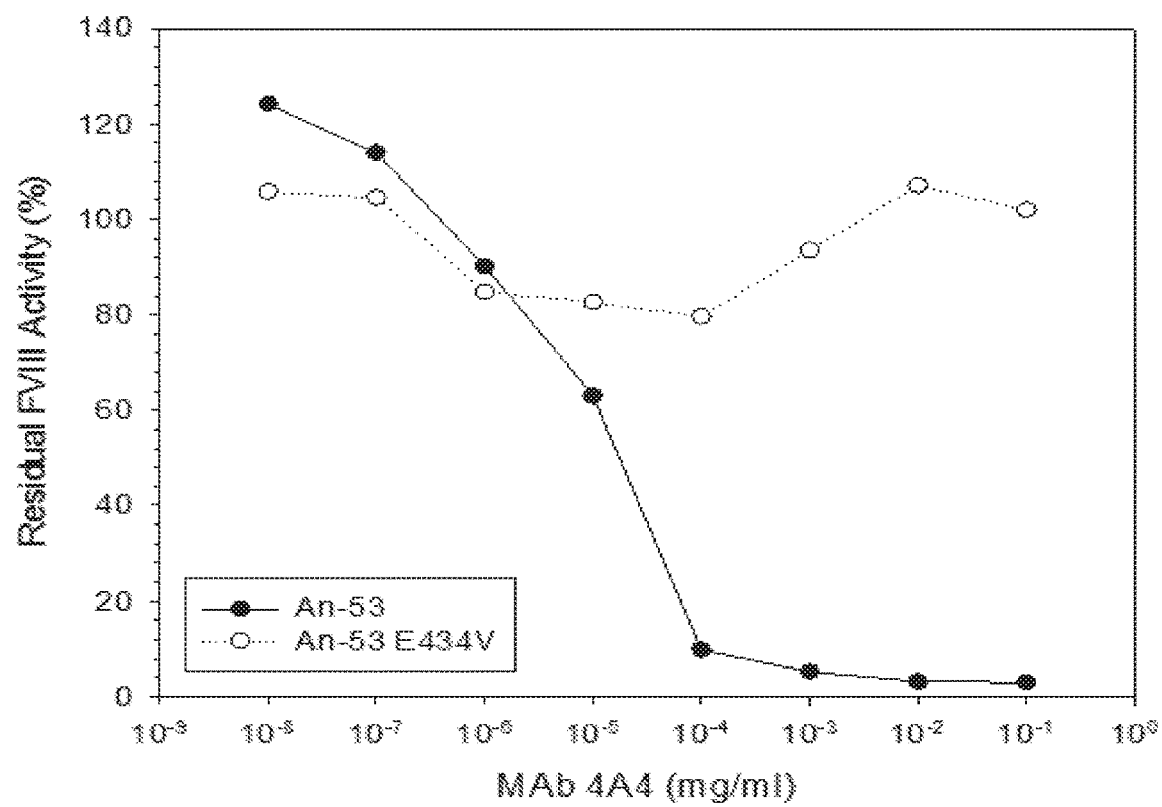
Figure 7:
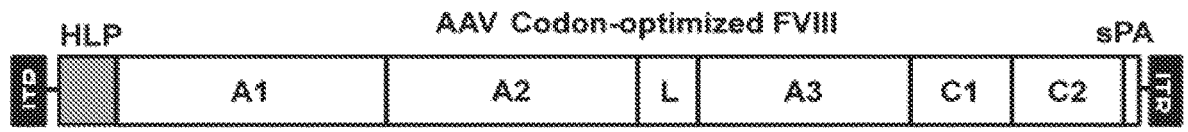
Figure 8:
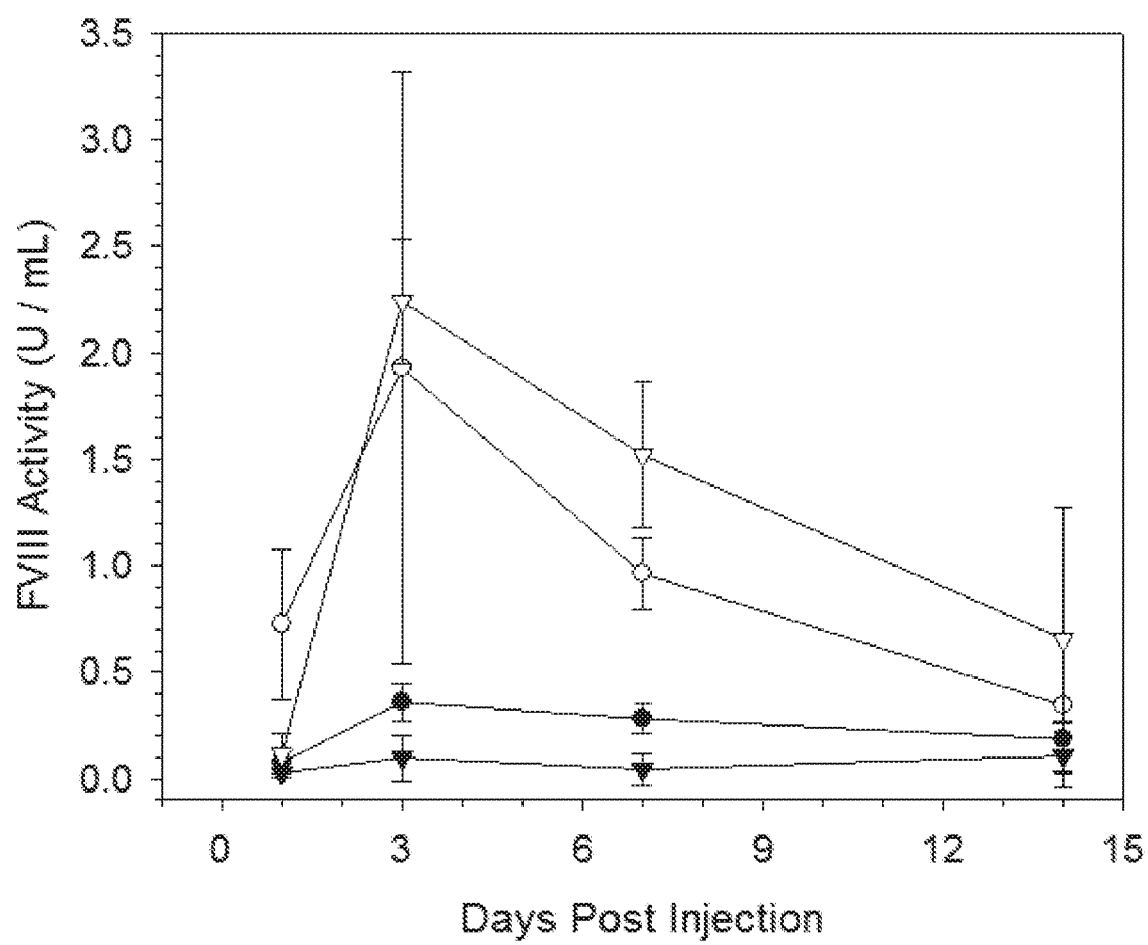
Figure 9:
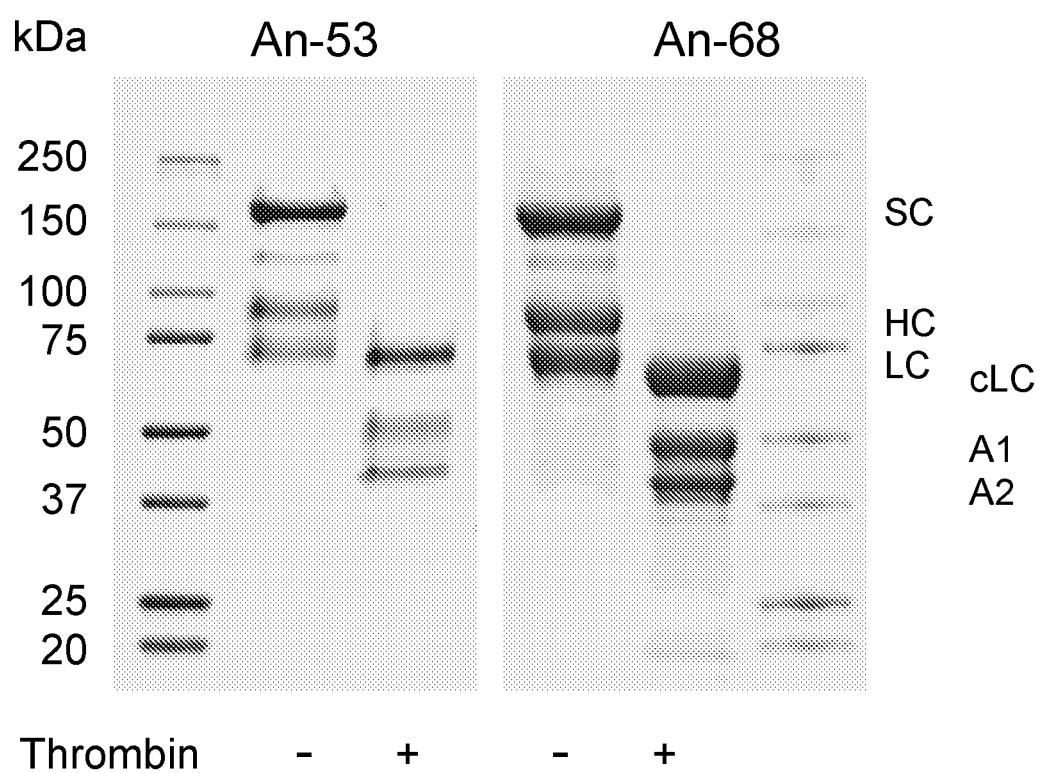

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

Prior to describing the various embodiments, the following definitions are provided and should be used unless otherwise indicated.

As used herein, a "non-naturally occurring" sequence is one for which no organisms produce or ever produced through the course of natural events. A protein is non-naturally occurring if one or more amino acids are substituted such that the entire amino acid sequence was never produced due to the course of natural events.

As used herein, an "ancestral mutations" refer to alterations in nucleic acid sequencing that results in amino acid substitutions in the corresponding protein when compared to the consensus human sequence, i.e., SEQ ID NO: 1. A position of the amino acid substitution can be identified by reference to numerical positions within SEQ ID NO: 1 with or without reference to the protein having the signal peptide. With regard to mutations, it is common to refer to the numbering system above wherein FVIII does not contain the signal peptide as it is typically cleaved during cellular processing. As used herein, a "unique ancestral mutation" refers to an ancestral mutation also not found in the sequence for any known primates or mammals.

The terms "protein" and "polypeptide" refer to compounds comprising amino acids joined via peptide bonds and are used interchangeably.

As used herein, where "amino acid sequence" is recited herein, it refers to an amino acid sequence of a protein molecule. An "amino acid sequence" can be deduced from the nucleic acid sequence encoding the protein. However, terms such as "polypeptide" or "protein" are not meant to limit the amino acid sequence to the deduced amino acid sequence, but include post-translational modifications of the deduced amino acid sequences, such as amino acid deletions, additions, and modifications such as glycosylations and addition of lipid moieties.

The term "nucleic acid" refers to a polymer of nucleotides, or polynucleotides. The term is used to designate a single molecule, or a collection of molecules. Nucleic acids may be single stranded or double stranded of self-complementary, and may include coding regions and regions of various control elements.

The terms "a nucleic acid sequence encoding" a specified polypeptide refers to a nucleic acid sequence comprising the coding region of a gene or in other words the nucleic acid sequence which encodes a protein. The coding region may be present in either a cDNA, genomic DNA, or RNA form. When present in a DNA form, the oligonucleotide, polynucleotide, or nucleic acid may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present disclosure may contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The term "chimera" when used in reference to a polypeptide of polynucleotide refers to the expression product of two or more coding sequences obtained from different genes, that have been cloned together and that, after translation, act as a single polypeptide sequence such that the single or whole polypeptide sequence, or nucleotide sequence, is not naturally occurring. Chimeric polypeptides are also referred to as "hybrid" polypeptides. The coding sequences include those obtained from the same or from different species of organisms.

The term "heterologous nucleic acid" refers to a nucleic acid that is not in its natural environment (i.e., has been altered by the hand of man). For example, a heterologous nucleic acid includes a gene from one species introduced into another species. A heterologous nucleic acid also includes a gene native to an organism that has been altered in some way (e.g., mutated, added in multiple copies, linked to a non-native promoter or enhancer sequence, etc.). Heterologous viral nucleic acids are distinguished from endogenous viral genes in that the heterologous gene sequences are typically joined to nucleotide sequences comprising regulatory elements such as promoters that are not found naturally associated with the gene for the protein encoded by the heterologous gene or with viral gene sequences in the chromosome, or are associated with portions of the chromosome not found in nature (e.g., genes expressed in loci where the gene is not normally expressed).

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (in other words, additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

In certain embodiments, term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity.

In certain embodiments, sequence "identity" refers to the number of exactly matching 5 amino acids or nucleotide (expressed as a percentage) in a sequence alignment between two sequences of the alignment calculated using the number of identical positions divided by the greater of the shortest sequence or the number of equivalent positions excluding overhangs wherein internal gaps are counted as an equivalent position. For example the polypeptides GGGGGG (SEQ ID NO: 278) and GGGGT (SEQ ID NO: 279) have a sequence identity of 4 out of 5 or 80%. For example, the 10 polypeptides GGGPPP (SEQ ID NO: 280) and GGGAPPP (SEQ ID NO: 281) have a sequence identity of 6 out of 7 or 85%. In certain embodiments, any recitation of sequence identity expressed herein may be substituted for sequence similarity. Percent "similarity" is used to quantify the similarity between two sequences of the alignment. This method is identical to determining the identity except that certain amino acids do not have to be identical to have a match. Amino acids are classified as matches if they are among 15 a group with similar properties according to the following amino acid groups: Aromatic—F Y W; hydrophobic—A V I L; Charged positive: R K H; Charged negative—D E; Polar—S T N Q.

The terms "vector" or "expression vector" refer to a recombinant nucleic acid containing a desired coding sequence and appropriate nucleic acid sequences necessary for the expression of the operably linked coding sequence in a particular host organism or expression system, e.g., cellular or cell-free. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

Protein "expression systems" refer to in vivo and in vitro and cell free systems. Systems for recombinant protein expression typically utilize cells transfecting with a DNA expression vector that contains the template. The cells are cultured under conditions such that they translate the desired protein. Expressed proteins are extracted for subsequent purification. In vivo protein expression systems using prokaryotic and eukaryotic cells are well known. Also, some proteins are recovered using denaturants and protein-refolding procedures. In vitro and cell-free protein expression systems typically use translation-compatible extracts of whole cells or compositions that contain components sufficient for transcription, translation and optionally post-translational modifications such as RNA polymerase, regulatory protein factors, transcription factors, ribosomes, tRNA cofactors, amino acids and nucleotides. In the presence of an expression vectors, these extracts and components can synthesize proteins of interest. Cell-free systems typically do not contain proteases and enable labeling of the protein with modified amino acids. Some cell free systems incorporated encoded components for translation into the expression vector. See, e.g., Shimizu et al., Cell-free translation reconstituted with purified components, 2001, Nat. Biotechnol., 19, 751-755 and Asahara & Chong, Nucleic Acids Research, 2010, 38(13): e141, both hereby incorporated by reference in their entirety.

In certain embodiments, the disclosure relates to the recombinant vectors comprising a nucleic acid encoding a polypeptide disclosed herein or chimeric protein thereof.

In certain embodiments, the recombinant vector optionally comprises a mammalian, human, insect, viral, bacterial, bacterial plasmid, yeast associated origin of replication or gene such as a gene or retroviral gene or lentiviral LTR, TAR, RRE, PE, SLIP, CRS, and INS nucleotide segment or gene selected from tat, rev, nef, vif, vpr, vpu, and vpx or structural genes selected from gag, pol, and env.

In certain embodiments, the recombinant vector optionally comprises a gene vector element (nucleic acid) such as a selectable marker region, lac operon, a CMV promoter, a hybrid chicken B-actin/CMV enhancer (CAG) promoter, tac promoter, T7 RNA polymerase promoter, SP6 RNA polymerase promoter, SV40 promoter, internal ribosome entry site (IRES) sequence, cis-acting woodchuck post regulatory regulatory element (WPRE), scaffold-attachment region (SAR), inverted terminal repeats (ITR), FLAG tag coding region, c-myc tag coding region, metal affinity tag coding region, streptavidin binding peptide tag coding region, poly-His tag coding region, HA tag coding region, MBP tag coding region, GST tag coding region, polyadenylation coding region, a beta globin polyA signal, SV40 polyadenylation signal, SV40 origin of replication, Col E1 origin of replication, f1 origin, pBR322 origin, or pUC origin, TEV protease recognition site, loxP site, Cre recombinase coding region, or a multiple cloning site such as having 5, 6, or 7 or more restriction sites within a continuous segment of less than 50 or 60 nucleotides or having 3 or 4 or more restriction sites with a continuous segment of less than 20 or 30 nucleotides.

A "selectable marker" is a nucleic acid introduced into a recombinant vector that encodes a polypeptide that confers a trait suitable for artificial selection or identification (report gene), e.g., beta-lactamase confers antibiotic resistance, which allows an organism expressing beta-lactamase to survive in the presence antibiotic in a growth medium. Another example is thymidine kinase, which makes the host sensitive to ganciclovir selection. It may be a screenable marker that allows one to distinguish between wanted and unwanted cells based on the presence or absence of an expected color. For example, the lac-z-gene produces a beta-galactosidase enzyme which confers a blue color in the presence of X-gal (5-bromo-4-chloro-3-indolyl-(3-D-galactoside). If recombinant insertion inactivates the lac-z-gene, then the resulting colonies are colorless. There may be one or more selectable markers, e.g., an enzyme that can complement to the inability of an expression organism to synthesize a particular compound required for its growth (auxotrophic) and one able to convert a compound to another that is toxic for growth. URA3, an orotidine-5' phosphate decarboxylase, is necessary for uracil biosynthesis and can complement ura3 mutants that are auxotrophic for uracil. URA3 also converts 5-fluoroorotic acid into the toxic compound 5-fluorouracil.

Additional contemplated selectable markers include any genes that impart antibacterial resistance or express a fluorescent protein. Examples include, but are not limited to, the following genes: ampr, camr, tetr, blasticidinr, neor, hygr, abxr, neomycin phosphotransferase type II gene (nptII), p-glucuronidase (gus), green fluorescent protein (gfp), egfp, yfp, mCherry, p-galactosidase (lacZ), lacZa, lacZAM15, chloramphenicol acetyltransferase (cat), alkaline phosphatase (phoA), bacterial luciferase (luxAB), bialaphos resistance gene (bar), phosphomannose isomerase (pmi), xylose isomerase (xylA), arabitol dehydrogenase (atlD), UDP-glucose:galactose-1-phosphate uridyltransferasel (galT), feedback-insensitive α subunit of anthranilate synthase (OASA1D), 2-deoxyglucose (2-DOGR), benzyladenine-N-3-glucuronide, E. coli threonine deaminase, glutamate 1-semialdehyde aminotransferase (GSA-AT), D-amino acidoxidase (DAAO), salt-tolerance gene (rstB), ferredoxin-like protein (pflp), trehalose-6-P synthase gene (AtTPS1), lysine racemase (lyr), dihydrodipicolinate synthase (dapA), tryptophan synthase beta 1 (AtTSB1), dehalogenase (dhlA), mannose-6-phosphate reductase gene (M6PR), hygromycin phosphotransferase (HPT), and D-serine ammonialyase (dsdA).

A "label" refers to a detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "label receptor" refers to incorporation of a heterologous polypeptide in the receptor. A label includes the incorporation of a radiolabeled amino acid or the covalent attachment of biotinyl moieties to a polypeptide that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionuclides (such as $^{35}S$ or $^{131}I$) fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

In certain embodiments, the nucleic acids disclosed herein may be a part of any genetic element (vector) which may be delivered to a host cell, e.g., naked DNA, a plasmid, phage, transposon, cosmid, episome, a protein in a non-viral delivery vehicle (e.g., a lipid-based carrier), virus, etc. which transfer the sequences carried thereon. In certain embodiments, a vector may be an adeno-associated virus or human adeno-associated virus (containing AAV genes or sequences) vector, e.g., having nucleic acid sequences derived from AAV1, AAV2, AAV3, AAV4, AAV5, AAV6, AAV7, AAV8, AAV9 serotypes or combinations. In certain embodiments, the nucleic acid sequences derived from AAV1, AAV2, AAV3, AAV4, AAV5, AAV6, AAV7, AAV8, AAV9 serotypes may be at least one or two or more genes or gene fragments of more than 1000, 500, 400, 300, 200, 100, 50, or 25 continuous nucleotides or nucleotides sequences with greater than 50, 60, 70, 80, 90, 95 or 99% identity to the gene or fragment. In certain embodiments, a vector may be a lentivirus based (containing lentiviral genes or sequences) vector, e.g., having nucleic acid sequences derived from VSVG or GP64 pseudotypes or both. In certain embodiments, the nucleic acid sequences derived from VSVG or GP64 pseudotypes may be at least one or two or more genes or gene fragments of more than 1000, 500, 400, 300, 200, 100, 50, or 25 continuous nucleotides or nucleotides sequences with greater than 50, 60, 70, 80, 90, 95 or 99% identity to the gene or fragment.

The selected vector may be delivered by any suitable method, including intravenous injection, ex-vivo transduction, transfection, electroporation, liposome delivery, membrane fusion techniques, high velocity DNA-coated pellets, viral infection and protoplast fusion. CpG DNA motifs are typically removed because they may lead to gene methylation and silencing. See Bird, DNA methylation and the frequency of CpG in animal DNA, 1980, Nucleic Acids Res, 8: 1499-1504. CpG removal also helps the vector evade immune detection, enhancing the safety and efficacy of the vector. See J Clin Invest. 2013, 123(7):2994-3001, entitled "CpG-depleted adeno-associated virus vectors evade immune detection."

Blood Coagulation Factors

The blood clothing system is a proteolytic cascade. Blood clotting factors are present in the plasma as a zymogen, in other words in an inactive form, which on activation undergoes proteolytic cleavage to release the active factor from the precursor molecule. The ultimate goal is to produce thrombin. Thrombin converts fibrinogen into fibrin, which forms a clot.

Factor X is the first molecule of the common pathway and is activated by a complex of molecules containing activated factor IX (FIXa), factor VIII, calcium, and phospholipids which are on the platelet surface. Factor VIII is activated by thrombin, and it facilitates the activation of factor X by FIXa. Factor VIII (FVIII), contains multiple domains (A1-A2-B-ap-A3-C1-C2) and circulates in blood in an inactivated form bound to von Willebrand factor (VWF). The C2 domain is involved with FVIII binding to VWF. Thrombin cleaves FVIII causing dissociation with VWF ultimately leading to fibrin formation through factor IX (FIX). Congenital hemophilia A is associated with genetic mutations in the FVIII gene and results in impaired clotting due to lower than normal levels of circulating FVIII. Hemophilia B is similarly associated with genetic mutations in the FIX gene.

A treatment option for a patient diagnosed with hemophilia A is the exogenous administration of recombinant FVIII sometimes referred to as FVIII replacement therapy. In some patients, this therapy can lead to the development of antibodies that bind to the administered FVIII protein. Subsequently, the FVIII-antibody bound conjugates, typically referred to as inhibitors, interfere with or retard the ability of FVIII to cause blood clotting. Inhibitory autoantibodies also sometimes occur spontaneously in a subject that is not genetically at risk of having hemophilia, termed acquired hemophilia. Inhibitory antibodies assays are typically performed prior to exogenous FVIII treatment in order to determine whether the anti-coagulant therapy will be effective.

A "Bethesda assay" has historically been used to quantitate the inhibitory strength the concentration of factor VIII binding antibodies. In the assay, serial dilutions of plasma from a patient, e.g., prior to having surgery, are prepared and each dilution is mixed with an equal volume of normal plasma as a source of FVIII. After incubating for a couple hours, the activities of factor VIII in each of the diluted mixtures are measured. Having antibody inhibitor concentrations that prevent factor VIII clotting activity after multiple repeated dilutions indicates a heightened risk of uncontrolled bleeding. Patients with inhibitor titers after about ten dilutions are felt to be unlikely to respond to exogenous FVIII infusions to stop bleeding. A Bethesda titer is defined as the reciprocal of the dilution that results in 50% inhibition of FVIII activity present in normal human plasma. A Bethesda titer greater than 10 is considered the threshold of response to FVIII replacement therapy.

In certain embodiments, the disclosure relates to methods of inducing blood clotting comprising administering an effective amount of a recombinant or chimeric protein disclosed herein or viral particle or capsid comprising a vector comprising a nucleic acid encoding a blood clotting factor as disclosed herein to a subject in need thereof.

In certain embodiments, the subject is diagnosed with hemophilia A or acquired hemophilia or unlikely to respond to exogenous FVIII infusions.

In certain embodiments, the protein, capsid, or vector is administered in combination with an immunosuppressive agent, e.g., ciclosporin, tacrolimus, sirolimus, cyclophosphamide, methotrexate, azathioprine, mercaptopurine, fluorouracil, mycophenolic acid, dactinomycin, fingolimod, T-cell receptor antibody or binding protein, muromonab-CD3, IL-2 receptor antibody or binding protein, basiliximab, daclizumab, recombinant IFN-beta, TNF-alpha antibody or binding protein, infliximab, etanercept, adalimumab, or combinations thereof.

In certain embodiments, modified cells are re-administered in combination with irradiation, busulfan, and/or anti-thymocyte globulin, e.g., when using lentiviral gene therapy targeting hematopoietic stem cells.

Treating patients with inhibitors to FVIII has also been accomplished by methods of immune tolerance induction (ITI) which typically involves the daily infusion of FVIII until circulating inhibitor/antibody levels decline. However, 20-30% of patients fail to become tolerant after an immune tolerance induction (ITI) therapy. Persistence of FVIII inhibitors is associated with increased risks of morbidity and mortality. In certain embodiments, the disclosure relates to methods of immune tolerance induction comprising administering an effective amount of a recombinant or chimeric protein disclosed herein or a vector or a capsid as disclosed herein to a subject in need thereof.

Vector-Mediated Gene Transfer

In certain embodiments, the disclosure relates to methods of treating a subject diagnosed with a genetic trait that results in expression of a mutated or truncated non-functional protein by administering an effective amount of a vector disclosed herein. In certain embodiments, the vector is configured to express a functional protein from the liver. In certain embodiments, the vector is configured to express a protein in any cells such as hematopoietic stem cells or other hematocytes in vivo or by ex vivo transduction.

As used herein, the liver specific promotor refers to the sequences in the 5' direction of the transcriptional start site of the protein to be produced. McIntosh et al. report an rAAV vector encoding a human factor VIII variant using a hybrid liver-specific promoter (HLP). Blood. 2013, 121(17):3335-44. Brown et al. report liver-directed adeno-associated viral vector delivery of a bioengineered FVIII. Molecular Therapy, Methods & Clinical Development (2014) 1, 14036.

In certain embodiments, the vector comprises a viral nucleic acid sequence of greater than 10, 20, 30, 40, 50, 100, or 200 nucleotides. In certain embodiments, the viral nucleic acid sequence is a segment of human adeno-associated virus (hAAV) of serotypes 1, 2, 3B, 4, 5, 6, 7, 8, 9 or combinations or variants thereof, typically comprising an AAV inverted terminal repeat.

Adeno-associated virus (AAV), Parvovirus family, is an icosahedral virus with single-stranded linear DNA genomes. The life cycle of AAV includes a latent phase at which AAV genomes, after infection, are site specifically integrated into host chromosomes and an infectious phase in which, following either adenovirus or herpes simplex virus infection, the integrated genomes are subsequently rescued, replicated, and packaged into infectious viruses. The properties of non-pathogenicity, broad host range of infectivity, including non-dividing cells, and potential site-specific chromosomal integration make AAV an attractive tool for gene transfer.

The nucleic acid and promotor sequences disclosed herein are useful in production of rAAV, and are also useful as antisense delivery vectors, gene therapy vectors, or vaccine vectors. In certain embodiments, the disclosure provides for gene delivery vectors, and host cells which contain the nucleic acid sequences disclosed herein.

In certain embodiments, the disclosure relates to virus particles, e.g., capsids, containing the nucleic acid sequences encoding promotors and proteins disclosed herein. The virus particles, capsids, and recombinant vectors are useful in delivery of a heterologous gene or other nucleic acid sequences to a target cell. The nucleic acids may be readily utilized in a variety of vector systems, capsids, and host cells. In certain embodiments, the nucleic acids are in vectors contained within a capsid comprising cap proteins, including AAV capsid proteins vp1, vp2, vp3 and hypervariable regions.

Adeno-associated virus (AAV) has a biphasic life cycle consisting of both a productive and a latent phase. In the presence of helper virus, Adenovirus (Ad), or Herpesvirus (HSV), AAV undergoes a productive infection. Lacking a helper virus, AAV latently infects by integration into the host genome. AAV is capable of undergoing site-specific integration into the human genome. The ability to integrate site specifically is one of the attractive features for using this virus as a vector for human gene therapy.

Inverted terminal repeats (ITRs) in AAVs are cis elements used for targeted integration. Traditional AAV-mediated site-specific integration uses the AAV Rep78/68 proteins and ITRs which contain the Rep-binding site (RBS) and AAVS1 which is a sequence present at the integration site. See Linden et al. (1996) entitled "The recombination signals for adeno-associated virus site-specific integration." Proc Natl Acad Sci USA 93(15):7966-7972.

AAV vectors typically contain a transgene expression cassette between the ITRs that replaces the rep and cap genes. Vector particles are produced by the co-transfection of cells with a plasmid containing the vector genome and a packaging/helper construct that expresses the rep and cap proteins in trans. During infection, AAV vector genomes enter the cell nucleus and can persist in multiple molecular states. One common outcome is the conversion of the AAV genome to a double-stranded circular episome by second-strand synthesis or complementary strand pairing.

The AAV ITRs, and other selected AAV components described herein, may be readily selected from among any AAV serotype, including, without limitation, AAV1, AAV2, AAV3, AAV4, AAV5, AAV6, AAV7, AAV8, AAV9 and function variants thereof. These ITRs or other AAV components may be readily isolated using techniques available to those of skill in the art from an AAV serotype. Such AAV may be isolated or obtained from academic, commercial, or public sources (e.g., the American Type Culture Collection, Manassas, Va.). Alternatively, the AAV sequences may be obtained through synthetic or other suitable means by reference to published sequences such as are available in the literature or in databases such as, e.g., GenBank, PubMed, or the like.

In certain embodiments, this disclosure provides for a nucleic acids disclosed herein the encoded proteins or wherein the nucleic acids are part of an expression cassette or transgene. See e.g., US Pat. App. Pub. 20150139953. In certain embodiments, the expression cassette is composed of a transgene and regulatory sequences, e.g., promotor and 5' and 3' AAV inverted terminal repeats (ITRs). In one desirable embodiment, the ITRs of AAV serotype 2 or 8 are used. However, ITRs from other suitable serotypes may be selected. An expression cassette is typically packaged into a capsid protein and delivered to a selected host cell.

In certain embodiments, the disclosure provides for a method of generating a recombinant adeno-associated virus (AAV) having an AAV serotype capsid, or a portion thereof. Such a method involves culturing a host cell which contains a nucleic acid sequence encoding an adeno-associated virus (AAV) serotype capsid protein; a functional rep gene; an expression cassette composed of AAV inverted terminal repeats (ITRs) and a transgene; and sufficient helper functions to permit packaging of the expression cassette into the AAV capsid protein. See e.g., US Pat. App. Pub. 20150139953.

The components for culturing in the host cell to package an AAV expression cassette in an AAV capsid may be provided to the host cell in trans. Alternatively, any one or more of the components (e.g., expression cassette, rep sequences, cap sequences, and/or helper functions) may be provided by a stable host cell which has been engineered to contain one or more of the required components using methods known to those of skill in the art. Most suitably, such a stable host cell will contain the component(s) under the control of an inducible promoter. However, the required component(s) may be under the control of a constitutive promoter. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contains the rep and/or cap proteins under the control of inducible promoters. Still other stable host cells may be generated by one of skill in the art.

Introduction into the host cell of the vector may be achieved by any means known in the art or as disclosed above, including transfection, infection, electroporation, liposome delivery, membrane fusion techniques, high velocity DNA-coated pellets, viral infection and protoplast fusion, among others. One or more of the adenoviral genes may be stably integrated into the genome of the host cell, stably expressed as episomes, or expressed transiently. The gene products may all be expressed transiently, on an episome or stably integrated, or some of the gene products may be expressed stably while others are expressed transiently. Furthermore, the promoters for each of the adenoviral genes may be selected independently from a constitutive promoter, an inducible promoter or a native adenoviral promoter. The promoters may be regulated by a specific physiological state of the organism or cell (i.e., by the differentiation state or in replicating or quiescent cells) or by exogenously added factors, for example.

Introduction of the molecules (as plasmids or viruses) into the host cell may be accomplished using techniques known to the skilled artisan. In preferred embodiment, standard transfection techniques are used, e.g., $CaPO_4$ transfection or electroporation, and/or infection by hybrid adenovirus/AAV vectors into cell lines such as the human embryonic kidney cell line HEK 293 (a human kidney cell line containing functional adenovirus E1 genes which provides trans-acting E1 proteins).

One of skill in the art will readily understand that the AAV techniques can be adapted for use in these and other viral vector systems for in vitro, ex vivo or in vivo gene delivery. The in certain embodiments the disclosure contemplates the use of nucleic acids and vectors disclosed herein in a variety of rAAV and non-rAAV vector systems. Such vectors systems may include, e.g., lentiviruses, retroviruses, poxviruses, vaccinia viruses, and adenoviral systems, among others.

For example, in certain embodiments, the disclosure contemplates expression of FVIII by lentiviral vectors through in vivo administration or ex vivo transduction. Allogenic or autologous CD34+ cells can be isolated and mixed ex vivo with a lentiviral vector having nucleic acids encoding a FVIII protein disclosed herein under conditions such that the lentiviral vector integrates into the cells nucleic acids, e.g. DNA, sufficiently to produce or allow production the encoded FVIII protein. The cells are then infused or re-infused into a subject, wherein the subject optionally received a myeloablative treatment, under conditions such that hematopoietic stem cells or resulting cells or hematocytes express the protein. See Cartier et al. Science. 2009, 326(5954):818-23. Sanber et al. report the construction of stable packaging cell lines for clinical lentiviral vector production. Sci Rep. 2015, 5:9021. Hu et al. report production of replication-defective human immunodeficiency type 1 virus vector particles using helper-dependent adenovirus vectors. See Mol Ther Methods Clin Dev. 2015, 2:15004.

Therapeutics

Recombinant or chimeric proteins and virus particles, capsids, or vectors encoding proteins disclosed herein can be delivered, e.g., to liver via the hepatic artery, the portal vein, or intravenously to yield therapeutic levels of therapeutic proteins or clotting factors in the blood. The recombinant or chimeric proteins and capsid or vector is preferably suspended in a physiologically compatible carrier, may be administered to a patient. Suitable carriers may be readily selected by one of skill in the art in view of the indication.

For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, sesame oil, and water.

Optionally, the compositions of the disclosure may contain other pharmaceutically acceptable excipients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The recombinant virus particles, capsids, or vectors are administered in sufficient amounts to transfect the cells and to provide sufficient levels of gene transfer and expression to provide a therapeutic benefit without undue adverse effects, or with medically acceptable physiological effects, which can be determined by those skilled in the medical arts. Conventional and pharmaceutically acceptable routes of administration include, but are not limited to, direct delivery to a desired organ (e.g., the liver (optionally via the hepatic artery) or lung), oral, inhalation, intranasal, intratracheal, intraarterial, intraocular, intravenous, intramuscular, subcutaneous, intradermal, and other parental routes of administration. Routes of administration may be combined, if desired.

Dosages of the recombinant or chimeric proteins and virus particles, capsids, or vectors will depend primarily on factors such as the condition being treated, the age, weight and health of the patient, and may thus vary among patients. For example, a therapeutically effective human dosage of the protein is generally in the range of from about 0.1 ml to about 100 ml of solution containing concentrations of from about $1\times10^9$ to $1\times10^{16}$ genomes, virus vectors, or gene modified cells produced by ex vivo transduction.

Therapeutic proteins encoded by the nucleic acids (e.g., operably in combination with promoters) reported herein include those used for treatment of hemophilia, including hemophilia hemophilia A (including Factor VIII and its variants, such as the light chain and heavy chain of the heterodimer and the B-deleted domain; U.S. Pat. Nos. 6,200,560 and 6,221,349). The Factor VIII gene codes for 2351 amino acids and the protein has six domains, designated from the amino to the terminal carboxy terminus as A1-A2-B-A3-C1-C2 [Wood et al, Nature, 312:330 (1984); Vehar et al., Nature 312:337 (1984); and Toole et al, Nature, 342:337 (1984)]. Human Factor VIII is processed within the cell to yield a heterodimer primarily comprising a heavy chain containing the A1, A2 and B domains and a light chain containing the A3, C1 and C2 domains. Both the single chain polypeptide and the heterodimer circulate in the plasma as inactive precursors, until activated by thrombin cleavage between the A2 and B domains, which releases the B domain and results in a heavy chain consisting of the A1 and A2 domains. The B domain is deleted in the activated procoagulant form of the protein. Additionally, in the native protein, two polypeptide chains ("a" and "b"), flanking the B domain, are bound to a divalent calcium cation.

Administration of only the chain defective is contemplated in patients because most persons with hemophilia contain a mutation or deletion in only one of the chains (e.g., heavy or light chain). Thus, in certain embodiments, the disclosure relates to recombinant or chimeric proteins of a light chain containing the A3, C1 and C2 domains or a heavy chain consisting of the A1 and A2 domains. In some embodiments, the therapeutic protein or as encoded by the nucleic acids (e.g., operably in combination with promoters) reported herein comprises the Factor VIII heavy chain which encodes the 19 amino acid signal sequence, as well as the human beta globin polyadenylation sequence or growth hormone (hGH) polyadenylation sequence. In alternative embodiments, the A1 and A2 domains, as well as 5 amino acids from the N-terminus of the B domain, and/or 8 amino acids of the C-terminus of the B domain, as well as the A3, C1 and C2 domains. In yet other embodiments, the protein or nucleic acids encoding Factor VIII is a heavy chain and light chain provided in a single protein or nucleic acid separated by 42 nucleic acids/14 amino acids of the B domain. See U.S. Pat. No. 6,200,560.

As used herein, a therapeutically effective amount is an amount of protein or vector that produces sufficient amounts of Factor VIII to decrease the time it takes for the blood of a subject to clot. Generally, severe hemophiliacs having less than 1% of normal levels of Factor VIII have a whole blood clotting time of greater than 60 minutes as compared to approximately 10 minutes for non-hemophiliacs.

The recombinant or chimeric proteins or vectors may contain an amino acid sequence or nucleic acid coding for fragments of Factor VIII which is itself not biologically active, yet when administered into the subject improves or restores the blood clotting time. For example, the Factor VIII protein comprises two polypeptide chains: a heavy chain and a light chain separated by a B-domain which is cleaved during processing. Co-transducing recipient cells with the Factor VIII heavy and light chains leads to the expression of biologically active Factor VIII. Administration of only the chain defective is contemplated in patients because most hemophiliacs contain a mutation or deletion in only one of the chains (e.g., heavy or light chain).

Thus, in certain embodiments, the disclosure relates to vectors disclosed herein having nucleic acids encoding a light chain containing the A3, C1 and C2 domains or a heavy chain consisting of the A1 and A2 domains.

Bioengineering Coagulation Factor VIII Through Ancestral Protein Reconstruction

The development of transformative hemophilia A therapeutics has been hindered by the size, instability, immunogenicity and biosynthetic inefficiency of coagulation factor VIII (FVIII). Through the study of FVIII orthologs from existing vertebrate species, unique molecular, cellular and biochemical properties that can overcome the limitations of human FVIII were discovered. This approach facilitated the development of recombinant porcine FVIII for acquired hemophilia A and has enabled low resolution mapping and bioengineering of functional sequence determinants into human FVIII.

A mammalian FVIII phylogenetic tree with corresponding ancestral node (An) sequences was constructed through Bayesian inference using both DNA and amino acid-based models in PAML Version 4.1 (FIG. 1). Initially, 14 An-FVIII sequences were selected for reconstruction and subsequent molecular, cellular, biochemical and immunological characterization. Each An-FVIII displayed activity in coagulation assays utilizing human hemophilia A plasma as a substrate thus demonstrating evolutionary mammalian compatibility. Infusion of highly purified preparations of several An-FVIIIs into hemophilia A mice also corrected the bleeding phenotype following a tail transection bleeding challenge confirming in vivo functionality.

To study biosynthetic efficiency, secreted FVIII activity and mRNA transcript levels were analyzed following transfection of An-FVIII plasmids into HEK293 and BHK-M cell lines. An-53, common ancestor to rodents and primates, and An-68, ancestor to a subset of current rodents, displayed the highest FVIII biosynthetic efficiencies that were 12 and 15 fold greater than human FVIII, respectively. These two An-FVIII sequences share 95 and 87% amino acid identity to human FVIII, respectively. In contrast, intermediate ancestors between An-53 and human FVIII, designated An-55, -56 and -57, do not display enhanced biosynthetic efficiency suggesting that the functional sequence determinant of high expression was lost during primate evolution.

Testing whether high expression ancestral FVIIIs would be enabling to gene therapy approaches, An-53, An-68 and human FVIII cDNAs were placed in an AAV expression cassette under the control of a liver-directed promoter and the resulting plasmid DNA was infused hydrodynamically into hemophilia A mice. An-53 and An-68, but not human FVIII vector treated animals, achieved sustained, therapeutic plasma FVIII activity levels over 4 weeks (0.1-0.6 IU/ml versus <0.01 IU/ml, respectively). Recombinant An-FVIIIs were expressed, purified and biochemically characterized by SDS-PAGE, specific activity, decay following thrombin activation and inhibitor recognition. Early mammalian and all primate lineage thrombin-activated An-FVIII(a) displayed half-lives between 1.5-2.2 min that were not distinguishable from human F VIII.

Modern murine, porcine, and ovine FVIIIa display significantly longer half-lives. An-68 and An-78 display prolonged half-lives of 16 and 7 min, respectively. Lastly, the immune recognition of An-FVIIIs by a panel of A2 and C2 domain targeting inhibitory murine monoclonal antibodies as well as hemophilia A inhibitor patient plasmas was examined and many examples of reduced reactivity were revealed, which may enable the development of less immunogenic FVIII products.

Factor VIII domain boundaries refer to the human FVIII amino acid sequence numbering as follows; residues 1-19 (Signal Sequence), 20-391 (A1), 392-759 (A2), 760-1667 (B), 1668-1708 (ap), 1709-2038 (A3), 2039-2191 (C1) and 2192-2351 (C2). Gitschier et al., Nature, 1984, 312, 326-330.

```
(SEQ ID NO: 1):
   1   MQIELSTCFF LCLLRFCFSA TRRYYLGAVE LSWDYMQSDL GELPVDARFP PRVPKSFPFN

61   TSVVYKKTLF VEFTDHLFNI AKPRPPWMGL LGPTIQAEVY DTVVITLKNM ASHPVSLHAV
       GVSYWKASEG AEYDDQTSQR EKEDDKVFPG GSHTYVWQVL KENGPMASDP LCLTYSYLSH
       VDLVKDLNSG LIGALLVCRE GSLAKEKTQT LHKFILLFAV FDEGKSWHSE TKNSLMQDRD
       AASARAWPKM HTVNGYVNRS LPGLIGCHRK SVYWHVIGMG TTPEVHSIFL EGHTFLVRNH

301   RQASLEISPI TFLTAQTLLM DLGQFLLFCH ISSHQHDGME AYVKVDSCPE EPQLRMKNNE
       EAEDYDDDLT DSEMDVVRFD DDNSPSFIQI RSVAKKHPKT WVHYIAAEEE DWDYAPLVLA

421   PDDRSYKSQY LNNGPQRIGR KYKKVRFMAY TDETFKTREA IQHESGILGP LLYGEVGDTL
       LIIFKNQASR PYNIYPHGIT DVRPLYSRRL PKGVKHLKDF PILPGEIFKY KWTVTVEDGP
       TKSDPRCLTR YYSSFVNMER DLASGLIGPL LICYKESVDQ RGNQIMSDKR NVILFSVFDE
       NRSWYLTENI QRFLPNPAGV QLEDPEFQAS NIMHSINGYV FDSLQLSVCL HEVAYWYILS
       IGAQTDFLSV FFSGYTFKHK MVYEDTLTLF PFSGETVFMS MENPGLWILG CHNSDFRNRG
       MTALLKVSSC DKNTGDYYED SYEDISAYLL SKNNAIEPRS FSQNSRHPST RQKQFNATTI

781   PENDIEKTDP WFAHRTPMPK IQNVSSSDLL MLLRQSPTPH GLSLSDLQEA KYETFSDDPS
       PGAIDSNNSL SEMTHFRPQL HHSGDMVFTP ESGLQLRLNE KLGTTAATEL KKLDFKVSST
       SNNLISTIPS DNLAAGTDNT SSLGPPSMPV HYDSQLDTTL FGKKSSPLTE SGGPLSLSEE
       NNDSKLLESG LMNSQESSWG KNVSSTESGR LFKGKRAHGP ALLTKDNALF KVSISLLKTN

1021   KTSNNSATNR KTHIDGPSLL IENSPSVWQN ILESDTEFKK VTPLIHDRML MDKNATALRL
       NHMSNKTTSS KNMEMVQQKK EGPIPPDAQN PDMSFFKMLF LPESARWIQR THGKNSLNSG
       QGPSPKQLVS LGPEKSVEGQ NFLSEKNKVV VGKGEFTKDV GLKEMVFPSS RNLFLTNLDN

1201   LHENNTHNQE KKIQEEIEKK ETLIQENVVL PQIHTVTGTK NFMKNLFLLS TRQNVEGSYD
       GAYAPVLQDF RSLNDSTNRT KKHTAHFSKK GEEENLEGLG NQTKQIVEKY ACTTRISPNT
       SQQNFVTQRS KRALKQFRLP LEETELEKRI IVDDTSTQWS KNMKHLTPST LTQIDYNEKE

1381   KGAITQSPLS DCLTRSHSIP QANRSPLPIA KVSSFPSIRP IYLTRVLFQD NSSHLPAASY
       RKKDSGVQES SHFLQGAKKN NLSLAILTLE MTGDQREVGS LGTSATNSVT YKKVENTVLP

1501   KPDLPKTSGK VELLPKVHIY QKDLFPTETS NGSPGHLDLV EGSLLQGTEG AIKWNEANRP
       GKVPFLRVAT ESSAKTPSKL LDPLAWDNHY GTQIPKEEWK SQEKSPEKTA FKKKDTILSL

1621   NACESNHAIA AINEGQNKPE IEVTWAKQGR TERLCSQNPP VLKRHQREIT RTTLQSDQEE
       IDYDDTISVE MKKEDFDIYD EDENQSPRSF QKKTRHYFIA AVERLWDYGM SSSPHVLRNR

1741   AQSGSVPQFK KVVFQEFTDG SFTQPLYRGE LNEHLGLLGP YIRAEVEDNI MVTFRNQASR
       PYSFYSSLIS YEEDQRQGAE PRKNFVKPNE TKTYFWKVQH HMAPTKDEFD CKAWAYFSDV

1861   DLEKDVHSGL IGPLLVCHTN TLNPAHGRQV TVQEFALFFT IFDETKSWYF TENMERNCRA
       PCNIQMEDPT FKENYRFHAI NGYIMDTLPG LVMAQDQRIR WYLLSMGSNE NIHSIHFSGH
       VFTVRKKEEY KMALYNLYPG VFETVEMLPS KAGIWRVECL IGEHLHAGMS TLFLVYSNKC
       QTPLGMASGH IRDFQITASG QYGQWAPKLA RLHYSGSINA WSTKEPFSWI KVDLLAPMII
       HGIKTQGARQ KFSSLYISQF IIMYSLDGKK WQTYRGNSTG TLMVFFGNVD SSGIKHNIFN

2161   PPIIARYIRL HPTHYSIRST LRMELMGCDL NSCSMPLGME SKAISDAQIT ASSYFTNMFA
       TWSPSKARLH LQGRSNAWRP QVNNPKEWLQ VDFQKTMKVT GVTTQGVKSL LTSMYVKEFL
       ISSSQDGHQW TLFFQNGKVK VFQGNQDSFT PVVNSLDPPL LTRYLRIHPQ SWVHQIALRM

2341   EVLGCEAQDL Y
```

HSQ is B domain deleted human factor VIII. ET3 is a B domain deleted FVIII hybrid that contains human and porcine domains, i.e., sequence (A1 and A3 porcine) with a linker in the deleted B domain. ET3 utilizes a 24 amino acid porcine sequence-derived OL linker sequence, i.e., porcine-derived sequence SFAQNSRPPSASAPKPPVLRRHQR (SEQ ID NO: 246). Both HSQ and ET3 contain the RHQR (SEQ ID NO: 245) recognition sequence for PACE/furin processing sequence for the B-domain.

In certain embodiments, the recombinant or chimeric FVIII protein further comprises a linker amino acid sequence between two and fifty, or two and twenty five, or two and fifteen amino acids between the A2 domain and the an activation peptide(ap) domain. In certain embodiments, the linker comprises RHQR (SEQ ID NO: 245), SRPPSASAPK (SEQ ID NO: 41), or SFAQNSRPPSASAP-KPPVLRRHQR (SEQ ID NO: 246).

In certain embodiments, the disclosure relates to FVIII proteins comprising one, two, more, or combinations of ancestral mutation(s). In certain embodiments, the disclosure relates to a recombinant or chimeric FVIII protein comprising one or more ancestral mutations wherein optionally one or more amino acids in B-domain are deleted, and wherein the sequence does not naturally occur.

```
The sequence for Node number 68 is: SEQ ID NO: 2
MQIALFTCFFLSLFNFCSSATRRYYLGAVELSWNYMQSDLLSVLHTDTRF

LPRMPTSFPFNTSIMYKKTVFVEYMDHLFNIAKPRPPWMGLLGPTIWTEV

HDTVVITLKNMASHPVSLHAVGVSYWKASEGAEYEDQTSQREKEDDKVFP

GESHTYVWQVLKENGPMASDPPCLTYSYLSHVDLVKDLNSGLIGALLVCK

EGSLSKERTQMLHQFVLLFAVFDEGKSWHSETKDSFTQAMDSASTRAWPK

MHTVNGYVNRSLPGLIGCHRKSVYWHVIGMGTTPEVHSIFLEGHTFLVRN

HRQASLEISPITFLTAQTLLIDLGQFLLFCHISSHKHDGMEAYVKVDSCP

EEPQWQKKNNEEMEDYDDDLDSEMDMFTLDDDNSPFIQIRSVAKKYPKTW

IHYISAEEEDWDYAPSVLTSDDGSYKSQYLSNGPHRIGRKYKKVRFIAYT

DETFKTRETIQHESGILGPLLYGEVGDTLLIIFKNQASRPYNIYPHGITD

VSPLHSRRLPRGIKHVKDLPIRPGEIFKYKWTVTVEDGPTKSDPRCLTRY

YSSFINPERDLASGLIGPLLICYKESVDQRGNQMMSDKRNVILFSVFDEN

QSWYITENMQRFLPNAADTQPQDPEFQASNIMHSINGYVFDSLQLTVCLH

EVAYWYILSVGAQTDFLSIFFSGYTFKHKMVYEDTLTLFPFSGETVFMSM

ENPGLWVLGCHNSDFRKRGMTALLKVSSCDKSTSDYYEEIYEDIPTQLVN

DNNVIEPRSFFQNSNHPNTRKKKFKATTIPENDIEKIEPQFGETAEMLKV

QSVSSSDLLMLLGQSPTPHGLSLSDNQEAIYEAIPDDHSPDAIDSNEGPS

KVTQLRPELHHSGKIVFTPEPGLQLRSNKNLETTIEVKWKKLDLQVSSLP

NNLMTTTILSDNLTATSEKTDSSGSPDMPVHFSSKLSTTAFGKKSYPLIG

SHVPLNISERNSDSNLLDATLMNNQESSLGDNISSMENDRLLKEKRFHGI

ALLTKDNTLFKDNISLMKTNKTYNHSTTNGKAHIDSPTSIENSTAVLQDT

ILKINSEIQEVTSLIHDGTLSGKNTTYLRLNHMLNRTTSSKNKEIFHQKD

EDPVPQDTENTIMPFFKMLFLPESANWMKRTNGNNSLNSEQGPSPKQLVY

LMLEKSVKNQNFLSEKNKVIVEQDEFTKDTGLKDMVFPSNMSIFLTTLAN

VQENDMHNQEKNIQEEIEKEALIEEKVVLPQVHIATGSKNFLKDIFFLGT

RQNVSLDEDIYVPVLQDISSINNSTNTVEIHMAHFFKRREDEETNSEGLV

NKTREMVKNYPSQKNIITQRSKRALGQFRLPLASTQWPQTMNYLTQSIIT

QIDHSKEGEKSITQSSLSDSSMIKSTTQTNSSGLHIVKTSAFPPTDLKRI

PFQDKFFHVLASSYTYDFKTKSSRIQESSHFLKETKINNSSLAILPWEMI

INQGKFASPGTSNTNSVTYKKLENIVLLKPVLPEESGKVELLPQVSIHEE

ELLPTETSHGSPGHLDLMKEVFLQKTQGPIKWNKAKRHGESELKGTTESS

EKTPSKLLDHLAWDNHYAAQIPKDKWKSKEKSPEITSIKREDTILSLNPH

ENNHSIVANEKQNWPQREATWVKQGQTQRLCSQNPPVLKRHQRELSALQS

EQEATDYDDSITIETNEDFDIYGEDIKQGPRSFQQKTRHYFIAAVERLWD

YGMSTSPHVLRNRDQSGNAPQFKKVVFQEFTDGSFSQPLYRGELNEHLGL

LGPYIRAEVEDNIMVTFKNQASRPYSFYSSLISYKEDQRQGEEPRRNFVK

PNETKIYFWKVQHHMAPTEDEFDCKAWAYFSDVDLERDMHSGLIGPLLIC

HTNTLNPAHGRQVAVQEFALFFTIFDETKSWYFTENVERNCKTPCNIQME

DPTLKENYRFHAINGYVMDTLPGLVMAQDQRIRWYLLSMGSNENIQSIHF

SGHVFTVRKKEEYKMAVYNLYPGVFETVEMLPSRAGIWRVECLIGEHLQA

GMSTLFLVYSKQCQIPLGMASGSIRDFQITASGHYGQWAPNLARLHHSGS

INAWSTKEPFSWIKVDLLTPMIIHGIKTQGARQKFSSLYISQFIIMYSLD

GKKWLSYRGNSTGTLMVFFGNVDSSGIKHNSFNPPIIARYIRLHPTHSSI

RSTLRMELMGCDLNSCSIPLGMENKVISDTQITASSYFTNMFATWSPSQA

RLHLQGRTNAWRPQVNDPKEWLQVDLQKTMKVTGIITQGVKSLFTSMFVK

EFLISSSQDGHHWTHILHNGKVKVFQGNQDSSTPMVNSLDPPLLTRYLRI

HPQIWEHQIALRLEILGCEAQQLY

Accordingly the sequences for sp-A1-A2-B-aq-A3-
C1-C2:
(signal peptide, sp domain, SEQ ID NO: 3)
MQIALFTCFFLSLFNFCSS (A1 domain SEQ ID NO: 4)
ATRRYYLGAVELSWNYMQSDLLSVLHTDTRFLPRMPTSFPFNTSIMYKKT

VFVEYMDHLFNIAKPRPPWMGLLGPTIWTEVHDTVVITLKNMASHPVSLH

AVGVSYWKASEGAEYEDQTSQREKEDDKVFPGESHTYVWQVLKENGPMAS

DPPCLTYSYLSHVDLVKDLNSGLIGALLVCKEGSLSKERTQMLHQFVLLF

AVFDEGKSWHSETKDSFTQAMDSASTRAWPKMHTVNGYVNRSLPGLIGCH

RKSVYWHVIGMGTTPEVHSIFLEGHTFLVRNHRQASLEISPITFLTAQTL

LIDLGQFLLFCHISSHKHDGMEAYVKVDSCPEEPQWQKKNNEEMEDYDDD

LDSEMDMFTLDDDNSPFIQIRS (A2 domain SEQ ID NO: 5)
VAKKYPKTWIHYISAEEEDWDYAPSVLTSDDGSYKSQYLSNGPHRIGRKY

KKVRFIAYTDETFKTRETIQHESGILGPLLYGEVGDTLLIIFKNQASRPY

NIYPHGITDVSPLHSRRLPRGIKHVKDLPIRPGEIFKYKWTVTVEDGPTK

SDPRCLTRYYSSFINPERDLASGLIGPLLICYKESVDQRGNQMMSDKRNV

ILFSVFDENQSWYITENMQRFLPNAADTQPQDPEFQASNIMHSINGYVFD
```

-continued

SLQLTVCLHEVAYWYILSVGAQTDFLSIFFSGYTFKHKMVYEDTLTLFPF

SGETVFMSMENPGLWVLGCHNSDFRKRGMTALLKVSSCDKSTSDYYEEIY

EDIPTQLVNDNNVIEPR (B domain SEQ ID NO: 6)
SFFQNSNHPNTRKKKFKATTIPENDIEKIEPQFGETAEMLKVQSVSSSDL

LMLLGQSPTPHGLSLSDNQEAIYEAIPDDHSPDAIDSNEGPSKVTQLRPE

LHHSGKIVFTPEPGLQLRSNKNLETTIEVKWKKLDLQVSSLPNNLMTTTI

LSDNLTATSEKTDSSGSPDMPVHFSSKLSTTAFGKKSYPLIGSHVPLNIS

ERNSDSNLLDATLMNNQESSLGDNISSMENDRLLKEKRFHGIALLTKDNT

LFKDNISLMKTNKTYNHSTTNGKAHIDSPTSIENSTAVLQDTILKINSEI

QEVTSLIHDGTLSGKNTTYLRLNHMLNRTTSSKNKEIFHQKDEDPVPQDT

ENTIMPFFKMLFLPESANWMKRTNGNNSLNSEQGPSPKQLVYLMLEKSVK

NQNFLSEKNKVIVEQDEFTKDTGLKDMVFPSNMSIFLTTLANVQENDMHN

QEKNIQEEIEKEALIEEKVVLPQVHIATGSKNFLKDIFFLGTRQNVSLDE

DIYVPVLQDISSINNSTNTVEIHMAHFFKRREDEETNSEGLVNKTREMVK

NYPSQKNIITQRSKRALGQFRLPLASTQWPQTMNYLTQSIITQIDHSKEG

EKSITQSSLSDSSMIKSTTQTNSSGLHIVKTSAFPPTDLKRIPFQDKFFH

VLASSYTYDFKTKSSRIQESSHFLKETKINNSSLAILPWEMIINQGKFAS

PGTSNTNSVTYKKLENIVLLKPVLPEESGKVELLPQVSIHEEELLPTETS

HGSPGHLDLMKEVFLQKTQGPIKWNKAKRHGESELKGTTESSEKTPSKLL

DHLAWDNHYAAQIPKDKWKSKEKSPEITSIKREDTILSLNPHENNHSIVA

NEKQNWPQREATWVKQGQTQRLCSQNPPVLKRHQR (ap domain SEQ ID NO: 7)
ELSALQSEQEATDYDDSITIETNEDFDIYGEDIKQGPR (A3 domain SEQ ID NO: 8)
SFQQKTRHYFIAAVERLWDYGMSTSPHVLRNRDQSGNAPQFKKVVFQEFT

DGSFSQPLYRGELNEHLGLLGPYIRAEVEDNIMVTFKNQASRPYSFYSSL

ISYKEDQRQGEEPRRNFVKPNETKIYFWKVQHHMAPTEDEFDCKAWAYFS

DVDLERDMHSGLIGPLLICHTNTLNPAHGRQVAVQEFALFFTIFDETKSW

YFTENVERNCKTPCNIQMEDPTLKENYRFHAINGYVMDTLPGLVMAQDQR

IRWYLLSMGSNENIQSIHFSGHVFTVRKKEEYKMAVYNLYPGVFETVEML

PSRAGIWRVECLIGEHLQAGMSTLFLVYSK (C1 domain SEQ ID NO: 9)
QCQIPLGMASGSIRDFQITASGHYGQWAPNLARLHHSGSINAWSTKEPFS

WIKVDLLTPMIIHGIKTQGARQKFSSLYISQFIIMYSLDGKKWLSYRGNS

TGTLMVFFGNVDSSGIKHNSFNPPIIARYIRLHPTHSSIRSTLRMELMGC

DLN (C2 domain SEQ ID NO: 10)
SCSIPLGMENKVISDTQITASSYFTNMFATWSPSQARLHLQGRTNAWRPQ

VNDPKEWLQVDLQKTMKVTGIITQGVKSLFTSMFVKEFLISSSQDGHHWT

HILHNGKVKVFQGNQDSSTPMVNSLDPPLLTRYLRIHPQIWEHQIALRLE

ILGCEAQQLY

The sequence for Node number 54 is: SEQ ID NO: 11
MQIELSTCFFLCLLQFSFSATRRYYLGAVELSWDYMQSDLLSELHVDTRF

PPRVPRSFPFNTSVMYKKTVFVEFTDHLFNIAKPRPPWMGLLGPTIQAEV

YDTVVITLKNMASHPVSLHAVGVSYWKASEGAEYDDQTSQREKEDDKVFP

GESHTYVWQVLKENGPMASDPPCLTYSYLSHVDLVKDLNSGLIGALLVCR

EGSLAKERTQTLHKFVLLFAVFDEGKSWHSETKDSLMQDMDSASARAWPK

MHTVNGYVNRSLPGLIGCHRKSVYWHVIGMGTTPEVHSIFLEGHTFLVRN

HRQASLEISPITFLTAQTLLMDLGQFLLFCHISSSHQHDGMEAYVKVDSCP

EEPQLRMKNNEEEEDYDDDLADSEMDVVRFDDDNSPSFIQIRSVAKKHPK

TWVHYIAAEEEDWDYAPSVLTPDDRSYKSQYLNNGPQRIGRKYKKVRFMA

YTDETFKTREAIQYESGILGPLLYGEVGDTLLIIFKNQASRPYNIYPHGI

TDVRPLHSGRLPKGVKHLKDLPILPGEIFKYKWTVTVEDGPTKSDPRCLT

RYYSSFINLERDLASGLIGPLLICYKESVDQRGNQMMSDKRNVILFSVFD

ENRSWYLTENMQRFLPNAAGVQPQDPEFQASNIMHSINGYVFDSLQLSVC

LHEVAYWYILSIGAQTDFLSVFFSGYTFKHKMVYEDTLTLFPFSGETVFM

SMENPGLWVLGCHNSDFRNRGMTALLKVSSCDRNTGDYYEDTYEDISTYL

LSENNVIEPRSFSQNSRHPSTRQKQFKATTIPENDIEKIDPQFGERTQML

KVQSVSSSDLLMLLGQSPTPHGLSLSDLQEATYEAIPDDHSPGAIDSNEG

PSEVAHLRPELHHSGDMVFTPEPGLQLRLNENLGTTIAVELKKLDLKVSS

SSNNLMTSPTIPSDNLAAGTEKTGSLGPPNMPVHFDSQLDTTVFGKKSSP

LIGSGVPLSLSERNNDSKLLEAALMNSQESSLGKNVSSMESDRLFKEKRA

HGPALLTKDNALFKVNISLVKTNKTSNNSTTNRKTHIDGPTLLIENSTSV

WQDILESDTEFQEVTSLIHDKMLMDKNTTALRLNHVSNKTTSSKNMEMVH

QKKEGPVPPDAENPDMSFFKMLFLPESANWIKRTHGKNSLNSGQGPSPKQ

LISLGSEKSVKDQNFLSEKNKVVGEDEFTKDTGLKEMIFPSSRNIFLTN

LANVHENDTHNQEKKIQEEIERKETLIQENVVLPQVYTVTGTKNFMKNLF

LLSTRQNVEGLDEGAYAPVLQDTRSLNDSTNRTEIHMAHFSKKREEENLE

GLGNQTKQMVEKYPSTTRMSPNPSQQNVITQRGKRALKQFRLPLEETELE

KGLIVDDTSTQWSKNMKYLTQSTLTQIDYNEKEKKAITQSPLSDCLMRNH

SITQTNSSALPIAKVSAFPSIRPTDLTRVPSQDNSSHLLASAYRKKSSGV

QESSHFLQGAKRNNLSLAILTLEMIGNQRKVGSLGTSATNSVMYKKLENT

VLLKPGLPEASGKVELLPKVHIHQKDLFPTETSNGSPGHLDLMEEILLQK

TQGAIKWNKTNRPGKVPFLKGATESSEKTPSKLLGPLAWDNQYATQIPKE

EWKSQEKSPENTAFKTKDTILSLNPCESNHAIAAINEGQDRPQREATWAK

QGGTGRLCSQNPPVLKRHQREITLTTLQSDQEEIDYDDTISIETKREDFD

IYGEDENQSPRSFQKKTRHYFIAAVERLWDYGMSRSPHVLRNRAQSGSVP

QFKKVVFQEFTDGSFTQPLYRGELNEHLGLLGPYIRAEVEDNIMVTFKNQ

ASRPYSFYSSLISYEEDQRQGAEPRKNFVKPNETKTYFWKVQHHMAPTKD

EFDCKAWAYFSDVDLEKDMHSGLIGPLLICHTNTLNPAHGRQVTVQEFAL

FFTIFDETKSWYFTENMERNCRAPCNIQMEDPTFKENYRFHAINGYVMDT

LPGLVMAQDQRIRWYLLSMGSNENIHSIHFSGHVFTVRKKEEYKMAVYNL

-continued

YPGVFETVEMLPSKAGIWRVECLIGEHLHAGMSTLFLVYSKQCQTPLGMA

SGHIRDFQITASGQYGQWAPKLARLHYSGSINAWSTKEPFSWIKVDLLAP

MIIHGIKTQGARQKFSSLYISQFIIMYSLDGKKWQTYRGNSTGTLMVFFG

NVDSSGIKHNIFNPPIIARYIRLHPTHYSIRSTLRMELMGCDLNSCSMPL

GMESKAISDAQITASSYFTNMFATWSPSQARLHLQGRTNAWRPQVNNPKE

WLQVDFQKTMKVTGITTQGVKSLLTSMYVKEFLISSSQDGHHWTLFFQNG

KVKVFQGNQDSFTPVVNSLDPPLLTRYLRIHPQSWVHQIALRLEVLGCEA

QQLY

Accordingly the sequences for sp-A1-A2-B-aq-A3-C1-C2:
(sp, Signal Peptide, SEQ ID NO: 12)
MQIELSTCFFLCLLQFSFS (A1 SEQ ID NO: 13)
ATRRYYLGAVELSWDYMQSDLLSELHVDTRFPPRVPRSFPFNTSVMYKKT

VFVEFTDHLFNIAKPRPPWMGLLGPTIQAEVYDTVVITLKNMASHPVSLH

AVGVSYWKASEGAEYDDQTSQREKEDDKVFPGESHTYVWQVLKENGPMAS

DPPCLTYSYLSHVDLVKDLNSGLIGALLVCREGSLAKERTQTLHKFVLLF

AVFDEGKSWHSETKDSLMQDMDSASARAWPKMHTVNGYVNRSLPGLIGCH

RKSVYWHVIGMTTPEVHSIFLEGHTFLVRNHRQASLEISPITFLTAQTL

LMDLGQFLLFCHISSHQHDGMEAYVKVDSCPEEPQLRMKNNEEEEDYDDD

LADSEMDVVRFDDDNSPSFIQIRS (A2 SEQ ID NO: 14)
VAKKHPKTWVHYIAAEEEDWDYAPSVLTPDDRSYKSQYLNNGPQRIGRKY

KKVRFMAYTDETFKTREAIQYESGILGPLLYGEVGDTLLIIFKNQASRPY

NIYPHGITDVRPLHSGRLPKGVKHLKDLPILPGEIFKYKWTVTVEDGPTK

SDPRCLTRYYSSFINLERDLASGLIGPLLICYKESVDQRGNQMMSDKRNV

ILFSVFDENRSWYLTENMQRFLPNAAGVQPQDPEFQASNIMHSINGYVFD

SLQLSVCLHEVAYWYILSIGAQTDFLSVFFSGYTFKHKMVYEDTLTLFPF

SGETVFMSMENPGLWVLGCHNSDFRNRGMTALLKVSSCDRNTGDYYEDTY

EDISTYLLSENNVIEPR (B SEQ ID NO: 15)
SFSQNSRHPSTRQKQFKATTIPENDIEKIDPQFGERTQMLKVQSVSSSDL

LMLLGQSPTPHGLSLSDLQEATYEAIPDDHSPGAIDSNEGPSEVAHLRPE

LHHSGDMVFTPEPGLQLRLNENLGTTIAVELKKLDLKVSSSSNNLMTSPT

IPSDNLAAGTEKTGSLGPPNMPVHFDSQLDTTVFGKKSSPLIGSGVPLSL

SERNNDSKLLEAALMNSQESSLGKNVSSMESDRLFKEKRAHGPALLTKDN

ALFKVNISLVKTNKTSNNSTTNRKTHIDGPTLLIENSTSVWQDILESDTE

FQEVTSLIHDKMLMDKNTTALRLNHVSNKTTSSKNMEMVHQKKEGPVPPD

AENPDMSFFKMLFLPESANWIKRTHGKNSLNSGQGPSPKQLISLGSEKSV

KDQNFLSEKNKVVVGEDEFTKDTGLKEMIFPSSRNIFLTNLANVHENDTH

NQEKKIQEEIERKETLIQENVVLPQVYTVTGTKNFMKNLFLLSTRQNVEG

LDEGAYAPVLQDTRSLNDSTNRTEIHMAHFSKKREEENLEGLGNQTKQMV

EKYPSTTRMSPNPSQQNVITQRGKRALKQFRLPLEETELEKGLIVDDTST

QWSKNMKYLTQSTLTQIDYNEKEKKAITQSPLSDCLMRNHSITQTNSSAL

PIAKVSAFPSIRPTDLTRVPSQDNSSHLLASAYRKKSSGVQESSHFLQGA

KRNNLSLAILTLEMIGNQRKVGSLGTSATNSVMYKKLENTVLLKPGLPEA

SGKVELLPKVHIHQKDLFPTETSNGSPGHLDLMEEILLQKTQGAIKWNKT

NRPGKVPFLKGATESSEKTPSKLLGPLAWDNQYATQIPKEEWKSQEKSPE

NTAFKTKDTILSLNPCESNHAIAAINEGQDRPQREATWAKQGGTGRLCSQ

NPPVLKRHQR (ap SEQ ID NO: 16)
EITLTTLQSDQEEIDYDDTISIETKREDFDIYGEDENQSPR (A3 SEQ ID NO: 17)
SFQKKTRHYFIAAVERLWDYGMSRSPHVLRNRAQSGSVPQFKKVVFQEFT

DGSFTQPLYRGELNEHLGLLGPYIRAEVEDNIMVTFKNQASRPYSFYSSL

ISYEEDQRQGAEPRKNFVKPNETKTYFWKVQHHMAPTKDEFDCKAWAYFS

DVDLEKDMHSGLIGPLLICHTNTLNPAHGRQVTVQEFALFFTIFDETKSW

YFTENMERNCRAPCNIQMEDPTFKENYRFHAINGYVMDTLPGLVMAQDQR

IRWYLLSMGSNENIHSIHFSGHVFTVRKKEEYKMAVYNLYPGVFETVEML

PSKAGIWRVECLIGEHLHAGMSTLFLVYSK (C1 SEQ ID NO: 18)
QCQTPLGMASGHIRDFQITASGQYGQWAPKLARLHYSGSINAWSTKEPFS

WIKVDLLAPMIIHGIKTQGARQKFSSLYISQFIIMYSLDGKKWQTYRGNS

TGTLMVFFGNVDSSGIKHNIFNPPIIARYIRLHPTHYSIRSTLRMELMGC

DLN (C2 SEQ ID NO: 19)
SCSMPLGMESKAISDAQITASSYFTNMFATWSPSQARLHLQGRTNAWRPQ

VNNPKEWLQVDFQKTMKVTGITTQGVKSLLTSMYVKEFLISSSQDGHHWT

LFFQNGKVKVFQGNQDSFTPVVNSLDPPLLTRYLRIHPQSWVHQIALRLE

VLGCEAQQLY

The sequence for Node number 53 is: SEQ ID NO: 20
MQIELSTCFFLCLLQFSFSATRRYYLGAVELSWDYMQSDLLSELHVDTRF

PPRVPRSFPFNTSVMYKKTVFVEFTDHLFNIAKPRPPWMGLLGPTIRAEV

YDTVVITLKNMASHPVSLHAVGVSYWKASEGAEYDDQTSQREKEDDKVFP

GESHTYVWQVLKENGPMASDPPCLTYSYLSHVDLVKDLNSGLIGALLVCR

EGSLAKERTQTLHQFVLLFAVFDEGKSWHSETKDSLTQAMDSASARAWPK

MHTVNGYVNRSLPGLIGCHRKSVYWHVIGMTTPEVHSIFLEGHTFLVRN

HRQASLEISPITFLTAQTLLMDLGQFLLFCHISSHQHDGMEAYVKVDSCP

EEPQLRMKNNEEEEDYDDDLYDSEMDVVRFDDDNSPPFIQIRSVAKKHPK

TWVHYIAAEEEDWDYAPSVLTPDDRSYKSQYLNNGPQRIGRKYKKVRFMA

YTDETFKTREAIQYESGILGPLLYGEVGDTLLIIFKNQASRPYNIYPHGI

TDVSPLHSGRLPKGVKHLKDLPILPGEIFKYKWTVTVEDGPTKSDPRCLT

RYYSSFINLERDLASGLIGPLLICYKESVDQRGNQMMSDKRNVILFSVFD

ENRSWYLTENMQRFLPNAAGVQPQDPEFQASNIMHSINGYVFDSLQLSVC

LHEVAYWYILSVGAQTDFLSVFFSGYTFKHKMVYEDTLTLFPPFSGETVFM

SMENPGLWVLGCHNSDFRNRGMTALLKVSSCDRNTGDYYEDTYEDIPTYL

```
LSENNVIEPRSFSQNSRHPSTRQKQFKATTIPENDIEKIDPQFGERTQML
KVQSVSSSDLLMLLGQSPTPHGLSLSDLQEATYEAIPDDHSPGAIDSNEG
PSEVAHLRPELHHSGDMVFTPEPGLQLRLNENLGTTIAVELKKLDLKVSS
SSNNLMTSPTIPSDNLAAGTEKTGSLGPPNMPVHFSSQLGTTVFGKKSSP
LIGSGVPLNLSERNNDSKLLEAALMNSQESSLGKNVSSMESDRLFKEKRV
HGPALLTKDNALFKVNISLVKTNKTSNNSTTNRKTHIDGPTLLIENSTSV
WQDIILESDTEFQEVTSLIHDEMLMDKNTTALRLNHVSNKTTSSKNMEMV
HQKKEGPVPPDAENPDMSFFKMLFLPESANWIKRTHGKNSLNSGQGPSPK
QLISLGSEKSVKDQNFLSEKNKVVVGEDEFTKDTGLKEMIFPNSRSIFLT
NLANVQENDTHNQEKKFQEEIERKETLIQENVVLPQVYTVTGTKNFLKNL
FLLSTRQNVEGLDEGTYAPVLQDTRSLNDSTNRAEIHMAHFSKRREEENL
EGLGNQTKQMVEKYPSTTRMSPNPSQQNVITQRGKRALKQFRLPLEETEL
EKGLIVDDTSTQWSKNMKYLTQSTLTQIDYNEKEKKAITQSPLSDCSMRN
HSITQTNSSALPIAKVSAFPSIRPTDLTKIPSQDNSSHLLASAYSYTFRE
KSSGVQESSHFLQGAKRNNLSLAILTLEMIRNQEKVGSLGTSATNSVMYK
KLENTVLLKPGLPEASGKVELLPKVHIHQEDLFPTETSNGSPGHLDLMEE
ILLQKTQGAIKWNKTNRPGKVPFLKGATESSEKTPSKLLGPLAWDNQYAT
QIPKEEWKSQEKSPKNTAFKTKDTILSLNPCENNHAIAAINEGQDRPQRE
ATWAKQGGTGRLCSQNPPVLKRHQREITLTTLQSEQEEIDYDDTISIETK
REDFDIYGEDENQGPRSFQKRTRHYFIAAVERLWDYGMSRSPHVLRNRAQ
SGSVPQFKKVVFQEFTDGSFTQPLYRGELNEHLGLLGPYIRAEVEDNIMV
TFKNQASRPYSFYSSLISYEEDQRQGAEPRKNFVKPNETKTYFWKVQHHM
APTKDEFDCKAWAYFSDVDLEKDMHSGLIGPLLICHTNTLNPAHGRQVTV
QEFALFFTIFDETKSWYFTENMERNCRAPCNIQMEDPTFKENYRFHAING
YVMDTLPGLVMAQDQRIRWYLLSMGSNENIHSIHFSGHVFTVRKKEEYKM
AVYNLYPGVFETVEMLPSKAGIWRVECLIGEHLHAGMSTLFLVYSKQCQT
PLGMASGHIRDFQITASGQYGQWAPKLARLHYSGSINAWSTKEPFSWIKV
DLLAPMIIHGIKTQGARQKFSSLYISQFIIMYSLDGKKWQTYRGNSTGTL
MVFFGNVDSSGIKHNIFNPPIIARYIRLHPTHYSIRSTLRMELMGCDLNS
CSMPLGMESKAISDAQITASSYFTNMFATWSPSQARLHLQGRTNAWRPQV
NNPKEWLQVDFQKTMKVTGITTQGVKSLLTSMYVKEFLISSSQDGHHWTL
FLQNGKVKVFQGNQDSFTPVVNSLDPPLLTRYLRIHPQSWVHQIALRLEV
LGCEAQQLY

Accordingly the sequences for sp-A1-A2-B-aq-A3-
C1-C2:
(sp, Signal Peptide, SEQ ID NO: 21)
MQIELSTCFFLCLLQFSFS (A1 SEQ ID NO: 22)
ATRRYYLGAVELSWDYMQSDLLSELHVDTRFPPRVPRSFPFNTSVMYKKT
VFVEFTDHLFNIAKPRPPWMGLLGPTIRAEVYDTVVITLKNMASHPVSLH
AVGVSYWKASEGAEYDDQTSQREKEDDKVFPGESHTYVWQVLKENGPMAS
DPPCLTYSYLSHVDLVKDLNSGLIGALLVCREGSLAKERTQTLHQFVLLF
AVFDEGKSWHSETKDSLTQAMDSASARAWPKMHTVNGYVNRSLPGLIGCH
```

```
RKSVYWHVIGMGTTPEVHSIFLEGHTFLVRNHRQASLEISPITFLTAQTL
LMDLGQFLLFCHISSHQHDGMEAYVKVDSCPEEPQLRMKNNEEEEDYDDD
LYDSEMDVVRFDDDNSPPFIQIRS (A2 SEQ ID NO: 23)
VAKKHPKTWVHYIAAEEEDWDYAPSVLTPDDRSYKSQYLNNGPQRIGRKY
KKVRFMAYTDETFKTREAIQYESGILGPLLYGEVGDTLLIIFKNQASRPY
NIYPHGITDVSPLHSGRLPKGVKHLKDLPILPGEIFKYKWTVTVEDGPTK
SDPRCLTRYYSSFINLERDLASGLIGPLLICYKESVDQRGNQMMSDKRNV
ILFSVFDENRSWYLTENMQRFLPNAAGVQPQDPEFQASNIMHSINGYVFD
SLQLSVCLHEVAYWYILSVGAQTDFLSVFFSGYTFKHKMVYEDTLTLFPF
SGETVFMSMENPGLWVLGCHNSDFRNRGMTALLKVSSCDRNTGDYYEDTY
EDIPTYLLSENNVIEPR (B SEQ ID NO: 24)
SFSQNSRHPSTRQKQFKATTIPENDIEKIDPQFGERTQMLKVQSVSSSDL
LMLLGQSPTPHGLSLSDLQEATYEAIPDDHSPGAIDSNEGPSEVAHLRPE
LHHSGDMVFTPEPGLQLRLNENLGTTIAVELKKLDLKVSSSSNNLMTSPT
IPSDNLAAGTEKTGSLGPPNMPVHFSSQLGTTVFGKKSSPLIGSGVPLNL
SERNNDSKLLEAALMNSQESSLGKNVSSMESDRLFKEKRVHGPALLTKDN
ALFKVNISLVKTNKTSNNSTTNRKTHIDGPTLLIENSTVWQDIILESDT
EFQEVTSLIHDEMLMDKNTTALRLNHVSNKTTSSKNMEMVHQKKEGPVPP
DAENPDMSFFKMLFLPESANWIKRTHGKNSLNSGQGPSPKQLISLGSEKS
VKDQNFLSEKNKVVVGEDEFTKDTGLKEMIFPNSRSIFLTNLANVQENDT
HNQEKKFQEEIERKETLIQENVVLPQVYTVTGTKNFLKNLFLLSTRQNVE
GLDEGTYAPVLQDTRSLNDSTNRAEIHMAHFSKRREEENLEGLGNQTKQM
VEKYPSTTRMSPNPSQQNVITQRGKRALKQFRLPLEETELEKGLIVDDTS
TQWSKNMKYLTQSTLTQIDYNEKEKKAITQSPLSDCSMRNHSITQTNSSA
LPIAKVSAFPSIRPTDLTKIPSQDNSSHLLASAYSYTFREKSSGVQESSH
FLQGAKRNNLSLAILTLEMIRNQEKVGSLGTSATNSVMYKKLENTVLLKP
GLPEASGKVELLPKVHIHQEDLFPTETSNGSPGHLDLMEEILLQKTQGAI
KWNKTNRPGKVPFLKGATESSEKTPSKLLGPLAWDNQYATQIPKEEWKSQ
EKSPKNTAFKTKDTILSLNPCENNHAIAAINEGQDRPQREATWAKQGGTG
RLCSQNPPVLKRHQR (ap SEQ ID NO: 25)
EITLTTLQSEQEEIDYDDTISIETKREDFDIYGEDENQGPR (A3 SEQ ID NO: 26)
SFQKRTRHYFIAAVERLWDYGMSRSPHVLRNRAQSGSVPQFKKVVFQEFT
DGSFTQPLYRGELNEHLGLLGPYIRAEVEDNIMVTFKNQASRPYSFYSSL
ISYEEDQRQGAEPRKNFVKPNETKTYFWKVQHHMAPTKDEFDCKAWAYFS
DVDLEKDMHSGLIGPLLICHTNTLNPAHGRQVTVQEFALFFTIFDETKSW
YFTENMERNCRAPCNIQMEDPTFKENYRFHAINGYVMDTLPGLVMAQDQR
IRWYLLSMGSNENIHSIHFSGHVFTVRKKEEYKMAVYNLYPGVFETVEML
PSKAGIWRVECLIGEHLHAGMSTLFLVYSK
```

(C1 SEQ ID NO: 27)
QCQTPLGMASGHIRDFQITASGQYGQWAPKLARLHYSGSINAWSTKEPFS

WIKVDLLAPMIIHGIKTQGARQKFSSLYISQFIIMYSLDGKKWQTYRGNS

TGTLMVFFGNVDSSGIKHNIFNPPIIARYIRLHPTHYSIRSTLRMELMGC

DLN (C2 SEQ ID NO: 28)
SCSMPLGMESKAISDAQITASSYFTNMFATWSPSQARLHLQGRTNAWRPQ

VNNPKEWLQVDFQKTMKVTGITTQGVKSLLTSMYVKEFLISSSQDGHHWT

LFLQNGKVKVFQGNQDSFTPVVNSLDPPLLTRYLRIHPQSWVHQIALRLE

VLGCEAQQLY

The sequence for Node number 50 is: SEQ ID NO: 29. The sequence for Node number 52 is: SEQ ID NO: 30. The sequence for Node number 57 is: SEQ ID NO: 31. The sequence for Node number 59 is: SEQ ID NO: 32. The sequence for Node number 65 is: SEQ ID NO: 33. The sequence for Node number 76 is: SEQ ID NO: 34. The sequence for Node number 78 is: SEQ ID NO: 35. The sequence for Node number 87 is: SEQ ID NO: 36. The sequence for Node number 90 is: SEQ ID NO: 37. The sequence for Node number 95 is: SEQ ID NO: 38.

SEQ ID NO: 29
MRIELPCCFFLCLLPFSFGATRRYYLGAVELSWDYVHSDLLSVLHVPTG

FPGRVGRKFPFSTSVRYKKTVFVEFTDHLFTIAKPRPPWMGLLGPTIRA

EVYDTVVVTLKNLASHPFSLHAVGVTYWKASEGAGYDDETSQREKEDDK

VDPGKTHTYVWEVLKDNGPTASDPPCLTYSYLSYVDLVKDLNSGLIGAL

LVCRPGALAKDGTQTLHEFVLLFAVFDEGKSWYPEPNESLTQALDTGTP

RPWPKLHTVNGYVNGSLPGLIGCHKRPVYWHVIGLGTTPEVHSIFLEGH

TFLVRNHRHATLEISPITFLTAQTLLTDLGRFLLFCHIPAHQHDGMEAY

VKVDVCPEEPKLRMRADAPEEDYYDDLYDLDMDVIRFDDDDSPPFIGVR

AFAKKHPKTWIHYIAAEEVDWDYAPIVPTYLDRSYKSQYLEAGPQRIGR

KYKKVRFVAYTDGTFKTRKVIQYDTGILGPLLYGEVGDTLLIVFKNLAS

RPYNIYPHGLTSVSPLHPGRLPKGVKHLKDLPILPGEIFKYKWTVTVED

GPTGSDPRCLTRYYYSFINPVRDLASGLIGPLLICYKESVDQRGNQMMS

DKRRFILFSVFDENRSWYLTENIQRFCPDAAGVQPQDPEFYASNVMHSI

NGYVFDNLHLKLCLHEVAYWYVLSVGAQTDFLSVFFSGYTFKHKMVFED

TLTLFPFSGETVFMSMEKPGLWVLGCLNPDFRDRGMWALLKVSSCDRDP

GLYYGDDYDLIPTYLLNENNVLEPRGFPKNKRWPRLCLRKFKAVTSPEK

DIEKLDPQFGERTQCLRAQPLKFSDLLMLLGQNPDPHGLSLSDLTEATY

EPIPYDSFPGPVGNSTGPSEVVHLRPELHHAGDAGFYPEGGLLLFGKER

LGPTVAVELKKLDLKLHKSVDNVMFSPTAPLDNLEKGLKGTGTLGPLKE

PVRFSGHLGPTVFGKKETGLIGSGVPLQLSDRDHDSRLLERVLLNDEES

PLGLNVTSLKPDRPFKDKRVHGPASLTKDNALFKGNITLVKLDKTPDNT

TTNRKTYVDGPALLKENGTPVWLDILENDTRFQEVASLGFYETFQDGKL

TAPGLDHVLNKTTSSKNGEVFFEKKVEPVPLDAERPPAPFFKDLFLPRT

ANWLLDTHGKADLRAGQGPSPKQLISLGSDKSGDEHFLSAKSKVRLGP

DKFTKGTGLLEMIFPGRKDIFLTSLVTVQENDTLILGKKFQEAIERKET

LIQENVDLPKLYVVAGTRNFLKDLFLLHTRTNLTLDGPDEGDYAPLLQD

TRYLNGKVPPAGVHLVHGSKLLEAADLEGLLHKTKRMVLDYPSTTRTAP

KPCDQNCITHRGKRALKQFGLPLEETELERGLVDKDRALKGRKNMGYLT

GGTLTKIDYNDRAKRLVARPPLVDCTARDHGVTGTDGPAGPIRGVSAFP

PIRPTDLTKLPSHDNSSHLPAAACGYTFREKSSGVRGGSHFLQGAKRTS

LTSAYLTLKTIRGEEKVSSLGTSADTPPTYKKLENTVLLKPGLPEVVGK

VEGLPKPHVWEADLFPTPTGNGTPGHLDLKEEWLLQKLQGAIKLSKVKR

PGDFPFLKGATEILEKRPSKLLGPLPWDGQYLTQILRDEWKLKHKSPKN

TVFKTKDAILPLSGCENVHGVDGINEGRDRLQKAATWAKQGGTERLCSR

EPPVLKNHKREITLTTLQPEKEKIDYDDYLKPETDRDDFDIYGEDENQG

PRTFTGRTRHYFIAAVERLWDYGMSRPPHFLRNRARGGRVPFFKKVVFR

GFLDGSFTQPLYRGELDEHLGLLGPYIRAEVDDVIMVTFKNLASRPYSF

YSSLLPYEGGLGQGSEPRKEVVKPGELRTYFWKVLPHMAPTVDEFDCKA

WAYFSDVDLEKDLHSGLVGPLLICRPGTLSPAFGRQLTVQEFALLFTIF

DETKSWYFTENMERNCPPPCQIQPDDPDFRRSYRFHAINGYVMDTLPGL

VMAQDQRVRWYLLSVGGTEDIHSVYFHGHVFTVRKKHEYRMGVYNLYPG

VFGTVEMLPSKPGIWRVECLVGEHLQAGMSTLFLVYDPKCQTPLGLASG

HIRDAQITASGQYGQWAPRLARLHYSGSVNAWSTKDPFSWIKVDLLRPM

ILHGIKTQGARQKFSSLYISQFIIFYGLDGKRWKRYRGNATGTLMVFFG

NVDATGVKHNRFNPPIIARYIRLHPTHYSIRTTLRMELIGCDLNSCSMP

LGMENKAISDAQITASSYFTNMFATWAPSQARLHLQGRTNAWRPKVNSP

KEWLQVDFEKTMRVTGIVTQGAKSLLTSMYVKEFLVSSSQDGHRWTPFL

QDGKVKVFKGNQDHFTPVVNSLDPPLLTRYLRIHPRRWVHHIALRLEFL

GCEAQQLY

SEQ ID NO: 30
MQIELSTCFFLCLLPFSFSATRRYYLGAVELSWDYMQSDLLSELHVDTR

FPPRVPRSFPFNTSVMYKKTVFVEFTDHLFNIAKPRPPWMGLLGPTIRA

EVYDTVVITLKNMASHPVSLHAVGVSYWKASEGAEYDDQTSQREKEDDK

VIPGESHTYVWQVLKENGPMASDPPCLTYSYLSHVDLVKDLNSGLIGAL

LVCREGSLAKERTQTLHEFVLLFAVFDEGKSWHSETNESLTQAMDSASA

RAWPKMHTVNGYVNRSLPGLIGCHRKSVYWHVIGMGTTPEVHSIFLEGH

TFLVRNHRQASLEISPITFLTAQTLLMDLGQFLLFCHISSHQHDGMEAY

VKVDSCPEEPQLRMKNNEEEEDYDDDLYDSDMDVVRFDDDNSPPFIQIR

SVAKKHPKTWVHYIAAEEEDWDYAPSVLTPNDRSYKSQYLNNGPQRIGR

KYKKVRFMAYTDETFKTREAIQYESGILGPLLYGEVGDTLLIIFKNQAS

RPYNIYPHGITDVSPLHSGRLPKGVKHLKDLPILPGEIFKYKWTVTVED

GPTKSDPRCLTRYYSSFINLERDLASGLIGPLLICYKESVDQRGNQMMS

DKRNVILFSVFDENRSWYLTENMQRFLPNAAGVQPQDPEFQASNIMHSI

NGYVFDSLQLSVCLHEVAYWYILSVGAQTDFLSVFFSGYTFKHKMVYED

TLTLFPFSGETVFMSMENPGLWVLGCHNSDFRNRGMTALLKVSSCDRNT

-continued

GDYYEDTYEDIPTYLLNENNVIEPRSFSQNSRHPSTRQKQFKATTTPEN
DIEKIDPQFGERTQLLKVQSVSSSDLLMLLGQSPTPHGLSLSDLQEATY
EAIPDDHSPGATESNEGPSEVAHLRPELHHSGDMVFTPEPGLQLRLNEN
LGTTITVELKKLDLKVSSSSNNLMTSPTIPSDNLAAGTEKTGSLGPPNM
PVHFSSQLGTIVFGKKSSPLIGSGVPLNLSERDNDSKLLEAALMNSQES
SLGKNVSSMESDRLFKEKRVHGPASLTKDNALFKVNISLVKTNKTPNNS
TTNRKTHIDGPTLLIENSTSVWQDILENDTEFQEVTSLIHDEMFMDKNT
TALGLNHVSNKTTSSKNMEMVHQKKEGPVPLDAENPDMSFFKMLFLPDS
ANWIKRTHGKNSLSSGQGPSPKQLISLGSEKSVKDQNFLSEKNKVVVGE
DEFTKDTGLKEMIFPNSKSIFLTNLANVQENDTHNQEKKFQEEIERKET
LIQENVVLPQVYTVTGTKNFLKNLFLLSTRQNVTVEGLDEGTYAPVLQD
TRSLNDSANRAGIHMAHFSKRREEAETNLEGLGNQTKQMVEKYPSTTRM
SPNPSQQNVITQRGKRALKQFRLPLEEIELERGLIVNDTSTQWSKNMKY
LTQGTLTQIDYNEKEKRAITQSPLSDCSMRNHSITQTNGSALPIAKVSA
FPSIRPTDLTKIPSQDNSSHLLASACSYTFREKSSGVQESSHFLQGAKR
NNLSLAILTLEMIRGQEKVSSLGTSATNPLMYKKLENTVLLKPGLPEAS
GKVELLPKVHVQEDLFPTETSNGSPGHLDLMEEILLQKTQGAIKLNKV
NRPGKVPFLKGATESSEKTPSKLLGPLAWDNQYATQIPREEWKSQEKSP
KNTAFKTKDTILPLNPCENNHAIAAINEGQDRPQREATWAKQGGTGRLC
SQNPPVLKRHQREITLTTLQPEQEKIDYDDTISIETKREDFDIYGEDEN
QGPRSFQKRTRHYFIAAVERLWDYGMSRSPHALRNRAQSGSVPQFKKVV
FQEFTDGSFTQPLYRGELNEHLGLLGPYIRAEVEDNIMVTFKNQASRPY
SFYSSLISYEEDQRQGAEPRKNFVKPNETKTYFWKVQHHMAPTKDEFDC
KAWAYFSDVDLEKDMHSGLIGPLLICRTNTLNPAHGRQVTVQEFALFFT
IFDETKSWYFTENMERNCRAPCNIQMEDPTFKENYRFHAINGYVMDTLP
GLVMAQDQRIRWYLLSMGSNENIHSIHFSGHVFTVRKKEEYKMAVYNLY
PGVFETVEMLPSKAGIWRVECLIGEHLQAGMSTLFLVYSKQCQTPLGMA
SGRIRDFQITASGQYGQWAPKLARLHYSGSINAWSTKDPFSWIKVDLLA
PMIIHGIKTQGARQKFSSLYISQFIIMYSLDGKKWQSYRGNSTGTLMVF
FGNVDSSGIKHNIFNPPIIARYIRLHPTHYSIRSTLRMELMGCDLNSCS
MPLGMESKAISDAQITASSYFTNMFATWSPSQARLHLQGRTNAWRPQVN
NPKEWLQVDFQKTMKVTGITTQGVKSLLTSMYVKEFLISSSQDGHHWTL
FLQNGKVKVFQGNQDSFTPVVNSLDPPLLTRYLRIHPQSWVHQIALRLE
VLGCEAQQLY

SEQ ID NO: 31
MQIELSTCFFLCLLRFCFSATRRYYLGAVELSWDYMQSDLGELPVDTRF
PPRVPRSFPFNTSVVYKKTVFVEFTDHLFNIAKPRPPWMGLLGPTIQAE
VYDTVVITLKNMASHPVSLHAVGVSYWKASEGAEYDDQTSQREKEDDKV
FPGGSHTYVWQVLKENGPMASDPLCLTYSYLSHVDLVKDLNSGLIGALL
VCREGSLAKEKTQTLHKFVLLFAVFDEGKSWHSETKNSLMQDRDAASAR
AWPKMHTVNGYVNRSLPGLIGCHRKSVYWHVIGMGTTPEVHSIFLEGHT

FLVRNHRQASLEISPITFLTAQTLLMDLGQFLLFCHISSHQHDGMEAYV
KVDSCPEEPQLRMKNNEEAEDYDDDLTDSEMDVVRFDDDNSPSFIQIRS
VAKKHPKTWVHYIAAEEEDWDYAPSVLAPDDRSYKSQYLNNGPQRIGRK
YKKVRFMAYTDETFKTREAIQHESGILGPLLYGEVGDTLLIIFKNQASR
PYNIYPHGITDVRPLYSRRLPKGVKHLKDFPILPGEIFKYKWTVTVEDG
PTKSDPRCLTRYYSSFINMERDLASGLIGPLLICYKESVDQRGNQIMSD
KRNVILFSVFDENRSWYLTENIQRFLPNPAGVQLEDPEFQASNIMHSIN
GYVFDSLQLSVCLHEVAYWYILSIGAQTDFLSVFFSGYTFKHKMVYEDT
LTLFPFSGETVFMSMENPGLWILGCHNSDFRNRGMTALLKVSSCDKNTG
DYYEDSYEDISTYLLSKNNAIEPRSFSQNSRHPSTRQKQFNATTIPEND
IEKTDPWFAHRTPMPKVQNVSSSDLLMLLRQSPTPHGLSLSDLQEAKYE
TFSDDPSPGAIDSNNSLSEMTHFRPQLHHSGDMVFTPEPGLQLRLNEKL
GTTAATELKKLDFKVSSTSNNLISTIPSDNLAAGTDNTSSLGPPNMPVH
YDSQLDTTLFGKKSSPLIESGGPLSLSEENNDSKLLESGLMNSQESSWG
KNVSSTESGRLFKEKRAHGPALLTKDNALFKVSISLLKTNKTSNNSATN
RKTHIDGPSLLIENSPSVWQNILESDTEFQKVTPLIHDRMLMDKNATAL
RLNHMSNKTTSSKNMEMVQQKKEGPIPPDAENPDMSFFKMLFLPESANW
IQRTHGKNSLNSGQGPSPKQLVSLGPEKSVEGQNFLSEKNKVVVGKGEF
TKDVGLKEMVFPSSRNLFLTNLDNLHENNTHNQEKKIQEEIERKETLIQ
ENVVLPQIHTVTGTKNFMKNLFLLSTRQNVEGSYEGAYAPVLQDFRSLN
DSTNRTKKHTAHFSKKGEEENLEGLGNQTKQIVEKYPRTTRISPNPSQQ
NFVTQRGKRALKQFRLPLEETELEKRIIVDDTSTQWSKNMKHLTPSTLT
QIDYNEKEKGAITQSPLSDCLTRSHSITQANRSPLPIAKVSSFPSIRPI
DLTRVLFQDNSSHLPAPSYRKKDSGVQESSHFLQGAKKNNLSLAILTLE
MTGDQREVGSLGTSATNSVTYKKVENTVLLKPGLPKTSGKVELLPKVHI
YQKDLFPTETSNGSPGHLDLVEGSLLQETEGAIKWNEANRPGKIPFLRV
ATESSAKTPSKLLGPLAWDNHYGTQIPKEEWKSQEKSPEKTAFKKKDTI
LSLNACESNHAIAAINEGQNKPEIEVTWAKQGGTERLCSQNPPVLKRHQ
REITLTTLQSDQEEIDYDDTISVEMKKEDFDIYDEDENQSPRSFQKKTR
HYFIAAVERLWDYGMSSSPHVLRNRAQSGSVPQFKKVVFQEFTDGSFTQ
PLYRGELNEHLGLLGPYIRAEVEDNIMVTFKNQASRPYSFYSSLISYEE
DQRQGAEPRKNFVKPNETKTYFWKVQHHMAPTKDEFDCKAWAYFSDVDL
EKDVHSGLIGPLLVCHTNTLNPAHGRQVTVQEFALFFTIFDETKSWYFT
ENMERNCRAPCNIQMEDPTFKENYRFHAINGYIMDTLPGLVMAQDQRIR
WYLLSMGSNENIHSIHFSGHVFTVRKKEEYKMAVYNLYPGVFETVEMLP
SKAGIWRVECLIGEHLHAGMSTLFLVYSNKCQTPLGMASGHIRDFQITA
SGQYGQWAPKLARLHYSGSINAWSTKEPFSWIKVDLLAPMIIHGIKTQG
ARQKFSSLYISQFIIMYSLDGKKWQTYRGNSTGTLMVFFGNVDSSGIKH
NIFNPPIIARYIRLHPTHYSIRSTLRMELMGCDLNSCSMPLGMESKAIS
DAQITASSYFTNMFATWSPSKARLHLQGRSNAWRPQVNNPKEWLQVDFQ

-continued
KTMKVTGITTQGVKSLLTSMYVKEFLISSSQDGHHWTLFFQNGKVKVFQ
GNQDSFTPVVNSLDPPLLTRYLRIHPQSWVHQIALRMEVLGCEAQELY SEQ ID NO: 32
MQIELSTCFFLCLLRFCFSATRRYYLGAVELSWDYMQSDLGELPVDARF
PPRVPKSFPFNTSVVYKKTVFVEFTDHLFNIAKPRPPWMGLLGPTIQAE
VYDTVVITLKNMASHPVSLHAVGVSYWKASEGAEYDDQTSQREKEDDKV
FPGGSHTYVWQVLKENGPMASDPLCLTYSYLSHVDLVKDLNSGLIGALL
VCREGSLAKEKTQTLHKFILLFAVFDEGKSWHSETKNSLMQDRDAASAR
AWPKMHTVNGYVNRSLPGLIGCHRKSVYWHVIGMGTTPEVHSIFLEGHT
FLVRNHRQASLEISPITFLTAQTLLMDLGQFLLFCHISSHQHDGMEAYV
KVDSCPEEPQLRMKNNEEAEDYDDDLTDSEMDVVRFDDDNSPSFIQIRS
VAKKHPKTWVHYIAAEEEDWDYAPLVLAPDDRSYKSQYLNNGPQRIGRK
YKKVRFMAYTDETFKTREAIQHESGILGPLLYGEVGDTLLIIFKNQASR
PYNIYPHGITDVRPLYSRRLPKGVKHLKDFPILPGEIFKYKWTVTVEDG
PTKSDPRCLTRYYSSFINMERDLASGLIGPLLICYKESVDQRGNQIMSD
KRNVILFSVFDENRSWYLTENIQRFLPNPAGVQLEDPEFQASNIMHSIN
GYVFDSLQLSVCLHEVAYWYILSIGAQTDFLSVFFSGYTFKHKMVYEDT
LTLFPPFSGETVFMSMENPGLWILGCHNSDFRNRGMTALLKVSSCDKNTG
DYYEDSYEDISAYLLSKNNAIEPRSFSQNSRHPSTRQKQFNATTIPEND
IEKTDPWFAHRTPMPKVQNVSSSDLLMLLRQSPTPHGLSLSDLQEAKYE
TFSDDPSPGAIDSNNSLSEMTHFRPQLHHSGDMVFTPESGLQLRLNEKL
GTTAATELKKLDFKVSSTSNNLISTIPSDNLAAGTDNTSSLGPPSMPVH
YDSQLDTTLFGKKSSPLTESGGPLSLSEENNDSKLLESGLMNSQESSWG
KNVSSTESGRLFKGKRAHGPALLTKDNALFKVSISLLKTNKTSNNSATN
RKTHIDGPSLLIENSPSVWQNILESDTEFQKVTPLIHDRMLMDKNATAL
RLNHMSNKTTSSKNMEMVQQKKEGPIPPDAENPDMSFFKMLFLPESASW
IQRTHGKNSLNSGQGPSPKQLVSLGPEKSVEGQNFLSEKNKVVGKGEF
TKDVGLKEMVFPSSRNLFLTNLDNLHENNTHNQEKKIQEEIERKETLIQ
ENVVLPQIHTVTGTKNFMKNLFLLSTRQNVEGSYEGAYAPVLQDFRSLN
DSTNRTKKHTAHFSKKGEEENLEGLGNQTKQIVEKYACTTRISPNTSQQ
NFVTQRSKRALKQFRLPLEETELEKRIIVDDTSTQWSKNMKHLTPSTLT
QIDYNEKEKGAITQSPLSDCLTRSHSIPQANRSPLPIAKVSSFPSIRPI
YLTRVLFQDNSSHLPAASYRKKDSGVQESSHFLQGAKKNNLSLAILTLE
MTGDQREVGSLGTSATNSVTYKKVENTVLPKPGLPKTSGKVELLPKVHI
YQKDLFPTETSNGSPGHLDLVEGSLLQETEGAIKWNEANRPGKIPFLRV
ATESSAKTPSKLLGPLAWDNHYGTQIPKEEWKSQEKSPEKTAFKKKDTI
LSLNACESNHAIAAINEGQNKPEIEVTWAKQGRTERLCSQNPPVLKRHQ
REITRTTLQSDQEEIDYDDTISVEMKKEDFDIYDEDENQSPRSFQKKTR
HYFIAAVERLWDYGMSSSPHVLRNRAQSGSVPQFKKVVFQEFTDGSFTQ
PLYRGELNEHLGLLGPYIRAEVEDNIMVTFKNQASRPYSFYSSLISYEE
DQRQGAEPRKNFVKPNETKTYFWKVQHHMAPTKDEFDCKAWAYFSDVDL -continued
EKDVHSGLIGPLLVCHTNTLNPAHGRQVTVQEFALFFTIFDETKSWYFT
ENMERNCRAPCNIQMEDPTFKENYRFHAINGYIMDTLPGLVMAQDQRIR
WYLLSMGSNENIHSIHFSGHVFTVRKKEEYKMALYNLYPGVFETVEMLP
SKAGIWRVECLIGEHLHAGMSTLFLVYSNKCQTPLGMASGHIRDFQITA
SGQYGQWAPKLARLHYSGSINAWSTKEPFSWIKVDLLAPMIIHGIKTQG
ARQKFSSLYISQFIIMYSLDGKKWQTYRGNSTGTLMVFFGNVDSSGIKH
NIFNPPIIARYIRLHPTHYSIRSTLRMELMGCDLNSCSMPLGMESKAIS
DAQITASSYFTNMFATWSPSKARLHLQGRSNAWRPQVNNPKEWLQVDFQ
KTMKVTGITTQGVKSLLTSMYVKEFLISSSQDGHHWTLFFQNGKVKVFQ
GNQDSFTPVVNSLDPPLLTRYLRIHPQSWVHQIALRMEVLGCEAQDLY SEQ ID NO: 33
MQIELSTCFFLCLLQFSFSATRRYYLGAVELSWDYMQSDLLSELHVDTR
FPPRMPRSFPFNTSVMYKKTVFVEFTDHLFNIAKPRPPWMGLLGPTIWA
EVYDTVVITLKNMASHPVSLHAVGVSYWKASEGAEYDDQTSQREKEDDK
VFPGESHTYVWQVLKENGPMASDPPCLTYSYLSHVDLVKDLNSGLIGAL
LVCREGSLAKERTQMLHQFVLLFAVFDEGKSWHSETKGSLTQAMDSASA
RAWPKMHTVNGYVNRSLPGLIGCHRKSVYWHVIGMGTTPEVHSIFLEGH
TFLVRNHRQASLEISPITFLTAQTLLMDLGQFLLFCHISSHQHDGMEAY
VKVDSCPEEPQLRMKNNEEEEDYDDDLLDSEMDVFRFDDDNSPPFIQIR
SVAKKHPKTWIHYIAAEEEDWDYAPSVLTSDDRSYKSQYLNNGPQRIGR
KYKKVRFMAYTDETFKTRETIQYESGILGPLLYGEVGDTLLIIFKNQAS
RPYNIYPHGITDVSPLHSGRLPKGVKHLKDLPILPGEIFKYKWTVTVED
GPTKSDPRCLTRYYSSFINLERDLASGLIGPLLICYKESVDQRGNQMMS
DKRNVILFSVFDENRSWYLTENMQRFLPNAAGVQPQDPEFQASNIMHSI
NGYVFDSLQLSVCLHEVAYWYILSVGAQTDFLSVFFSGYTFKHKMVYED
TLTLFPPFSGETVFMSMENPGLWVLGCHNSDFRNRGMTALLKVSSCDRNT
GDYYEDTYEDIPTYLLSENNVIEPRSFSQNSRHPSTRQKQFKATTIPEN
DIEKIDPQFGERTQMLKVQSVSSSDLLMLLGQSPTPHGLSLSDLQEATY
EAIPDDHSPGAIDSNEGPSEVAHLRPELHHSGDIVFTPEPGLQLRLNEN
LGTTIAVELKKLDLKVSSSPNNLMTSPTIPSDNLAAGTEKTGSLGPPNM
PVHFSSQLSTTVFGKKSSPLIGSGVPLNLSERNNDSKLLEAALMNSQES
SLGKNVSSMESDRLFKEKRVHGPALLTKDNALFKVNISLIKTNKTSNNS
TTNRKTHIDGPTLLIENSTSVWQDTILESDTEFQEVTSLIHDEMLMDKN
TTALRLNHVSNKTTSSKNMEMVHQKKEGPVPPDAENPDMSFFKMLFLPE
SANWIKRTHGKNSLNSGQGPSPKQLISLGSEKSVKDQNFLSEKNKVVVG
EDEFTKDTGLKEMIFPNNRSIFLTNLANVQENDTHNQEKKFQEEIERKE
ALIQENVVLPQVYTVTGTKNFLKNLFLLSTRQNIGLDEGTYAPVLQDTR
SLNDSTNRAEIHMAHFSKRREEEETNLEGLGNQTKQMVEKYPSTTRMSP
NPSQQNVITQRGKRALKQFRLPLEETELEKGLIVDDTSTQWSKNMKYLT
QSTLTQIDYNEKEKKAITQSPLSDSPMRNHSITQMNSSALPIAKISAFP
SIRPTDLTKIPSQDNSSHFLASAYNYTFREKSSGVQESSHFLQGAKRNN -continued LSLAILPLEMIRNQEKVGSLGTSATNSVMYKKLENTVLLKPGLPEASGK
VELLPKVPIHQEDLFPTETSHGSPGHLDLMEEILLQKTQGAIKWNKTNR
PGKVPFLKGATESSEKTPSKLLGPLAWDNQYATQIPKEEWKSQEKSPKN
TAFKTKDTILSLNPCENNHAIAAINEGQDRPQREATWAKQGGTGRLCSQ
NPPVLKRHQREITLTTLQSEQEEIDYDDTISIETKREDFDIYGEDENQG
PRSFQKRTRHYFIAAVERLWDYGMSRSPHVLRNRDQSGSVPQFKKVVFQ
EFTDGSFTQPLYRGELNEHLGLLGPYIRAEVEDNIMVTFKNQASRPYSF
YSSLISYKEDQRQGAEPRKNFVKPNETKTYFWKVQHHMAPTKDEFDCKA
WAYFSDVDLEKDMHSGLIGPLLICHTNTLNPAHGRQVTVQEFALFFTIF
DETKSWYFTENMERNCRAPCNIQMEDPTFKENYRFHAINGYVMDTLPGL
VMAQDQRIRWYLLSMGSNENIHSIHFSGHVFTVRKKEEYKMAVYNLYPG
VFETVEMLPSKAGIWRVECLIGEHLHAGMSTLFLVYSKQCQIPLGMASG
HIRDFQITASGQYGQWAPKLARLHYSGSINAWSTKEPFSWIKVDLLAPM
IIHGIKTQGARQKFSSLYISQFIIMYSLDGKKWQTYRGNSTGTLMVFFG
NVDSSGIKHNIFNPPIIARYIRLHPTHYSIRSTLRMELMGCDLNSCSMP
LGMESKAISDAQITASSYFTNMFATWSPSQARLHLQGRTNAWRPQVNNP
KEWLQVDFQKTMKVTGIITQGVKSLLTSMFVKEFLISSSQDGHHWTLFL
QNGKVKVFQGNQDSFTPVVNSLDPPLLTRYLRIHPQSWVHQIALRLEVL
GCEAQQLY SEQ ID NO: 34
MQIELSTCFFLCLLPFSFSATRRYYLGAVELSWDYMQSELLSELHVDTR
FPPRVPRSFPFNTSVMYKKTVFVEFTDHLFNIAKPRPPWMGLLGPTIRA
EVYDTVVITLKNMASHPVSLHAVGVSYWKASEGAEYEDQTSQREKEDDK
VIPGESHTYVWQVLKENGPMASDPPCLTYSYLSHVDLVKDLNSGLIGAL
LVCREGSLAKERTQTLHEFVLLFAVFDEGKSWHSETNESLTQAMDPASA
RAQPEMHTVNGYVNRSLPGLIGCHKKSVYWHVIGMGTTPEVHSIFLEGH
TFLVRNHRQASLEISPITFLTAQTLLMDLGQFLLFCHISSHQHDGMEAY
VKVDSCPEEPQLRMKNNEEEEDYDDDLYDSDMDVVRFDDDNSPPFIQIR
SVAKKHPKTWVHYIAAEEEDWDYAPSVLTPNDRSYKSLYLNNGPQRIGR
KYKKVRFMAYTDETFKTREAIQYESGILGPLLYGEVGDTLLIIFKNQAS
RPYNIYPHGITDVSPLHSGRLPKGVKHLKDMPILPGEIFKYKWTVTVED
GPTKSDPRCLTRYYSSFVNLERDLASGLIGPLLICYKESVDQRGNQMMS
DKRNVILFSVFDENRSWYLTENMQRFLPNADGVQPQDPEFQVSNIMHSI
NGYVFDSLQLSVCLHEVAYWYILSVGAQTDFLSVFFSGYTFKHKMVYED
TLTLFPFSGETVFMSMENPGLWVLGCHNSDFRNRGMTALLKVSSCDRNT
GDYYEDTYEDIPTSLLNENNVIEPRSFSQNSRHPSTRQKQFKATTTPEN
DIEKIDPQSGERTQLLKVQSVSSSDLLMLLGQNPTPHGLSLSDLQEATY
EADDHLPGAIERNKGPSEVAHLRPELHHSGDRVFTPEPELQLRLNENLG
TTITVELKKLDLKISSSSNNLMTSPTIPSDKLAAGTEKTGSLGPPNMPV
HFSSQLGTIVFGKNSSHLIGSGVPLGLSEGDNDSKLLEAALMNSQESSL
GENVLSMESDRLFKEERVHGPASLTKDNALFKVNISLVKTNKAPINSTT -continued NRKTHIDGPTLLIENSTSVWQDIILESNTEFQEVTSLIHDETFMDKNTT
ALGLNHVSNKTTSSKNMEMVHQKKEGPVPLGAENPDTSFFKMLFLPDSA
NWIKRTHGKNSLSSGQRPSPKQLTSLGSEKSVKDQNFLSEKNKVVVGED
EFTKDTGLKEMIFPNSKSIFLTNLANVQENDTHNQEKKSQEEIERKEKL
IQENVVLPQVYTVTGTKNFLKNLFLLSTKQNVEGLDEGTYTPILQDTRS
LNDSANRAGIHMAHFSKIREEANLEGLGNQTKQMVEKYPSTTRMSPNPS
QQNVITQRGKRALKQFRLPLEEIKLERGVILNDTSTQWSKNMKYLTQGT
LTQIEYNEKEKRAITQSLLSDCSMRSHGIIQTNGSALPIAKVSAFPSIR
PTDLTKIPSQDNSSHLLASACSYTFRERSSGVQESSHFLQGAKRNNLSL
AFLTLEMIRGQEKISSLGKSATNPLMYKKLENTVLLKPGLSEASGKVEL
LPKVHVHQEDSFPTKTSNGSPGHLDLMEEIFLQKTQGPVKLNKVNRPGK
VPFLKWATESSEKTPSKLLGPLAWDNQYATQIPREEWKSQEKSQKNTAF
KTKDTILPLDPCENNHSIAAINEGQDKPQREATWAKQGGTGRLCSQNPP
VLKRHQREITLTTLQPEEDKIDYDDTFSIETKREDFDIYGEDENQGPRS
FQKRTRHYFIAAVERLWDYGMSRSPHALRNRAQSGSVPQFKKVVFQEFT
DGSFTQPLYRGELNEHLGLLGPYIRAEVEDNIMVTFKNQASRPYSFYSS
LISYEEDQRQGAEPRKKFVKPNETKIYFWKVQHHMAPTKDEFDCKAWAY
FSDVDLEKDMHSGLIGPLLICRTNTLNPAHGRQVTVQEFALFFTIFDET
KSWYFTENMERNCRAPCNIQMEDPTFKENYRFHAINGYVMDTLPGLVMA
QDQRIRWYLLSMGSNENIHSIHFSGHVFTVRKKEEYKMAVYNLYPGVFE
TVEMLPSKAGIWRIECLIGEHLQAGMSTLFLVYSKKCQTPLGMASGRIR
DFQITASGQYGQWAPKLARLHYSGSINAWSTKDPFSWIKVDLLAPMIIH
SIMTQGARQKFSSLYISQFIIMYSLDGKKWQSYRGNSTGTLMVFFGNVD
SSGIKHNIFNPPIIARYIRLHPTHYSIRSTLRMELMGCDLNSCSMPLGM
ENKAISDAQITASSYLNNMFATWSPSQARLHLQGRTNAWRPQVNNPKEW
LQVDFQKTMKVTGITTQGVKSLLTSMYVKEFLISSSQDGENWTLFLQNG
KVKVFQGNQDSFTPVVNSLDPPLLTRYLRIHPQSWAHQIALRLEVLGCE
AQQLY SEQ ID NO: 35
MQIELSTCFFLCLLPFSFSAIRRYYLGAVELSWDYMQSELLSELHVDTR
FPPRVPRSFPFNTSVMYKKTVFVEFTDQLFNIAKPRPPWMGLLGPTIQA
EVYDTVVITLKNMASHPVSLHAVGVSYWKSSEGAEYEDQTSQREKEDDK
VIPGKSHTYVWQVLKENGPTASDPPCLTYSYLSHVDLVKDLNSGLIGAL
LVCREGSLTKERTQTLHEFVLLFAVFDEGKSWHSGKNESLTQAMDPASA
RAQPAMHTINGYINRSLPGLIGCHKKSVYWHVIGMGTTPEVHSIFLEGH
TFLVRNHRQASLEISPITFLTAQTLLMDLGQFLLFCHISSHQHDGMEAY
VKVDSCPEEPQLRMKNNEEEEDYDDDLYDSDMDVVRFDGDNAPPFIQIR
SVAKKHPKTWVHYIAAEEEDWDYAPSVLTSNDRSYKSLYLNNGPQRIGR
KYKKVRFIAYTDETFKTREAIQYESGILGPLLYGEVGDTLLIIFKNQAS
RPYNIYPHGITDVSPLHSGRFPKGVKHLKDMPILPGEIFKYKWTVTVED
GPTKSDPRCLTRYYSSFVNLEKDLASGLIGPLLICYKESVDQRGNQMMS -continued
DKRNVILFSVFDENQSWYLTENIQRFLPNADGVQPQDPEFQVSNIMHSI
NGYVFDSLQLSVCLHEVAYWYILSVGAQTDFLSVFFSGYTFKHKMVYED
TLTLFPFSGETVFMSMENPGLWVLGCHNSDFRNRGMTALLKVYSCDRNT
GDYYEDTYEDIPTFLLNENNVIEPRSFSQNSRHPSTRQKQFKATTTPEN
DIEKIDPQSGERTQLLKEQSVSSSDLLMLLGQNPTPHGLSLSDLQEARN
EADDHLPGAIERNKGPSEVAHLRPELHHSGERVFTPEPELPLRLNENLG
TTITVELKKLDFKISSSSNNLMTSPTIPSDKLSAGTEKTGSLGPPNMPV
NFSSQLGTIVFGKNSSHFIGSGVPLGLSEEDNDSKLLEAALMNSQESSL
GENVLSMESDRLFKEERVHGPASLTKDDALFKVNISLVKTNKAPVNSTT
NRKTHIDDPTLLIENSTSVWQDIILESNTEFQEVTSLIHDETFMDKNTT
ALGLNHVSNKTTSSKNMEMVHQKKEGPVPLDAEYPDTSFFKTLFLPDST
NWIKRTHGKNSLSSGQRPSPKQLTSSGSEKSVKDQNFLSEKNKVVVGED
EFSKDTGLKEMIFPNSKSIFLTNLANVQENDTHNQEKKSQEEIERKEKL
IQENVVLPQVYTVTGTKNFLKNLFLLSTKQNVEGLDEGTYTPVLQDTRS
LNDSAKRAGIHMAHFSKIREEANLEGLGNQTKQMVEKYPSTTRMSPNPS
QQNVIPQRGKRDLKQFRLPLEEIKLERGVILNDTSTQWSKNMKYLTQGT
FTQIEYNKKEKRAITQSFLSDCSMRSHGIIQTNGSALPIAKVSAFPSIR
PTDLTKIPSQDNSSHLPASACSYTFGERSSGVQESSHFLQGAKRNNLSL
AFLTLEMIRGQKISTLGKSATNPLMYKKLENTVLLKPGLSEASGKVEF
LPKVHVQEDFFPTKTSNGSPAHLDLREEIFLQKTQGLVKLNKVNRPGK
VPPFLKWATESSEKTPSKLLGPLAWDNQYATLIPREEWKSLEKSQKNTAF
KTKDTILPLDPCENNHSIAAINEGQDKPQREATWVKQGGTGRLCSQNPP
VLKRHQREITLTTFQPEEDKIDYDDTFSIETKREDFDIYGEDENQGPRS
FQKRTRHYFIAAVERLWDYGMSRSPHALRNRAQNGDVPQFKKVVFQEFT
DGSFTQPLYRGELNEHLGLLGPYIRAEVEDNIMVTFKNQASRPYSFYSS
LISYEEDQRQGAEPRKKFVKPNETKIYFWKVQHHMAPTKDEFDCKAWAY
FSDVDLEKDVHSGLIGPLLICRTNTLNAAHGRQVTVQEFALFFTIFDET
KSWYFTENMERNCRAPCNIQMEDPTFKENYRFHAINGYVMDTLPGLVMA
QDQRIRWYLLSMGSNENIHSIHFSGHVFTVRKKEEYKMAVYNLYPGVFE
TVEMLPSKVGIWRIECLIGEHLQAGMSTLFLVYSKKCQTPLGMASGRIR
DFQITASGQYGQWAPKLARLHYSGSINAWSTKDPFSWIKVDLLAPMIIH
SIMTQGARQKFSSLYISQFIIMYSLDGKKWQSYRGNSTGTLMVFFGNVD
SSGIKHNIFNPPIIARYIRLHPTHYSIRSTLRMELMGCDLNSCSMPLGM
ENKAISDAQITASSHLSNMFATWSPSQARLHLQGRTNAWRPQVNNPKEW
LQVDFQKTMKVTGITTQGVKSLLTSMYVKEFLISSSQDGNNWTLFLQNG
KVKVFQGNQDSFTPVVNALDPPLFTRYLRIHPQSWAHHIALRLEVLGCE
AQQLY SEQ ID NO: 36
MQIELSTCFFLCLLPFSFSATRRYYLGAVELSWDYMQSELLSELHVDTR
FSPRVPRSLPFNTSVMYKKTVFVEFTDHLFNIAKPRPPWMGLLGPTIRA
EVYDTVVITLKNMASHPVSLHAVGVSYWKASEGAEYEDQTSQKEKEDDK
VIPGESHTYVWQVLKENGPMASDPPCLTYSYFSHVDLVKDLNSGLIGAL
LVCKEGSLAKERTQTLHEFVLLFAVFDEGKSWHSETNESLTQSAQAQHE
MHTVNGYVNRSLPGLTGCHKKSVYWHVIGMGTTPEVHSIFLEGHTFLVR
NHRQASLEISPITFLTAQTFLMDLGQFLLFCHISSHQHDGMEAYVKVDS
CPEEPQLRMKNNEEEEDYDDDLYDSDMDVVRFDGDNSSPFIQIRSVAKK
HPKTWVHYIAAEEEDWDYAPSAPTPNDRSYKNLYLNNGPQRIGRKYKKV
RFMAYTDETFKTREAIQYESGILGPLLYGEVGDTLLIIFKNQASRPYNI
YPHGITDVSPLHSGRLPKGVKHLKDMPILPGEIFKYKWTVTVEDGPTKS
DPRCLTRYYSSFINLERDLASGLIGPLLICYKESVDQRGNQMMSDKRNV
ILFSVFDENRSWYLTENMQRFLPNADAVQPHDPEFQVSNIMHSINGYVF
DNLQLSVCLHEVAYWYILSVGAQTDFLSVFFSGYTFKHKMVYEDTLTLF
PFSGETVFMSMENPGLWVLGCHNSDFRNRGMTALLKVSSCNRNTGDYYE
DTYEDIPTSLLNENNVIEPRSFSQNSRHPSTRQKQFKATTTPENDIEKI
DPQSGERTQLLKVQSVSSSDLLMLLGQNPTPHGLFLSDLQEATHEADDH
LLGAIERNKGPSEVASLRPELHHSGDRVFTPEPELQLRLNENLGTTVTV
ELKKLDLKISSSSDNLMTSPTIPSDKLAAGTEKTGSLGPPNMSVHFNSH
LGTIVFGKNSSHLIESGVPLGLSEGDNDSKLLEAALMNSQESSLGENVL
SMESNRLFKEERVHGPASLIKDNALFKVNISLVKTNKAPINSTTNRKTH
VDVPTLLIENSTSVWQDIILESNTEFQEVTSLIHNETFMDRNTTALGLN
HVSNKTTSSKNVEMVHQKKEGPVPLGAENPDLSFFKILFLPDSANWIKR
THGKNSLSSGQRPSPKQLTSLGSEKSVKDQNFLSEKKVVVGEDEFTKDT
GLKEMIFPNSKSIFFTNLANVQENDTYNQEKKSQEEIERKEKLTQENVV
LPQVYTVTGTKNFLKNLFLTKQNVTEGLDEGTYPILQDTRSLNDSAH
RAGIHMAHFSKIREEANLEGLGNQTKQMVERFPSTTRMSPNPSQHNVIT
QRGKRALKQPRLSLEEIKFERGVILNDTSTQWSKNMNYLTQGTLTQIEY
NEKEKRAITQSLLSDCSMRNHGTIQMNDSALPIAKVSAFPSIRHTDLTK
IPSQDNSSHLPASACSYTFRERSSGVQESSHFLQGAKRNNLSLAFLTLE
MIRGQGKFSSLGKSATNPMYKKLENTVLLKPGLSEASGKVELLPKVHV
HQEDSFPTKTSNDSPGHLDLMEKIFLQKTQGPVKLNKVNRPGKVPFLKW
ATESSEKIPSKLLGPLAWDNHYATQIPREEWKSQKKSQKNTAFKTKDTI
LPLGPCENNHSIAAINEGQDKPQREATWAKQGETGRLCSQNPPVSKRHQ
REITLTTLQPEEDKIEYDDTFSIEMKREDFDIYGEDENQGLRSFQKRTR
HYFIAAVERLWDYGMSRSPHALRNRAQSGDVPQFKKVVFQEFTDGSFTQ
PLYRGELNEHLGLLGPYIRAEVEDNIMVTFKNQASRPYSFYSSLISYEE
DQRQGAEPRKKFVNPNETKIYFWKVQHHMAPTKDEFDCKAWAYFSDVDL
EKDVHSGLIGPLLICRSNTLNPAHGRQVTVQEFALFFTIFDETKSWYFT
ENMERNCRAPCNIQKEDPTFKENYRFHAINGYVMDTLPGLVMAQDQKIR
WYLLSMGSNENIHSIHFSGHVFTVRKKEEYKMAVYNLYPGVFETVEMLP
SKVGIWRIECLIGEHLQAGMSTLFLVYSKKCQTPLGMASGHIRDFQITA
SGQYGQWAPKLARLHYSGSINAWSTKDPFSWIKVDLLAPMIIHSIMTQG
ARQKFSSLYISQFIIMYSLDGKKWQSYRGNSTGTLMVFFGNVDSSGIKH NIFNPPIIARYIRLHPTHYSIRSTLRMELMGCDLNSCSMPLGMENKAIS
DAQITASSYLNSMFATWSPSQARLHLQGRTNAWRPQANNPKEWLQVDFQ
KTMKVTGITTQGVKSLLTSMYVKEFLISSSQDGENWTLFLQNGKVKVFQ
GNQDSFTPVVNSLDPPLLTRYLRIHPQSWAHQIALRLEVLGCEAQQLY SEQ ID NO: 37
MQIELSTCFFLCLLPFSFSATRRYYLGTVELSWDYMQSELLSELHVDTR
FPPRVPRSFPFNPSVMYKKTVFVEFTDHLFNIAKPRPPWMGLLGPTIRA
EVYDTVVITLKNMASHPVSLHAVGVSYWKASEGAEYEDQTSQREKEDDK
VIPGESYTYVWQVLKENGPMASDPPCLTYSYLSHVDLVKDLNSGLIGAL
LVCREGSLAKERTQTLHEFVLLFAVFDEGKSWHSETNESLTQAMDPASA
RAQPEMHTVNGYVNRSLPGLIGCHKKSVYWHVIGMGTTPEVHSIFLEGH
TFLVRNHRQASLEISPISFLTAQTLLMDLGQFLLFCHISSHQHDGMEAY
VKVDSCPEEPQLRMKNNEEEEDYDDDLYDSDMDVVRFDGDNSPPFIQIR
SVAKKHPKTWVHYIAAEEEDWDYAPSVLTPNDRSYKSLYLNNGPQQIGR
KYKKARFMAYTDETFKTREAIQYESGILGPLLYGEVGDTLLIIFKNQAS
RPYNIYPHGITDVSPLHSGRLPKGVKHLKDMPILPGEIFKYKWTVTVED
GPTKSDPRCLTRYYSSFVNLERDLASGLIGPLLICYKESVDQRGNQMMS
DKRNVILFSVFDENRSWYLTENMQRFLPNADGVQPQDPEFQVSNIMHSI
NGYVFDSLQLSVCLHEVAYWYILSVGAQTDFLSVFFSGYTFKHKMVYED
TLTLFPFSGETVFMSMENPGLWVLGCHNSDFRNRGMTALLKVSSCNRNT
GDYYEDTYEDIPTSLLNENNVIEPRSFSQNSRHPSTRQKQFKATTTPEN
DVEKIDLRSGERTQLLKVQSVSSSDLLMLLGQNPTPHALSLSDLQEVTY
EADDHLPGTIERNKGPSEVAHLRPELHHSGDRVFTPEPELQLRLNENLG
TTITVELKKLDLKISSSSNNLMISPTIPSDKLAAGTEKTGSLGPPNMPV
HFSSQLGTIVFGKNSSHLIESAVPLGLSEGDNDSKLIEAALMNSQESSL
EENVLSMESDRLFKEERVHGPVSLTKDNALFKVNFSLVKTNKAPINSTT
NRKTHIDGPTLLIENSTSVWQDIILESNSGFQEVTSLIHDETFMDKNTT
ALGLNHVSNKTTSSKNMEMVHQKKEDPAPLGAENPDISFFKMLFLPDSA
NWIKRTHCKNSLSSGQRPSPKQLTSLGSEKSVKDQNFLSEKNKVVVGED
EFTKDTGLKEMIFPNSKSIFLTNLANVQENDTHNQEKNSQEEIERKEKL
IQKNVVLPQVYTVTGTKNFLKNLFLLSTKQNVEGLDEGTYTPILQDTRS
LNESANRARIHMAHFSKIREEANLEGLGNQTKQMVEKYPSTTRMSPNPR
QQNVITHHGKRALKQFRLPQEEIKLERGVILNDTSTQWSKNMKYLTQGT
LTQIEYNEKEKRAITQSLLSDCSVRSHGIIQTNGSALPIAKVSAFPSIR
PTDLTKIPSQDNSSHLLASACSYTFREKSSGIQESSHFLQGAKRNNLSL
AFLTLEMIRGQKISSLGKLSEASGKVELLPKVHVHQEDSFPTKTSNGS
PGHLDLMEEIFLQKTQGPVKLNKVNRPGKIPFLKWAAESSEKTPSKLLG
PLATQIPREEWNSQEKSQKNKAFKTKDTISPLDPCENNHSIAAINKGQD
KPQREATWAKQEETGRLCSQNPPVLKRHQRQITLTTVQPEEDKIDYDDT
FSTETKREDFDIYGEDENQDPRSFQKRTRHYFIAAVERLWDYGMSRSPH
ALRNRAQSGDVPQFKKVVFQEFTDGSFTQPLYRGELNEHLGLLGPYIRA EVEDNIMVTFKNQASRPYSFYSSLISYEDDQRQGAEPRKKFVKPNETEV
YFWKVQHHMAPTKDEFDCKAWAYFSDVDLDKDVHSGLVGPLLICRANTL
NPAHGRQVTVQEFALFFTIFDETKSWYFTENMERNCRAPCNIQMEDPTF
KENYRFHAINGYVMDTLPGLVMAQDQRIRWYLLSMGSNENIHSIHFSGH
VFTVRKKEEYKMAVYNLYPGVFETVEMLPSKVGIWRIECLIGEHLQAGM
STLFLVYSKKCQTPLGMASGHIRDFQITASGQYGQWAPKLARLHYSGSI
NAWSTKDPFSWIKVDLLAPMIIHSIMTQGARQKFSSLYISQFIIMYSLD
GKKWQSYRGNSTGTLMVFFGNVDSSGIKHNIFNPPIIARYIRLHPTHYS
IRSTLRMELMGCDLNSCSMPLGMENKAIADAQITASSYLNNMFATWSPS
QARLHLQGRTNAWRPRVNNPKEWLQVDFQKTMKVTGITTQGVKSLLTSM
YVKEFLISSSQDGHNWTLFLQNGKVKVFQGNQDSFTPVVNSLDPPLLTR
YLRIHPQSWGHQIALRLEVLGCEAQQLY SEQ ID NO: 38
MQIELSVCFFLCLLPFSFSATRRYYLGAVELSWDYMQSDLLSELHVDTRL
LPRVPRSFPFNTSVMFKKTVFVEFTDHLFNIAKPRPPWMGLLGPTIRAEV
YDTVIITLKNMASHPVSLHAVGVSYWKASEGAEYDDKTSQREKEDDKVIP
GESHTYIWQVLKENGPMASDPPCLTYSYLSHVDLVKDLNSGLIGALLVCR
EGSLAKERTQTLHEFVLLFAVFDEGKSWHSEANESLAQGVDSASTRPWPK
MYTVNGYVNRSLPGLIGCHRKSVYWHVIGMGTTPEVHSIFLEGHTFLVRN
HRQASLEISPITFLTAQTLLMDLGQFLLFCHIPSHQHDGMEAYVKVDSCP
EEPQLRKKNNEEEEDYEDDLYDSDMDVLRFDDDNSPPFIQIRSVAKKHPK
TWIHYIAAEEEDWDYAPAVLPSTDRSYKSQYLNNGTQRIGRKYKKVRFIA
YTDETFQTREAIQYESGILGPLLYGEVGDTLLIIFKNQASRPYNIYPHGI
TNVSPLHSGRLPKGVKHLKDLQIMPGEIFKYKWTVTVEDGPTKSDPRCLT
RYYSSFINLERDLASGLIGPLLICYKESVDQRGNQMMSDKRNVILFSVFD
ENRSWYLTENMQRFLPNAAGVQPQDPEFQASNMMYSINGYVFDNLQLSVC
LHEVAYWYILSVGAQTDFLSVFFSGYTFKHKMVFEDTLTLFPFSGETVFM
SMENPGLWVLGCHNSDFRNRGMTALLKVSSCDRNTDDYYEDTYEDIPTYL
LNENSVIEPRSFSQNSRHPSPRQKQFKATTAPENDIEKMDPRFGERTQLL
KAQSVSSSDLLMLLGQSPTPHGLSLSDLQEAKYEAIPDDPSPGAIENKEG
PSEVAHLRPELHHSEDMVFTPEPGLQLRLNENLETTITEDLKKLDLKVSS
SSNNVMTSPISSSDNLPADTEKTDSLGPLNTPVHFSSQLGTILFGKKSSP
LIGSGVPLNLSERDNDSTLLEAALMSSQESSLGKKVSSMESDRLFKEKKV
HGPASLTKDNALFKVNISLVKTNKTPNNSTTNRKTHIDGPTLLNENSTSG
WQDILKNDTEFQEVTSLIHNEMFMDKNTTALGLNHVSNKTTSSKDMEMVH
QKKEDPVSLDAENPDMSFFKMLFLPDSANWIKRTHGKNSLSSEQGPSPKQ
LISLGSENSVKDQNFLSEKNKVAVGEDEFTKDTGFKEMIFPNSKSIFLTN
LANVQENDTQNQEKKFQEEIERKETLIQENVGLPQVFPVTGTKNFLKTLF
LLSTRQNVTVEGLDEGTYAPVLQDTRSLNDSANRLGLHMAHFSKRREEAN
LEGLRNQTKQMVEKYPSPTRMSPNPSQQNAITQRSKRALKQFGPPLEEIE
LERGLIVNDTSTLQSRNMKYLTQGTLTQIDYNEKEKRAITQSPLSDCSMR

NHVITQTNGSALPIAKTSAFPSIRPTDLTKIPSQDNSSHLLSSACNYTFR

EKSSGVQESSHFLQGAKRNNLSSAILTLDMIRGQEKVISLSATDPLMYKK

LENTVLLKPGLPEASGKVELLPKIHVHQEDPFPTETSNGSPGHLDLMEEI

LLQKTQGAIKLNKVNRPGKVPFLKGATESSEKTLPKLLGPLAWDNQYATQ

ISREEWQSQEKSPKNTAFNTKDTISPLNPCENNHAIAAINEGQDRLQKEA

TWAKQGETERLCSENPPVLKHHPREITLTALQQEQEKIDYDDALSIETKR

EDFDIYGEDENQGPRSFQKKTRHYFIAAVERLWDYGMSKSPHALRNRAQS

GSVPQFKKVVFQEFTDGSFTQPLYRGELNEHLGLLGPYIRAEVEDNIMVT

FKNQASRPYSFYSSLISYEEDQRQGTEPRKNLVKPNETKTYFWKVQHHMA

PTKDEFDCKAWAYFSDVDLEKDLHSGLIGPLLICRTNTLNPAHGRQLTVQ

EFALFFTIFDETKSWYFTENMERNCKAPCNIQMEDPTFKKNYRFHAINGY

VMDTLPGLVMAQDQRIRWYLLSMGSNENIHSIHFSGHVFTVRKKEEYKMA

VYNLYPGVFETVEMLPSKAGIWRVECLIGEHLQAGMSTLFLVYSKECQTP

LGMASGRIRDSQITASGHYGQWAPKLARLHYTGSINAWSTKDPFSWIKVD

LLAPMIIHGIKTQGARQKLSSLYISQFIIMYSLDGKKWQSYRGNSTGTLM

VFFGNVDSSGIKHNIFNPPIIAQYIRLHPTHHSIRSTLRMELMGCDLNSC

SMPLGMESKAISDAQITASSYFTNMFATWSPSQARLHLQGRTNAWRPQVN

NPKEWLQVDFQKTMKVTGITTQGAKSLLTSMYVKEFLISSSQDGHHWTLF

LQNGKVKVFQGNQDSFTPVVNSLDPPLLTRYLRIYPQSWVHQIALRLEVL

GCQSQQHY

SEQ ID NO: 39
MQIALFTCFFLSLFNFCSSATRRYYLGAVELSWNYMQSDLLSVLHTDTRF

LPRMPTSFPFNTSIMYKKTVFVEYMDHLFNIAKPRPPWMGLLGPTIWTEV

HDTVVITLKNMASHPVSLHAVGVSYWKASEGAEYEDQTSQREKEDDKVFP

GESHTYVWQVLKENGPMASDPPCLTYSYLSHVDLVKDLNSGLIGALLVCK

EGSLSKERTQMLHQFVLLFAVFDEGKSWHSETKDSFTQAMDSASTRAWPK

MHTVNGYVNRSLPGLIGCHRKSVYWHVIGMGTTPEVHSIFLEGHTFLVRN

HRQASLEISPITFLTAQTLLIDLGQFLLFCHISSHKHDGMEAYVKVDSCP

EEPQWQKKNNEEMEDYDDDLDSEMDMFTLDDDNSPFIQIRSVAKKYPKTW

IHYISAEEEDWDYAPSVLTSDDGSYKSQYLSNGPHRIGRKYKKVRFIAYT

DVTFKTRETIQHESGILGPLLYGEVGDTLLIIFKNQASRPYNIYPHGITD

VSPLHSRRLPRGIKHVKDLPIRPGEIFKYKWTVTVEDGPTKSDPRCLTRY

YSSFINPERDLASGLIGPLLICYKESVDQRGNQMMSDKRNVILFSVFDEN

QSWYITENMQRFLPNAADTQPQDPEFQASNIMHSINGYVFDSLQLTVCLH

EVAYWYILSVGAQTDFLSIFFSGYTFKHKMVYEDTLTLFPFSGETVFMSM

ENPGLWVLGCHNSDFRKRGMTALLKVSSCDKSTSDYYEEIYEDIPTQLVN

DNNVIEPRSFFQNPPVLKRHQRELSALQSEQEATDYDDSITIETNEDFDI

YGEDIKQGPRSFQQKTRHYFIAAVERLWDYGMSTSPHVLRNRDQSGNAPQ

FKKVVFQEFTDGSFSQPLYRGELNEHLGLLGPYIRAEVEDNIMVTFKNQA

SRPYSFYSSLISYKEDQRQGEEPRRNFVKPNETKIYFWKVQHHMAPTEDE

FDCKAWAYFSDVDLERDMHSGLIGPLLICHTNTLNPAHGRQVAVQEFALF

FTIFDETKSWYFTENVERNCKTPCNIQMEDPTLKENYRFHAINGYVMDTL

PGLVMAQDQRIRWYLLSMGSNENIQSIHFSGHVFTVRKKEEYKMAVYNLY

PGVFETVEMLPSRAGIWRVECLIGEHLQAGMSTLFLVYSKQCQIPLGMAS

GSIRDFQITASGHYGQWAPNLARLHHSGSINAWSTKEPFSWIKVDLLTPM

IIHGIKTQGARQKFSSLYISQFIIMYSLDGKKWLSYRGNSTGTLMVFFGN

VDSSGIKHNSFNPPIIARYIRLHPTHSSIRSTLRMELMGCDLNSCSIPLG

MENKVISDTQITASSYFTNMFATWSPSQARLHLQGRTNAWRPQVNDPKEW

LQVDLQKTMKVTGIITQGVKSLFTSMFVKEFLISSSQDGHHWTHILHNGK

VKVFQGNQDSSTPMVNSLDPPLLTRYLRIHPQIWEHQIALRLEILGCEAQ

QLY

SEQ ID NO: 40
MQIELSTCFFLCLLQFSFSATRRYYLGAVELSWDYMQSDLLSELHVDTRF

PPRVPRSFPFNTSVMYKKTVFVEFTDHLFNIAKPRPPWMGLLGPTIRAEV

YDTVVITLKNMASHPVSLHAVGVSYWKASEGAEYDDQTSQREKEDDKVFP

GESHTYVWQVLKENGPMASDPPCLTYSYLSHVDLVKDLNSGLIGALLVCR

EGSLAKERTQTLHQFVLLFAVFDEGKSWHSETKDSLTQAMDSASARAWPK

MHTVNGYVNRSLPGLIGCHRKSVYWHVIGMTTPEVHSIFLEGHTFLVRN

HRQASLEISPITFLTAQTLLMDLGQFLLFCHISSHQHDGMEAYVKVDSCP

EEPQLRMKNNEEEEDYDDDLYDSEMDVVRFDDDNSPPFIQIRSVAKKHPK

TWVHYIAAEEEDWDYAPSVLTPDDRSYKSQYLNNGPQRIGRKYKKVRFMA

YTDVTFKTREAIQYESGILGPLLYGEVGDTLLIIFKNQASRPYNIYPHGI

TDVSPLHSGRLPKGVKHLKDLPILPGEIFKYKWTVTVEDGPTKSDPRCLT

RYYSSFINLERDLASGLIGPLLICYKESVDQRGNQMMSDKRNVILFSVFD

ENRSWYLTENMQRFLPNAAGVQPQDPEFQASNIMHSINGYVFDSLQLSVC

LHEVAYWYILSVGAQTDFLSVFFSGYTFKHKMVYEDTLTLFPFSGETVFM

SMENPGLWVLGCHNSDFRNRGMTALLKVSSCDRNTGDYYEDTYEDIPTYL

LSENNVIEPRSFSQNPPVLKRHQREITLTTLQSEQEEIDYDDTISIETKR

EDFDIYGEDENQGPRSFQKRTRHYFIAAVERLWDYGMSRSPHVLRNRAQS

GSVPQFKKVVFQEFTDGSFTQPLYRGELNEHLGLLGPYIRAEVEDNIMVT

FKNQASRPYSFYSSLISYEEDQRQGAEPRKNFVKPNETKTYFWKVQHHMA

PTKDEFDCKAWAYFSDVDLEKDMHSGLIGPLLICHTNTLNPAHGRQVTVQ

EFALFFTIFDETKSWYFTENMERNCRAPCNIQMEDPTFKENYRFHAINGY

VMDTLPGLVMAQDQRIRWYLLSMGSNENIHSIHFSGHVFTVRKKEEYKMA

VYNLYPGVFETVEMLPSKAGIWRVECLIGEHLAGMSTLFLVYSKQCQTP

LGMASGHIRDFQITASGQYGQWAPKLARLHYSGSINAWSTKEPFSWIKVD

LLAPMIIHGIKTQGARQKFSSLYISQFIIMYSLDGKKWQTYRGNSTGTLM

VFFGNVDSSGIKHNIFNPPIIARYIRLHPTHYSIRSTLRMELMGCDLNSC

SMPLGMESKAISDAQITASSYFTNMFATWSPSQARLHLQGRTNAWRPQVN

NPKEWLQVDFQKTMKVTGITTQGVKSLLTSMYVKEFLISSSQDGHHWTLF

LQNGKVKVFQGNQDSFTPVVNSLDPPLLTRYLRIHPQSWVHQIALRLEVL

GCEAQQLY

SEQ ID NO: 42:

MQIALFTCFFLSLFNFCSSATRRYYLGAVELSWNYMQSDLLSVLHTDTRF

LPRMPTSFPFNTSIMYKKTVFVEYMDHLFNIAKPRPPWMGLLGPTIWTEV

HDTVVITLKNMASHPVSLHAVGVSYWKASEGAEYEDQTSQREKEDDKVFP

GESHTYVWQVLKENGPMASDPPCLTYSYLSHVDLVKDLNSGLIGALLVCK

EGSLSKERTQMLHQFVLLFAVFDEGKSWHSETKDSFTQAMDSASTRAWPK

MHTVNGYVNRSLPGLIGCHRKSVYWHVIGMGTTPEVHSIFLEGHTFLVRN

HRQASLEISPITFLTAQTLLIDLGQFLLFCHISSHKHDGMEAYVKVDSCP

EEPQWQKKNNEEMEDYDDDLDSEMDMFTLDDDNSPFIQIRSVAKKHPKTW

VHYIAAEEEDWDYAPLVLAPDDRSYKSQYLNNGPQRIGRKYKKVRFMAYT

DVTFKTREAIQHESGILGPLLYGEVGDTLLIIFKNQASRPYNIYPHGITD

VRPLYSRRLPKGVKHLKDFPILPGEIFKYKWTVTVEDGPTKSDPRCLTRY

YSSFVNMERDLASGLIGPLLICYKESVDQRGNQIMSDKRNVILFSVFDEN

RSWYLTENIQRFLPNPAGVQLEDPEFQASNIMHSINGYVFDSLQLSVCLH

EVAYWYILSIGAQTDFLSVFFSGYTFKHKMVYEDTLTLFPFSGETVFMSM

ENPGLWILGCHNSDFRNRGMTALLKVSSCDKNTGDYYEDSYEDISAYLLS

KNNAIEPRSFAQNSRPPSASAPKPPVLKRHQRELSALQSEQEATDYDDSI

TIETNEDFDIYGEDIKQGPRSFQQKTRHYFIAAVERLWDYGMSTSPHVLR

NRDQSGNAPQFKKVVFQEFTDGSFSQPLYRGELNEHLGLLGPYIRAEVED

NIMVTFKNQASRPYSFYSSLISYKEDQRQGEEPRRNFVKPNETKIYFWKV

QHHMAPTEDEFDCKAWAYFSDVDLERDMHSGLIGPLLICHTNTLNPAHGR

QVAVQEFALFFTIFDETKSWYFTENVERNCKTPCNIQMEDPTLKENYRFH

AINGYVMDTLPGLVMAQDQRIRWYLLSMGSNENIQSIHFSGHVFTVRKKE

EYKMAVYNLYPGVFETVEMLPSRAGIWRVECLIGEHLQAGMSTLFLVYSK

KCQTPLGMASGHIRDFQITASGQYGQWAPKLARLHYSGSINAWSTKEPFS

WIKVDLLAPMIIHGIKTQGARQKFSSLYISQFIIMYSLDGKKWQTYRGNS

TGTLMVFFGNVDSSGIKHNIFNPPIIARYIRLHPTHYSIRSTLRMELMGC

DLNSCSMPLGMESKAISDAQITASSYFTNMFATWSPSKARLHLQGRSNAW

RPQVNNPKEWLQVDFQKTMKVTGVTTQGVKSLLTSMYVKEFLISSSQDGH

QWTLFFQNGKVKVFQGNQDSFTPVVNSLDPPLLTRYLRIHPQSWVHQIAL

RMEVLGCEAQDLY

In certain embodiments, the disclosure contemplate recombinant, chimeric, non-naturally occurring sequences comprising one or more of the sequences of four or more continuous amino acids found in Ancestral Nodes disclosed herein, e.g., 68 or 53.

In certain embodiments, the sp domain comprises one or more sequences selected from; IALF (SEQ ID NO: 44), FFLS (SEQ ID NO: 45), FLSL (SEQ ID NO: 46), LSLF (SEQ ID NO: 47), SLFN (SEQ ID NO: 48), LFNF (SEQ ID NO: 49), FNFC (SEQ ID NO: 50), NFCS (SEQ ID NO: 51), FCSS (SEQ ID NO: 52), CSSA (SEQ ID NO: 53), SSAT (SEQ ID NO: 54).

In certain embodiments, the A1 domain comprises one or more sequences selected from; LSWN (SEQ ID NO: 55), WNYM (SEQ ID NO: 56), NYMQ (SEQ ID NO: 57), DLLS (SEQ ID NO: 58), LLSV (SEQ ID NO: 59), LSVL (SEQ ID NO: 60), SVLH (SEQ ID NO: 61), VLHT (SEQ ID NO: 62), LHTD (SEQ ID NO: 63), HTDT (SEQ ID NO: 64), TDTR (SEQ ID NO: 65), TRFL (SEQ ID NO: 66), RFLP (SEQ ID NO: 67), FLPR (SEQ ID NO: 68), LPRM (SEQ ID NO: 69), PRMP (SEQ ID NO: 70), RMPT (SEQ ID NO: 71), PTSF (SEQ ID NO: 72), TSFP (SEQ ID NO: 73), NTSI (SEQ ID NO: 74), TSIM (SEQ ID NO: 75), SIMY (SEQ ID NO: 76), IMYK (SEQ ID NO: 77), MYKK (SEQ ID NO: 78), FVEY (SEQ ID NO: 79), VEYM (SEQ ID NO: 80), EYMD (SEQ ID NO: 81), YMDH (SEQ ID NO: 82), MDHL (SEQ ID NO: 83), DHLF (SEQ ID NO: 84), PTIW (SEQ ID NO: 85), TIWT (SEQ ID NO: 86), IWTE (SEQ ID NO: 87), WTEV (SEQ ID NO: 88), TEVH (SEQ ID NO: 89), EVHD (SEQ ID NO: 90), VHDT (SEQ ID NO: 91), HDTV (SEQ ID NO: 92), FPGE (SEQ ID NO: 93), PGES (SEQ ID NO: 94), GESH (SEQ ID NO: 95), ESHT (SEQ ID NO: 96), LVCK (SEQ ID NO: 97), VCKE (SEQ ID NO: 98), CKEG (SEQ ID NO: 99), GSLS (SEQ ID NO: 100), SLSK (SEQ ID NO: 101), LSKE (SEQ ID NO: 102), SKER (SEQ ID NO: 103), RTQM (SEQ ID NO: 104), TQML (SEQ ID NO: 105), QMLH (SEQ ID NO: 106), MLHQ (SEQ ID NO: 107), LHQF (SEQ ID NO: 108), HQFV (SEQ ID NO: 109), QFVL (SEQ ID NO: 110), KDSF (SEQ ID NO: 111), DSFT (SEQ ID NO: 112), SFTQ (SEQ ID NO: 113), FTQA (SEQ ID NO: 114), TQAM (SEQ ID NO: 115), QAMD (SEQ ID NO: 116), AMDS (SEQ ID NO: 117), MDSA (SEQ ID NO: 118), DSAS (SEQ ID NO: 119), SAST (SEQ ID NO: 120), ASTR (SEQ ID NO: 121), STRA (SEQ ID NO: 122), TRAW (SEQ ID NO: 123), LLID (SEQ ID NO: 124), LIDL (SEQ ID NO: 125), IDLG (SEQ ID NO: 126), SSHK (SEQ ID NO: 127), SHKH (SEQ ID NO: 128), HKHD (SEQ ID NO: 129), KHDG (SEQ ID NO: 130), EPQW (SEQ ID NO: 131), PQWQ (SEQ ID NO: 132), QWQK (SEQ ID NO: 133), WQKK (SEQ ID NO: 134), QKKN (SEQ ID NO: 135), KKNN (SEQ ID NO: 136), NEEM (SEQ ID NO: 137), EEME (SEQ ID NO: 138), EMED (SEQ ID NO: 139), MEDY (SEQ ID NO: 140), DDLD (SEQ ID NO: 141), DLDS (SEQ ID NO: 142), LDSE (SEQ ID NO: 143), EMDM (SEQ ID NO: 144), MDMF (SEQ ID NO: 145), DMFT (SEQ ID NO: 146), MFTL (SEQ ID NO: 147), FTLD (SEQ ID NO: 148), TLDD (SEQ ID NO: 149), LDDD (SEQ ID NO: 150).

In certain embodiments, the ap domain comprises one or more sequences selected from; LSAL (SEQ ID NO: 151), SALQ (SEQ ID NO: 152), ALQS (SEQ ID NO: 153), LQSE (SEQ ID NO: 154), QSEQ (SEQ ID NO: 155), SEQE (SEQ ID NO: 156), EQEA (SEQ ID NO: 157), QEAT (SEQ ID NO: 158), EATD (SEQ ID NO: 159), ATDY (SEQ ID NO: 160), TDYD (SEQ ID NO: 161), YDDS (SEQ ID NO: 162), DDSI (SEQ ID NO: 163), DSIT (SEQ ID NO: 164), SITI (SEQ ID NO: 165), ITIE (SEQ ID NO: 166), TIET (SEQ ID NO: 167), IETN (SEQ ID NO: 168), ETNE (SEQ ID NO: 169), TNED (SEQ ID NO: 170), NEDF (SEQ ID NO: 171), DIYG (SEQ ID NO: 172), IYGE (SEQ ID NO: 173), YGED (SEQ ID NO: 174), GEDI (SEQ ID NO: 175), EDIK (SEQ ID NO: 176), DIKQ (SEQ ID NO: 177), IKQG (SEQ ID NO: 178), KQGP (SEQ ID NO: 179), QGPR (SEQ ID NO: 180).

In certain embodiments, the A3 domain comprises one or more sequences selected from; MSTS (SEQ ID NO: 181), STSP (SEQ ID NO: 182), TSPH (SEQ ID NO: 183), RNRD (SEQ ID NO: 184), NRDQ (SEQ ID NO: 185), RDQS (SEQ ID NO: 186), DQSG (SEQ ID NO: 187), QSGN (SEQ ID NO: 188), SGNA (SEQ ID NO: 189), GNAP (SEQ ID NO: 190), NAPQ (SEQ ID NO: 191), APQF (SEQ ID NO: 192), GSFS (SEQ ID NO: 193), SFSQ (SEQ ID NO: 194), FSQP (SEQ ID NO: 195), SQPL (SEQ ID NO: 196), ISYK (SEQ ID NO: 197), SYKE (SEQ ID NO: 198), YKED (SEQ ID NO: 199), KEDQ (SEQ ID NO: 200), RQGE (SEQ ID NO: 201), QGEE (SEQ ID NO: 202), GEEP (SEQ ID NO: 203), EEPR (SEQ ID NO: 204), EPRR (SEQ ID NO: 205), PRRN (SEQ ID NO: 206), RRNF (SEQ ID NO: 207), RNFV (SEQ ID NO: 208), ETKI (SEQ ID NO: 209), TKIY (SEQ ID NO: 210), KIYF (SEQ ID NO: 211), IYFW (SEQ ID NO: 212), DLER (SEQ ID NO: 213), LERD (SEQ ID NO: 214), ERDM (SEQ ID NO: 215), RDMH (SEQ ID NO: 216), DMHS (SEQ ID NO: 217), MHSG (SEQ ID NO: 218), LICH (SEQ ID NO: 219), ICHT (SEQ ID NO: 220), CHTN (SEQ ID NO: 221), HTNT (SEQ ID NO: 222), TNTL (SEQ ID NO: 223), TLNP (SEQ ID NO: 224), LNPA (SEQ ID NO: 225), NPAH (SEQ ID NO: 226), PAHG (SEQ ID NO: 227), RQVA (SEQ ID NO: 228), QVAV (SEQ ID NO: 229), VAVQ (SEQ ID NO: 230), AVQE (SEQ ID NO: 231), RNCK (SEQ ID NO: 232), NCKT (SEQ ID NO: 233), CKTP (SEQ ID NO: 234), KTPC (SEQ ID NO: 235), TPCN (SEQ ID NO: 236), ENIQ (SEQ ID NO: 237), NIQS (SEQ ID NO: 238), IQSI (SEQ ID NO: 239), QSIH (SEQ ID NO: 240), LPSR (SEQ ID NO: 241), PSRA (SEQ ID NO: 242), SRAG (SEQ ID NO: 243), RAGI (SEQ ID NO: 244).

In certain embodiments, the recombinant or chimeric protein comprises one or more of the sequences found to be unique in Ancestral Nodes 53 selected from in the sp domain, CLLQ (SEQ ID NO: 247), LLQF (SEQ ID NO: 248), LQFS (SEQ ID NO: 249), QFSF (SEQ ID NO: 250). In the A1 domain LLSE (SEQ ID NO: 251), LSEL (SEQ ID NO: 252), ELHV (SEQ ID NO: 253), RVPR (SEQ ID NO: 254), VPRS (SEQ ID NO: 255), PTIR (SEQ ID NO: 256), TIRA (SEQ ID NO: 257), IRAE (SEQ ID NO: 258), NEEE (SEQ ID NO: 259), EEED (SEQ ID NO: 260), CDRN (SEQ ID NO: 261), EDTY (SEQ ID NO: 262), PTYL (SEQ ID NO: 263), LSEN (SEQ ID NO: 264). In the activation peptide domain, ITLT (SEQ ID NO: 265), SIET (SEQ ID NO: 266), IETK (SEQ ID NO: 267), ETKR (SEQ ID NO: 268), TKRE (SEQ ID NO: 269), KRED (SEQ ID NO: 270), REDF (SEQ ID NO: 271), QKRT (SEQ ID NO: 272). In the A3 domain, VEQL (SEQ ID NO: 273), EGLW (SEQ ID NO: 274), GMSR (SEQ ID NO: 275), MSRS (SEQ ID NO: 276), SRSP (SEQ ID NO: 277).

Ancestral Protein Reconstruction

Recombinant porcine FVIII was approved by the FDA for the treatment of hemophilia A patients who have developed an autoimmune response to endogenous FVIII. Porcine FVIII displays reduce cross-reactivity toward antibody inhibitors developed against human FVIII. It is desirable to find FVIII sequences that have improved activity because it is possible that the frequency of infusion may be lessened while still achieving full prophylaxis. Murine FVIII (mFVIII) has displayed the longest observed half-life following activation.

A phylogenetic tree was constructed based on known orthologous FVIII sequences. Ancestral FVIII sequences were reconstructed and expressed in multiple cell lines. The ancestral FVIII sequences produced functional proteins that complexed with human coagulation factors. A sequence for the common ancestor of primates and rodents demonstrates higher biosynthesis/secretion than more evolved primates. Several ancestral FVIII sequences are expressed at greater levels than human FVIII in transient and recombinant expression systems.

Recombinant Proteins with the B domain deleted were produced.

The B-domain deleted sequence for Node number 68 having the E434V mutation is:

```
                                        SEQ ID NO: 39
MQIALFTCFFLSLFNFCSSATRRYYLGAVELSWNYMQSDLLSVLHTDTRF

LPRMPTSFPFNTSIMYKKTVFVEYMDHLFNIAKPRPPWMGLLGPTIWTEV

HDTVVITLKNMASHPVSLHAVGVSYWKASEGAEYEDQTSQREKEDDKVFP

GESHTYVWQVLKENGPMASDPPCLTYSYLSHVDLVKDLNSGLIGALLVCK

EGSLSKERTQMLHQFVLLFAVFDEGKSWHSETKDSFTQAMDSASTRAWPK

MHTVNGYVNRSLPGLIGCHRKSVYWHVIGMGTTPEVHSIFLEGHTFLVRN

HRQASLEISPITFLTAQTLLIDLGQFLLFCHISSHKHDGMEAYVKVDSCP

EEPQWQKKNNEEMEDYDDDLDSEMDMFTLDDDNSPFIQIRSVAKKYPKTW

IHYISAEEEDWDYAPSVLTSDDGSYKSQYLSNGPHRIGRKYKKVRFIAYT

DV [E434V mutation]

TFKTRETIQHESGILGPLLYGEVGDTLLIIFKNQASRPYNIYPHGITDVS

PLHSRRLPRGIKHVKDLPIRPGEIFKYKWTVTVEDGPTKSDPRCLTRYYS

SFINPERDLASGLIGPLLICYKESVDQRGNQMMSDKRNVILFSVFDENQS

WYITENMQRFLPNAADTQPQDPEFQASNIMHSINGYVFDSLQLTVCLHEV

AYWYILSVGAQTDFLSIFFSGYTFKHKMVYEDTLTLFPFSGETVFMSMEN

PGLWVLGCHNSDFRKRGMTALLKVSSCDKSTSDYYEEIYEDIPTQLVNDN

NVIEPRSFFQN [B-domain deletion]

PPVLKRHQRELSALQSEQEATDYDDSMETNEDFDIYGEDIKQGPRSFQQK

TRHYFIAAVERLWDYGMSTSPHVLRNRDQSGNAPQFKKVVFQEFTDGSFS

QPLYRGELNEHLGLLGPYIRAEVEDNIMVTFKNQASRPYSFYSSLISYKE

DQRQGEEPRRNFVKPNETKIYFWKVQHHMAPTEDEFDCKAWAYFSDVDLE

RDMHSGLIGPLLICHTNTLNPAHGRQVAVQEFALFFTIFDETKSWYFTEN

VERNCKTPCNIQMEDPTLKENYRFHAINGYVMDTLPGLVMAQDQRIRWYL

LSMGSNENIQSIHFSGHVFTVRKKEEYKMAVYNLYPGVFETVEMLPSRAG

IWRVECLIGEHLQAGMSTLFLVYSKQCQIPLGMASGSIRDFQITASGHYG

QWAPNLARLHHSGSINAWSTKEPFSWIKVDLLTPMIIHGIKTQGARQKFS

SLYISQFIIMYSLDGKKWLSYRGNSTGTLMVFFGNVDSSGIKHNSFNPPI

IARYIRLHPTHSSIRSTLRMELMGCDLNSCSIPLGMENKVISDTQITASS

YFTNMFATWSPSQARLHLQGRTNAWRPQVNDPKEWLQVDLQKTMKVTGII

TQGVKSLFTSMFVKEFLISSSQDGHHWTHILHNGKVKVFQGNQDSSTPMV

NSLDPPLLTRYLRIHPQIWEHQIALRLEILGCEAQQLY

The B-domain deleted sequence for Node number 53
having E434V mutation is: SEQ ID NO: 40
MQIELSTCFFLCLLQFSFSATRRYYLGAVELSWDYMQSDLLSELHVDTRF

PPRVPRSFPFNTSVMYKKTVFVEFTDHLFNIAKPRPPWMGLLGPTIRAEV

YDTVVITLKNMASHPVSLHAVGVSYWKASEGAEYDDQTSQREKEDDKVFP

GESHTYVWQVLKENGPMASDPPCLTYSYLSHVDLVKDLNSGLIGALLVCR

EGSLAKERTQTLHQFVLLFAVFDEGKSWHSETKDSLTQAMDSASARAWPK

MHTVNGYVNRSLPGLIGCHRKSVYWHVIGMGTTPEVHSIFLEGHTFLVRN

HRQASLEISPITFLTAQTLLMDLGQFLLFCHISSHQHDGMEAYVKVDSCP
```

-continued

EEPQLRMKNNEEEEDYDDDLYDSEMDVVRFDDDNSPPFIQIRSVAKKHPK

TWVHYIAAEEEDWDYAPSVLTPDDRSYKSQYLNNGPQRIGRKYKKVRF

MAYTDV [E434V mutation]

TFKTREAIQYESGILGPLLYGEVGDTLLIIFKNQASRPYNIYPHGITDVS

PLHSGRLPKGVKHLKDLPILPGEIFKYKWTVTVEDGPTKSDPRCLTRYYS

SFINLERDLASGLIGPLLICYKESVDQRGNQMMSDKRNVILFSVFDENRS

WYLTENMQRFLPNAAGVQPQDPEFQASNIMHSINGYVFDSLQLSVCLHEV

AYWYILSVGAQTDFLSVFFSGYTFKHKMVYEDTLTLFPFSGETVFMSMEN

PGLWVLGCHNSDFRNRGMTALLKVSSCDRNTGDYYEDTYEDIPTYLLSEN

NVIEPRSFSQN [B-domain deletion]

PPVLKRHQREITLTTLQSEQEEIDYDDTISIETKREDFDIYGEDENQGPR

SFQKRTRHYFIAAVERLWDYGMSRSPHVLRNRAQSGSVPQFKKVVFQEFT

DGSFTQPLYRGELNEHLGLLGPYIRAEVEDNIMVTFKNQASRPYSFYSSL

ISYEEDQRQGAEPRKNFVKPNETKTYFWKVQHHMAPTKDEFDCKAWAYFS

DVDLEKDMHSGLIGPLLICHTNTLNPAHGRQVTVQEFALFFTIFDETKSW

YFTENMERNCRAPCNIQMEDPTFKENYRFHAINGYVMDTLPGLVMAQDQR

IRWYLLSMGSNENIHSIHFSGHVFTVRKKEEYKMAVYNLYPGVFETVEML

PSKAGIWRVECLIGEHLHAGMSTLFLVYSKQCQTPLGMASGHIRDFQITA

SGQYGQWAPKLARLHYSGSINAWSTKEPFSWIKVDLLAPMIIHGIKTQGA

RQKFSSLYISQFIIMYSLDGKKWQTYRGNSTGTLMVFFGNVDSSGIKHNI

FNPPIIARYIRLHPTHYSIRSTLRMELMGCDLNSCSMPLGMESKAISDAQ

ITASSYFTNMFATWSPSQARLHLQGRTNAWRPQVNNPKEWLQVDFQKTMK

VTGITTQGVKSLLTSMYVKEFLISSSQDGHHWTLFLQNGKVKVFQGNQDS

FTPVVNSLDPPLLTRYLRIHPQSWVHQIALRLEVLGCEAQQLY

Biosynthetic Rates of Ancestral FVIII Molecules

Constructs within the ancestral mammalian Orders—Primates, Rodentia and Perissodactyla were reconstructed through gene transfer and expression in human embryonic kidney (HEK) 293 and baby hamster kidney (BHK) mammalian cell lines. Each construct displayed detectable FVIII activity as determined by one-stage coagulation assay. This assay utilizes human FVIII-deficient plasma in combination with a test substance to generate a macroscopic clot capable of physically trapping a metal ball being pulled by magnetic forces. This assay also confirmed the compatibility of each An-FVIII with human coagulation factor IXa, for which FVIII serves as a cofactor, as well as factor X, the substrate of factor IXa. Following transient transfection of HEK293T-17 cells with plasmid DNA encoding the An-FVIII variants, 11-, 9-, and 4-fold enhanced FVIII activity was observed from the cells expressing the inferred primate ancestors An-54, -53, and -52, respectively, relative to existing human FVIII. However, the closest inferred An-57 shares 99% identity to hFVIII and did not display a significant difference in activity. Within the non-primate groups, An-68 demonstrated the greatest activity at 14-fold relative to hFVIII while An-65, -78, and -76 did not display different secreted activity concentrations. Of note, porcine FVIII (pFVIII) and the human porcine hybrid ET3 demonstrated 8 and 7-fold increased activity, respectively.

In Vivo $ED_{50}$ Determination of Recombinant an-FVIII

To study the in vivo efficacy of $ED_{50}$ of two An-FVIII sequences, An-53 and An-68, secreted protein was purified to homogeneity using two-step ion exchange FPLC. Purity of the protein was confirmed using SDS-PAGE, and specific activities of An-53 and An-68 were measured as 18,500 and 8770 U/mg, respectively. Hemophilia A E16 mice of 8-12 weeks were administered a single dose of FVIII and challenged via tail transection 15 minutes following injection. For the Dixon up-and-down method, doses were determined a priori based upon previous investigation of human FVIII $ED_{50}$. A bleeding event was defined as blood loss exceeding the mean plus standard deviation of wildtype C57BL/6 mice following the same challenge. Completion of this study revealed that An-53 and An-68 yielded $ED_{50}$ values of 88.6 and 47.2 U/kg, respectively. The resulting efficacies mirror the differences in specific activities.

TABLE 1

ED50 determination of An-53 and An-68 by Dixon up-and-down method via murine tail transection bleeding challenge.
Dixon Up-and-Down Method for Small Samples

| Factor VIII | Dose (U/mL) | Log (Dose) | Response: X = Bleed ○ = No Bleed | | | | | |
|---|---|---|---|---|---|---|---|---|
| An-53 | 100 | 2 | | ○ | | | | X |
| | 63.1 | 1.8 | X | | ○ | | X | |
| | 39.8 | 1.6 | | | | X | | |
| An-68 | 63.1 | 1.8 | ○ | | ○ | | | |
| | 39.8 | 1.6 | | X | | ○ | | X |
| | 25.1 | 1.4 | | | | | X | |
| Saline | 0 | N/A | X | X | | | | |
| hFVIII | 200 | 2.3 | ○ | ○ | | | | |

Antigenicity of Ancestral FVIII

An obstacle in the treatment of hemophilia A patients with protein replacement is the development of inhibitors. In naïve hemophilia A populations, infusions of picomolar concentrations of exogenous FVIII is sufficient to generate a robust adaptive immune response. Efforts to identify and remove immunogenic epitopes within human FVIII have largely utilized a panel of well characterized mouse anti-human monoclonal antibodies (MAbs).

Using a subset of MAbs with inhibitor titers over 1000 BU/mg and specificity targeting the A2 and C2 domains, ancestral FVIII were tested as an antigenic substrate via ELISA. Despite sharing 95% identity to modern human, An-53 displays markedly reduced cross-reactivity within the A2 and C2 domains. All group A MAbs are known to bind a major epitope in the highly immunogenic 484-508 loop of human FVIII, however, only MAbs 4A4 and G32 demonstrate cross-reactivity to An-53 (FIG. 5). These MAbs were explored for inhibitor titers against An-53 and show that G32 has an inhibitory titer 45-fold less compared to human FVIII while 4A4 has an equivalent titer against both human and An-53. An-53 has 4 residue substitutions within the 484-508 loop which may explain the absence of cross reactivity and/or inhibition by these potent A2 domain inhibitors. In addition to the 484-508 epitope, homolog scanning mutagenesis of human FVIII with porcine FVIII has previously shown that a major epitope of 4A4 lies within residues 403-444, but has not been defined. Alignment of several FVIII A2 domain sequences either possessing or lacking the 4A4 epitope allows for the identification of 4 residues that may be responsible for altered binding affinity. Three of these residues, Asp403, Gln410, and Asn414 are distal to the 484-508 surface loop and therefore unlikely to contribute significant binding energy. However, Glu434 is within close proximity to Ile508. Mutation of E434 to valine as observed in porcine FVIII resulted in a >4,000 fold reduction in 4A4 inhibition to undetectable levels as measured by modified Bethesda assay (FIG. 6).

Hydrodynamic Delivery of Two an-53 Plasmid DNA (Encoding AN-53 and AN-56) in an AAV Expression Cassette The use of AAV as a gene therapy application for hemophilia A has been explored extensively by many academic and commercial laboratories and recently advanced into clinical testing. An AAV-based product for hemophilia A has progressed beyond pre-clinical investigation. The major limitation to all gene therapy protocols for hemophilia A, both AAV and lentiviral, has continued to be the low level biosynthesis of FVIII at clinical achievable or predictably-safe vector doses. Given the enhanced biosynthesis observed for An-53 and An-56, despite high identity to human FVIII, in recombinant cell line systems, their utility was investigated in vivo following nucleic acid delivery to the liver of hemophilia A mice as a preclinical proxy for liver-directed AAV gene therapy.

An-53, An-56 and ET3 cDNAs were subcloned into an AAV expression cassette under the liver-specific HLP promoter (FIG. 7). Hemophilia A E16 mice were administered 3 μg linearized plasmid DNA (pDNA) diluted in TransIT®-EE delivery solution. A total volume equaling 10% of the mouse body weight was injected via tail vein within 4-7 seconds. Hydrodynamic injection results in DNA uptake predominantly in hepatocytes with other organs minimally affected. By placing transcriptional control under the HLP promoter, liver specificity was increase to better mimic the tropism of several AAV serotypes in clinical testing (e.g. AAV8).

Plasma FVIII levels were monitored over two weeks following injection. Peak FVIII levels were observed at day 3 for all constructs tested. Compared to the high-expression human/porcine hybrid ET3, An-53 demonstrated significantly increased and superphysiological peak FVIII levels of 2.37 units/mL. Interestingly, An-56 levels were detectable but did not exceed 0.06 units/mL throughout the experiment, suggesting that the sequence specificities allowing for enhanced biosynthesis in BHK-M cells did not convey an advantage in mouse hepatocytes. Using this system, liver codon optimized human FVIII at 3 μg per mouse was insufficient to yield detectable FVIII levels in empirical studies. The specific activity of An-53 generated in vivo was analyzed via an ELISA using cross-reactive anti-human MAbs compared to a recombinant An-53 standard curve. The FVIII produced de novo demonstrated a specific activity of 13,000±5100 U/mg.

High DNA requirement in a hydrodynamic setting can be paralleled to the viral titer required to achieve therapeutic levels of FVIII. Therefore, hydrodynamic injections were conducted using two doses, a repeat of 3 μg and 4-fold lower DNA dose at 0.75 μg per mouse. Following hydrodynamic injection, ET3 DNA was observed to display the predicted dose response. An-53 DNA produced similar FVIII activity levels at 4-fold lower DNA dose. See FIG. 8.

Human and Ancestral Chimeric Sequences

It is contemplated that ancestral and human chimeric protein can be produced. In certain embodiments, the disclosure contemplates that the human FVIII B domain deleted sequences can be replaced with Ancestral A1 and A3 sequences e.g., sp-A1 (node 68)-A2 (Human E434V mutation)-(B-partially deleted Human)-linker-ap-A3 (node 68)-C1-C2 (human)

SEQ ID NO: 42:

MQIALFTCFFLSLFNFCSSATRRYYLGAVELSWNYMQSDLLSVLHTDTRF

LPRMPTSFPFNTSIMYKKTVFVEYMDHLFNIAKPRPPWMGLLGPTIWTEV

HDTVVITLKNMASHPVSLHAVGVSYWKASEGAEYEDQTSQREKEDDKVFP

GESHTYVWQVLKENGPMASDPPCLTYSYLSHVDLVKDLNSGLIGALLVCK

EGSLSKERTQMLHQFVLLFAVFDEGKSWHSETKDSFTQAMDSASTRAWPK

MHTVNGYVNRSLPGLIGCHRKSVYWHVIGMGTTPEVHSIFLEGHTFLVRN

HRQASLEISPITFLTAQTLLIDLGQFLLFCHISSHKHDGMEAYVKVDSCP

EEPQWQKKNNEEMEDYDDDLDSEMDMFTLDDDNSPFIQIRSVAKKHPKTW

VHYIAAEEEDWDYAPLVLAPDDRSYKSQYLNNGPQRIGRKYKKVRFMAYT

DV [E434V mutation]

TFKTREAIQHESGILGPLLYGEVGDTLLIIFKNQASRPYNIYPHGITDVR

PLYSRRLPKGVKHLKDFPILPGEIFKYKWTVTVEDGPTKSDPRCLTRYYS

SFVNMERDLASGLIGPLLICYKESVDQRGNQIMSDKRNVILFSVFDENRS

WYLTENIQRFLPNPAGVQLEDPEFQASNIMHSINGYVFDSLQLSVCLHEV

AYWYILSIGAQTDFLSVFFSGYTFKHKMVYEDTLTLFPFSGETVFMSMEN

PGLWILGCHNSDFRNRGMTALLKVSSCDKNTGDYYEDSYEDISAYLLSKN

NAIEPRSFAQN [B-domain deletion]

SRPPSASAPK [linker]

PPVLKRHQRELSALQSEQEATDYDDSMETNEDFDIYGEDIKQGPRSFQQK

TRHYFIAAVERLWDYGMSTSPHVLRNRDQSGNAPQFKKVVFQEFTDGSFS

QPLYRGELNEHLGLLGPYIRAEVEDNIMVTFKNQASRPYSFYSSLISYKE

DQRQGEEPRRNFVKPNETKIYFWKVQHHMAPTEDEFDCKAWAYFSDVDLE

RDMHSGLIGPLLICHTNTLNPAHGRQVAVQEFALFFTIFDETKSWYFTEN

VERNCKTPCNIQMEDPTLKENYRFHAINGYVMDTLPGLVMAQDQRIRWYL

LSMGSNENIQSIHFSGHVFTVRKKEEYKMAVYNLYPGVFETVEMLPSRAG

IWRVECLIGEHLQAGMSTLFLVYSKKCQTPLGMASGHIRDFQITASGQYG

QWAPKLARLHYSGSINAWSTKEPFSWIKVDLLAPMIIHGIKTQGARQKFS

SLYISQFIIMYSLDGKKWQTYRGNSTGTLMVFFGNVDSSGIKHNIFNPPI

IARYIRLHPTHYSIRSTLRMELMGCDLNSCSMPLGMESKAISDAQITASS

YFTNMFATWSPSKARLHLQGRSNAWRPQVNNPKEWLQVDFQKTMKVTGVT

TQGVKSLLTSMYVKEFLISSSQDGHQWTLFFQNGKVKVFQGNQDSFTPVV

NSLDPPLLTRYLRIHPQSWVHQIALRMEVLGCEAQDLY.

The invention claimed is:

1. A recombinant or chimeric FVIII protein, comprising, in an N- to C-terminal direction, an A1 domain, an A2 domain, a linker, an ap domain, an A3 domain, a C1 domain, and a C2 domain, wherein the protein has a B-domain deletion with the A2 and ap domains joined by the linker, and wherein the protein has FVIII activity, and:
   the A1 domain has an amino acid sequence at least 96% identical to SEQ ID NO: 22;
   the A2 domain has an amino acid sequence at least 96% identical to SEQ ID NO: 23;
   the ap domain has an amino acid sequence at least 96% identical to SEQ ID NO: 25;
   the A3 domain has an amino acid sequence at least 96% identical to SEQ ID NO: 26;
   the C1 domain has an amino acid sequence at least 96% identical to SEQ ID NO: 27; and
   the C2 domain has an amino acid sequence at least 96% identical to SEQ ID NO: 28.

2. The protein of claim 1, wherein:
   the A1 domain has an amino acid sequence at least 99% identical to SEQ ID NO: 22;
   the A2 domain has an amino acid sequence at least 99% identical to SEQ ID NO: 23;
   the ap domain has an amino acid sequence at least 99% identical to SEQ ID NO: 25;
   the A3 domain has an amino acid sequence at least 99% identical to SEQ ID NO: 26;
   the C1 domain has an amino acid sequence at least 99% identical to SEQ ID NO: 27; and the C2 domain has an amino acid sequence at least 99% identical to SEQ ID NO: 28.

3. The protein of claim 1 wherein the A2 domain comprises a glutamate or a valine residue at FVIII position 453, wherein the FVIII position is according to a FVIII protein sequence set forth as SEQ ID NO: 1.

4. The protein of claim 1, wherein the linker comprises an amino acid sequence between two and fifty amino acids in length.

5. The protein of claim 1 comprising the amino acid sequence set forth as SEQ ID NO: 40 without the signal peptide of residues 1-19.

6. A nucleic acid encoding the protein of claim 1.

7. A pharmaceutical composition comprising the protein of claim 1.

8. A method of inducing blood clotting comprising administering an effective amount of a pharmaceutical composition of claim 7 to a subject in need thereof.

9. The protein of claim 3, comprising the valine residue at FVIII position 453.

10. The protein of claim 3, comprising the glutamate residue at FVIII position 453.

11. The protein of claim 1, wherein the linker comprises an amino acid sequence set forth as SFSQNPPVLKRHQR (residues 761-774 of SEQ ID NO: 40).

12. The protein of claim 2, wherein the linker comprises an amino acid sequence set forth as SFSQNPPVLKRHQR (residues 761-774 of SEQ ID NO: 40).

13. The protein of claim 1, comprising an amino acid sequence at least 96% identical to SEQ ID NO: 40 without the signal peptide of residues 1-19.

14. The protein of claim 13, comprising an amino acid sequence at least 99% identical to SEQ ID NO: 40 without the signal peptide of residues 1-19.

15. The protein of claim 14, comprising the amino acid sequence set forth as SEQ ID NO: 40 without the signal peptide of residues 1-19 and further comprising a glutamate residue at FVIII position 453, wherein the FVIII position is according to the FVIII protein sequence set forth as SEQ ID NO: 1.

16. The protein of claim 1, wherein
  the A1 domain has the amino acid sequence set forth as SEQ ID NO: 22;
  the A2 domain has the amino acid sequence set forth as SEQ ID NO: 23, further comprising a glutamate residue at FVIII position 453, wherein the FVIII position is according to a FVIII protein sequence set forth as SEQ ID NO: 1;
  the ap domain has the amino acid sequence set forth as SEQ ID NO: 25;
  the A3 domain has the amino acid sequence set forth as SEQ ID NO: 26;
  the C1 domain has the amino acid sequence set forth as SEQ ID NO: 27; and
  the C2 domain has the amino acid sequence set forth as SEQ ID NO: 28.

17. The protein of claim 16, wherein the linker comprises the amino acid sequence set forth as SFSQNPPVLKRHQR (residues 761-774 of SEQ ID NO: 40).

18. The protein of claim 4, wherein the linker comprises a PACE/furin processing sequence set forth as RHQR (SEQ ID NO: 245).

* * * * *